(12) United States Patent
Parthasaradhi Reddy et al.

(10) Patent No.: US 9,067,966 B2
(45) Date of Patent: Jun. 30, 2015

(54) LUPEOL-TYPE TRITERPENE DERIVATIVES AS ANTIVIRALS

(75) Inventors: Bandi Parthasaradhi Reddy, Hyderabad (IN); Vedula Manohar Sharma, Hyderabad (IN); Kura Rathnakar Reddy, Hyderabad (IN); Musku Madhanmohan Reddy, Hyderabad (IN); Nelli Yella Reddy, Hyderabad (IN); Lanka VL Subrahmanyam, Hyderabad (IN)

(73) Assignee: HETERO RESEARCH FOUNDATION, HETERO DRUGS LTD. (IN)

( * ) Notice: Subject to any disclaimer, the term of this patent is extended or adjusted under 35 U.S.C. 154(b) by 521 days.

(21) Appl. No.: 12/829,483

(22) Filed: Jul. 2, 2010

(65) Prior Publication Data

US 2011/0015196 A1 Jan. 20, 2011

Related U.S. Application Data

(60) Provisional application No. 61/251,933, filed on Oct. 15, 2009.

(30) Foreign Application Priority Data

Jul. 14, 2009 (IN) .............................. 1670/CHE/2009
Mar. 8, 2010 (IN) ............................... 587/CHE/2010

(51) Int. Cl.
| | |
|---|---|
| *A61K 31/56* | (2006.01) |
| *A61K 31/58* | (2006.01) |
| *C07J 43/00* | (2006.01) |
| *C07J 53/00* | (2006.01) |
| *C07J 63/00* | (2006.01) |
| *C07J 69/00* | (2006.01) |

(52) U.S. Cl.
CPC ................ *C07J 63/008* (2013.01); *C07J 69/00* (2013.01)

(58) Field of Classification Search
CPC ................................. C07J 63/008; C07J 69/00
USPC ..................... 540/107; 514/169, 176; 552/510
See application file for complete search history.

(56) References Cited

U.S. PATENT DOCUMENTS

| | | | |
|---|---|---|---|
| 5,679,828 A | 10/1997 | Lee et al. | |
| 6,670,345 B1 | 12/2003 | Ramadoss et al. | |
| 7,923,573 B2 | 4/2011 | Tamaki et al. | |
| 2004/0204389 A1 | 10/2004 | Chen et al. | |
| 2006/0194774 A1 | 8/2006 | Selzer et al. | |
| 2006/0205697 A1 | 9/2006 | Robinson et al. | |
| 2008/0207573 A1 | 8/2008 | Yager | |
| 2008/0214516 A1 | 9/2008 | Selzer et al. | |
| 2011/0152229 A1 | 6/2011 | Chen et al. | |
| 2011/0218204 A1 | 9/2011 | Parthasaradhi Reddy et al. | |
| 2014/0221328 A1 | 8/2014 | Parthasaradhi Reddy et al. | |

FOREIGN PATENT DOCUMENTS

| | | |
|---|---|---|
| CA | 2223513 A1 | 12/1996 |
| CN | 1861627 A | 11/2006 |
| CN | 101287744 A | 10/2008 |
| WO | 0046235 A1 | 8/2000 |
| WO | 02091858 A1 | 11/2002 |
| WO | 2004072092 A1 | 8/2004 |
| WO | 2005090380 A1 | 9/2005 |
| WO | 2006053255 A2 | 5/2006 |
| WO | 2006105356 A2 | 10/2006 |
| WO | 2007002411 A1 | 1/2007 |
| WO | 2007141383 A1 | 12/2007 |
| WO | 2007141390 A1 | 12/2007 |
| WO | 2007141391 A1 | 12/2007 |
| WO | 2007141392 A2 | 12/2007 |
| WO | 2008057420 A2 | 5/2008 |
| WO | 2008091532 A1 | 7/2008 |
| WO | 2008127364 A2 | 10/2008 |
| WO | 2009082818 A1 | 7/2009 |
| WO | 2009082819 A1 | 7/2009 |
| WO | 2009100532 A1 | 8/2009 |
| WO | 2010132334 A1 | 11/2010 |
| WO | 2011007230 A2 | 1/2011 |
| WO | 2011007230 A3 | 1/2011 |

OTHER PUBLICATIONS

Antimonova, A.N. et al., Synthesis of Betulonic Acid Amides, Chemistry of Natural Compounds, 2008, vol. 44, No. 3, pp. 327-333.
Sun, i. et al., Anti-AIDS Agents, 34. Synthesis and Structure-Activity Relationships of Betulin Derivatives as Anti-HIV Agents, J. Med. Chem. 1998, vol. 41, pp. 4648-4657.
Zhu, YM, et al., Synthesis and Anti-HIV Activity Oleanolic Acid Derivatives, Bioorganic & Medicinal Chemistry Letters, 2001, vol. 11, pp. 3115-3118.
Hashimoto, F. et al., Anti-AIDS Agents—XXVIL. Synthesis and Anti-HIV Activity of Betulinic Acid and Dihydrobetulinic Acid Derivatives, Bioorganic & Medicinal Chemistry, 1997, vol. 5, No. 12, pp. 2133-2143.
Qian, K. et al., Anti-AIDS Agents 81. Design, Synthesis, and Structure—Activity Relationship Study of Betulinic Acid and Moronic Acid Derivatives as Potent HIV Maturation Inhibitors, J. Med. Chem., 2010, vol. 53, pp. 3133-3141.
International Search Report for PCT/IB2010/001677 dated Jul. 5, 2010 and Written Opinion.
International Search Report of PCT/IB2011/054183 dated Sep. 22, 2011 and Written Opinion.
Kashiwada, Y. et al., Betulinic Acid and Dihydrobetulinic Acid Derivatives as Potent Anti-HIV Agents, J. Med. Chem, 1996, 1016-1017, vol. 39.

(Continued)

*Primary Examiner* — Barbara P Badio
(74) *Attorney, Agent, or Firm* — Cantor Colburn LLP

(57) ABSTRACT

The invention relates to novel lupeol-type triterpene derivatives and related compounds, and pharmaceutical compositions useful for therapeutic treatment of viral diseases and particularly HIV mediated diseases.

15 Claims, No Drawings

(56) References Cited

OTHER PUBLICATIONS

Moglioni, A.G. et al, Divergent Routes to Chiral Cyclobutane Synthons from (-)-α-Pinene and Their Use in the Stereoselective Synthesis of Dehydro Amino Acids, J. Org. Chem, 2000, 3934-3940, vol. 65.

Kanamoto, T. et al., Anti-Human Immunodeficiency Virus Activity of YK-FH312 (a Betulinic Acid Derivative), a Novel Compound Blocking Viral Maturation, Antimicrobial Agents and Chemotherapy, Apr. 2001, 1225-1230, vol. 45, No. 4.

Popik, W. et al., Human Immunodeficiency Virus Type 1 Uses Lipid Raft-Colocalized CD4 and Chemokine Receptors for Productive Entry into CD4+ T Cells, Journal of Virology, May 2002, 4709-4722, vol. 76, No. 10.

Aguado, G.P. et al., Enantiodivergent synthesis of cyclobutyl-(Z)-α, β-dehydro-α-amino acid derivatives from (-)-cispinononic acid, Tetrahedron Asymmetry, 2003, 217-223, vol. 14.

Li, F. et al., PA-457: A potent HIV inhibitor that disrupts core condensation by targeting a late step in Gag processing, Proc. Natl. Acad. Sci., Nov. 11, 2003, 13555-13560, vol. 100, No. 23.

Zhou, J. et al., Small-Molecule Inhibition of Human Immunodeficiency Virus Type 1 Replication by Specific Targeting of the Final Step of Virion Maturation, Journal of Virology, Jan. 2004, 922-929, Vo. 78, No. 2.

Zhou, J., et al., Inhibition of HIV-1 Maturation via Drug Association with the Viral Gag Protein in Immature HIV-1 Particles*, Journal of Biological Chemistry, Dec. 23, 2005, 42149-42155, vol. 280, No. 51.

Sakalian, M. et al., 3-O-(3',3'-Dimethysuccinyl) Betulinic Acid Inhibits Maturation of the Human Immunodeficiency Virus Type 1 Gag Precursor Assembled In Vitro, Journal of Virology, Jun. 2006, 5716-5722, vol. 80, No. 12.

Aguilera, J. et al., Stereodivergent snythesis of the first bis-cyclobutane) γ-dipeptides and mixed γ-oligomers, Tetrahedron Asymmetry, 2008, 302-308, vol. 19.

LUPEOL-TYPE TRITERPENE DERIVATIVES AS ANTIVIRALS

This application claims the benefit of Indian Provisional Patent Application Nos. 1670/CHE/2009 filed on 14 Jul. 2009 and 587/CHE/2010 filed on 8 Mar. 2010; and U.S. Provisional Patent Application No. 61/251,933 filed on 15 Oct. 2009, all of which are incorporated herein by reference in their entirety.

FIELD OF THE INVENTION

The present invention relates to novel lupeol-type triterpene derivatives and related compounds, compositions useful for therapeutic treatment of viral diseases and particularly HIV mediated diseases.

BACKGROUND OF THE INVENTION

The Human Immunodeficiency Virus (HIV) has now been established as the causative agent of the Acquired Immunodeficiency Syndrome (AIDS) for over 20 years (Science 1983, 220, 868-871; N. Eng. J. Med. 1984, 311, 1292-1297). AIDS is characterized by the destruction of the immune system, particularly of CD4+T-cells. HIV is a retrovirus, and the HIV life cycle encompasses several crucial steps, starting from the attachment of the virus to the host cell membrane and finishing with the release of progeny virons from the cell.

The natural compound betulinicacid acid, isolated from *Syzygium clavifolium* and several other plant species was found to possess anti-HIV activity. Chemical modifications were undertaken by several research groups in an attempt to identify potent anti-HIV agents by making semi-synthetic analogs of betulinic acid, leading to the discovery of bevirimat as a compound with a novel mechanism of action (J. Nat. Prod. 199457(2):243-7; J. Med. Chem. 1996, 39(5), 1016). Further studies shown that bevirimat acts by disrupting Gag processing (Proc. Natl. Acad. Sci. USA 2003, 100(23):13555-60; Antimicrob. Agents. Chemother. 2001, 45(4), 1225-30; J. Virol. 2004, 78(2): 922-9; J. Biol. Chem. 2005, 280(51):42149-55; J. Virol. 2006, 80(12): 5716-22) and to be a first-in-class maturation inhibitor with a potent activity against HIV-1.

Encouraged by these developments, medicinal chemists started exploring betulinic acid derivatives and related compounds intensively for their therapeutic activities. For example, the patent publication WO 2008057420 describes extended triterpene derivatives as antiretroviral agents; WO 2007141391 describes Betulin derived compounds useful as antiprotozoal agents; WO 2007141390 describes preparation of betulin derived compounds as antiviral agents; WO 2008127364 describes preparation of betulinic acid derivatives for use in antiviral and anticancer pharmaceutical compositions; US 20080207573 describes preparation of triterpene derivatives for therapeutic use in the treatment of viral infections; WO 2007141389 describes preparation of betulin derived compounds as antibacterial agents; US 20040204389 describes anti-HIV agents with dual sites of action; WO 2007/002411 describes antiviral compounds; CN 1861627 describes antitumor agents; WO 2006053255 describes novel betulin derivatives, preparation thereof and use thereof; WO 2009/082818 describes novel C-21 keto lupine derivatives preparation and use thereof; and WO 2006105356 describes methods of manufacturing bioactive 3-esters of betulinic aldehyde and betulinic acid.

Similarly WO 2009/082819, WO 2009/100532 disclosed 17 β lupine derivatives as anti-HIV agents.

Some more references disclose betulinic acid related compounds. For example, WO 2007141383 describes betulin derivatives as antifeedants for plant pests; U.S. Pat. No. 6,670,345 describes use of betulinic acid and its derivatives for inhibiting cancer growth and process for the manufacture of betulinic acid; WO 2002091858 describes anxiolytic marcgraviaceae compositions containing betulinic acid, betulinic acid derivatives, and methods of preparation and use; WO 2000046235 describes preparation of novel betulinic acid derivatives for use as cancer growth inhibitors and WO 2007141392 describes cosmetic and pharmaceutical compositions comprising betulonic acid and betulin derivatives.

Given the fact of the world wide epidemic level of AIDS, there is a strong continued need for new effective drugs for treatment of HIV infected patentis, disease conditions and/or disorders mediated by HIV by discovering new compounds with novel structures and/or mechanism of action(s).

SUMMARY OF THE INVENTION

The present invention relates to the compounds of the formula (1):

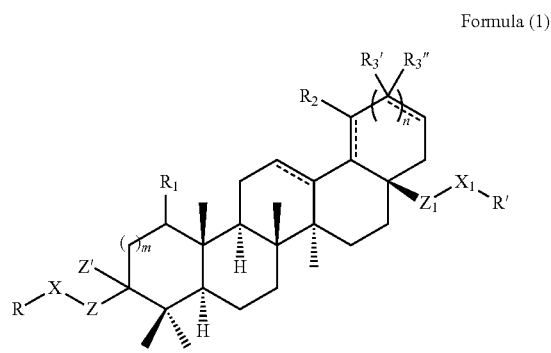

Formula (1)

wherein,
R can be H, substituted or unsubstituted alkyl, substituted or unsubstituted aryl, substituted or unsubstituted cycloalkyl, or substituted or unsubstituted heterocyclyl and preferably R can be substituted by $R^a$;

R' can be H, substituted or unsubstituted alkyl, substituted or unsubstituted aryl, substituted or unsubstituted cycloalkyl, substituted or unsubstituted cycloalkenyl, substituted or unsubstituted heterocyclyl, substituted or unsubstituted alkyloxy, or substituted or unsubstituted aryloxy and preferably R' can be substituted by $R^a$;

X and $X_1$ independently can be selected from a bond, —O—, —NR"—, —C(O)—, —C(O)$_2$—, —(CH$_2$)$_n$—, or —C(O)NR"—;

Z and $Z_1$ are independently can be selected from a bond, —C(O)—, —(CH$_2$)$_n$—, —O—, —S—, —SO$_2$—, or —NR"—;

Z' can be H, substituted or unsubstituted alkyl or Z and Z' can be together with the attached carbon to form oxo (C═O) and when Z and Z' together with the attached carbon form oxo (C═O) then X and R are absent;

n can be an integer 0-2;
m can be an integer 0-2;
" ≡ " can be single bond or double bond;

$R_1$ can be H, C(O)$_2$R", or substituted or unsubstituted alkyl;

$R_2$ can be H, substituted or unsubstituted alkyl, substituted or unsubstituted alkenyl, substituted or unsubstituted alkynyl, or substituted or unsubstituted cycloalkyl;

R₃' and R₃" independently can be selected from H, or substituted or unsubstituted alkyl and when "═══" is a double bond then one of R₃' or R₃" is absent;

R^a can be H, OH, halogen, NR", C(O)₂R", CH₂OR", C(O)NR" or substituted or unsubstituted alkyl; and each R" can be independently selected from H, substituted or unsubstituted alkyl, substituted or unsubstituted amino, substituted or unsubstituted aryl, substituted or unsubstituted cycloalkyl, or substituted or unsubstituted heterocyclyl; and a proviso that one of the R or R' is substituted or unsubstituted 4 or 5 membered cycloalkyl group, and if R or R' is 4 membered cycloalkyl group then at least one of the carbon atom of the 4 membered cycloalkyl group must be substituted by two identical groups and which are selected from alkyl or halogen wherein most preferably alkyl is methyl and halo is fluorine.

Pharmaceutically acceptable salts of the compounds of the formula (1) are also contemplated. Likewise, pharmaceutically acceptable solvates, including hydrates, of the compounds of the formula (1) are contemplated.

It should be understood that formula (1) structurally encompasses all stereoisomers, including enantiomers, diastereomers, racemates, and combinations thereof, which may be contemplated from the chemical structure of the genus described herein.

Also contemplated are prodrugs of the compounds of the formula (1), including ester prodrugs.

According to one embodiment, there is provided a compound of formula (1), wherein X is —C(O)—.

According to one embodiment, there is provided a compound of formula (1), wherein X is —C(O)NR"—.

According to one embodiment, there is provided a compound of formula (1), wherein X is a bond.

According to one embodiment, there is provided a compound of formula (1), wherein Z is O.

According to one embodiment, there is provided a compound of formula (1), wherein Z' is H.

According to one embodiment, there is provided a compound of formula (1), wherein R is H.

According to one embodiment, there is provided a compound of formula (1), wherein R is substituted or unsubstituted cyclobutyl.

According to one embodiment, there is provided a compound of formula (1), wherein R is substituted or unsubstituted cyclopentyl.

According to one embodiment, there is provided a compound of formula (1), wherein R is substituted or unsubstituted alkyl.

According to one embodiment, there is provided a compound of formula (1), wherein R is H, —C((CH₃)₂)—CO₂H, —C((CH₃)₂)—CH2-CO₂H, —CH₂—CH2-CO₂H, —CH2-CO₂H and CH₃.

According to one embodiment, there is provided a compound of formula (1), wherein Z₁ is a bond.

According to one embodiment, there is provided a compound of formula (1), wherein X₁ is —C(O)NR"— and —C(O)₂—.

According to one embodiment, there is provided a compound of formula (1), wherein R' is H.

According to one embodiment, there is provided a compound of formula (1), wherein R' is substituted or unsubstituted alkyl.

According to one embodiment, there is provided a compound of formula (1), wherein R' is substituted or unsubstituted cyclobutyl.

According to one embodiment, there is provided a compound of formula (1), wherein R' is substituted or unsubstituted cyclopentyl.

According to one embodiment, there is provided a compound of formula (1), wherein R" is H.

According to one embodiment, there is provided a compound of formula (1), wherein R₁ is H.

According to one embodiment, there is provided a compound of formula (1), wherein R₂ is propene.

According to one embodiment, there is provided a compound of formula (1), wherein "═══" is single bond;

According to one embodiment, there is provided a compound of formula (1), wherein n is 0.

According to one embodiment, there is provided a compound of formula (1), wherein m is 0 and 1.

Accordingly, one aspect of the present invention provides compounds of formula (1A):

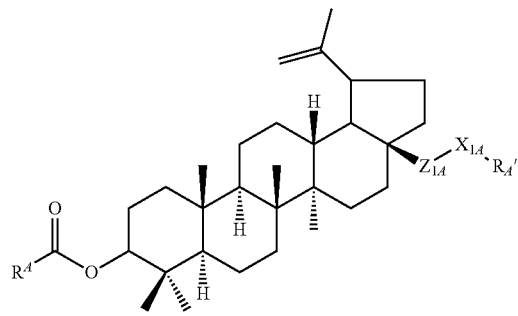

Formula (1A)

wherein,

R^A can be substituted or unsubstituted alkyl or substituted or unsubstituted cycloalkyl; wherein cycloalkyl is a 4 or 5 membered ring system and substituents in each occurrence is independently selected from H, halo, C₁-C₄ alkyl, CO—O—R_b, —CH2-O—R_b, CO—NHR_b, or CON(R_b)₂; and preferably substituted or unsubstituted alkyl of R^A can be selected from:

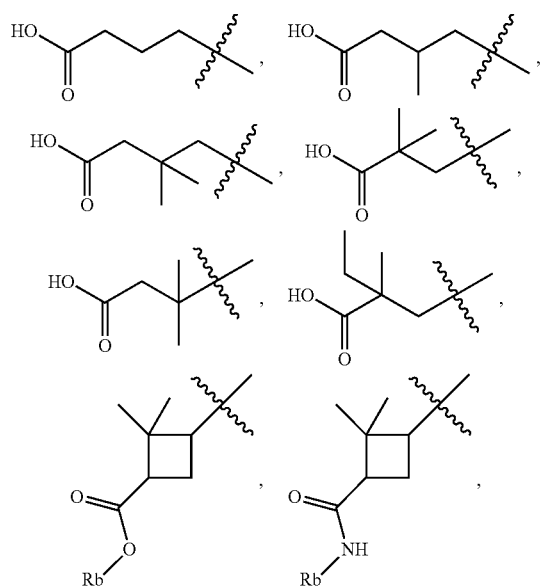

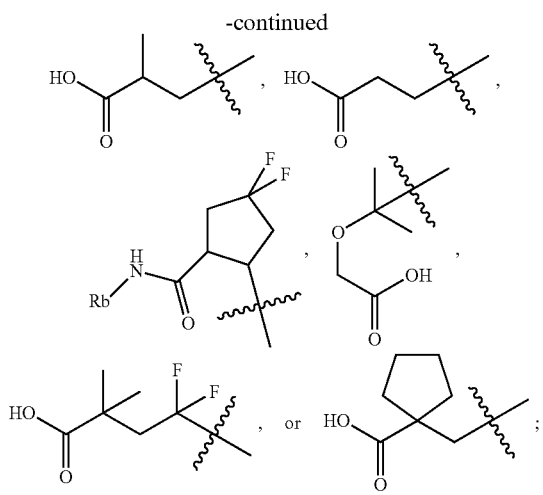

$R_A'$ can be H, substituted or unsubstituted alkyl, substituted or unsubstituted aryl, substituted or unsubstituted cycloalkyl, and preferably $R_A'$ can be substituted by $R^a$;

$X_{1A}$ can be a bond, —O—, —NR"—, —C(O)—, —C(O)$_2$—, or —C(O)NR"—;

$Z_{1A}$ can be a bond, —C(O)—, —O—, —S—, —SO$_2$—, or —NR"—;

$R^a$ can be H, OH, halogen, NR", C(O)$_2$R", CH$_2$OR", C(O)NR" or substituted or unsubstituted alkyl;

$R_b$ can be H, or substituted or unsubstituted alkyl; and each R" can be independently selected from H, substituted or unsubstituted alkyl, substituted or unsubstituted amino, substituted or unsubstituted aryl, substituted or unsubstituted cycloalkyl, or substituted or unsubstituted heterocyclyl; and a proviso that one of the $R^A$ or $R_A'$ is substituted or unsubstituted 4 or 5 membered cycloalkyl group, and if $R^A$ or $R_A'$ is 4 membered cycloalkyl group then at least one of the carbon atom of the 4 membered cycloalkyl group must be substituted by two identical groups and which are selected from alkyl or halogen wherein most preferably alkyl is methyl and halo is fluorine.

Pharmaceutically acceptable salts of the compounds of the formula (1A) are also contemplated. Likewise, pharmaceutically acceptable solvates, including hydrates, of the compounds of the formula (1A) are contemplated.

It should be understood that formula (1A) structurally encompasses all stereoisomers, including enantiomers and diastereomers, which may be contemplated from the chemical structure of the genus described herein.

Also contemplated are prodrugs of the compounds of the formula (1A), including ester prodrugs.

According to one embodiment, there is provided a compound of formula (1A), wherein $R^A$ is substituted or unsubstituted cyclobutyl.

According to one embodiment, there is provided a compound of formula (1A), wherein $R^A$ is CH$_2$—C((CH$_3$)$_2$)—CO$_2$H, and CH$_3$.

According to one embodiment, there is provided a compound of formula (1A), wherein $R_A'$ is substituted or unsubstituted cyclobutyl.

According to one embodiment, there is provided a compound of formula (1A), wherein $R_A'$ is H, CH$_2$—C((CH$_3$)$_2$)—CO$_2$H, and CH$_3$.

Also the present invention relates to the compounds of the formula (2):

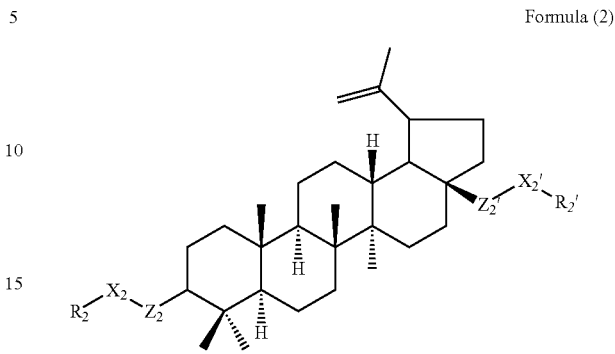

Formula (2)

wherein, $R_2$ can be H, substituted or unsubstituted alkyl, substituted or unsubstituted aryl, or substituted or unsubstituted cycloalkyl and preferably $R_2$ can be substituted by $R^a$;

$R_2'$ can be H, substituted or unsubstituted alkyl, substituted or unsubstituted aryl, substituted or unsubstituted cycloalkyl, substituted or unsubstituted heterocyclyl, substituted or unsubstituted alkyloxy, or substituted or unsubstituted aryloxy and preferably $R_2'$ can be substituted by $R^a$;

$X_2$ and $X_2'$ are independently can be selected from a bond, —O—, —NR"—, —C(O)—, —C(O)$_2$—, —(CH$_2$)$_n$—, or —C(O)NR"—;

n can be 0-3;

$Z_2$ and $Z_2'$ are independently can be selected from a bond, —C(O)—, —O—, or —NR"—;

$R^a$ can be H, OH, halogen, N(R")$_2$, C(O)R", C(O)$_2$R", CH$_2$OR", C(O)N(R")$_2$ or substituted or unsubstituted alkyl;

each R" can be independently selected from H, —[CH(R''')]$_p$C(O)$_2$R''', substituted or unsubstituted alkyl, substituted or unsubstituted amino, substituted or unsubstituted aryl, substituted or unsubstituted cycloalkyl, or substituted or unsubstituted heterocyclyl;

p can be 0-3; and each R''' can be independently selected from H, substituted or unsubstituted alkyl, or substituted or unsubstituted cycloalkyl; and a proviso that one of the $R_2$ or $R_2'$ is substituted or unsubstituted 4 or 5 membered cycloalkyl group, and if $R_2$ or $R_2'$ is 4 membered cycloalkyl group then at least one of the carbon atom of the 4 membered cycloalkyl group must be substituted by two identical groups and which are selected from alkyl or halogen wherein most preferably alkyl is methyl and halo is fluorine.

Pharmaceutically acceptable salts of the compounds of the formula (2) are also contemplated. Likewise, pharmaceutically acceptable solvates, including hydrates, of the compounds of the formula (2) are contemplated.

It should be understood that the formula (2) structurally encompasses all stereoisomers, including enantiomers and diastereomers, which may be contemplated from the chemical structure of the genus described herein.

Also contemplated are prodrugs of the compounds of the formula (2), including ester prodrugs.

According to one embodiment, there is provided a compound of formula (2), wherein $Z_2$ is O.

According to one embodiment, there is provided a compound of formula (2), wherein $X_2$ is a bond, —C(O)— and —C(O)—CH$_2$—.

According to one embodiment, there is provided a compound of formula (2), wherein $R_2$ is H, —C(($CH_3)_2$)—$CO_2H$, —C(($CH_3)_2$)—CH2-$CO_2H$, —$CH_2$—CH2-$CO_2H$, —CH2-$CO_2H$ and $CH_3$.

According to one embodiment, there is provided a compound of formula (2), wherein $R_2$ is substituted or unsubstituted cyclobutyl.

According to one embodiment, there is provided a compound of formula (2), wherein $Z_2'$ is a bond.

According to one embodiment, there is provided a compound of formula (2), wherein $X_2'$ is a bond, —C(O)$_2$— and —C(O)NR"—.

According to one embodiment, there is provided a compound of formula (2), wherein $R_2'$ is H, substituted or unsubstituted cyclobutyl and ethyl piperidine-4-carboxylate.

According to one embodiment, there is provided a compound of formula (2), wherein R" is H.

According to one embodiment, there is provided a compound of formula (2), wherein $R^a$ is substituted or unsubstituted alkyl and C(O)R". In this embodiment, preferably R" is OH, —[CH(R''')]$_p$C(O)$_2$Me, —[CH(R''')]$_p$C(O)$_2$H, benzyl, morpholine, piperidine, ethyl piperidine-4-carboxylate, N-ethyl piperazine, and pyrrolidine.

According to one embodiment, there is provided a compound of formula (2), wherein R''' is H, methyl, isopropyl and isobutyl.

According to one embodiment, there is provided a compound of formula (2), wherein p is 1 and 2.

Accordingly, one more aspect of the present invention provides the compounds of formula (2A):

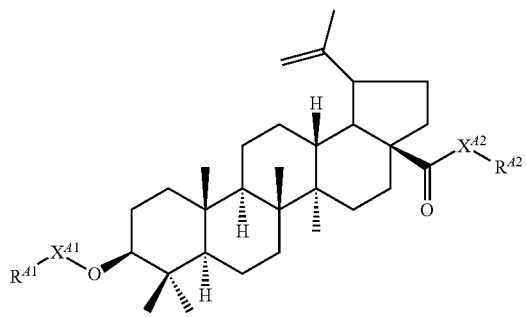

Formula (2A)

wherein, $X^{41}$ can be a bond, or —C(O)—;

$X^{42}$ can be a bond, O or NH;

$R^{41}$ can be H, substituted or unsubstituted alkyl, substituted or unsubstituted aryl,

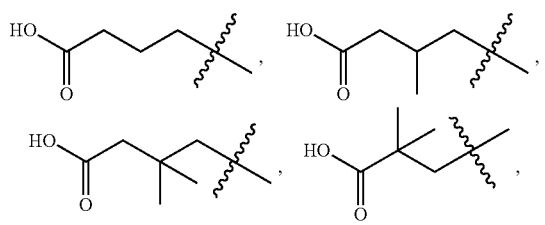

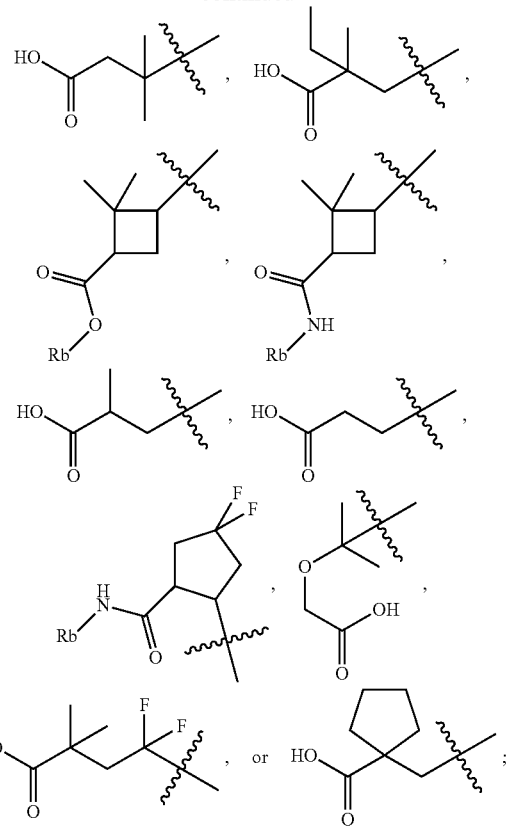

$R^{42}$ can be H, substituted or unsubstituted alkyl, substituted or unsubstituted amino, substituted or unsubstituted cycloalkyl, substituted or unsubstituted cycloalkenyl, substituted or unsubstituted heterocyclyl, or substituted or unsubstituted aryl and preferably $R^{42}$ can be substituted by R'''; and each R''' can be substituted or unsubstituted alkyl, substituted or unsubstituted heterocyclyl, wherein heterocycle is nitrogen containing heterocycle and is bonded through nitrogen atom, substituted or unsubstituted N contained heterocyclylalkyl (wherein alkyl is bonded to ring nitrogen atom of heterocycle), substituted or unsubstituted aralkyl or substituted or unsubstituted phenyl.

Pharmaceutically acceptable salts of the compounds of the formula (2A) are also contemplated. Likewise, pharmaceutically acceptable solvates, including hydrates, of the compounds of the formula (2A) are contemplated.

It should be understood that the formula (2A) structurally encompasses all stereoisomers, including enantiomers, diastereomers, racemates, and combinations thereof which may be contemplated from the chemical structure of the genus described herein.

Also contemplated are prodrugs of the compounds of the formula (2A), including ester prodrugs.

According to one embodiment, there is provided a compound of formula (2A), wherein $X^{41}$ is a bond and —C(O)—.

According to one embodiment, there is provided a compound of formula (2A), wherein $R^{41}$ is H and substituted or unsubstituted alkyl.

According to one embodiment, there is provided a compound of formula (2A), wherein $R^{41}$ is H and substituted or unsubstituted cycloalkyl.

According to one embodiment, there is provided a compound of formula (2A), wherein $R^{41}$ is H, —C(($CH_3)_2$)—$CO_2H$, —C(($CH_3)_2$)—CH2-$CO_2H$, —$CH_2$—CH2-$CO_2H$, —CH2-$CO_2H$ and $CH_3$.

According to one embodiment, there is provided a compound of formula (2A), wherein $X^{A2}$ is a bond and NH.

According to one embodiment, there is provided a compound of formula (2A), wherein $R^{A2}$ is

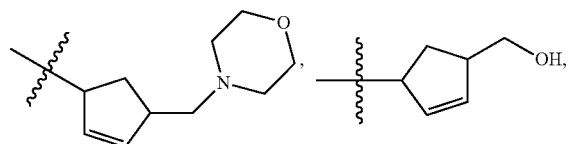

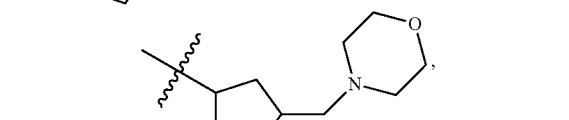

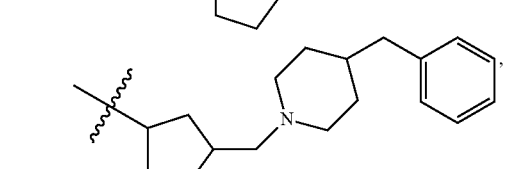

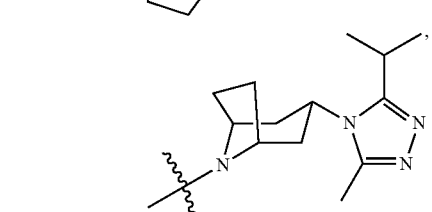

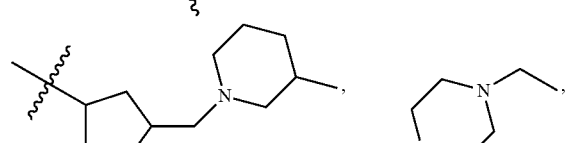

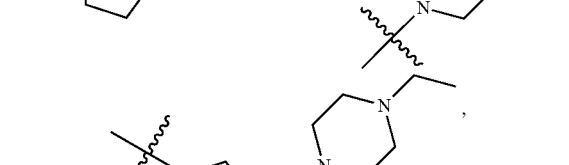

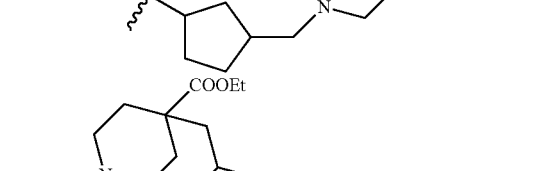

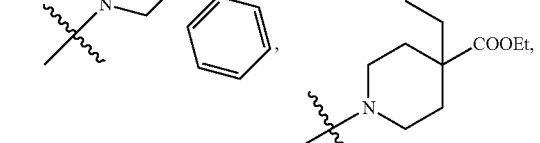

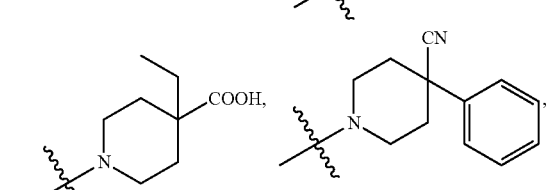

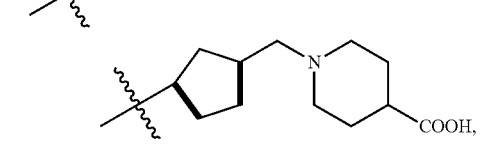

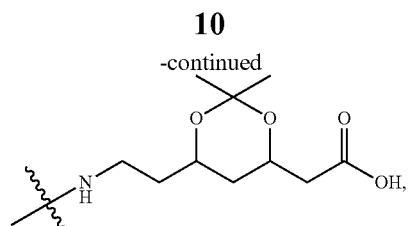

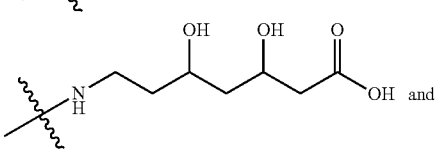, and

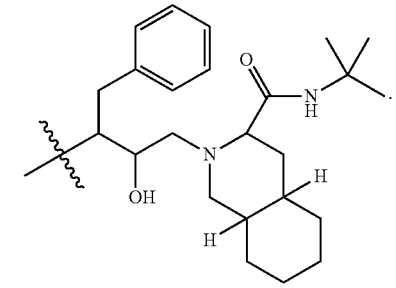

Also the present invention relates to the intermediate compounds of the formula (3):

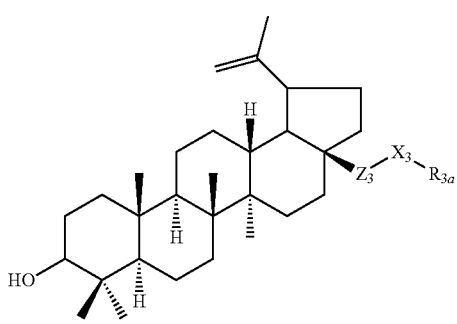

Formula (3)

wherein, $R_{3a}$ can be H, substituted or unsubstituted alkyl, substituted or unsubstituted aryl, substituted or unsubstituted cycloalkyl, substituted or unsubstituted cycloalkenyl, substituted or unsubstituted heterocyclyl, substituted or unsubstituted alkyloxy, or substituted or unsubstituted aryloxy and preferably $R_{3a}$ can be substituted by $R^a$;

$X_3$ can be selected from a bond, —O—, —NR"—, —C(O)—, —C(O)$_2$—, —(CH$_2$)$_n$, or —C(O)NR"—;

n can be 0-3;

$Z_3$ can be selected from a bond, —O—, or —NR"—;

$R^a$ can be H, OH, halogen, N(R")$_2$, C(O)R", C(O)$_2$R", CH$_2$OR", C(O)N(R")$_2$ or substituted or unsubstituted alkyl;

each R" can be independently selected from H, —[CH(R''')]$_p$C(O)$_2$R''', substituted or unsubstituted alkyl, substituted or unsubstituted amino, substituted or unsubstituted aryl, substituted or unsubstituted cycloalkyl, or substituted or unsubstituted heterocyclyl;

p can be 0-3; and each R''' can be independently selected from H, substituted or unsubstituted alkyl, or substituted or unsubstituted cycloalkyl; and a proviso that $R_{3a}$ is substituted or unsubstituted 4 or 5 membered cycloalkyl group, and if $R_{3a}$ is 4 membered cycloalkyl group then at least one of the carbon atom of the 4 membered cycloalkyl group must be substituted by two identical groups and which are selected from alkyl or halogen wherein most preferably alkyl is methyl and halo is fluorine.

Pharmaceutically acceptable salts of the compounds of the formula (3) are also contemplated. Likewise, pharmaceutically acceptable solvates, including hydrates, of the compounds of the formula (3) are contemplated.

It should be understood that the formula (3) structurally encompasses all stereoisomers, including enantiomers, diastereomers, racemates, and combinations thereof, which may be contemplated from the chemical structure of the genus described herein.

Also contemplated are prodrugs of the compounds of the formula (3), including ester prodrugs.

Below are the representative compounds, which are illustrative in nature only and are not intended to limit to the scope of the invention (Nomenclature has been generated from Chem. Draw Ultra 11.0 version):

(1R,3aS,5aR,5bR,7aR,9S,11aR,11bR,13aR,13bR)-9-acetoxy-5a,5b,8,8,11a-pentamethyl-1-(prop-1-en-2-yl)icosahydro-1H-cyclopenta[a]chrysene-3a-carboxylic acid (Compound 1), (1S,3R)-benzyl 3-((1R,3aS,5aR,5bR,7aR,9S,11aR,11bR,13aR,13bR)-9-acetoxy-5a,5b,8,8,11a-pentamethyl-1-(prop-1-en-2-yl)icosahydro-1H-cyclopenta[a]chrysene-3a-carboxamido)-2,2-dimethylcyclobutanecarboxylate (Compound 2), (1R,3aS,5aR,5bR,7aR,9S,11aR,11bR,13aR,13bR)-9-((1R,3S)-3-(tert-butoxycarbonyl)-2,2-dimethylcyclobutanecarbonyloxy)-5a,5b,8,8,11a-pentamethyl-1-(prop-1-en-2-yl)icosahydro-1H-cyclopenta[a]chrysene-3a-carboxylic acid (Compound 3), (1R,3aS,5aR,5bR,7aR,9S,11aR,11bR,13aR,13bR)-9-((1R,3S)-3-carboxy-2,2-dimethylcyclobutanecarbonyloxy)-5a,5b,8,8,11a-pentamethyl-1-(prop-1-en-2-yl)icosahydro-1H-cyclopenta[a]chrysene-3a-carboxylic acid (Compound 4), (1S,3R)-3-((1R,3aS,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysene-3a-carboxamido)-2,2-dimethylcyclobutanecarboxylic acid (Compound 5), (1R,2S,3aR,5aR,5bR,7aS,10R,12aR,12bR)-2-(3-carboxy-3-methylbutanoyloxy)-3,3,5a,5b,12b-pentamethyl-10-(prop-1-en-2-yl)icosahydrodicyclopenta[a,i]phenanthrene-1,7a-dicarboxylic acid (Compound 6), (1R,3aS,5aR,5bR,7aR,9S,11aR,11bR,13aR,13bR)-3a-((1S,3R)-2,2-dimethyl-3-(morpholine-4-carbonyl)cyclobutylcarbamoyl)-5a,5b,8,8,11a-pentamethyl-1-(prop-1-en-2-yl)icosahydro-1H-cyclopenta[a]chrysen-9-yl acetate (Compound 7), (1R,3aS,5aR,5bR,7aR,9S,11aR,11bR,13aR,13bR)-N-((1S,3R)-2,2-dimethyl-3-(morpholine-4-carbonyl)cyclobutyl)-9-hydroxy-5a,5b,8,8,11a-pentamethyl-1-(prop-1-en-2-yl)icosahydro-1H-cyclopenta[a]chrysene-3a-carboxamide (Compound 8), 4-((1R,3aS,5aR,5bR,7aR,9S,11aR,11bR,13aR,13bR)-3a-((1S,3R)-2,2-dimethyl-3-(morpholine-4-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid (Compound 9), (1R,3aS,5aR,5bR,7aR,9S,11aR,11bR,13aR,13bR)-3a-((1S,3R)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yl acetate (Compound 10), (1R,3aS,5aR,5bR,7aR,9S,11aR,11bR,13aR,13bR)-N-((1S,3R)-2,2-dimethyl-3-(piperidine-1-carbonyl)cyclobutyl)-9-hydroxy-5a,5b,8,8,11a-pentamethyl-1-(prop-1-en-2-yl)icosahydro-1H-cyclopenta[a]chrysene-3a-carboxamide (Compound 11), 4-((1R,3aS,5aR,5bR,7aR,9S,11aR,11bR,13aR,13bR)-3a-((1S,3R)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid (Compound 12), (1R,3aS,5aR,5bR,7aR,9S,11aR,11bR,13aR,13bR)-3a-((1S,3R)-2,2-dimethyl-3-(pyrrolidine-1-carbonyl)cyclobutylcarbamoyl)-5a,5b,8,8,11a-pentamethyl-1-(prop-1-en-2-yl)icosahydro-1H-cyclopenta[a]chrysen-9-yl acetate (Compound 13), (1R,3aS,5aR,5bR,7aR,9S,11aR,11bR,13aR,13bR)-N-((1S,3R)-2,2-dimethyl-3-(pyrrolidine-1-carbonyl)cyclobutyl)-9-hydroxy-5a,5b,8,8,11a-pentamethyl-1-(prop-1-en-2-yl)icosahydro-1H-cyclopenta[a]chrysene-3a-carboxamide (Compound 14), 4-((1R,3aS,5aR,5bR,7aR,9S,11aR,11bR,13aR,13bR)-3a-((1S,3R)-2,2-dimethyl-3-(pyrrolidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid (Compound 15), (1R,3aS,5aR,5bR,7aR,9S,11aR,11bR,13aR,13bR)-3a-((1R,3S)-2,2-dimethyl-3-(morpholine-4-carbonyl)cyclobutylcarbamoyl)-5a,5b,8,8,11a-pentamethyl-1-(prop-1-en-2-yl)icosahydro-1H-cyclopenta[a]chrysen-9-yl acetate (Compound 16), (1R,3aS,5aR,5bR,7aR,9S,11aR,11bR,13aR,13bR)-N-((1R,3S)-2,2-dimethyl-3-(morpholine-4-carbonyl)cyclobutyl)-9-hydroxy-5a,5b,8,8,11a-pentamethyl-1-(prop-1-en-2-yl)icosahydro-1H-cyclopenta[a]chrysene-3a-carboxamide (Compound 17), (1R,3aS,5aR,5bR,7aR,9S,11aR,11bR,13aR,13bR)-9-((1S,3R)-3-(benzyloxycarbonyl)-2,2-dimethylcyclobutanecarbonyloxy)-5a,5b,8,8,11a-pentamethyl-1-(prop-1-en-2-yl)icosahydro-1H-cyclopenta[a]chrysene-3a-carboxylic acid (Compound 18), (1R,3aS,5aR,5bR,7aR,9S,11aR,11bR,13aR,13bR)-9-((1S,3R)-3-carboxy-2,2-dimethylcyclobutanecarbonyloxy)-5a,5b,8,8,11a-pentamethyl-1-(prop-1-en-2-yl)icosahydro-1H-cyclopenta[a]chrysene-3a-carboxylic acid (Compound 19), (1R,3aS,5aR,5bR,7aR,9S,11aR,11bR,13aR,13bR)-5a,5b,8,8,11a-pentamethyl-3a-((1R,3S)-3-morpholinomethyl)cyclopentylcarbamoyl)-1-(prop-1-en-2-yl)icosahydro-1H-cyclopenta[a]chrysen-9-yl acetate (Compound 20), (1R,3aS,5aR,5bR,7aR,9S,11aR,11bR,13aR,13bR)-5a,5b,8,8,11a-pentamethyl-3a-((1S,4R)-4-(morpholinomethyl)cyclopent-2-enylcarbamoyl)-1-(prop-1-en-2-yl)-icosahydro-1H-cyclopenta[a]chrysen-9-yl acetate (Compound 21), ((1R,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysen-3a-yl)(3-(3-isopropyl-5-methyl-4H-1,2,4-triazol-4-yl)-8-azabicyclo[3.2.1]octan-8-yl)methanone (Compound 22), (1R,3aS,5aR,5bR,7aR,9S,11aR,11bR,13aR,13bR)-9-hydroxy-5a,5b,8,8,11a-pentamethyl-N-((1R,3S)-3-(morpholinomethyl)cyclopentyl)-1-(prop-1-en-2-yl)icosahydro-1H-cyclopenta[a]chrysene-3a-carboxamide (Compound 23), 2,2-dimethyl-4-oxo-4-((1R,3aS,5aR,5bR,7aR,9S,11aR, 11bR,13aR,13bR)-5a,5b,8,8,11a-pentamethyl-3a-((1R, 3S)-3-(morpholinomethyl)cyclopentylcarbamoyl)-1-(prop-1-en-2-yl)icosahydro-1H-cyclopenta[a]chrysen-9-yloxy)butanoic acid (Compound 24), ((1R,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysen-3a-yl)(3-(3-isopropyl-5-methyl-4H-1,2,4-triazol-4-yl)-8-azabicyclo[3.2.1]octan-8-yl)methanone (Compound 25), (1R,3aS,5aR,5bR,7aR,9S,11aR,11bR,13aR,13bR)-9-hydroxy-5a,5b,8,8,11a-pentamethyl-N-((1S,4R)-4-(morpholinomethyl)cyclopent-2-enyl)-1-(prop-1-en-2-yl)icosahydro-1H-cyclopenta[a]chrysene-3a-carboxamide (Compound 26), (1R,3aS,5aR,5bR,7aR,9S,11aR,11bR,13aR,13bR)-3a-(4-(hydroxymethyl)cyclopent-2-enylcarbamoyl)-5a,5b,8,8, 11a-pentamethyl-1-(prop-1-en-2-yl)icosahydro-1H-cyclopenta[a]chrysen-9-yl acetate (Compound 27), (1R,3aS,5aR,5bR,7aR,9S,11aR,11bR,13aR,13bR)-9-hydroxy-N-(4-(hydroxymethyl)cyclopent-2-enyl)-5a,5b,8, 8,11a-pentamethyl-1-(prop-1-en-2-yl)icosahydro-1H-cyclopenta[a]chrysene-3a-carboxamide (Compound 28), (1R,3aS,5aR,5bR,7aR,9S,11aR,11bR,13aR,13bR)-3a-((2S, 3R)-4-((3S,4aS,8aS)-3-(tert-butylcarbamoyl)octahydroisoquinolin-2(1H)-yl)-3-hydroxy-1-phenylbutan-2-ylcarbamoyl)-5a,5b,8,8,11a-pentamethyl-1-(prop-1-en-2-yl)icosahydro-1H-cyclopenta[a]chrysen-9-yl acetate (Compound 29), (3S,4aS,8aS)-N-tert-butyl-2-((2R,3S)-2-hydroxy-3-((1R, 3aS,5aR,5bR,7aR,9S,11aR,11bR,13aR,13bR)-9-hydroxy-5a,5b,8,8,11a-pentamethyl-1-(prop-1-en-2-yl) icosahydro-1H-cyclopenta[a]chrysene-3a-carboxamido)-4-phenylbutyl)decahydroisoquinoline-3-carboxamide (Compound 30), (1R,3aS,5aR,5bR,7aR,9S,11aR,11bR,13aR,13bR)-3a-((1R, 3S)-3-((4-benzylpiperidin-1-yl)methyl)cyclopentylcarbamoyl)-5a,5b,8,8,11a-pentamethyl-1-(prop-1-en-2-yl) icosahydro-1H-cyclopenta[a]chrysen-9-yl acetate (Compound 31), (1R,3aS,5aR,5bR,7aR,9S,11aR,11bR,13aR,13bR)-N-((1R, 3S)-3-((4-benzylpiperidin-1-yl)methyl)cyclopentyl)-9-hydroxy-5a,5b,8,8,11a-pentamethyl-1-(prop-1-en-2-yl) icosahydro-1H-cyclopenta[a]chrysene-3a-carboxamide (Compound 32), 5-((1R,3aS,5aR,5bR,7aR,9S,11aR,11bR,13aR,13bR)-3a-((1R,3S)-3-((4-benzylpiperidin-1-yl)methyl)cyclopentylcarbamoyl)-5a,5b,8,8,11a-pentamethyl-1-(prop-1-en-2-yl)icosahydro-1H-cyclopenta[a]chrysen-9-yloxy)-5-oxopentanoic acid (Compound 33), (1R,3aS,5aR,5bR,7aR,9S,11aR,11bR,13aR,13bR)-3a-((1R, 3S)-3-((4-ethylpiperazin-1-yl)methyl)cyclopentylcarbamoyl)-5a,5b,8,8,11a-pentamethyl-1-(prop-1-en-2-yl) icosahydro-1H-cyclopenta[a]chrysen-9-yl acetate (Compound 34), (1R,3aS,5aR,5bR,7aR,9S,11aR,11bR,13aR,13bR)-N-((1R, 3S)-3-((4-ethylpiperazin-1-yl)methyl)cyclopentyl)-9-hydroxy-5a,5b,8,8,11a-pentamethyl-1-(prop-1-en-2-yl) icosahydro-1H-cyclopenta[a]chrysene-3a-carboxamide (Compound 35), 4-((1R,3aS,5aR,5bR,7aR,9S,11aR,11bR,13aR,13bR)-3a-((1R,3S)-3-((4-ethylpiperazin-1-yl)methyl)cyclopentylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid (Compound 36), Methyl 3-((1S,3R)-3-((1R,3aS,5aR,5bR,7aR,9S,11aR, 11bR,13aR,13bR)-9-acetoxy-5a,5b,8,8,11a-pentamethyl-1-(prop-1-en-2-yl)icosahydro-1H-cyclopenta[a]chrysene-3a-carboxamido)-2,2-dimethylcyclobutanecarboxamido) propanoate (Compound 37), 3-((1S,3R)-3-((1R,3aS,5aR,5bR,7aR,9S,11aR,11bR,13aR, 13bR)-9-hydroxy-5a,5b,8,8,11a-pentamethyl-1-(prop-1-en-2-yl)icosahydro-1H-cyclopenta[a]chrysene-3a-carboxamido)-2,2-dimethylcyclobutanecarboxamido) propanoic acid (Compound 38), (S)-methyl 2-((1S,3R)-3-((1R,3aS,5aR,5bR,7aR,9S,11aR, 11bR,13aR,13bR)-9-acetoxy-5a,5b,8,8,11a-pentamethyl-1-(prop-1-en-2-yl)icosahydro-1H-cyclopenta[a]chrysene-3a-carboxamido)-2,2-dimethylcyclobutanecarboxamido)-3-methylbutanoate (Compound 39), (S)-2-((1S,3R)-3-((1R,3aS,5aR,5bR,7aR,9S,11aR,11bR, 13aR,13bR)-9-hydroxy-5a,5b,8,8,11a-pentamethyl-1-(prop-1-en-2-yl)icosahydro-1H-cyclopenta[a]chrysene-3a-carboxamido)-2,2-dimethylcyclobutanecarboxamido)-3-methylbutanoic acid (Compound 40), (S)-methyl 2-((1S,3R)-3-((1R,3aS,5aR,5bR,7aR,9S,11aR, 11bR,13aR,13bR)-9-acetoxy-5a,5b,8,8,11a-pentamethyl-1-(prop-1-en-2-yl)icosahydro-1H-cyclopenta[a]chrysene-3a-carboxamido)-2,2-dimethylcyclobutanecarboxamido)-4-methylpentanoate (Compound 41), (S)-2-((1S,3R)-3-((1R,3aS,5aR,5bR,7aR,9S,11aR,11bR, 13aR,13bR)-9-hydroxy-5a,5b,8,8,11a-pentamethyl-1-(prop-1-en-2-yl)icosahydro-1H-cyclopenta[a]chrysene-3a-carboxamido)-2,2-dimethylcyclobutanecarboxamido)-4-methylpentanoic acid (Compound 42), (1R,3aS,5aR,5bR,7aR,9S,11aR,11bR,13aR,13bR)-3a-((1R, 3S)-2,2-dimethyl-3-(pyrrolidine-1-carbonyl)cyclobutylcarbamoyl)-5a,5b,8,8,11a-pentamethyl-1-(prop-1-en-2-yl)icosahydro-1H-cyclopenta[a]chrysen-9-yl acetate (Compound 43), (1R,3aS,5aR,5bR,7aR,9S,11aR,11bR,13aR,13bR)-N-(1R, 3S)-2,2-dimethyl-3-(pyrrolidine-1-carbonyl)cyclobutyl)-9-hydroxy-5a,5b,8,8,11a-pentamethyl-1-(prop-1-en-2-yl) icosahydro-1H-cyclopenta[a]chrysene-3a-carboxamide (Compound 44), 4-((1R,3aS,5aR,5bR,7aR,9S,11aR,11bR,13aR,13bR)-3a-((1R,3S)-2,2-dimethyl-3-(pyrrolidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid (Compound 45), (1R,3aS,5aR,5bR,7aR,9S,11aR,11bR,13aR,13bR)-3a-((1R, 3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yl acetate (Compound 46), (1R,3aS,5aR,5bR,7aR,9S,11aR,11bR,13aR,13bR)-N-((1R, 3S)-2,2-dimethyl-3-(piperidine-1-carbonyl)cyclobutyl)-9-hydroxy-5a,5b,8,8,11a-pentamethyl-1-(prop-1-en-2-yl) icosahydro-1H-cyclopenta[a]chrysene-3a-carboxamide (Compound 47), 4-((1R,3aS,5aR,5bR,7aR,9S,11aR,11bR,13aR,13bR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid (Compound 48), (1R,3aS,5aR,5bR,7aR,9S,11aR,11bR,13aR,13bR)-5a,5b,8, 8,11a-pentamethyl-3a-((1R,3S)-3-((3-methylpiperidin-1-yl)methyl)cyclopentylcarbamoyl)-1-(prop-1-en-2-yl) icosahydro-1H-cyclopenta[a]chrysen-9-yl acetate (Compound 49), (1R,3aS,5aR,5bR,7aR,9S,11aR,11bR,13aR,13bR)-9-hydroxy-5a,5b,8,8,11a-pentamethyl-N-((1R,3S)-3-((3-methylpiperidin-1-yl)methyl)cyclopentyl)-1-(prop-1-en-2- yl)icosahydro-1H-cyclopenta[a]chrysene-3a-carboxamide (Compound 50), 2,2-dimethyl-4-oxo-4-((1R,3aS,5aR,5bR,7aR,9S,11aR, 11bR,13aR,13bR)-5a,5b,8,8,11a-pentamethyl-3a-((1R, 3S)-3-((3-methylpiperidin-1-yl)methyl)cyclopentylcarbamoyl)-1-(prop-1-en-2-yl)icosahydro-1H-cyclopenta[a]chrysen-9-yloxy)butanoic acid (Compound 51), (1R,3aS,5aR,5bR,7aR,9S,11aR,11bR,13aR,13bR)-3a-(4-ethylpiperazine-1-carbonyl)-5a,5b,8,8,11a-pentamethyl-1-(prop-1-en-2-yl)icosahydro-1H-cyclopenta[a]chrysen-9-yl acetate (Compound 52), 4-ethylpiperazin-1-yl)((1R,3aS,5aR,5bR,7aR,9S,11aR, 11bR,13aR,13bR)-9-hydroxy-5a,5b,8,8,11a-pentamethyl-1-(prop-1-en-2-yl)icosahydro-1H-cyclopenta[a]chrysen-3a-yl)methanone (Compound 53), 3-(((1R,3aS,5aR,5bR,7aR,9S,11aR,11bR,13aR,13bR)-3a-(4-ethylpiperazine-1-carbonyl)-5a,5b,8,8,11a-pentamethyl-1-(prop-1-en-2-yl)icosahydro-1H-cyclopenta[a]chrysen-9-yloxy)carbonyl)-2,2-dimethylcyclobutanecarboxylic acid (Compound 54), Ethyl 4-((1R,3aS,5aR,5bR,7aR,9S,11aR,11bR,13aR,13bR)-9-acetoxy-5a,5b,8,8,11a-pentamethyl-1-(prop-1-en-2-yl)icosahydro-1H-cyclopenta[a]chrysene-3a-carbonyl)-1-benzylcyclohexanecarboxylate (Compound 55), Ethyl 1-benzyl-4-((1R,3aS,5aR,5bR,7aR,9S,11aR,11bR, 13aR,13bR)-9-hydroxy-5a,5b,8,8,11a-pentamethyl-1-(prop-1-en-2-yl)icosahydro-1H-cyclopenta[a]chrysene-3a-carbonyl)cyclohexanecarboxylate (Compound 56), 4-((1R,3aS,5aR,5bR,7aR,9S,11aR,11bR,13aR,13bR)-3a-(4-benzyl-4-(ethoxycarbonyl)piperidine-1-carbonyl)-5a, 5b,8,8,11a-pentamethyl-1-(prop-1-en-2-yl)icosahydro-1H-cyclopenta[a]chrysen-9-yloxy)-2,2-dimethyl-4-oxobutanoic acid (Compound 57), (1S,3R)-1-tert-butyl 3-((1R,3aS,5aR,5bR,7aR,9S,11aR, 11bR,13aR,13bR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yl)2,2-dimethylcyclobutane-1,3-dicarboxylate (Compound 58), (1S,3R)-3-(((1R,3aS,5aR,5bR,7aR,9S,11aR,11bR,13aR, 13bR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)carbonyl)-2,2-dimethylcyclobutanecarboxylic acid (Compound 59), (1S,3R)-1-tert-butyl 3-((1R,3aS,5aR,5bR,7aR,9S,11aR, 11bR,13aR,13bR)-3a-((1S,3R)-2,2-dimethyl-3-(morpholine-4-carbonyl)cyclobutylcarbamoyl)-5a,5b,8,8,11a-pentamethyl-1-(prop-1-en-2-yl)icosahydro-1H-cyclopenta[a]chrysen-9-yl)2,2-dimethylcyclobutane-1,3-dicarboxylate (Compound 60), (1S,3R)-3-(((1R,3aS,5aR,5bR,7aR,9S,11aR,11bR,13aR, 13bR)-3a-((1S,3R)-2,2-dimethyl-3-(morpholine-4-carbonyl)cyclobutylcarbamoyl)-5a,5b,8,8,11a-pentamethyl-1-(prop-1-en-2-yl)icosahydro-1H-cyclopenta[a]chrysen-9-yloxy)carbonyl)-2,2-dimethylcyclobutanecarboxylic acid (Compound 61), 4-((1R,3aS,5aR,5bR,7aR,9S,11aR,11bR,13aR,13bR)-3a-((1S,3R)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-4-oxobutanoic acid (Compound 62), (1S,3R)-1-tert-butyl 3-((1R,3aS,5aR,5bR,7aR,9S,11aR, 11bR,13aR,13bR)-3a-((1S,3R)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yl)2,2-dimethylcyclobutane-1,3-dicarboxylate (Compound 63), (1S,3R)-3-(((1R,3aS,5aR,5bR,7aR,9S,11aR,11bR,13aR, 13bR)-3a-((1S,3R)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)carbonyl)-2,2-dimethylcyclobutanecarboxylic acid (Compound 64), 5-((1R,3aS,5aR,5bR,7aR,9S,11aR,11bR,13aR,13bR)-3a-((1S,3R)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-5-oxopentanoic acid (Compound 65), (1R,3aS,5aR,5bR,7aR,9S,11aR,11bR,13aR,13bR)-3a-((1S, 3R)-3-(4-ethylpiperazine-1-carbonyl)-2,2-dimethylcyclobutylcarbamoyl)-5a,5b,8,8,11a-pentamethyl-1-(prop-1-en-2-yl)icosahydro-1H-cyclopenta[a]chrysen-9-yl acetate (Compound 66), (1R,3aS,5aR,5bR,7aR,9S,11aR,11bR,13aR,13bR)-N-((1S, 3R)-3-(4-ethylpiperazine-1-carbonyl)-2,2-dimethylcyclobutyl)-9-hydroxy-5a,5b,8,8,11a-pentamethyl-1-(prop-1-en-2-yl)icosahydro-1H-cyclopenta[a]chrysene-3a-carboxamide (Compound 67), 4-((1R,3aS,5aR,5bR,7aR,9S,11aR,11bR,13aR,13bR)-3a-((1S,3R)-3-(4-ethylpiperazine-1-carbonyl)-2,2-dimethylcyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid (Compound 68), (1R,3aS,5aR,5bR,7aR,9S,11aR,11bR,13aR,13bR)-3a-((1R, 3S)-3-(4-ethylpiperazine-1-carbonyl)-2,2-dimethylcyclobutylcarbamoyl)-5a,5b,8,8,11a-pentamethyl-1-(prop-1-en-2-yl)icosahydro-1H-cyclopenta[a]chrysen-9-yl acetate (Compound 69), (1R,3aS,5aR,5bR,7aR,9S,11aR,11bR,13aR,13bR)-N-((1R, 3S)-3-(4-ethylpiperazine-1-carbonyl)-2,2-dimethylcyclobutyl)-9-hydroxy-5a,5b,8,8,11a-pentamethyl-1-(prop-1-en-2-yl)icosahydro-1H-cyclopenta[a]chrysene-3a-carboxamide (Compound 70), 4-((1R,3aS,5aR,5bR,7aR,9S,11aR,11bR,13aR,13bR)-3a-((1R,3S)-3-(4-ethylpiperazine-1-carbonyl)-2,2-dimethylcyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid (Compound 71), Ethyl 1-((1R,3aS,5aR,5bR,7aR,9S,11aR,11bR,13aR,13bR)-9-acetoxy-5a,5b,8,8,11a-pentamethyl-1-(prop-1-en-2-yl)icosahydro-1H-cyclopenta[a]chrysene-3a-carbonyl)-4-ethylpiperidine-4-carboxylate (Compound 72), Ethyl 4-ethyl-1-((1R,3aS,5aR,5bR,7aR,9S,11aR,11bR, 13aR,13bR)-9-hydroxy-5a,5b,8,8,11a-pentamethyl-1-(prop-1-en-2-yl)icosahydro-1H-cyclopenta[a]chrysene-3a-carbonyl)piperidine-4-carboxylate (Compound 73), 4-((1R,3aS,5aR,5bR,7aR,9S,11aR,11bR,13aR,13bR)-3a-(4-(ethoxycarbonyl)-4-ethylpiperidine-1-carbonyl)-5a, 5b,8,8,11a-pentamethyl-1-(prop-1-en-2-yl)icosahydro- 1H-cyclopenta[a]chrysen-9-yloxy)-2,2-dimethyl-4-oxobutanoic acid (Compound 74), (1R,3aS,5aR,5bR,7aR,9S,11aR,11bR,13aR,13bR)-3a-(4-cyano-4-phenylpiperidine-1-carbonyl)-5a,5b,8,8,11a-pentamethyl-1-(prop-1-en-2-yl)icosahydro-1H-cyclopenta[a]chrysen-9-yl acetate (Compound 75), 1-((1R,3aS,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysene-3a-carbonyl)-4-phenylpiperidine-4-carbonitrile (Compound 76), 4-((1R,3aS,5aR,5bR,7aR,9S,11aR,11bR,13aR,13bR)-3a-(4-cyano-4-phenylpiperidine-1-carbonyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid (Compound 77), Tert-butyl 2-(6-(2-((1R,3aS,5aR,5bR,7aR,9S,11aR,11bR,13aR,13bR)-9-acetoxy-5a,5b,8,8,11a-pentamethyl-1-(prop-1-en-2-yl)icosahydro-1H-cyclopenta[a]chrysene-3a-carboxamido)ethyl)-2,2-dimethyl-1,3-dioxan-4-yl)acetate (Compound 78), Tert-butyl 2-(6-(2-((1R,3aS,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysene-3a-carboxamido)ethyl)-2,2-dimethyl-1,3-dioxan-4-yl)acetate (Compound 79), 4-((1R,3aS,5aR,5bR,7aR,9S,11aR,11bR,13aR,13bR)-3a-(2-(6-(2-tert-butoxy-2-oxoethyl)-2,2-dimethyl-1,3-dioxan-4-yl)ethylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid (Compound 80), 7-((1R,3aS,5aR,5bR,7aR,9S,11aR,11bR,13aR,13bR)-9-(3-carboxy-3-methylbutanoyloxy)-5a,5b,8,8,11a-pentamethyl-1-(prop-1-en-2-yl)icosahydro-1H-cyclopenta[a]chrysene-3a-carboxamido)-3,5-dihydroxyheptanoic acid (Compound 81), 5-((1R,3aS,5aR,5bR,7aR,9S,11aR,11bR,13aR,13bR)-3a-((1R,3S)-3-((4-benzylpiperidin-1-yl)methyl)cyclopentylcarbamoyl)-5a,5b,8,8,11a-pentamethyl-1-(prop-1-en-2-yl)icosahydro-1H-cyclopenta[a]chrysen-9-yloxy)-3,3-dimethyl-5-oxopentanoic acid (Compound 82), ((1R,3aS,5aR,5bR,7aR,9S,11aR,11bR,13aR,13bR)-9-acetoxy-5a,5b,8,8,11a-pentamethyl-1-(prop-1-en-2-yl)icosahydro-1H-cyclopenta[a]chrysene-3a-carbonyl)-4-ethylpiperidine-4-carboxylic acid (Compound 83), 4-ethyl-1-((1R,3aS,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysene-3a-carbonyl)piperidine-4-carboxylic acid (Compound 84), 1-((1R,3aS,5aR,5bR,7aR,9S,11aR,11bR,13aR,13bR)-9-(3-carboxy-3-methylbutanoyloxy)-5a,5b,8,8,11a-pentamethyl-1-(prop-1-en-2-yl)icosahydro-1H-cyclopenta[a]chrysene-3a-carbonyl)-4-ethylpiperidine-4-carboxylic acid (Compound 85), 1-(((1S,3R)-3-((1R,3aS,5aR,5bR,7aR,9S,11aR,11bR,13aR,13bR)-9-(3-carboxy-3-methylbutanoyloxy)-5a,5b,8,8,11a-pentamethyl-1-(prop-1-en-2-yl)icosahydro-1H-cyclopenta[a]chrysene-3a-carbonyl)cyclopentyl)methyl)piperidine-4-carboxylic acid (Compound 86), 4-((1R,3aS,5aR,5bR,7aR,9S,11aR,11bR,13aR,13bR)-3a-((1R,3S)-3-(benzyloxycarbonyl)-2,2-dimethylcyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid (Compound 87), (1S,3R)-3-((1S,3aS,5aR,5bR,7aR,9S,11aR,11bR,13aR,13bR)-9-(3-carboxy-3-methylbutanoyloxy)-1-isopropyl-5a,5b,8,8,11a-pentamethylicosahydro-1H-cyclopenta[a]chrysene-3a-carboxamido)-2,2-dimethylcyclobutanecarboxylic acid (Compound 88), (1R,3S)-1-benzyl 3-((1R,3aS,5aR,5bR,7aR,9S,11aR,11bR,13aR,13bR)-3a-((1S,3R)-3-(4-(ethoxycarbonyl)piperidine-1-carbonyl)-2,2-dimethylcyclobutylcarbamoyl)-5a,5b,8,8,11a-pentamethyl-1-(prop-1-en-2-yl)icosahydro-1H-cyclopenta[a]chrysen-9-yl)2,2-dimethylcyclobutane-1,3-dicarboxylate (Compound 89), (1R,3S)-3-(((1R,3aS,5aR,5bR,7aR,9S,11aR,11bR,13aR,13bR)-3a-((1S,3R)-3-(4-(ethoxycarbonyl)piperidine-1-carbonyl)-2,2-dimethylcyclobutylcarbamoyl)-5a,5b,8,8,11a-pentamethyl-1-(prop-1-en-2-yl)icosahydro-1H-cyclopenta[a]chrysen-9-yloxy)carbonyl)-2,2-dimethylcyclobutanecarboxylic acid (Compound 90), (1R,3S)-1-benzyl 3-((1R,3aS,5aR,5bR,7aR,9S,11aR,11bR,13aR,13bR)-3a-((1R,3S)-3-(benzyloxycarbonyl)-2,2-dimethylcyclobutylcarbamoyl)-5a,5b,8,8,11a-pentamethyl-1-(prop-1-en-2-yl)icosahydro-1H-cyclopenta[a]chrysen-9-yl)2,2-dimethylcyclobutane-1,3-dicarboxylate (Compound 91), (1S,3R)-3-((1R,3aS,5aR,5bR,7aR,9S,11aR,11bR,13aR,13bR)-9-((1S,3R)-3-carboxy-2,2-dimethylcyclobutanecarbonyloxy)-5a,5b,8,8,11a-pentamethyl-1-(prop-1-en-2-yl)icosahydro-1H-cyclopenta[a]chrysene-3a-carboxamido)-2,2-dimethylcyclobutanecarboxylic acid (Compound 92), (1R,3S)-1-benzyl 3-((1R,3aS,5aR,5bR,7aR,9S,11aR,11bR,13aR,13bR)-3a-(4-(ethoxycarbonyl)piperidine-1-carbonyl)-5a,5b,8,8,11a-pentamethyl-1-(prop-1-en-2-yl)icosahydro-1H-cyclopenta[a]chrysen-9-yl)2,2-dimethylcyclobutane-1,3-dicarboxylate (Compound 93), 5-((1R,3aS,5aR,5bR,7aR,9S,11aR,11bR,13aR,13bR)-3a-((1R,3S)-3-((4-benzylpiperidin-1-yl)methyl)cyclopentylcarbamoyl)-5a,5b,8,8,11a-pentamethyl-1-(prop-1-en-2-yl)icosahydro-1H-cyclopenta[a]chrysen-9-yloxy)-3,3-dimethyl-5-oxopentanoic acid (Compound 94), 2,2-dimethyl-4-oxo-4-((1R,3aS,5aR,5bR,7aR,9S,11aR,11bR,13aR,13bR)-5a,5b,8,8,11a-pentamethyl-3a-((1S,4R)-4-(morpholinomethyl)cyclopent-2-enylcarbamoyl)-1-(prop-1-en-2-yl)icosahydro-1H-cyclopenta[a]chrysen-9-yloxy)butanoic acid (Compound 95), 4-oxo-4-((1R,3aS,5aR,5bR,7aR,9S,11aR,11bR,13aR,13bR)-5a,5b,8,8,11a-pentamethyl-3a-(3-(piperidin-1-yl)methyl)cyclopentylcarbamoyl)-1-(prop-1-en-2-yl)icosahydro-1H-cyclopenta[a]chrysen-9-yloxy)butanoic acid (Compound 96), (1R,3aS,5aR,5bR,7aR,9S,11aR,11bR,13aR,13bR)-N-(2,2-dimethyl-3-(3-morpholino-3-oxopropylcarbamoyl)cyclobutyl)-9-hydroxy-5a,5b,8,8,11a-pentamethyl-1-(prop-1-en-2-yl)icosahydro-1H-cyclopenta[a]chrysene-3a-carboxamide (Compound 97), (1R,3aS,5aR,5bR,7aR,9S,11aR,11bR,13aR,13bR)-N-(2,2-dimethyl-3-(3-oxo-3-(pyrrolidin-1-yl)propylcarbamoyl)cyclobutyl)-9-hydroxy-5a,5b,8,8,11a-pentamethyl-1-(prop-1-en-2-yl)icosahydro-1H-cyclopenta[a]chrysene-3a-carboxamide (Compound 98), 4-((1R,3aS,5aR,5bR,7aR,9S,11aR,11bR,13aR,13bR)-3a-((1R,3S)-3-((4-benzylpiperidin-1-yl)methyl)cyclopentylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid (Compound 99), or pharmaceutically acceptable salts, solvates, including hydrates and prodrugs of compounds are also contemplated.

Also below are the some representative compounds (shown in Table 1), which are illustrative in nature only and are not intended to limit to the scope of the invention:

TABLE 1

| Structure | IUPAC Name (Nomenclature has been generated from Chem. Draw Ultra 11.0 version) |
|---|---|
| 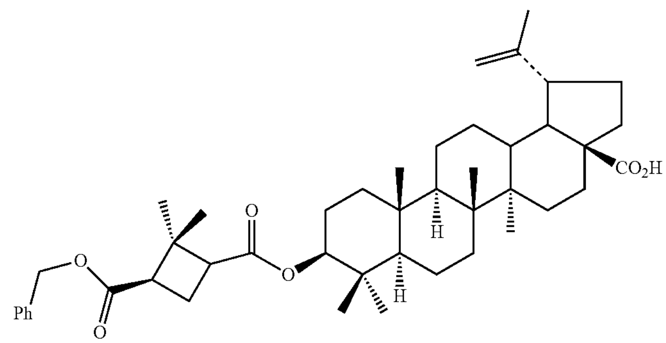 | (1R,3aS,5aR,5bR,7aR,9S,11aR,11bR)-9-((3R)-3-(benzyloxycarbonyl)-2,2-dimethylcyclobutanecarbonyloxy)-5a,5b,8,8,11a-pentamethyl-1-(prop-1-en-2-yl)icosahydro-1H-cyclopenta[a]chrysene-3a-carboxylic acid |
| 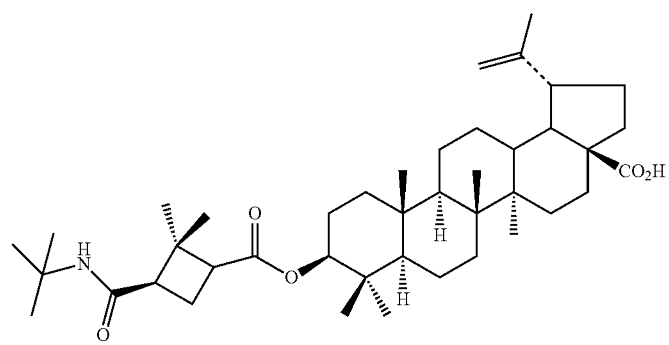 | (1R,3aS,5aR,5bR,7aR,9S,11aR,11bR)-9-((3R)-3-(tert-butylcarbamoyl)-2,2-dimethylcyclobutanecarbonyloxy)-5a,5b,8,8,11a-pentamethyl-1-(prop-1-en-2-yl)icosahydro-1H-cyclopenta[a]chrysene-3a-carboxylic acid |
| 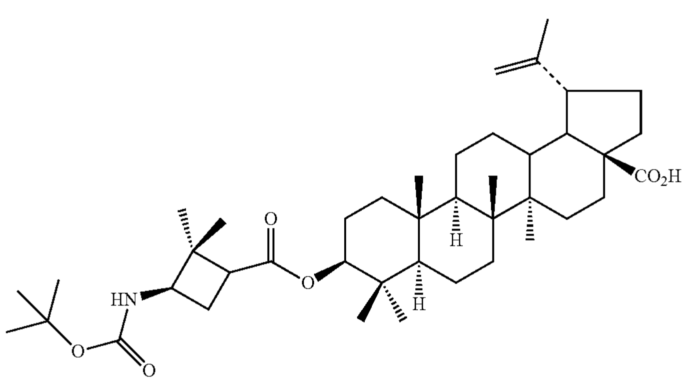 | (1R,3aS,5aR,5bR,7aR,9S,11aR,11bR)-9-((3R)-3-(tert-butoxycarbonylamino)-2,2-dimethylcyclobutanecarbonyloxy)-5a,5b,8,8,11a-pentamethyl-1-(prop-1-en-2-yl)icosahydro-1H-cyclopenta[a]chrysene-3a-carboxylic acid |
| 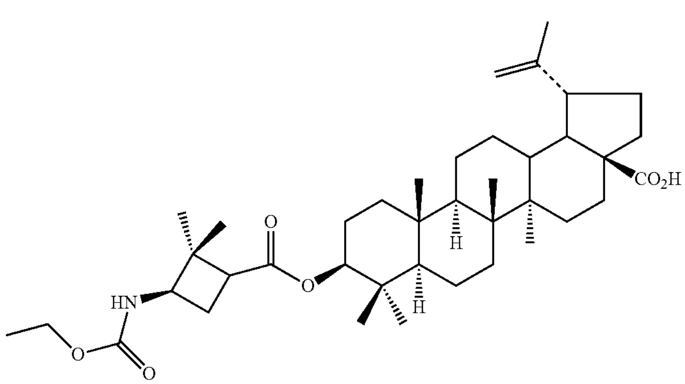 | (1R,3aS,5aR,5bR,7aR,9S,11aR,11bR)-9-((3R)-3-(ethoxycarbonylamino)-2,2-dimethylcyclobutanecarbonyloxy)-5a,5b,8,8,11a-pentamethyl-1-(prop-1-en-2-yl)icosahydro-1H-cyclopenta[a]chrysene-3a-carboxylic acid |

TABLE 1-continued

| Structure | IUPAC Name (Nomenclature has been generated from Chem. Draw Ultra 11.0 version) |
|---|---|
| 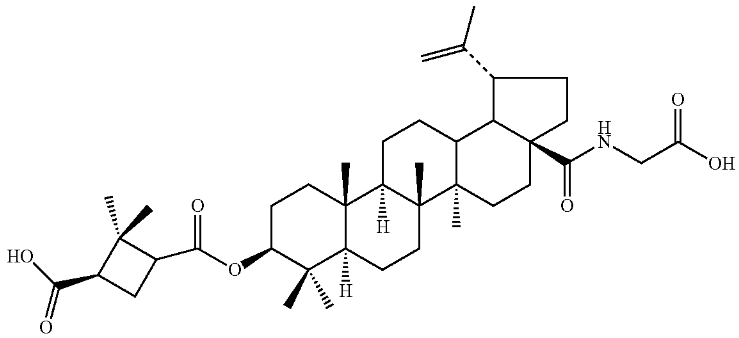 | (1R)-3-(((1R,3aS,5aR,5bR,7aR,9S,11aR,11bR)-3a-(carboxymethylcarbamoyl)-5a,5b,8,8,11a-pentamethyl-1-(prop-1-en-2-yl)icosahydro-1H-cyclopenta[a]chrysen-9-yloxy)carbonyl)-2,2-dimethylcyclobutanecarboxylic acid |
| 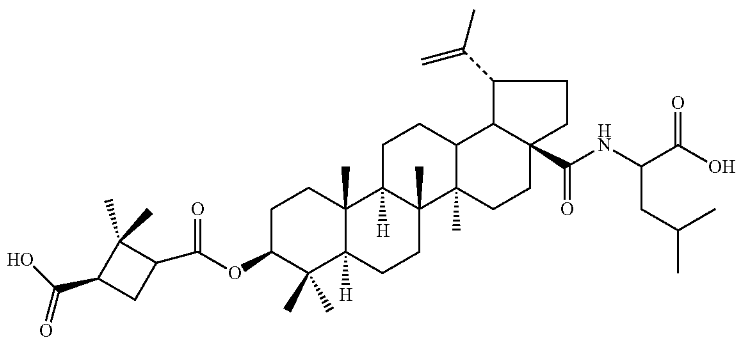 | (1R)-3-(((1R,3aS,5aR,5bR,7aR,9S,11aR,11bR)-3a-(1-carboxy-3-methylbutylcarbamoyl)-5a,5b,8,8,11a-pentamethyl-1-(prop-1-en-2-yl)icosahydro-1H-cyclopenta[a]chrysen-9-yloxy)carbonyl)-2,2-dimethylcyclobutanecarboxylic acid |
| 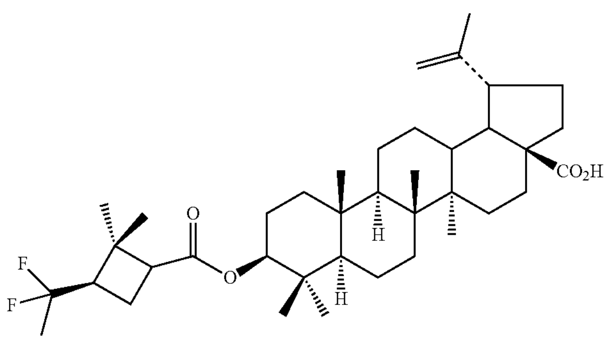 | (1R,3aS,5aR,5bR,7aR,9S,11aR,11bR)-9-((3R)-3-(1,1-difluoroethyl)-2,2-dimethylcyclobutanecarbonyloxy)-5a,5b,8,8,11a-pentamethyl-1-(prop-1-en-2-yl)icosahydro-1H-cyclopenta[a]chrysene-3a-carboxylic acid |
| 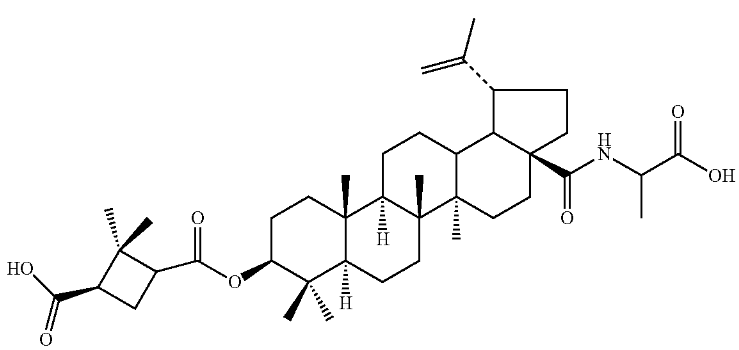 | (1R)-3-(((1R,3aS,5aR,5bR,7aR,9S,11aR,11bR)-3a-(1-carboxyethylcarbamoyl)-5a,5b,8,8,11a-pentamethyl-1-(prop-1-en-2-yl)icosahydro-1H-cyclopenta[a]chrysen-9-yloxy)carbonyl)-2,2-dimethylcyclobutanecarboxylic acid |

TABLE 1-continued

| Structure | IUPAC Name (Nomenclature has been generated from Chem. Draw Ultra 11.0 version) |
|---|---|
| 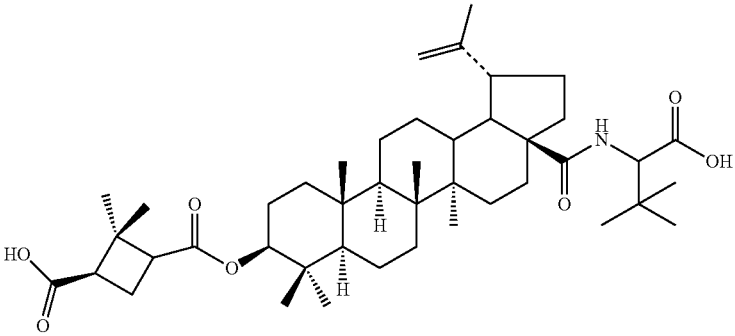 | (1R)-3-(((1R,3aS,5aR,5bR,7aR,9S,11aR,11bR)-3a-(1-carboxy-2,2-dimethylpropylcarbamoyl)-5a,5b,8,8,11a-pentamethyl-1-(prop-1-en-2-yl)icosahydro-1H-cyclopenta[a]chrysen-9-yloxy)carbonyl)-2,2-dimethylcyclobutanecarboxylic acid |
| 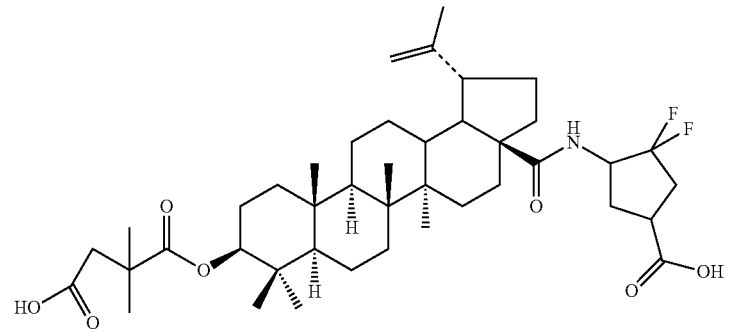 | 4-((1R,3aS,5aR,5bR,7aR,9S,11aR,11bR)-9-(3-carboxy-2,2-dimethylpropanoyloxy)-5a,5b,8,8,11a-pentamethyl-1-(prop-1-en-2-yl)icosahydro-1H-cyclopenta[a]chrysene-3a-carboxamido)-3,3-difluorocyclopentanecarboxylic acid |
| 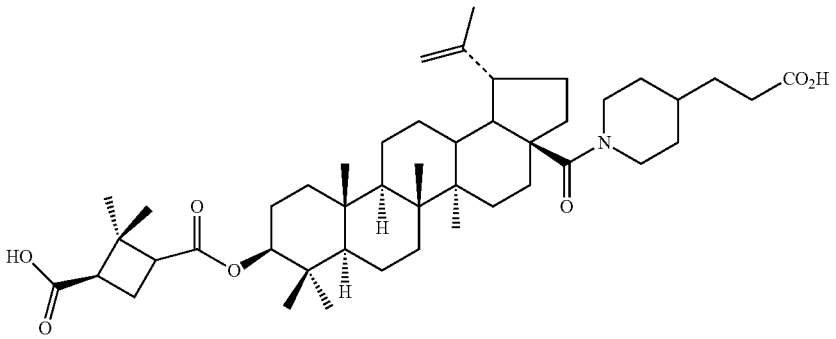 | (1R)-3-(((1R,3aS,5aR,5bR,7aR,9S,11aR,11bR)-3a-(4-(2-carboxyethyl)piperidine-1-carbonyl)-5a,5b,8,8,11a-pentamethyl-1-(prop-1-en-2-yl)icosahydro-1H-cyclopenta[a]chrysen-9-yloxy)carbonyl)-2,2-dimethylcyclobutanecarboxylic acid |
| 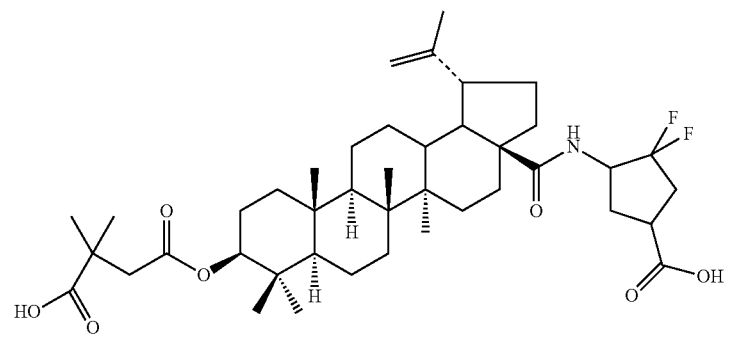 | 4-((1R,3aS,5aR,5bR,7aR,9S,11aR,11bR)-9-(3-carboxy-3-methylbutanoyloxy)-5a,5b,8,8,11a-pentamethyl-1-(prop-1-en-2-yl)icosahydro-1H-cyclopenta[a]chrysene-3a-carboxamido)-3,3-difluorocyclopentanecarboxylic acid |

TABLE 1-continued

| Structure | IUPAC Name (Nomenclature has been generated from Chem. Draw Ultra 11.0 version) |
|---|---|
| 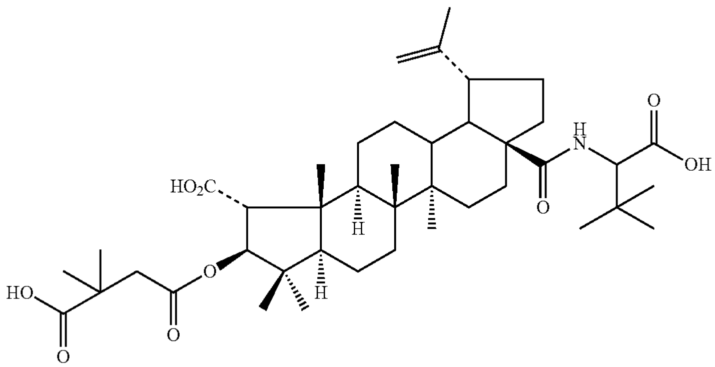 | (1R,2S,3aR,5aR,5bR,7aS,10R,12aR,12bR)-7a-(1-carboxy-2,2-dimethylpropylcarbamoyl)-2-(3-carboxy-3-methylbutanoyloxy)-3,3,5a,5b,12b-pentamethyl-10-(prop-1-en-2-yl)icosahydrodicyclopenta[a,i]phenanthrene-1-carboxylic acid |
| | (1R,2S,3aR,5aR,5bR,7aS,10R,12aR,12bR)-2-(3-carboxy-3-methylbutanoyloxy)-7a-(1-carboxyethylcarbamoyl)-3,3,5a,5b,12b-pentamethyl-10-(prop-1-en-2-yl)icosahydrodicyclopenta[a,i]phenanthrene-1-carboxylic acid | or pharmaceutically acceptable salts, solvates, including hydrates and prodrugs of compounds are also contemplated.

The present invention also provides a pharmaceutical composition that includes at least one compound of described herein and at least one pharmaceutically acceptable excipient (such as a pharmaceutically acceptable carrier or diluent). Preferably, the pharmaceutical composition comprises a therapeutically effective amount of at least one compound described herein. The compound(s) present in the composition may be associated with a pharmaceutically acceptable excipient (such as a carrier or a diluent) or may be diluted by a carrier, or enclosed within a carrier which may be in the form of a capsule, sachet, paper, or other container.

The compounds and pharmaceutical compositions described herein are useful in the treatment of diseases, conditions and/or disorders mediated by viral infections.

The present invention further provides a method of treating a disease, condition and/or disorder mediated by viral infections in a subject in need thereof by administering to the subject one or more compounds described herein in the amount effective to cause that infection.

Also provided herein are processes for preparing compounds described herein.

The invention provides a method for preventing, ameliorating or treating a HIV mediated disease, disorder or syndrome in a subject in need thereof comprising administering to the subject a therapeutically effective amount of a compound of the invention. The invention further provides a method, wherein the HIV mediated disease, disorder or syndrome is like AIDS, AIDS related complex, or a syndrome characterized by symptoms such as pesistant generalized limphadenopathy, fever and weight loss, or an etroviral infection genetically related to AIDS.

Anti HIV inhibitory potential of the compounds of present invention may be demonstrated by any one or more methodologies known in the art, such as by using the assays described in Mosmann T, December 1983, *Journal of immunological methods*, 65 (1-2), 55-63 and *SPC Cole, cancer chemotherapy and Pharmacology*, 1986, 17, 259-263.

DETAILED DESCRIPTION OF THE INVENTION

The present invention provides lupeol-type triterpene derivatives and related compounds, which may be used as antiviral particularly as anti-HIV compounds and processes for the synthesis of these compounds. Pharmaceutically acceptable salts, pharmaceutically acceptable solvates, enantiomers, diastereomers, together with pharmaceutically acceptable carriers, excipients or diluents, which can be used for the treatment of diseases, condition and/or disorders mediated by viral infections, are also provided.

The following definitions apply to the terms as used herein:

The terms "halogen" or "halo" includes fluorine, chlorine, bromine, or iodine.

The term "alkyl" refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl (isopropyl), n-butyl, n-pentyl, and 1,1-dimethylethyl (t-butyl).

The term "alkenyl" refers to an aliphatic hydrocarbon group containing a carbon-carbon double bond and which may be a straight or branched chain having from 2 to about 10 carbon atoms, e.g., ethenyl, 1-propenyl, 2-propenyl (allyl), iso-propenyl, 2-methyl-1-propenyl, 1-butenyl, and 2-butenyl.

The term "halo alkyl" is used to denote a group comprised of an alkyl group substituted with halogen atom, where alkyl group is as defined above and halogen is used to denote fluorine, chlorine, bromine or iodine, an example of such group is trifluoromethyl, difluoromethyl.

The term "acyl group" is used to denote a linear or branched aliphatic acyl group (preferably a $C_{2-6}$ alkanoyl group) or an aromatic acyl group, which contains 2 to 10 carbon atoms. Examples include an acetyl group, a propionyl group, a pivaloyl group, a butyryl group, an isobutyryl group, a valeryl group and a benzoyl group, with an acetyl group being preferred.

The term "alkoxy group" is used to denote a linear or branched alkoxy group containing 1 to 6 carbon atoms. Preferred are $C_{1-4}$ alkoxy groups including a methoxy group, an ethoxy group, a propoxy group, an isopropoxy group, an n-butoxy group, an isobutoxy group and a tert-butoxy group.

The term "alkoxycarbonyl group" is used to denote a structure composed of a linear or branched $C_{1-5}$ alkoxy group and a carbonyl group. Preferred are $C_{2-5}$ alkoxycarbonyl groups including a methoxycarbonyl group, an ethoxycarbonyl group, a propoxycarbonyl group, an isopropoxycarbonyl group and a butoxycarbonyl group. Among them, a methoxycarbonyl group is preferred.

The term "cycloalkyl" denotes a non-aromatic mono or multicyclic ring system of from 3 to about 12 carbon atoms, such as cyclopropyl, cyclobutyl, cyclopentyl, and cyclohexyl. Examples of multicyclic cycloalkyl groups include, but are not limited to, perhydronapthyl, adamantyl and norbornyl groups, bridged cyclic groups and spirobicyclic groups, e.g., spiro (4,4) non-2-yl.

The term "cycloalkenyl" refers to a cyclic ring-containing radical having from 3 to about 8 carbon atoms with at least one carbon-carbon double bond, such as cyclopropenyl, cyclobutenyl, and cyclopentenyl.

The term "cycloalkylalkyl" refers to a cyclic ring-containing radical having from 3 to about 8 carbon atoms directly attached to an alkyl group. The cycloalkylalkyl group may be attached to the main structure at any carbon atom in the alkyl group that results in the creation of a stable structure. Non-limiting examples of such groups include cyclopropylmethyl, cyclobutylethyl, and cyclopentylethyl.

The term "aryl" refers to an aromatic radical having from 6 to 14 carbon atoms such as phenyl, naphthyl, tetrahydronapthyl, indanyl, and biphenyl.

The term "arylalkyl" refers to an aryl group as defined above directly bonded to an alkyl group as defined above, e.g., —$CH_2C_6H_5$ and —$C_2H_5C_6H_5$.

"Substituted" refers to 1-3 substituents on the same position or on different positions with the same groups or different groups.

"Alkynyl" refers to alkynyl groups having from 2 to 6 carbon atoms and having at least one alkynyl saturation, example for such group includes acetylenyl, propargyl.

The terms "heterocyclyl" and "heterocyclic ring" refer to a stable 3- to 15-membered ring radical which consists of carbon atoms and from one to five heteroatoms selected from nitrogen, phosphorus, oxygen and sulfur. For purposes of this invention, the heterocyclic ring radical may be a monocyclic, bicyclic or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated (i.e., heterocyclic or heteroaryl). Examples of such heterocyclic ring radicals include, but are not limited to, tetrazoyl, tetrahydroisouinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, oxazolidinyl, triazolyl, isoxazolyl, isoxasolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzothiazolyl, benzooxazolyl, furyl, tetrahydrofurtyl, tetrahydropyranyl, thienyl, benzothienyl, thiamorpholinyl, thiamorpholinyl sulfoxide, thiamorpholinyl sulfone, dioxaphospholanyl, oxadiazolyl. The heterocyclic ring radical may be attached to the main structure at any heteroatom or carbon atom that results in the creation of a stable structure.

The term "heterocyclylalkyl" refers to a heterocyclic ring radical directly bonded to an alkyl group. The heterocyclylalkyl radical may be attached to the main structure at any carbon atom in the alkyl group that results in the creation of a stable structure.

The term "heteroaryl" refers to an aromatic heterocyclic ring radical. The heteroaryl ring radical may be attached to the main structure at any heteroatom or carbon atom that results in the creation of a stable structure.

The term "heteroarylalkyl" refers to a heteroaryl ring radical directly bonded to an alkyl group. The heteroarylalkyl radical may be attached to the main structure at any carbon atom in the alkyl group that results in the creation of a stable structure.

Unless otherwise specified, the term "substituted" as used herein refers to substitution with any one or any combination of the following substituents: hydroxy, halogen, carboxyl, cyano, nitro, oxo (=O), thio (=S), substituted or unsubstituted alkyl, haloalkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenylalkyl, substituted or unsubstituted cycloalkenyl, substituted or unsubstituted amino, substituted or unsubstituted aryl, substituted or unsubstituted heteroaryl, substituted or unsubstituted heterocyclylalkyl ring, substituted or unsubstituted heteroarylalkyl, substituted or unsubstituted heterocyclic ring, substituted or unsubstituted guanidine, —$COOR^x$, —$C(O)R^x$, —$C(S)R^x$, —$C(O)NR^xR^y$, —$C(O)ONR^xR^y$, —$NR^x$-$CONR^yR^x$, —$N(R^x)SOR^y$, —$N(R^x)SO_2R^y$, —(=N—N($R^x$)$R^y$), —$NR^xC(O)OR^y$, —$NR^xR^y$, —$NR^xC(O)R^y$, —$NR^xC(S)R^y$, —$NR^xC(S)NR^yR^z$, —$SONR^xR^y$, —$SO_2NR^xR^y$, —$OR^x$, —$OR^xC(O)NR^yR^z$, —$R^xC(O)OR^y$, —$OC(O)R^x$, —$OC(O)NR^xR^y$, —$R^xNR^yC(O)R^x$, —$R^xOR^y$, —$R^xC(O)OR^y$, —$R^xC(O)NR^yR^z$, —$R^xC(O)R^y$, —$R^xOC(O)R^y$, —$SR^x$, —$SOR^x$, —$SO_2R^x$, and —$ONO_2$, wherein $R^x$, $R^y$ and $R^z$ are independently selected from hydrogen, substituted or unsubstituted alkyl, haloalkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted heterocyclylalkyl ring, substituted or unsubstituted heteroarylalkyl, or substituted or unsubstituted heterocyclic ring. The substituents in the aforementioned "substituted" groups cannot be further substituted. For example, when the substituent on "substituted alkyl" is "substituted aryl", the substituent on "substituted aryl" cannot be "substituted alkenyl".

The term "prodrug" means a compound that is transformed in vivo to yield a compound of Formula (I), (IA), (2), (2A) or a pharmaceutically acceptable salt, hydrate or solvate, or metabolite of the compound. The transformation may occur by various mechanisms, such as through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

The term "treating" or "treatment" of a state, disease, disorder or condition includes:

(1) preventing or delaying the appearance of clinical symptoms of the state, disease, disorder or condition developing in a subject that may be afflicted with or predisposed to the state, disease, disorder or condition but does not yet experience or display clinical or subclinical symptoms of the state, disease, disorder or condition;

(2) inhibiting the state, disease, disorder or condition, i.e., arresting or reducing the development of the state, disease, disorder or condition or at least one clinical or subclinical symptom thereof; or (3) relieving the state, disease, disorder or condition, i.e., causing regression of the state, disease, disorder or condition or at least one of its clinical or subclinical symptoms.

The benefit to a subject receiving treatment is either statistically significant or at least perceptible to the subject or to the physician.

The term "subject" includes mammals (especially humans) and other animals, such as domestic animals (e.g., household pets including cats and dogs) and non-domestic animals (such as wildlife).

A "therapeutically effective amount" means the amount of a compound that, when administered to a subject for treating a state, disease, disorder or condition, is sufficient to effect such treatment. The "therapeutically effective amount" will vary depending on the compound, the state, disease, disorder or condition and its severity and the age, weight, physical condition and responsiveness of the subject receiving treatment.

The compounds of the present invention may form salts. Non-limiting examples of pharmaceutically acceptable salts forming part of this invention include salts derived from inorganic bases salts of organic bases salts of chiral bases, salts of natural amino acids and salts of non-natural amino acids. Certain compounds of the present invention are capable of existing in stereoisomeric forms (e.g., diastereomers, enantiomers, racemates, and combinations thereof). With respect to the overall compounds described by the Formula (1), (1A), (2) or (2A), the present invention extends to these stereoisomeric forms and to mixtures thereof. To the extent prior art teaches synthesis or separation of particular stereoisomers, the different stereoisomeric forms of the present invention may be separated from one another by the methods known in the art, or a given isomer may be obtained by stereospecific or asymmetric synthesis. Tautomeric forms and mixtures of compounds described herein are also contemplated.

Pharmaceutically acceptable solvates includes hydrates and other solvents of crystallization (such as alcohols). The compounds of the present invention may form solvates with low molecular weight solvents by methods known in the art.

Pharmaceutical Compositions

The pharmaceutical compositions provided in the present invention include at least one compound described herein and at least one pharmaceutically acceptable excipient (such as a pharmaceutically acceptable carrier or diluent). Preferably, the contemplated pharmaceutical compositions include a compound(s) described herein in an amount sufficient to treat viral infection in a subject.

The subjects contemplated include, for example, a living cell and a mammal, including human. The compound of the present invention may be associated with a pharmaceutically acceptable excipient (such as a carrier or a diluent) or be diluted by a carrier, or enclosed within a carrier which can be in the form of a capsule, sachet, or other container.

Examples of suitable carriers include, but are not limited to, water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone.

The carrier or diluent may include a sustained release material, such as, for example, glyceryl monostearate or glyceryl distearate, alone or mixed with a wax.

The pharmaceutical composition may also include one or more pharmaceutically acceptable auxiliary agents, wetting agents, emulsifying agents, suspending agents, preserving agents, salts for influencing osmotic pressure, buffers, sweetening agents, flavoring agents, colorants, or any combination of the foregoing. The pharmaceutical composition of the invention may be formulated so as to provide quick, sustained, or delayed release of the active ingredient after administration to the subject by employing procedures known in the art.

The pharmaceutical compositions described herein may be prepared, e.g., as described in *Remington: The Science and Practice of Pharmacy*, 20$^{th}$ Ed., 2003 (Lippincott Williams & Wilkins). For example, the active compound can be mixed with a carrier, or diluted by a carrier, or enclosed within a carrier, which may be in the form of an ampoule, capsule, sachet, or other container. When the carrier serves as a diluent, it may be a solid, semi-solid, or liquid material that acts as a vehicle, excipient, or medium for the active compound. The active compound can be adsorbed on a granular solid container, for example, in a sachet.

The pharmaceutical compositions may be, for example, capsules, tablets, aerosols, solutions, suspensions, liquids, gels, or products for topical application.

The route of administration may be any route which effectively transports the active compound to the appropriate or desired site of action. Suitable routes of administration include, but are not limited to, oral, nasal, pulmonary, buccal, subdermal, intradermal, transdermal, parenteral, rectal, depot, subcutaneous, intravenous, intraurethral, intramuscular, intranasal, ophthalmic (such as with an ophthalmic solution) or topical (such as with a topical ointment). The oral route is preferred.

Solid oral formulations include, but are not limited to, tablets, capsules (soft or hard gelatin), dragees (containing the active ingredient in powder or pellet form), troches and lozenges. Tablets, dragees, or capsules having talc and/or a carbohydrate carrier or binder or the like are particularly suitable for oral application. Preferable carriers for tablets, dragees, or capsules include lactose, cornstarch, and/or potato starch. A syrup or elixir can be used in cases where a sweetened vehicle can be employed.

A typical tablet that may be prepared by conventional tabletting techniques may contain: (1) Core: Active compound (as free compound or salt thereof), 250 mg colloidal silicon dioxide (AEROSIL®), 1.5 mg microcrystalline cellulose (AVICEL®), 70 mg modified cellulose gum (AC-DI-SOL®), and 7.5 mg magnesium stearate; (2) Coating: HPMC, approx. 9 mg Mywacett 9-40 T and approx. 0.9 mg acylated monoglyceride.

Liquid formulations include, but are not limited to, syrups, emulsions, soft gelatin and sterile injectable liquids, such as aqueous or non-aqueous liquid suspensions or solutions.

For parenteral application, particularly suitable are injectable solutions or suspensions, preferably aqueous solutions with the active compound dissolved in polyhydroxylated castor oil.

Methods of Screening

Antiviral HIV activity and cytotoxicity of compounds present invention can be measured in parallel by following the methods published in the literature.

The cytotoxic effect of compounds can be analyzed by measuring the proliferation of cells using the 3-(4,5-Dimethylthiazol-2-yl)-2,5-diphenyl tetrazlium bromide (MTT) staining. Cells ($5 \times 10^3$ cells/well) will be incubated in in 96 well plates in the presence or absence of compounds. At the end of treatment, 20 µl of MTT (5 mg/ml in PBS) will be added to each well and incubated for an additional 4 hours at 37° C. The purple-blue MTT formazan precipitate will be dissolved in a triplex reagent containing 10% SDS, 5% isobutanol and 10 mmol/lit HCl. The activity of mitochondria, reflecting cellular growth and viability, will be evaluated by measuring the optical density at 570 nm on micro titer plate.

Action of compounds on replication of HIV in Sup-T1 cells can be determined by the method published by Roda Rani et al., 2006 (Archives of Biochemistry and Biophysics, Volume 456, Issue 1, 1 Dec. 2006, Pages 79-92).

Briefly, $1 \times 10^6$ Sup-T1 cells with 100% cell viability will be seeded in RPMI 1640, 0.1% FBS four 12 well plates. Increasing concentrations of Epap-1 peptides will be added to the cells and will be infected with $HIV1_{93\ IN\ 101}$ each at final concentration of virus equivalent to 2 ng of p24 per ml. The infected cells will be incubated at 37 C and 5% CO2 incubator for 2 hours. After 2 hrs the cells will be pelleted at 350 g for 10 min, supernatant will be discarded and cell will be held with RPMI 1640 containing 10% FBS. The cells will be resuspended in the same medium with increasing concentrations of Epap-1 peptides and will be incubated for 96 hours. The cells will be supplemented with peptides at every 24 hours. The supernatants will be collected after 96 hours and analyzed using P24 antigen capture assay kit (SAIC Fredrick). The infection in the absence of Epap-1 will be considered to be 0% inhibition Azidothymidine (AZT) will be taken as positive control.

Action of compound on virus entry and quantification of virus entered can be done in terms of GFP expression by the following the methods published J. Virol. 72, 6988 (1998) by in Cecilia et al., and Analytical Biochemistry Volume 360, Issue 2, 15 Jan. 2007, Pages 315-317 (Dyavar S. Ravi and Debashis Mitra).

Briefly, cells will be seeded in to wells of 24 well plates 1 day prior to the experiment. The cells will be transfected with Tat-reporter. The virus inoculum will be adjusted to 1,000-4,000 TCID 50/ml in assay medium (DMEM, 10% FCS, glutamine and antibiotics), 50 µl aliquots will be incubated with serial dilutions of compounds (50 µl) for 1 hr at 37° C. The reporter expression will be quantified at appropriate time calculated inhibitory doses referrers to the concentration of these agents in this preincubation mixture.

Other relevant references useful for screening antiviral HIV activity are: Averett, D. R. 1989. Anti-HIV compound assessment by two novel high capacity assays. J. Virol. Methods 23: 263-276; Schwartz, O., et al. 1998; A rapid and simple colorimeric test for the study of anti HIV agents. AIDS Res. and Human Retroviruses, 4(6):441-447; Daluge, S. M., et al. 1994. 5-Chloro-2',3'-deoxy-3' fluorouridine (935U83), a selective anti human immunodeficiency virus agent with an improved metabolic and toxicological profile; Antimicro. Agents and Chemotherapy, 38(7):1590-1603; H. Mitsuya and S. Border, Inhibition of the in vitro infectivity and cytopathic effect of human T-lymphotropic virus type lymphadenopathy-associated virus (HLTV-III/LAV) by 2,3'-dideoxynucleosides, Proc. Natl. Acad. Sci. USA, 83, 1911-15 (1986); Pennington et al., Peptides 1990; Meek T. D et al., Inhibition of HIV-1 protease in infected T-lymphocytes by synthetic peptide analogues, Nature, 343, p 90 (1990); Weislow et al., J. Natl. Cancer Inst. 81, 577-586, 1989; T. Mimoto et al., J. Med. Chem., 42, 1789-1802, 1999; Uckun et al 1998, Antimicrobial Agents and Chemotherapy 42:383; for P24 antigen assay Erice et al., 1993, Antimicrob. Ag. Chemotherapy 37: 385-383; Koyanagi et al., Int. J. Cancer, 36, 445-451, 1985; Balzarini et al. AIDS (1991), 5, 21-28; Connor et al., Journal of virology, 1996, 70, 5306-5311; Popik et al., Journal of virology, 2002, 76, 4709-4722; Harrigton et al., Journal of Virology Methods, 2000, 88, 111-115; Roos et al., Virology 2000, 273, 307-315; Fedyuk N. V. et al; Problems of Virology 1992, (3)P135; Mosmann T, December 1983, Journal of immunological methods, 65 (1-2), 55-63; SPC Cole, cancer chemotherapy and Pharmacology, 1986, 17, 259-263.

Methods of Treatment

The present invention provides compounds and pharmaceutical formulations thereof that are useful in the treatment of diseases, conditions and/or disorders mediated by viral infections. The connection between therapeutic effect and antiviral is illustrated. For example, PCT publication Nos. WO 01//07646, WO 01/65957, or WO 03/037908; US publication Nos. U.S. Pat. No. 4,598,095 or US 2002/0068757; EP publication Nos. EP0989862 or EP 0724650; *Bioorganic & Medicinal Chemistry Letters,* 16, (6), 1712-1715, 2006; and references cited therein, all of which are incorporated herein by reference in their entirety and for the purpose stated.

The present invention further provides a method of treating a disease, condition and/or disorder mediated by viral infections in a subject in need thereof by administering to the subject a therapeutically effective amount of a compound or a pharmaceutical composition of the present invention.

Diseases, conditions, and/or disorders that are mediated by viral infections are believed to include, but are not limited to, HIV infection, HBV, HCV, a retroviral infection genetically related to HIV, AIDS, inflammatory disease, respiratory disorders (including adult respiratory distress syndrome (ARDS), bronchitis, chronic bronchitis, chronic obstructive pulmonary disease, cystic fibrosis, asthma, emphysema, rhinitis and chronic sinusitis), inflammatory bowel disease (including Crohn's disease and ulcerative colitis), multiple sclerosis, rheumatoid arthritis, graft rejection (in particular but not limited to kidney and lung allografts), endometriosis, type I diabetes, renal diseases, chronic pancreatitis, inflammatory lung conditions, chronic heart failure and bacterial infections (in particular but not limited to tuberculosis).

The compounds of the present invention can obtain more advantageous effects than additive effects in the prevention or treatment of the above diseases when using suitably in combination with the above drugs. Also, the administration dose can be decreased in comparison with administration of either drug alone, or adverse effects of co administrated drugs other than antiviral can be avoided or declined.

Methods of Preparation

The compounds described herein may be prepared by techniques known in the art. In addition, the compounds described herein may be prepared by following the reaction sequence as depicted in Scheme-1 to 6. Further, in the following schemes, where specific bases, acids, reagents, solvents, coupling agents, etc., are mentioned, it is understood that other bases, acids, reagents, solvents, coupling agents etc., known in the art may also be used and are therefore included within the present invention. Variations in reaction conditions, for example, temperature and/or duration of the reaction, which may be used as known in the art, are also within the scope of the present invention. All the stereo isomers of the compounds in these schemes, unless otherwise specified, are also encompassed within the scope of this invention.

Compounds of the present invention can be synthesized from naturally occurring Betulinic acid, Ceanothic acid, Moronic acid, or Oleanolic acid. Key intermediates required for synthesizing analogues are either commercially available, or can be prepared by the methods published in the literature. For example, the key intermediates in the present invention were prepared by modifying the procedures published in *Journal of organic chemistry* 2000, 65, 3934-3940; *Tetrahedron: asymmetry* 2008, 19, 302-308; or *Tetrahedron: asymmetry* 2003, 14, 217-223.

vebinone was oxidized with an oxidizing agent like ruthenium chloride/sodium periodate in a solvent system like CCl4-ACN—H2O to give the carboxylic acid of compounds of formula 1. The carboxylic acid of compounds of formula 1 is protected with a protecting agent to give the acid protected compounds of formula 2. A protecting group is introduced by reacting alkyl halides in the presence of a base like potassium carbonate or cesium carbonate or by reacting a compound of formula 1 with alcohols in the presence of a dehydrating agent like DCC/DMAP or refluxing in the presence of an acid catalyst. A wide range of solvents can be used to conduct this reaction including DMF, THF, DCM, toluene or the like. A compound of the formula 2, on Schmidt rearrangement promoted by treatment with sodium azide and methane sulphonic acid or the like, gives protected amino acid compounds of formula 3. The N-acyl of compounds of formula 3 is hydrogenolysed in the presence of Pd—C/EtOAc or the like to give the N-acyl amino acid of compounds of formula 4. The N-acyl amino acid of compounds of formula 4 can be acid hydrolyzed in the presence of hydrogen chloride or the like and treated with BOC anhydride in the appropriate reagent to give corresponding carbamate, more particularly, the tertiary butyl carbamate of compounds of formula 5. The tertiary butyl carbamate of compounds of formula 5 can be benzylated to give the tertiary butyl carbamate of benzylated compounds of formula 6 in presence of cesium carbonate or the like in the solvents such as DMF or the like. The tertiary butyl carbamate of benzylated compounds of formula 6 can be treated for BOC removal in the presence of TFA in solvents such as, DCM or the like to give the salt of benzylated of compound of formula 7.

Scheme 1

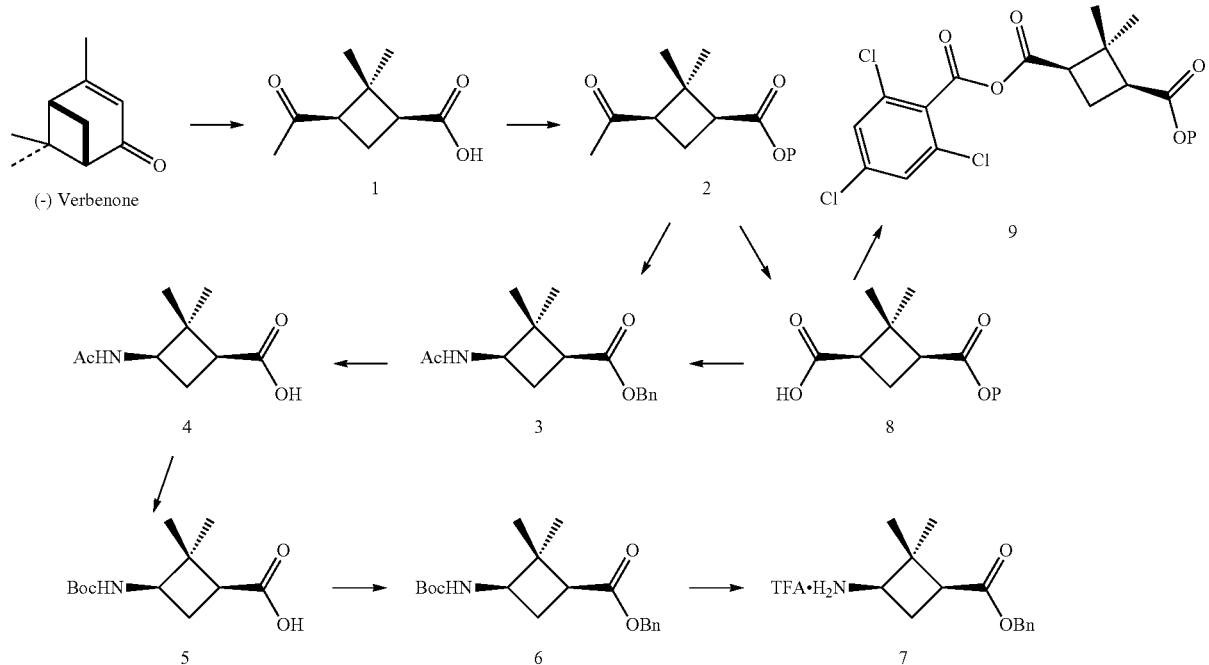

The compound of Formula (7), (wherein, P is a protecting group (for example alkyl or aralkylyl protecting methyl, ethyl, propyl, isopropyl, benzyl or tertiorybutyl) can be prepared as shown in Scheme 1. Commercially available Lieben degradation of the methyl ketone functional group of compound of formula 2 by using aqueous sodium hypobromite in the solvent such as, dioxane or the like, furnish compound of formula 8. 2,4,6-trichloro benzoyl ester compound of formula 9 was obtained by reacting benzoylchloride in presence of DIPEA or the like in solvents such as THF, or the like.

carboxylic halide of formula 12 in presence of acid halides such as thionyl chloride, oxalyl chloride, phosphorous bromide, phosphorous oxy bromide or the like occurs in an inert solvent like benzene or DCM or the like. Reacting a C-28 carboxylic halide of formula 12 with a compound of formula 7 in the presence of triethyl amine or the like occurs in an inert solvent such as DCM or the like to give the compounds of formula 13 [Formula (1), when n and m is 0, "- - -" is no bond, Z is O, $X_1$ is NH, Z' and $R_1$ is H, X and $Z_1$ is CO, $R_2$ is iso-propylene, R is methyl, and R' is substituted cyclobutyl].

Esterifying a C-3 alcohol of the compound of the formula 10 by reacting with the compound of formula 9 gives a compound of formula 14 [Formula (1A), when $Z_{1A}$ is CO, $X_{1A}$ is O, $R_A'$ is H, and $R^A$ is substituted cyclobutyl] in presence of a base like triethylamine in the solvents such as DCM or THF.

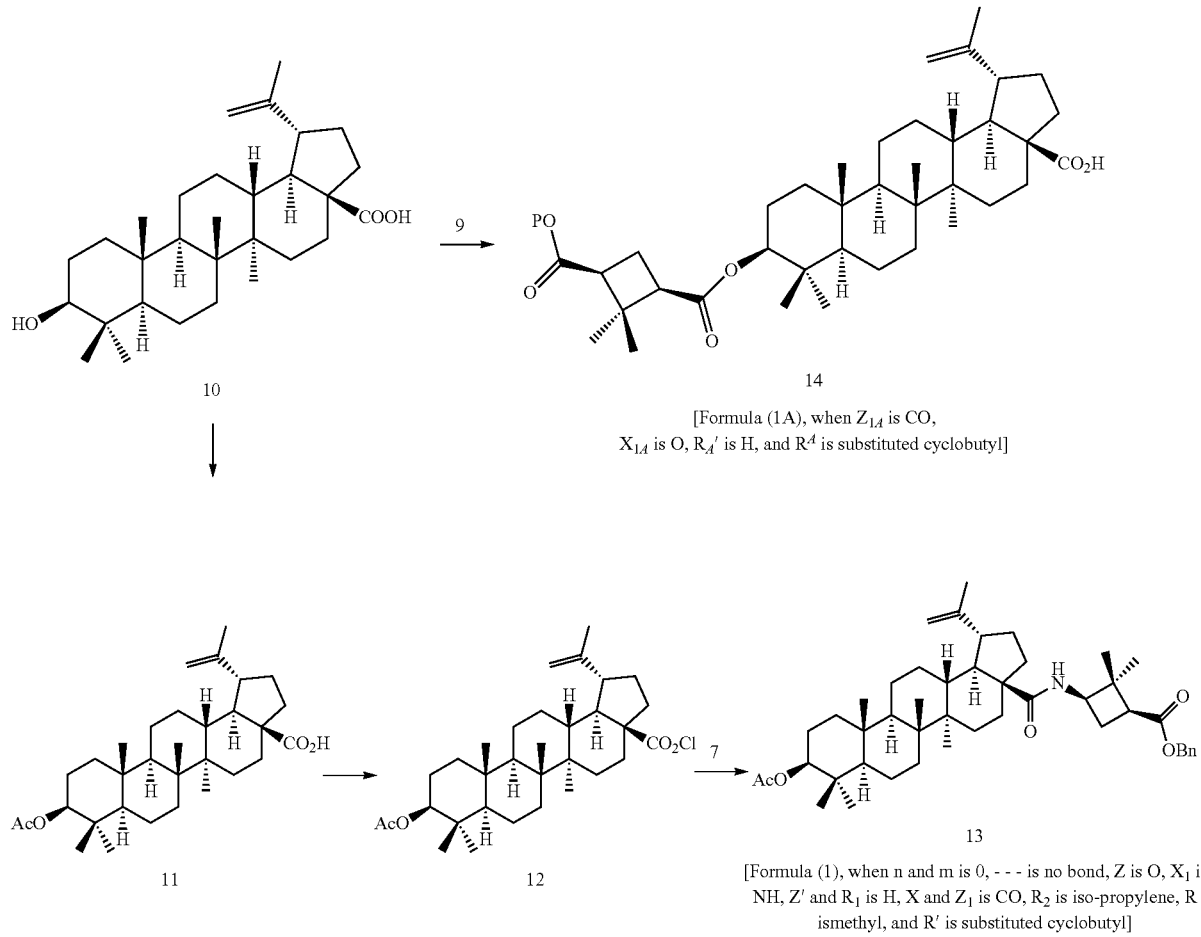

Scheme 2

[Formula (1A), when $Z_{1A}$ is CO, $X_{1A}$ is O, $R_A'$ is H, and $R^A$ is substituted cyclobutyl]

[Formula (1), when n and m is 0, - - - is no bond, Z is O, $X_1$ is NH, Z' and $R_1$ is H, X and $Z_1$ is CO, $R_2$ is iso-propylene, R is methyl, and R' is substituted cyclobutyl]

Compounds 13 and 14 of general formula (1), (wherein, P, R, R', X and $X_1$, Z and $Z_1$, Z', n, m, "----", $R_1$, $R_2$, $R_3'$ and $R_3''$, $R^a$, and R" are same as defined above) can be prepared as described in Scheme 2. The steps of providing a triterpene betulinic acid or ceanotheic acid comprising a C-3 alcohol, C-28 and or C2-carboxyl acid of compound 13 or 14 include: reacting a C-3 alcohol with a suitable ester fixating reagents like anhydrides, acid halides or mixed anhydrides in the presence of a base like triethyl amine, diisopropyl ethyl mine, or pyridine in an inert solvent like DCM, toluene, THF or a basic solvent like pyridine with or without addition of a catalyst like DMAP. For example a C-3 alcohol of compounds of the formula 10 can be protected by an acetyl group in the presence of acetic anhydride in solvents such as pyridine or the like, to give the C-3 acetyl of compounds of formula 11. Converting the C-3 acetyl compound of formula 11 to C-28

Scheme 3

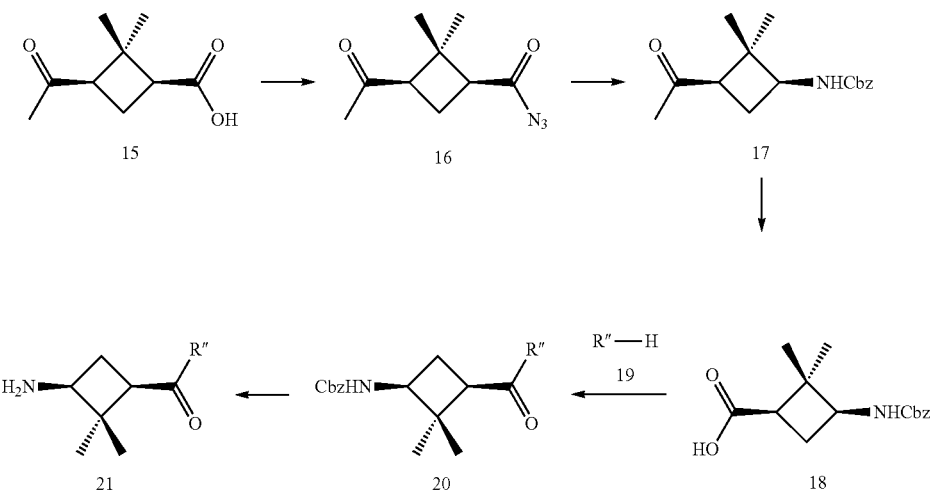

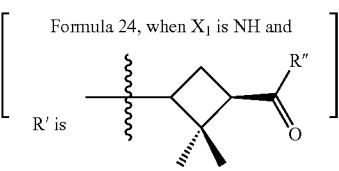

The compounds of Formula (21), (wherein, R″ is as defined above) can be prepared by following the procedures published as shown in Scheme 1. Commercially available verbenone can be oxidized with an oxidizing agent like ruthenium chloride/sodium periodate in a solvent system like CCl₄-ACN—H₂O to give the carboxylic acid of compounds of formula 15. Curtius rearrangement with sodium azide or (PhO)2P(O)N3, followed by N-protection affords the N-protected aminoketone of formula 17. A halo form reaction using substrate 17 under NaOBr, dioxane with aq conditions give compounds of formula 18. The acid compounds of formula 18 can be reacted with compounds of formula 19 to give the N-protected compounds of formula 20 in presence of coupling reagents such as 1-Ethyl-3-(3-Dimethylaminopropyl) carbodiimide (EDCI), 1-hydroxybenzotrazolehydrate (HOBT), O-benzotrazol-1-yl-N,N,N′,N′-tetramethyluroniumhexafluorophosphate (HBTU) or the like and a base for example, triethylamine, diisopropylethylamine, sodium carbonate, potassium carbonate, or the like in the solvents, for example, ethylactate, dichloromethane, acetonitrile, tetrahydrofuran, dioxane or mixtures thereof. The N-protected compounds of formula 20 can be deprotected to give the deprotected amine compounds of formula 21 in presence of hydrogenating agents such as, for example, Pd—C/EtOAc or the like.

Scheme-4

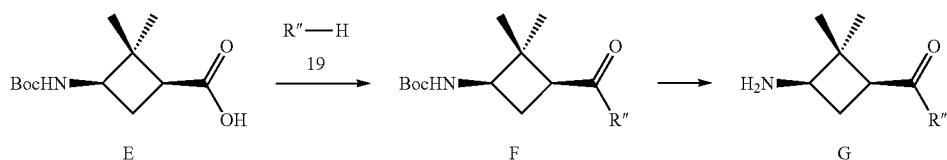

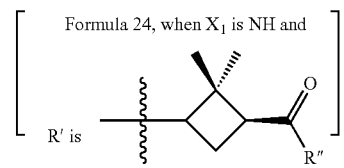

Compounds of Formula (G), (wherein, R" is as defined above) can be prepared by following the procedures published as shown in Scheme 4. The acid compounds of formula E can be reacted with compounds of formula 19 to give the N-protected compounds of formula F in presence of coupling reagents such as 1-Ethyl-3-(3-Dimethylaminopropyl)carbodiimide (EDCI), 1-hydroxybenzotrazolehydrate (HOBT), O-benzotrazol-1-yl-N,N,N',N'-tetramethyluronium-hexafluorophosphate (HBTU) or the like and a base for example, DMAP, triethylamine, diisopropylethylamine, sodium carbonate, potassium carbonate, or the like in the solvents, for example, ethylactate, dichloromethane, acetonitrile, tetrahydrofuran, dioxane or mixtures thereof. The N-protected compounds of formula F can be deprotected to give the deprotected amine compounds of formula G in presence of acids such as, for example, trifluoroacetic acid, HCl or the like.

phorous bromide, phosphorous oxy bromide or the like can be performed in an inert solvent like benzene or DCM or the like without added solvent. C-28 carboxylic halide of the C-3 oxy-protected compounds of formula 23 can be reacted with the amine compounds of formula 24 in the presence of triethyl amine or the like in an inert solvents such as DCM or the like to give the O-protected compounds of formula 25. The O-protected compounds of formula 25 can be hydrolyzed to give the hydroxyl compounds of formula 26 in presence of base such as, for example, metal hydroxides, metal caronates or bicarbonates in MeOH, EtOH or MeOH-THF or the like solvents. The hydroxy compounds of formula 26 can be reacted with acid anhydride compounds, half protected diacids or their mixed anhydrides or acid chlorides of formula 27

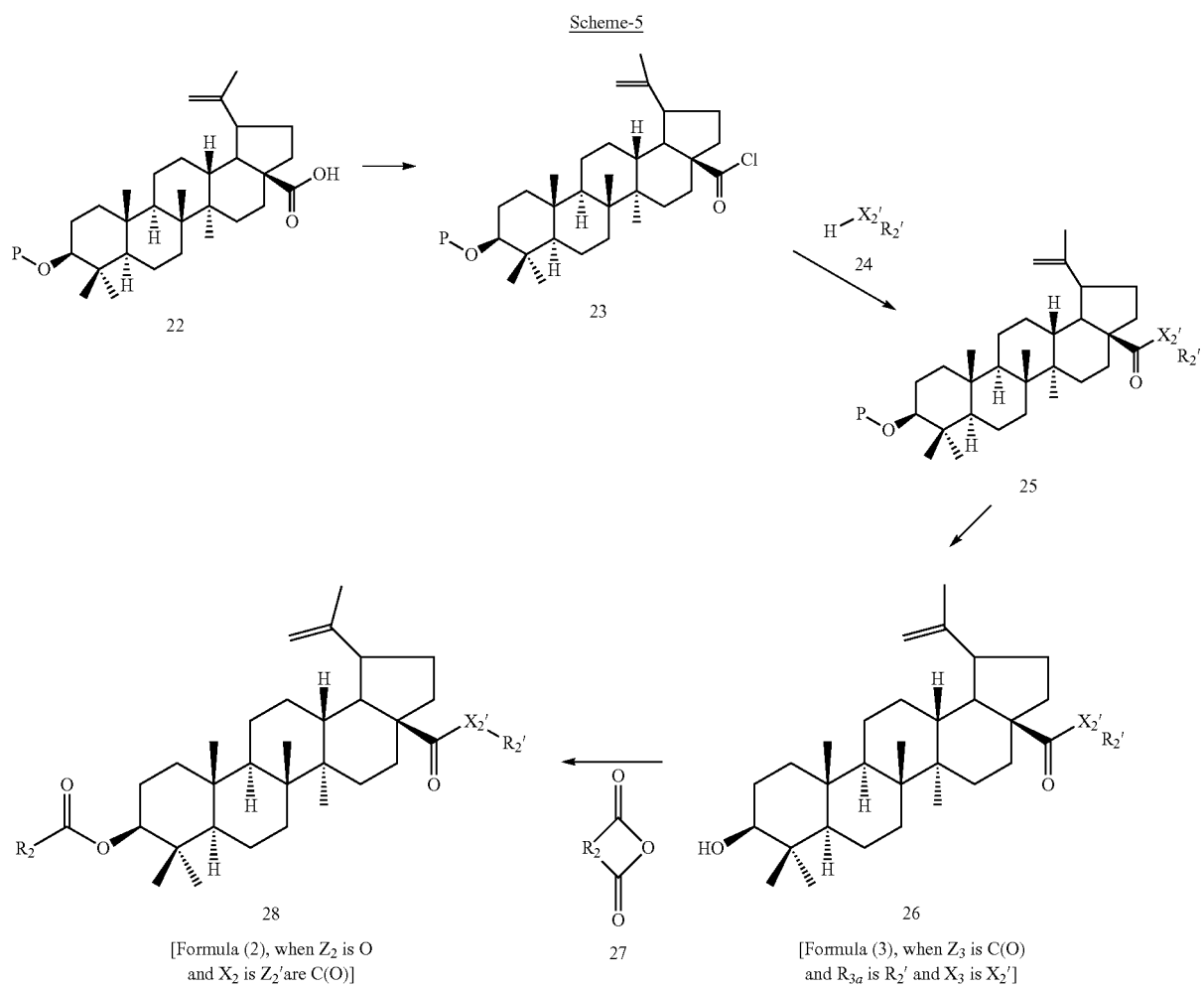

The compounds of Formula (28) (Formula (2), when $Z_2$ is O) can be prepared as shown in Scheme 5. The C-3 hydroxy-protected compounds of formula 22 can be converted to C-28 carboxylic halide compounds of formula 23 in presence of acid halides such as thionyl chloride, oxalyl chloride, phosto give the final compound of formula 28 [Formula (2), when $Z_2$ is O and $Z_2'$ and $X_2'$ are C(O)] in the presence a base like triethyl amine, 4-Dimethylaminopyridine, diisopropyl ethyl mine or pyridine or the like in the solvents such as for example, DCM, toluene, THF or the like.

Scheme-6

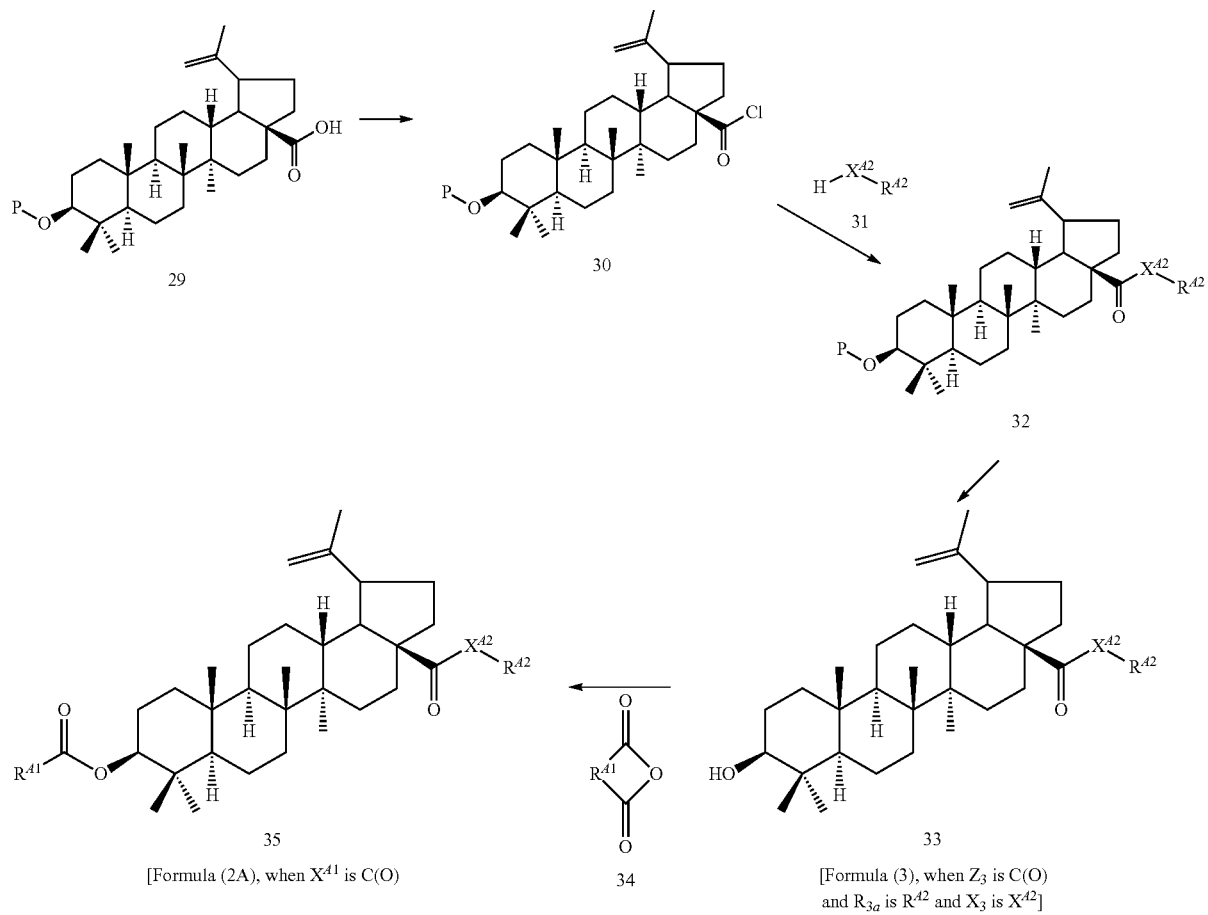

The compounds of Formula (35) (Formula (2A), when $X^{41}$ is C(O)) can be prepared by the above procedure as shown in Scheme 6. The C-3 hydroxy-protected compounds of formula 29 can be converted to C-28 carboxylic halide of the C-3 oxy-protected compounds of formula 30 in presence of acid halides such as thionyl chloride, oxalyl chloride, phosphorous bromide, phosphorous oxy bromide or the like can be performed in an inert solvent like benzene or DCM or the like without added solvent. C-28 carboxylic halide of the C-3 oxy-protected compounds of formula 30 can be reacted with the amine compounds of formula 31 in the presence of triethyl amine or the like in an inert solvents such as DCM or the like to give the O-protected compounds of formula 32. The O-protected compounds of formula 32 can be hydrolyzed to give the hydroxyl compounds of formula 33 by hydrolyzing with a base like metal hydroxide, metal carbonates or bicarbonates and the like in a protic solvent like alcohol or a combination of solvents for example, MeOH:THF or the like. The hydroxyl compounds of formula 33 can be reacted with acid anhydride compounds of formula 34 or partially protected diacids or mixed anhydrides, acid halides to give the final compound of formula (35) (Formula (2A), when $X^{41}$ is C(O)) in the presence a base like triethyl amine, 4-Dimethylaminopyridine, diisopropyl ethyl mine or pyridine or the like in the solvents such as for example, DCM, toluene, THF or the like.

EXPERIMENTAL

The present invention is further illustrated by the following examples, which are not to be construed in any way as imposing limitations upon the scope of this disclosure, but rather are intended to be illustrative only. On the contrary, it is to be clearly understood that resort may be had to various other embodiments, modifications, and equivalents thereof which, after reading the description herein, may suggest themselves to one of ordinary skill in the art without departing from the spirit of the present invention. Thus, the skilled artisan will appreciate how the experiments and Examples may be further implemented as disclosed by variously altering the following examples, substituents, reagents, or conditions.

INTERMEDIATES

Intermediate 1

Synthesis of (1S,3R)-3-acetyl-2,2-dimethylcyclobutanecarboxylic acid

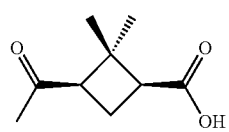

A stirred solution of verbenone (about 10 g, 66.57 mmol) in $CCl_4$: ACN: $H_2O$ (140 ml) $NaIO_4$ (56.9 g, 266.3 mmol) followed by RuCl₃.H₂O (catalytic) were added at 0° C. and allowed to stir at room temperature for about 12 hours. After completion of the reaction (monitored by TLC), reaction mixture was diluted with EtOAc (about 200 ml), filtered through celite bed and the organic layer was separated, the aqueous layer extracted with EtOAc (100 ml×2) combined the organic layers dried with Na₂SO₄ and concentrated under reduced pressure. The resulting crude was stirred in hexane. Solid was filtered and dried under vacuum (8.56 g). ¹H NMR (300 MHZ, CDCl₃): δ 2.91-2.77 (m, 2H), 2.63 (q, 1H, J=9 Hz), 2.07 (s, 3H), 1.86-1.95 (m, 1H), 1.40 (s, 3H), 0.97 (s, 3H). Mass: [M+1]⁺ 171 (10%), [M+Na]⁺ 193 (72%). IR (KBr, cm⁻¹): 3218, 1737, 1694, 1467, 1368, 1283, 1174, 1080, 836, 703. M.R: 109.5° C.-120.7° C.

Intermediate 2

Synthesis of (1S,3R)-benzyl 3-acetyl-2,2-dimethylcyclobutanecarboxylate

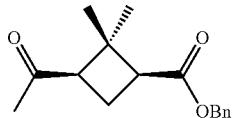

A stirred solution of (1S,3R)-3-acetyl-2,2-dimethylcyclobutanecarboxylic acid (6.0 g, 35.29 mmol) in DMF (20 ml) at 0° C., Cs₂CO₃ (13.8 g, 42.34 mmol) followed by BnBr (5.06 ml, 42.34 mmol) were added slowly portion wise. The reaction was stirred at room temperature for about 2 hours. After completion of the reaction (monitored by TLC), the reaction mixture was diluted with EtOAc (100 ml) and washed with water (50 ml), brine (50 ml) and dried with Na₂SO₄. The solvent was evaporated and purified by silica gel column (60-120, elution 4% EtOAc in hexane) to afford title compound as a pale yellow syrup. Wt: 5.6 g; Yield: 61.5%; ¹H NMR (300 MHZ, CDCl₃): δ 7.42-7.31 (m, 5H), 5.13 (s, 2H), 2.93-2.81 (m, 2H), 2.68 (q, 1H, J=10.5 Hz,), 2.05 (s, 3H), 1.97-1.88 (m, 1H), 1.43 (s, 3H), 0.87 (s, 3H); Mass: [M+1]⁺ 261 (20%), [M+Na]⁺ 283 (87%); IR (KBr, cm⁻¹): 2889, 1732, 1708, 1498, 1456, 1329, 1279, 1183, 1027, 954, 752, 698.

Intermediate 3

Synthesis of (1S,3R)-benzyl 3-acetamido-2,2-dimethylcyclobutanecarboxylate

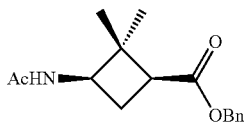

A stirred solution of (1S,3R)-benzyl 3-acetyl-2,2-dimethylcyclobutanecarboxylate (1.5 g, 5.76 mmol) in monoglyme (18.75 ml) at −45° C., NaN₃ (1.12 g, 17.30 mmol), MeSO₃H (10.5 ml), were added drop wise slowly and the reaction was allowed to stir at room temperature for about 48 hours. After completion of the reaction (monitored by TLC), the reaction mixture was neutralized with aqueous ammonia solution. Solvent was evaporated and diluted with DCM. Organic layer was washed with water, brine dried over Na₂SO₄. The solvent was evaporated under reduced pressure and the resulting crude purified by silica gel column (60/120 mesh, elution: 30% EtOAc in Hexane) to afford the title compound as off white solid. Wt: 1.3 g; Yield: 82.2%; ¹H NMR (300 MHZ, CD₃OD): δ 7.42-7.31 (m, 5H), 5.59 (d, 1H, J=5.7 Hz), 5.12 (s, 2H), 4.13 (q, 1H, J=9.3 Hz), 2.69-2.63 (m, 1H), 2.38-2.34 (m, 1H), 2.13-2.06 (m, 1H), 2.05 (s, 3H), 1.30 (s, 3H), 0.86 (s, 3H). Mass: [M+1]⁺ 276 (100%), [M+Na]⁺ 298 (66%); IR (KBr, cm⁻¹): 3270, 2963, 2866, 1728, 1647, 1571, 1455, 1303, 1151, 1071, 1019, 961, 755, 742; M.R: 85.6° C.-97.5° C.

Intermediate 4

Synthesis of (1S,3R)-3-acetamido-2,2-dimethylcyclobutanecarboxylic acid

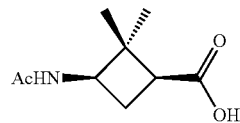

A stirred solution of (1S,3R)-benzyl 3-acetamido-2,2-dimethylcyclobutanecarboxylate (0.650 g, 2.36 mmol) in EtOAc (10 ml) at room temperature, 10% Pd/C (catalytic amount) were added and the reaction mixture was stirred under H₂ gas atmosphere at room temperature for about 1 hour. After completion of the reaction (monitored by TLC), the reaction mixture was filtered through celite bed. The obtained filtrate was concentrated under reduced pressure to afford title compound as an off white solid. Wt: 0.240 g; Yield: 54.9%; ¹H NMR (300 MHZ, CD₃OD): δ 8.09 (d, J=3.0 Hz, 1H), 4.08-3.96 (m, 1H), 2.62-2.58 (m, 1H), 2.20-2.15 (m, 2H), 1.93 (s, 3H), 1.26 (s, 3H), 0.92 (s, 3H); Mass: [M+1]⁺ 186 (70%), [M+Na]⁺ 208 (93%). IR (KBr, cm⁻¹): 3349, 2962, 1697, 1624, 1557, 1428, 1377, 1257, 1075, 988, 920, 736; M.R: 194.7° C.-216.2° C.

Intermediate 5

Synthesis of (1S,3R)-3-(tert-butoxycarbonylamino)-2,2-dimethylcyclobutanecarboxylic acid

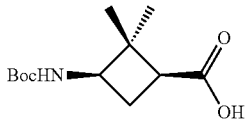

A stirred suspension of (1S,3R)-3-acetamido-2,2-dimethylcyclobutanecarboxylic acid (0.5 g, 2.702 mmol) in 3N HCl (about 8 ml) was refluxed for about 2 hours. After completion of the reaction (monitored by TLC), the solvent was evaporated and basified (P^H=8-9) with 2N NaOH. Dioxane (3 ml), followed by (Boc)₂O (1.24 ml, 5.405 mmol) were added at about 0° C. The reaction was allowed to stir at room temperature for about 16 hours. After completion of the reaction (monitored by TLC), the reaction mixture was acidified with 1N HCl and extracted with EtOAc, the organic layer was washed with water, brine and dried over Na₂SO₄. Organic layer was concentrated under reduced pressure then the resulting crude was purified by silica gel column (100-200 mesh, elution: 30% EtOAc in Hexane) to afford the title compound as off white solid. Wt: 0.500 g; Yield: 72.6%; ¹H NMR (300 MHZ, CD₃OD): δ 3.75-3.704 (m, 1H), 2.55-2.52 (m, 1H), 2.19-2.06 (m, 2H), 1.43 (s, 9H), 1.25 (s, 3H), 0.92 (s, 3H); Mass: [M+Na]⁺ 266 (100%); IR (KBr, cm⁻¹): 3300, 3249, 2967, 1701, 1643, 1479, 1403, 1265, 1159, 1109, 1029, 858, 778; M.R: 142.8° C.-149.0° C.

Intermediate 6

Synthesis of (1S,3R)-benzyl 3-(tert-butoxycarbonylamino)-2,2-dimethylcyclobutanecarboxylate

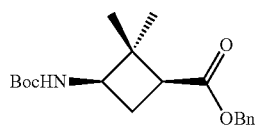

A stirred solution of (1S,3R)-3-(tert-butoxycarbonylamino)-2,2-dimethylcyclobutanecarboxylic acid (0.5 g, 2.05 mmol) in DMF (about 5 ml), Cs₂CO₃ (0.804 g, 2.47 mmol) and BnBr (0.3 ml, 2.47 mmol) were added slowly portion wise at about 0° C., then the reaction was stirred at room temperature for about 2 hours. After completion of the reaction (monitored by TLC), the reaction mixture was diluted with EtOAc and washed with water, brine and dried over Na₂SO₄. The solvent was evaporated and purified by silica gel column (60-120 mesh, elution 4% EtOAc in hexane) to afford title compound as a pale yellow syrup. Wt: 0.35 g; Yield: 51%; ¹H NMR (300 MHZ, CDCl₃): δ 7.39-7.28 (m, 5H), 5.12 (Brs, 2H), 4.60 (Brs, 1H), 3.88-3.79 (m, 1H), 2.65-2.53 (m, 1H), 2.38-2.27 (m, 1H), 2.01-1.99 (m, 1H), 1.43 (s, 9H), 1.28 (s, 3H), 0.86 (s, 3H); IR (KBr, cm⁻¹): 3387, 2962, 1710, 1523, 1456, 1366, 1253, 1173, 1079, 1009, 979, 746, 698.

Intermediate 7

Synthesis of (1S,3R)-benzyl 3-amino-2,2-dimethylcyclobutanecarboxylate trifluoroacetic acid

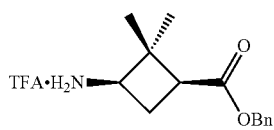

(1S,3R)-benzyl-(tert-butoxycarbonylamino)-2,2-dimethylcyclobutanecarboxylate (about 0.210 g, 0.63 mmol) was stirred in TFA:DCM (1:4) (3 ml) solution at 0° C. and allowed to reach room temperature in 30 minutes. After completion of the reaction the solvent was evaporated and the crude was dissolved in DCM and basified with Et₃N (about 0.26 ml, 1.89 mmol) then the resulting solution immediately used as such for the next reaction.

Intermediate 8

Synthesis of (1S,3R)-tert-butyl 3-acetyl-2,2-dimethylcyclobutanecarboxylate

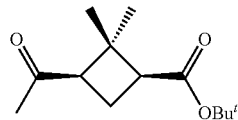

To a stirred ice cooled solution of (1S,3R)-3-acetyl-2,2-dimethylcyclobutanecarboxylic acid (3.0 g, 17.65 mmol) in THF (5 ml), t-BuOH (5.1 ml, 52.94 mmol) and DMAP (0.036 g, 0.176 mmol) in THF (3 ml) were added followed by DCC (4.4 g, 21.2 mmol) in dry THF (2 ml) was added slowly. Then the reaction was stirred at room temperature for about 36 hours. After completion of the reaction (monitored by TLC), the reaction mixture was filtered through a celite bed and washed with DCM. The filtrate was washed with 5% HCl, water, aqueous NaHCO₃ and dried over Na₂SO₄. The solvent was evaporated and purified by silica gel column (60-120, elution 10% EtOAc in hexane) to afford title compound as a pale yellow syrup. Wt: 2.4 g; Yield: 60%; ¹H NMR (300 MHZ, CDCl₃): δ 2.84 (m, 1H), 2.70-2.51 (m, 2H), 2.06 (s, 3H), 1.89-1.80 (m, 1H), 1.41 (s, 12H), 0.93 (s, 3H); Mass: [M+Na]⁺ 249 (100%).

Intermediate 9

Synthesis of (1R,3S)-3-(tert-butoxycarbonyl)-2,2-dimethylcyclobutanecarboxylic acid

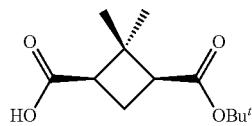

A stirred solution of (1S,3R)-tert-butyl 3-acetyl-2,2-dimethylcyclobutanecarboxylate (2.4 g, 10.62 mmol) in dioxane (270 ml) aqueous NaOBr solution (about 180 ml) was added slowly at about 0° C. and stirred at the same temperature for about 3 hours then allowed to stirred at room temperature for about 4 hours (the yellow colored solution turned to white color). After completion of the reaction (monitored by TLC), the reaction mixture was washed with methyl t-butyl ether (3×150 ml), the aqueous layer was adjusted p^H (2-3) with 1N HCl and the aqueous layer was extracted with EtOAc and dried over Na₂SO₄ and the solvent was evaporated to afford title compound as an off white liquid. Wt: 1.9 g; Yield: 78%; ¹H NMR (300 MHZ, CDCl₃): δ 2.82-2.67 (m, 2H), 2.57-2.50 (m, 1H), 2.04-1.98 (m, 1H), 1.42 (s, 9H), 1.34 (s, 3H), 1.05 (s, 3H); IR (KBr, cm⁻¹): 3205, 1731, 1694, 1460, 1371, 1236, 1157, 1108, 846, 721; Mass: [M+Na]⁺ 251 (40%).

Intermediate 10

Synthesis of (1R,3S)-3-(tert-butoxycarbonyl)-2,2-dimethylcyclobutanecarboxylic 2,4,6-trichlorobenzoic anhydride

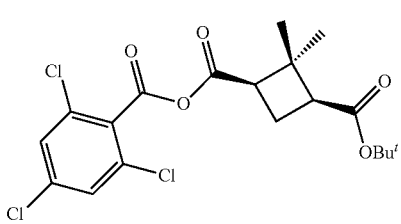

To a stirred solution of (1R,3S)-3-(tert-butoxycarbonyl)-2,2-dimethylcyclobutanecarboxylic acid (about 0.450 g, 1.97 mmol) and DIPEA (about 1.01 ml, 5.92 mmol) in THF (about 4 ml) and 2,4,6-trichloro benzoyl chloride (0.35 ml, 2.17 mmol) were added at 0° C. and the reaction mixture was allowed to stir at room temperature for about 6 hours, after completion of the reaction (monitored by TLC), the solvent was evaporated and crude product proceeded as such for the next reaction.

Intermediate 11

Synthesis of ((1R,3S)-3-amino-2,2-dimethylcyclobutyl)(morpholino)methanone

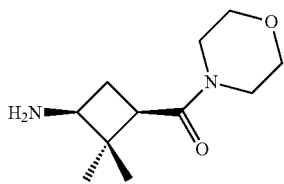

Step 1: Synthesis of (1S,3R)-3-acetyl-2,2-dimethylcyclobutanecarbonyl azide

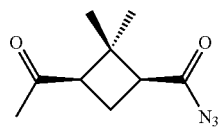

A stirred solution of (1S,3R)-3-acetyl-2,2-dimethylcyclobutanecarboxylic acid (1.0 g, 5.88 mmol) in acetone (20 ml), $Et_3N$ (1.6 ml, 11.76 mmol) and ethyl chloroformate (1.12 ml, 11.76 mmol) were added slowly by portion wise at about 0° C. and stirred for about 3 hours. After completion of the reaction (monitored by TLC), $NaN_3$ (0.84 g, 12.93 mmol) dissolved in minimum amount of water was added to reaction mixture at 0° C. and the reaction mixture was allowed to stir at room temperature for about 1.5 hours. After completion of the reaction (monitored by TLC), the reaction mixture was extracted with DCM and washed with water, brine and dried over $Na_2SO_4$ and benzyl alcohol (0.95 ml, 8.82 mmol) then the solvent was evaporated and the crude product was processed for next reaction immediately without characterization (considering as 100% yield proceeded for next reaction). Crude wt: 1.147 g (100% yield).

Step 2: Synthesis of benzyl (1S,3R)-3-acetyl-2,2-dimethylcyclobutylcarbamate

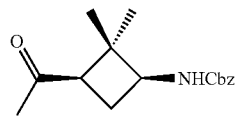

A stirred solution of (1S,3R)-3-acetyl-2,2-dimethylcyclobutanecarbonyl azide (Step 1, 1.147 g, 5.88 mmol) in toluene (20 ml) benzyl alcohol (0.95 ml mmol, 8.82 mmol) was added at room temperature and stirred at reflux temperature for about 4 hours. After completion of the reaction (monitored by TLC), the solvent was evaporated under reduced pressure and the resulting crude was purified by silicagel column (60/120 mesh, elution: 5% EtOAc in Hexane) to afford the title compound as a liquid. Wt: 1.3 g; Yield: 81.2%; $^1H$ NMR (300 MHz, $CDCl_3$): δ 7.38-7.29 (m, 5H), 5.08 (q, 2H, J=12 Hz), 4.80 (d, 1H, J=8.0 Hz), 3.92 (q, 1H, J=9.3 Hz), 2.77-2.71 (m, 1H), 2.16-2.08 (m, 1H), 2.07 (s, 3H), 1.40 (s, 3H), 0.82 (s, 3H); Mass: $[M+1]^+$ 276 (10%), $[M+Na]^+$ 298 (100%); IR (KBr, $cm^{-1}$): 3338, 2956, 2927, 1703, 1648, 1530, 1460, 1370, 1282, 1254, 1183, 1042, 944.

Step 3: Synthesis of (1R,3S)-3-(benzyloxycarbonylamino)-2,2-dimethylcyclobutanecarboxylic acid

To a stirred solution of benzyl (1S,3R)-3-acetyl-2,2-dimethylcyclobutylcarbamate (Step 2, 1.3 g, 4.72 mmol) in dioxane (90 ml): water (30 ml) aq. NaOBr solution (80 ml) was added slowly at about −5° C. and stirred at the same temperature for about 5 hours. After completion of the reaction (monitored by TLC), the reaction mixture was washed with methyl t-butyl ether and the aqueous layer was adjusted $p^H$ (2-3) with 1N HCl and extracted with EtOAc, dried over $Na_2SO_4$ and the solvent was evaporated then the resulting crude was purified by silica gel column (100-200 mesh, elution: 20% EtOAc in Hexane) to afford the title compound as a semi solid. Wt: 1.2 g; Yield: 92%; $^1H$ NMR (300 MHZ, $CDCl_3$): δ 7.38-7.31 (m, 5H), 5.09 (q, 2H, J=10.8 Hz), 4.89 (d, 1H, J=8.4 Hz), 3.98-3.89 (m, 1H), 2.64-2.53 (m, 1H), 2.51-2.26 (m, 2H), 1.32 (s, 3H), 0.98 (s, 3H). IR (KBr, $cm^{-1}$): 3411, 3351, 2961, 1705, 1532, 1456, 1412, 1343, 1256, 1044, 1003, 776, 697; Mass: $[M+Na]^+$ 300 (100%).

NaOBr solution: A solution of NaOH (9.4 g, 233.6 mmol) in $H_2O$ (180 ml) $Br_2$ (3.3 ml, 63.72 mmol) was added at 0° C. slowly, the yellow colored NaOBr solution formed which was used immediately for the reaction.

Step 4: Synthesis of benzyl (1S,3R)-2,2-dimethyl-3-(morpholine-4-carbonyl)cyclobutylcarbamate

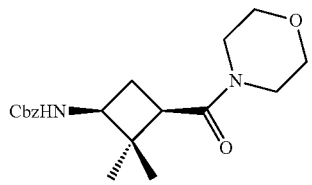

To a stirred solution of (1R,3S)-3-(benzyloxycarbonylamino)-2,2-dimethylcyclobutanecarboxylic acid (Step 3, 0.9 g, 3.25 mmol) in DCM (5 ml) EDCI (0.747 g, 3.89 mmol) and HOBt (0.527 g, 3.89 mmol) were added at about 0° C., after 10 minutes morpholine (0.6 ml, 6.5 mmol) and Et$_3$N (2.3 ml, 16.26 mmol) were added drop wise and the reaction mixture was stirred at room temperature for about 8 hours. After completion of the reaction (monitored by TLC), the reaction mixture was diluted with DCM and washed with water, saturated NaHCO$_3$ solution, water, 1N HCl, water and saturated brine and the organic layer was concentrated under reduced pressure, the resulting crude purified by silica gel column (100-200 mesh, elution 90% EtOAC in hexane) to afford the title compound as a syrup. Wt: 0.6 g; Yield: 53.4%; $^1$H NMR (300 MHz, CD$_3$OD): δ 7.40-7.22 (m, 5H), 5.19 (d, 1H, J=8.7 Hz), 5.08 (q, 2H, J=12.0 Hz), 3.95 (q, 1H, J=9.0 Hz), 3.79-3.38 (m, 8H), 2.80 (t, 1H, J=8.4 Hz), 2.49-2.35 (m, 1H), 2.34-2.20 (m, 1H), 1.33 (s, 3H), 0.89 (s, 3H); Mass: [M+1]$^+$ 347 (10%), [M+Na]$^+$ 346 (100%).

Step 5: Synthesis of ((1R,3S)-3-amino-2,2-dimethyl-cyclobutyl)(morpholino)methanone

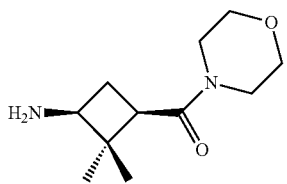

To a stirred solution of benzyl (1S,3R)-2,2-dimethyl-3-(morpholine-4-carbonyl)cyclobutylcarbamate (step 4, 0.60 g, 1.73 mmol) in EtOAc (10 ml) 10% Pd/C (catalytic amount) was added at room temperature and the reaction mixture was stirred under H$_2$ gas atmosphere at room temperature for about 12 hours. After completion of the reaction (monitored by TLC) the reaction mixture was filtered through a celite bed, the obtained filtrate was concentrated under reduced pressure to afford free amine as a liquid which was proceeded as such for the next reaction without characterization. Wt: 0.331 g: Yield: 90%.

Intermediate 12

Synthesis of ((1R,3S)-3-amino-2,2-dimethylcyclobutyl)(piperidin-1-yl)methanone

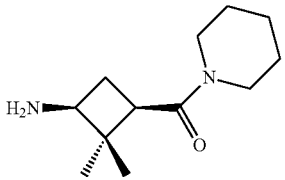

3

Step 1: Synthesis of benzyl (1S,3R)-2,2-dimethyl-3-(piperidine-1-carbonyl)cyclobutylcarbamate

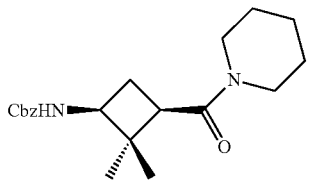

To a stirred solution of (1R,3S)-3-(benzyloxycarbonylamino)-2,2-dimethylcyclobutanecarboxylic acid (Intermediate 1-Step 3, 0.650 g, 2.346 mmol) in DCM (5 ml) EDCI (0.674 g, 3.519 mmol) and HOBt (0.475 g, 3.519 mmol) were added at 0° C., after 10 minutes piperidine (0.46 ml, 4.692 mmol) and Et$_3$N (0.65 ml, 4.692 mmol) were added drop wise and the reaction mixture was stirred at room temperature for about 12 hours. After completion of the reaction (monitored by TLC), the reaction mixture was diluted with DCM and washed with water, saturated NaHCO$_3$ solution, water, 1N HCl, water and saturated brine and the organic layer was concentrated under reduced pressure. The resulting crude was purified by a silica gel column (100-200 mesh, elution 20% EtOAC in hexane) to afford the title compound as an off white solid. Wt: 0.393 g; Yield: 48.6%; $^1$H NMR (300 MHz, CDCl$_3$): δ 7.40-7.28 (m, 5H), 5.18-4.99 (m, 3H), 3.97-3.87 (m, 1H), 3.77-3.67 (m, 1H), 3.49-3.28 (m, 3H), 2.83 (t, 1H, J=8.4 Hz), 2.47-2.20 (m, 2H), 3.65-3.41 (m, 6H), 1.35 (s, 3H), 0.87 (s, 3H); Mass: [M+1]$^+$ 345 (10%), [M+Na]$^+$ 367 (100%); IR (KBr, cm$^{-1}$): 3315, 3013, 2931, 2855, 1719, 1622, 1534, 1443, 1369, 1255, 1236, 1219, 1125, 1040, 853, 746, 697; M.R: 145.2° C.-150.8° C.

Step 2: Synthesis of ((1R,3S)-3-amino-2,2-dimethyl-cyclobutyl)(piperidin-1-yl)methanone

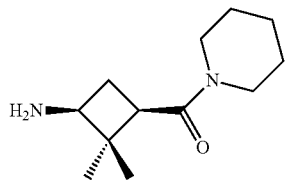

10% Pd/C (catalytic amount) was added to a stirred solution of benzyl (1S,3R)-2,2-dimethyl-3-(piperidine-1-carbonyl)cyclobutylcarbamate (step 1, 0.393 g, 1.14 mmol) in EtOAc (10 ml) at room temperature and the reaction mixture was stirred under H$_2$ gas atmosphere at room temperature for about 12 hours. After completion of the reaction (monitored by TLC) the reaction mixture was filtered through celite bed, the obtained filtrate was concentrated under reduced pressure to afford free amine as a liquid which was proceeded as such for next reaction without characterization. Wt: 0.230 g: Yield: 95%.

Intermediate 13

Synthesis of ((1R,3S)-3-amino-2,2-dimethylcyclobutyl)(pyrrolidin-1-yl)methanone

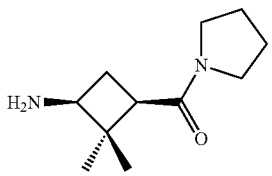

Step 1: Synthesis of benzyl (1S,3R)-2,2-dimethyl-3-(pyrrolidine-1-carbonyl)cyclobutylcarbamate

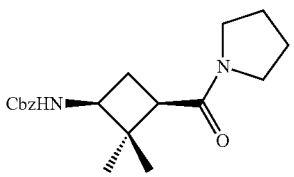

To a stirred solution of (1R,3S)-3-(benzyloxycarbonylamino)-2,2-dimethylcyclobutanecarboxylic acid (Intermediate 1-Step 3, 0.650 g, 2.346 mmol) in DCM (5 ml) EDCI (0.674 g, 3.519 mmol) and HOBt (0.475 g, 3.519 mmol) were added at about 0° C., after 10 minutes pyrrolidine (0.40 ml, 4.692 mmol) and Et₃N (0.65 ml, 4.692 mmol) were added drop wise and the reaction mixture was stirred at room temperature for about 12 hours. After completion of the reaction (monitored by TLC), the reaction mixture was diluted with DCM and washed with water, saturated NaHCO₃ solution, water, 1N HCl, water and saturated brine and the organic layer was concentrated under reduced pressure, the resulting crude purified by silica gel column (100-200 mesh, elution 20% EtOAC in hexane) to afford the title compound as an off white solid. Wt: 0.600 g; Yield: 77.5%; $^1$H NMR (300 MHz, CDCl₃): δ 7.40-7.28 (m, 5H), 5.18-4.99 (m, 3H), 3.97-3.87 (m, 1H), 3.77-3.67 (m, 1H), 3.49-3.28 (m, 3H), 2.83 (t, 1H, J=8.4 Hz), 2.47-2.20 (m, 2H), 3.65-3.41 (m, 6H), 1.35 (s, 3H), 0.87 (s, 3H); Mass: [M+1]⁺ 331 (20%), [M+Na]⁺ 353 (100%); IR (KBr, cm⁻¹): 3304, 3035, 2954, 1716, 1618, 1529, 1497, 1439, 1387, 1368, 1311, 1253, 1222, 1159, 1041, 912, 753.

Step 2: Synthesis of ((1R,3S)-3-amino-2,2-dimethylcyclobutyl)(pyrrolidin-1-yl)methanone

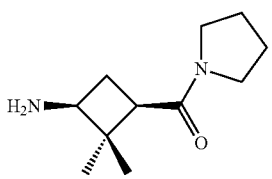

To a stirred solution of benzyl (1S,3R)-2,2-dimethyl-3-(pyrrolidine-1-carbonyl)cyclobutylcarbamate (Step 1, 0.600 g, 1.818 mmol) in EtOAc (10 ml) 10% Pd/C (catalytic amount) was added at room temperature and the reaction mixture was stirred under H₂ gas atmosphere at room temperature for about 12 hours. After completion of the reaction (monitored by TLC), the reaction mixture was filtered through a celite bed, the obtained filtrate was concentrated under reduced pressure to afford free amine as a liquid which was processed as such for the next reaction without characterization. Wt: 0.282 g: Yield: 80%.

Intermediate 14

Synthesis of ((1S,3R)-3-amino-2,2-dimethylcyclobutyl)(morpholino)methanone

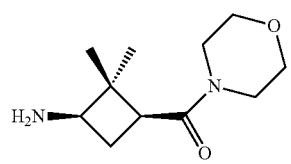

Step 1: Synthesis of tert-butyl (1R,3S)-2,2-dimethyl-3-(morpholine-4-carbonyl)cyclobutylcarbamate

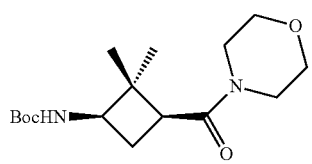

To a stirred solution of (1S,3R)-3-(tert-butoxycarbonylamino)-2,2-dimethylcyclobutanecarboxylic acid (Intermediate 1-Step 3, 0.3 g, 1.23 mmol) in DCM (5 ml) EDCI (0.237 g, 1.23 mmol) and HOBt (0.167 g, 1.23 mmol) were added at about 0° C., after 10 minutes morpholine (0.2 ml, 2.469 mmol) and Et₃N (0.9 ml, 6.2 mmol) were added drop wise and the reaction mixture was stirred at room temperature for about 16 hours. After completion of the reaction (monitored by TLC), the reaction mixture was diluted with DCM and washed with water, saturated NaHCO₃ solution, water, 1N HCl, water and saturated brine and the organic layer was concentrated under reduced pressure, the resulting crude purified by a silica gel column (100-200 mesh, elution 90% EtOAC in hexane) to afford the title compound as a syrup. Wt: 0.205 g; Yield: 53.1%; $^1$H NMR (300 MHz, CDCl₃): δ 4.75 (d, 1H, J=8.4 Hz), 3.90-3.40 (m, 8H), 2.83-2.74 (m, 1H), 2.40-2.21 (m, 2H), 1.43 (s, 9H), 1.32 (s, 3H), 0.89 (s, 3H).

Step 2: Synthesis of ((1S,3R)-3-amino-2,2-dimethylcyclobutyl)(morpholino)methanone

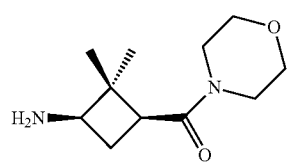

Tert-butyl (1R,3S)-2,2-dimethyl-3-(morpholine-4-carbonyl)cyclobutylcarbamate (Step 1, 0.260 g, 0.833 mmol) was taken in TFA:DCM (1:4) (3 ml) at 0° C.-room temperature and stirred for 1 hour. After completion of the reaction the solvent was evaporated and the crude dissolved in DCM and basified with Et$_3$N (0.7 ml, 5.0 mmol). The resulting solution as such used for next reaction immediately. Wt: 0.176 g.

Intermediate 15

Synthesis of (1S,3R)-3-(benzyloxycarbonyl)-2,2-dimethylcyclobutanecarboxylic acid

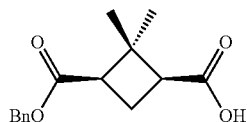

Step 1: synthesis of (1S,3R)-tert-butyl 3-acetyl-2,2-dimethylcyclobutanecarboxylate

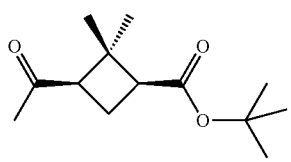

To a stirred ice cooled solution of (1S,3R)-3-acetyl-2,2-dimethylcyclobutanecarboxylic acid (16.0 g, 94.117 mmol) in THF (160 ml) DMAP (1.148 g, 9.409 mmol) and DCC (23.265 g, 112.93 mmol) were added, followed by t-butyl alcohol (27.63 ml, 282.34 mmol) was added drop wise. The reaction mixture was stirred at room temperature for 36 hours. After completion of the reaction (monitored by TLC), the reaction mixture was diluted with EtOAc and filtered through a celite bed and washed with EtOAc. The filtrate was as such concentrated and purified by silica gel column (100-200 mesh, elution 10% EtOAc in hexane) to afford the title compound as a solid. Wt: 15.0 g: Yield: 70%; $^1$H NMR (300 MHz, CDCl$_3$): δ 2.86-2.74 (m, 1H), 2.70-2.50 (m, 2H), 2.04 (s, 3H), 1.89-1.78 (m, 1H), 1.42, 1.40 (2s, 12H), 0.91 (s, 3H); Mass: [M+Na]$^+$ 249 (100%).

Step 2: Synthesis of (1R,3S)-3-(tert-butoxycarbonyl)-2,2-dimethylcyclobutanecarboxylic acid

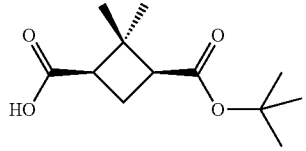

A stirred solution of (1S,3R)-tert-butyl 3-acetyl-2,2-dimethylcyclobutanecarboxylate (step 1, 15.0 g, 66.371 mmol) in dioxane (1450 ml), aq. NaOBr solution (920 ml) was added slowly drop wise at about 0° C. and stirred for about 3 hours and again stirred at room temperature for about 4 hours. After completion of the reaction (monitored by TLC), the reaction mixture was washed with methyl t-butyl ether. The aqueous layer was adjusted p$^H$ (2-3) with 1N HCl and extracted with EtOAc, the organic layer was washed with water and brine, dried over Na$_2$SO$_4$. The solvent was evaporated to afford the title acid as an off white solid. Wt: 7.2 g: Yield: 47.5%; $^1$H NMR (300 MHz, CDCl$_3$): δ 2.83-2.68 (m, 2H), 2.59-2.48 (m, 1H), 2.08-1.97 (m, 1H), 1.44 (s, 9H), 1.34 (s, 3H), 1.06 (s, 3H); IR (KBr, cm$^{-1}$): 3207, 2873, 1731, 1694, 1472, 1462, 1371, 1312, 1286, 1251, 1179, 1157, 1108, 1090, 1017, 904, 846, 742, 721, 620; Mass: [M+Na]$^+$ 251 (100%); M.R: 119.1-123.0° C.

NaOBr solution: A solution of NaOH (57.0 g, 1426.9 mmol) in H$_2$O (910 ml), Br$_2$ (19 ml, 371.6 mmol) were added at 0° C. slowly, the yellow colored NaoBr solution formed which was used immediately for the reaction.

Step 3: Synthesis of (1R,3S)-1-benzyl 3-tert-butyl 2,2-dimethylcyclobutane-1,3-dicarboxylate

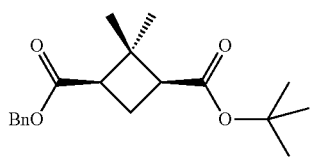

To a stirred solution of (1R,3S)-3-(tert-butoxycarbonyl)-2,2-dimethylcyclobutanecarboxylic acid (step 2, 0.200 g) in DMF (5 ml) Cs2CO3 (0.371 g) was added at about 0° C. under nitrogen atmosphere. After 30 minutes, BnBr (0.11 ml) was added by drop wise to the reaction mixture and stirred for about 2 hours at room temperature. After completion of the reaction (monitored by TLC), the reaction mixture was diluted with ethyl acetate and washed with water. The organic layer was washed with brine, dried over MgSO4 and concentrated under reduced pressure to give crude product which upon column chromatography afforded the title compound (150 mg, 53.9% Yield). $^1$H NMR (300 MHz, CDCl$_3$): δ 7.37-7.34 (5H, m), 5.12 (2H, d, J=3.9 Hz), 2.80 (1H, t, J=8.1 Hz), 2.768-2.52 (2H, m), 2.0 (1H, m), 1.44 (9H, m), 1.32 (3H, s), 0.953 (3H, s); Mass: [M+Na]$^+$ 341.2 (100%).

Step 4: Synthesis of (1S,3R)-3-(benzyloxycarbonyl)-2,2-dimethylcyclobutanecarboxylic acid

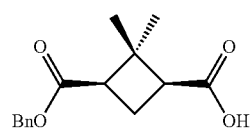

To a solution of (1R,3S)-1-benzyl 3-tert-butyl 2,2-dimethylcyclobutane-1,3-dicarboxylate (step 3, 1.0 g) dioxane-HCl (10 ml) was added at about 0° C. under nitrogen atmosphere. The reaction mixture was stirred for about 12 hours at room temperature. After completion of the reaction (monitored by TLC), the reaction mixture was diluted with ethyl acetate and washed with water. The organic layer was washed with brine, dried over Na$_2$SO$_4$ and concentrated under reduced pressure to give crude product, which upon column chromatography to afford the title compound (800 mg, 97.2% Yield). $^1$H NMR (300 MHz, CDCl$_3$): δ 7.35 (5H, s), 5.12 (2H, d, J=2.7 Hz), 2.84 (2H, m), 2.63 (1H, m), 2.0 (1H, m), 1.35 (3H, s), 0.99 (3H, s); Mass: [M+H]⁺ 263.1 (20%), 285.1 [M+Na]⁺.

Intermediate 16

Synthesis of 3-(morpholinomethyl)cyclopentanamine

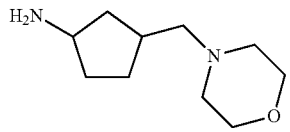 [SMILES: NC1CCC(CN2CCOCC2)C1]

Step 1: Synthesis of tert-butyl (1S,4R)-4-(hydroxymethyl)cyclopent-2-enylcarbamate

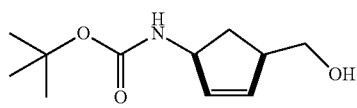

To a stirred solution of ((1S,4R)-4-aminocyclopent-2-enyl)methanol 2,3-dihydroxysuccinate salt (about 10.0 g, 38.02 mmol) in THF (100 ml) sodium carbonate (about 6.38 g, 76.04 mmol) was added at room temperature and cooled to about 0° C. After ten minutes, di-tert-butyl dicarbonate (about 9.1 g, 41.82) was added and stirred the reaction at room temperature for about 12 hours. Completion of the reaction monitored by TLC. Reaction mixture was diluted with water and extracted with DCM, the organic layer was dried over Na₂SO₄ and concentrated under reduced pressure to furnish the title compound (11.5 g) as light yellow liquid. ES Mass: 213 [M+1] 214 (100%).

Step 2: Synthesis of tert-butyl (1R,3S)-3-(hydroxymethyl)cyclopentylcarbamate

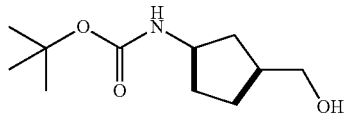

To a stirred solution of tert-butyl (1S,4R)-4-(hydroxymethyl)cyclopent-2-enylcarbamate (step 1, about 10.0 g) in ethanol (150 ml) 10% palladium on carbon (about 1.0 g) was added and kept under hydrogen atmosphere. Reaction mass was stirred for about 16 hours. Completion of the reaction was monitored by TLC. After completion of the reaction, the reaction mixture was filtered through high-flow bed and washed with ethanol. The filtrate was concentrated under reduced pressure to furnish the title compound (7.5 g) as a light yellow liquid. ES Mass: 215 [M+1] 216 (100%).

Step 3: Synthesis of ((1S,3R)-3-(tert-butoxycarbonylamino)cyclopentyl)methyl 4-methylbenzenesulfonate

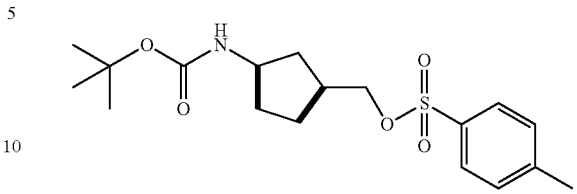

To a stirred solution of tert-butyl (1R,3S)-3-(hydroxymethyl)cyclopentylcarbamate (Step 2, about 4.5 g, 21.12 mmol) in DCM (50 ml), triethyl amine (about 9.5 ml, 68.1 mmol) was added at room temperature and cooled to about 0° C. After ten minutes, 4-methylbenzene-1-sulfonyl chloride (about 6.0 g) was added and stirred the reaction at room temperature for about 6 hours. Completion of the reaction was monitored by TLC. The reaction mixture was neutralized with saturated NaHCO₃ and extracted with DCM, the organic layer was dried over Na₂SO₄ and concentrated under reduced pressure to furnish the title compound (5.5 g) as light yellow liquid. 1H NMR (300 MHz, CDCl3): 1.45 (s, 9H); 246-2.55 (m, 4H); 2.90-2.91 (m, 1H); 3.95-3.98 (m, 2H); 4.59-4.70 (m, 2H); 5.66-5.77 (m, 2H); 7.34-7.37 (d, J=9 Hz, 2H); 7.77-7.80 (d, J=9 Hz, 2H); ES Mass: 369 [M+1] 370 (100%).

Step 4: Synthesis of tert-butyl (1R,3S)-3-(morpholinomethyl)cyclopentylcarbamate

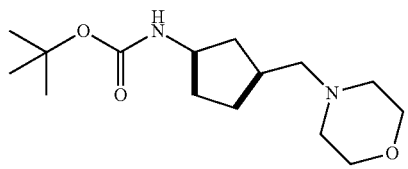

To a stirred solution of ((1S,3R)-3-(tert-butoxycarbonylamino)cyclopentyl)methyl 4-methylbenzenesulfonate (step 3, about 0.5 g) in DCM (50 ml), potassium carbonate (about 0.3 g) was added at room temperature and cooled to about 0° C. After ten minutes, morpholine (1 ml) was added and stirred the reaction at room temperature for about 6 hours. Completion of the reaction was monitored by TLC. The reaction mixture was neutralized and extracted with DCM, the organic layer was dried over Na₂SO₄ and concentrated under reduced pressure to furnish the title compound (0.60 g) as a light yellow liquid. 1H NMR (300 MHz, CDCl3): 1.24-1.29 (m, 1H); 1.39-1.40 (s, 9H); 2.29-2.60 (m, 7H); 2.79-2.80 (m, 1H); 3.70-3.73 (m, 4H); 4.63 (S, 1H); 5.37-5.39 (d, J=6 Hz, 1H); 5.72-5.81 (m, 2H); ES Mass: 283 (100%) [M+1].

Step 5: Synthesis of (1R,3S)-3-(morpholinomethyl)cyclopentanamine

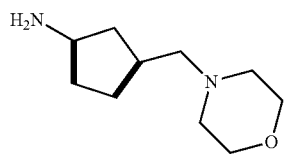

Tert-butyl (1R,3S)-3-(morpholinomethyl)cyclopentylcarbamate (Step 4, 0.6) was treated with trifluoroacetic acid (2 ml) and the obtained compound of 3-(morpholinomethyl)

cyclopentanamine was used directly for synthesizing final compounds given in example section without further purification.

Intermediate 17

Synthesis of (1S,4R)-4-(morpholinomethyl)cyclopent-2-enamine

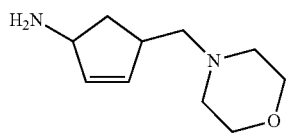 [SMILES: NC1C=CC(CN2CCOCC2)C1]

Step 1: Synthesis of ((1R,4S)-4-(tert-butoxycarbonylamino)cyclopent-2-enyl)methyl 4-methylbenzenesulfonate

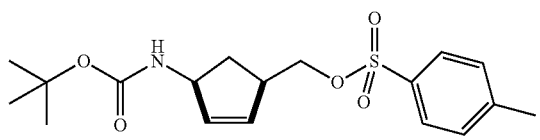

To a stirred solution of tert-butyl (1S,4R)-4-(hydroxymethyl)cyclopent-2-enylcarbamate (Intermediate 6-step 2, about 4.5 g, 21.12 mmol) in DCM (50 ml) triethyl amine (about 9.5 ml, 68.1 mmol) was added at room temperature and cooled to about 0° C. After ten minutes, 4-methylbenzene-1-sulfonyl chloride (about 6.0 g) was added and stirred the reaction at room temperature for about 6 hours and completion of the reaction was monitored by TLC. Reaction mixture was neutralized with saturated NaHCO$_3$ and extracted with DCM, the organic layer was dried over Na$_2$SO$_4$ and concentrated under reduced pressure to furnish the title compound (5.5 g) as a light yellow liquid. $^1$H NMR (300 MHz, CDCl$_3$): 1.45 (s, 9H); 246-2.55 (m, 4H); 2.90-2.91 (m, 1H); 3.95-3.98 (m, 2H); 4.59-4.70 (m, 2H); 5.66-5.77 (m, 2H); 7.34-7.37 (d, J=9 Hz, 2H); 7.77-7.80 (d, J=9 Hz, 2H).

Step 2: Synthesis of tert-butyl (1S,4R)-4-(morpholinomethyl)cyclopent-2-enylcarbamate

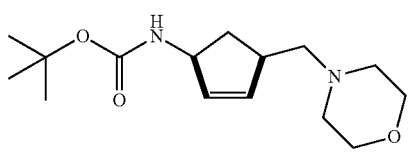

To a stirred solution of ((1R,4S)-4-(tert-butoxycarbonylamino)cyclopent-2-enyl)methyl 4-methylbenzenesulfonate (step 1, about 0.5 g) in DCM (50 ml) potassium carbonate (about 0.3 g) was added at room temperature and cooled to about 0° C. After ten minutes, morpholine (3 ml) was added and stirred the reaction at room temperature for about 6 hours then completion of the reaction monitored by TLC. The reaction mixture was neutralized and extracted with DCM, the organic layer was dried over Na$_2$SO$_4$ and concentrated under reduced pressure to furnish the title compound (0.5 g) as light yellow liquid. $^1$H NMR (300 MHz, CDCl$_3$: 1.24-1.29 (m, 1H); 1.39-1.40 (s, 9H); 2.29-2.60 (m, 7H); 2.79-2.80 (m, 1H); 3.70-3.73 (m, 4H); 4.63 (S, 1H); 5.37-5.39 (d, J=6 Hz, 1H); 5.72-5.81 (m, 2H); ES Mass: 283 (100%), [M+1].

Step 3: Synthesis of (1S,4R)-4-(morpholinomethyl)cyclopent-2-enamine

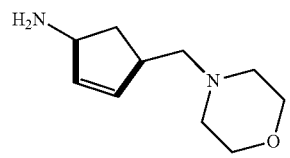

Tert-butyl (1R,3S)(morpholinomethyl)cyclopentylcarbamate (step 2) was treated with trifluoroacetic acid and the obtained compound of (1S,4R)-4-(morpholinomethyl)cyclopent-2-enamine was used directly for synthesizing the final compounds in the example section without further purification.

Intermediate 18

Synthesis of (1R,3S)-3-((4-benzylpiperidin-1-yloxy)methyl)cyclopentanamine

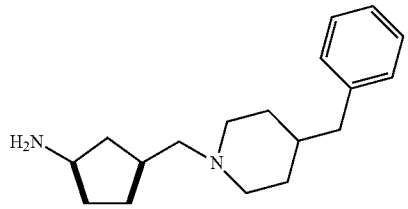

Step 1: Synthesis of ((1S,3R)-3-(tert-butoxycarbonylamino)cyclopentyl)methyl 4-methylbenzenesulfonate

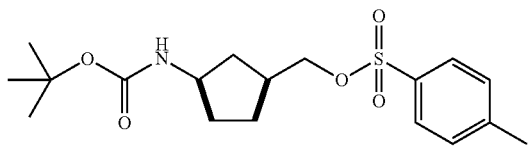

To a stirred solution of N-((1R,3S)-3-(hydroxymethyl)cyclopentyl)-3,3-dimethylbutanamide (Intermediate 16-step 2, 4.5 g, 21.12. mmol) in DCM (50 ml) triethyl amine (about 9.5 ml, 68.1 mmol) was added at room temperature and cooled to about 0° C. After ten minutes, 4-methylbenzene-1-sulfonyl chloride (about 6.0 g) was added and stirred the reaction at room temperature for about 6 hours and completion of the reaction was monitored by TLC. Reaction mixture was neutralized with saturated NaHCO$_3$ and extracted with DCM, the organic layer was dried over Na$_2$SO$_4$ and concentrated under reduced pressure to furnish the title compound (5.5 g) as a light yellow liquid. $^1$H NMR (300 MHz, CDCl$_3$): 1.45 (s, 9H); 2.46-2.55 (m, 4H); 2.90-2.91 (m, 1H); 3.95-3.98 (m, 2H); 4.59-4.70 (m, 2H); 5.66-5.77 (m, 2H); 7.34-7.37 (d, J=9 Hz, 2H); 7.77-7.80 (d, J=9 Hz, 2H).

Step 2: Synthesis of tert-butyl (1R,3S)-3-((4-benzylpiperidin-1-yl)methyl)cyclopentylcarbamate

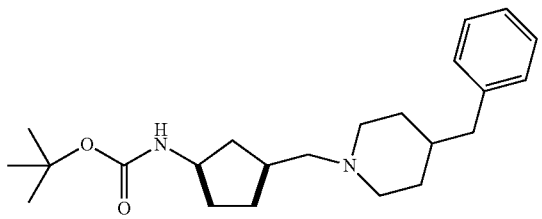

To a stirred solution of ((1R,4S)-4-(tert-butoxycarbonylamino)cyclopent-2-enyl)methyl 4-methylbenzenesulfonate (step 1, about 0.5 g) in DCM (50 ml), potassium carbonate (about 0.3 g) was added at room temperature and cooled to about 0° C. After ten minutes, 4-benzylpiperidine (0.17 g) was added and stirred the reaction at room temperature for about 6 hours. Completion of the reaction was monitored by TLC. The reaction mixture was neutralized and extracted with DCM, the organic layer was dried over $Na_2SO_4$ and concentrated under reduced pressure to furnish the title compound (0.45 g) as light yellow liquid. $^1$H NMR (300 MHz, $CDCl_3$: 1.24-1.29 (m, 1H); 1.39-1.40 (s, 9H); 2.29-2.60 (m, 7H); 2.79-2.80 (m, 1H); 3.70-3.73 (m, 4H); 4.63 (S, 1H); 5.37-5.39 (d, J=6 Hz, 1H); 5.72-5.81 (m, 2H).

Step 3: Synthesis of (1R,3S)-3-((4-benzylpiperidin-1-yloxy)methyl)cyclopentanamine

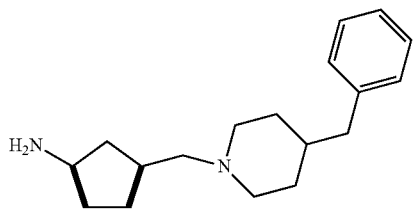

N-((1R,3S)-3-((4-benzylpiperidin-1-yloxy)methyl)cyclopentyl)-3,3-dimethylbutanamide (step 2, 0.5 g) was treated with trifluoroacetic acid (3 ml) and the obtained compound of (1R,3S)-3-((4-benzylpiperidin-1-yloxy)methyl)cyclopentanamine (0.25 g) was used directly for synthesizing final compounds in the example section without further purification.

Intermediate 19

Synthesis of (1R,3S)-3-((4-ethylpiperazin-1-yl)methyl)cyclopentanamine

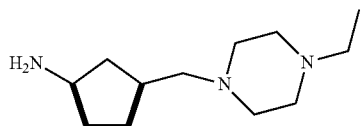

Step 1: Synthesis of tert-butyl (1R,3S)-3-((4-ethylpiperazin-1-yl)methyl)cyclopentylcarbamate

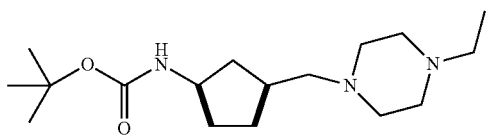

To a stirred solution of ((1S,3R)-3-(tert-butoxycarbonylamino)cyclopentyl)methyl 4-methylbenzenesulfonate (Intermediate 18-step 2, about 0.5 g) in DCM (50 ml) potassium carbonate (about 0.3 g) was added at room temperature and cooled to about 0° C. After ten minutes, 1-ethyl piperazine (0.23 g) was added and stirred the reaction at room temperature for about 6 hours then completion of the reaction monitored by TLC. The reaction mixture was neutralized and extracted with DCM, the organic layer was dried over $Na_2SO_4$ and concentrated under reduced pressure to furnish the title compound (0.3 g) as a pale yellow solid. $^1$H NMR (300 MHz, $CDCl_3$: 1.09-1.24 (m, 3H); 1.39 (s, 9H); 2.29-2.60 (m, 4H); 2.79-2.80 (m, 10H); 3.06-3.18 (m, 6H); 3.70-3.73 (m, 1H); ES Mass: 312 (100%) [M+1].

Step 2: Synthesis of (1R,3S)-3-((4-ethylpiperazin-1-yl)methyl)cyclopentanamine N-((1R,3S)-3-((4-ethylpiperazin-1-yl)methyl)cyclopentyl)-3,3-dimethylbutanamide (step 1, 0.5 g) was treated with trifluoroacetic acid and the obtained compound of (1R,3S)-3-((4-ethylpiperazin-1-yl)methyl)cyclopentanamine was used directly for synthesizing final compounds in example section without further purification.

Intermediate 20

Synthesis of (1R,3S)-3-((3-methylpiperidin-1-yl)methyl)cyclopentanamine

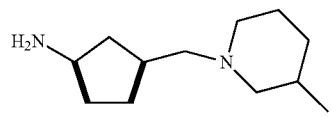

Step 1: Synthesis of tert-butyl (1R,3S)-3-((3-methylpiperidin-1-yl)methyl)cyclopentylcarbamate

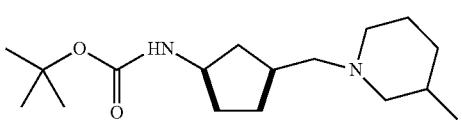

To a stirred solution of ((1S,3R)-3-(tert-butoxycarbonylamino)cyclopentyl)methyl 4-methylbenzenesulfonate (Intermediate 18-step 2, about 0.5 g) in DCM (50 ml) potassium carbonate (about 0.3 g) was added at room temperature and cooled to about 0° C. After ten minutes, 3-methylpiperidine (0.21 g) was added and stirred the reaction at room temperature for about 6 hours and completion of the reaction was monitored by TLC. The reaction mixture was neutralized and extracted with DCM, the organic layer was dried over Na₂SO₄ and concentrated under reduced pressure to furnish the title compound (0.29 g) as a pale yellow solid. ¹H NMR (300 MHz, CDCl₃: 1.08-1.09 (m, 3H); 1.24-1.29 (m, 1H); 1.39-1.40 (s, 9H); 2.29-2.60 (m, 6H); 2.79-2.80 (m, 8H); 3.70-3.73 (m, 4H); ES Mass: 297 (100%), [M+1].

Step 2: Synthesis of (1R,3S)-3-((3-methylpiperidin-1-yl)methyl)cyclopentanamine

Tert-butyl (1R,3S)-3-((3-methylpiperidin-1-yl)methyl)cyclopentylcarbamate (step 1, 0.2 g) was treated with trifluoroacetic acid and the obtained compound of (1R,3S)-3-((3-methylpiperidin-1-yl)methyl)cyclopentanamine was used directly for synthesizing the final compounds in the example section without further purification.

Intermediate 21

Synthesis of ethyl 4-ethylpiperidine-4-carboxylate

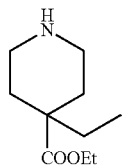

Step 1: Synthesis of 1-tert-butyl 4-ethyl piperidine-1,4-dicarboxylate

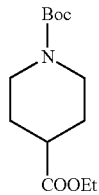

To a stirred solution of ethyl piperidine-4-carboxylate (10.0 g, 63.69 mmol) in 50 ml THF sodium bicarbonate (8.0 g, 95.5 mmol) was added at room temperature and cooled to 0° C. After ten minutes, di-tert-butyl dicarbonate (15.27 g, 70.05 mmol) was added and stirred the reaction at room temperature for 14 hours. After completion of the reaction (monitored by TLC), the reaction mixture was diluted with water and extracted with DCM, the organic layer was dried over Na₂SO₄ and concentrated under reduced pressure to furnish the title compound (11.4 g) as a light yellow liquid. ¹H NMR (300 MHz, CDCl₃): 1.23-1.28 (t, 3H); 1.45 (s, 9H); 1.60-1.68 (m, 3H); 1.85-1.90 (d, J=15 Htz, 2H); 2.41-2.46 (m, 1H); 2.83-2.87 (m, 2H); 4.04-4.17 (m, 3H); ES Mass: 258 (100%), [M+1].

Step 2: Synthesis of 1-tert-butyl 4-ethyl 4-benzylpiperidine-1,4-dicarboxylate

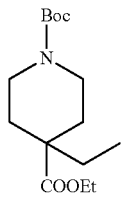

Diisopropyl ethylamine (6.5 ml) in dry THF (25 ml) was cooled to −10° C. then N-butyl lithium (1.6 molar, 23 ml) was added drop wise under nitrogen atmosphere and maintain the reaction at −10° C. for 45 minutes then cool the reaction to −75° C. for 15 minutes then 1-tert-butyl 4-ethyl piperidine-1,4-dicarboxylate (Above step 1, 5 g in 30 ml THF) was added and stirred the reaction at same temp for 30 minutes, again raise the reaction temperature to −35° C. and stirred for 45 minutes then again cool the reaction to −75° C. then ethyl iodide (3.5 g in 20 ml THF) was added drop wise and slowly allowed the reaction to room temperature and stirred the reaction at room temperature for about 12 hours. After completion of the reaction (monitored by TLC), the reaction mixture was quenched with saturated ammonium chloride and extracted with ethyl acetate. The organic layer was washed with saturated NaHCO₃ followed by brine and the organic layer dried over Na₂SO₄ and concentrated under reduced pressure. The residue was purified by silica gel column chromatography using 3% ethyl acetate in hexane as eluent to furnish the title compound as a light yellow color liquid. ¹H NMR (300 MHz, CDCl₃): 1.16-1.18 (t, 3H); 1.44 (s, 9H); 2.07-2.11 (m, 2H); 2.28 (s, 1H); 2.82 (s, 2H); 2.92-2.95 (m, 1H); 3.46-3.52 (m, 3H); 4.09-4.11 (m, 2H); ES Mass: 308 (100%) [M+Na].

Step 3: Synthesis of ethyl 4-ethylpiperidine-4-carboxylate

To a stirred solution of 1-tert-butyl 4-ethyl 4-ethylpiperidine-1,4-dicarboxylate (above step 2, 4.5 g, 12.96 mmol) in 50 ml DCM was cooled to 0° C. After ten minutes trifluoro acetic acid (6.0 g) was added and stirred the reaction at room temperature for about 6 hours. Upon completion of the reaction (monitored by TLC), the reaction mixture was neutralized with saturated NaHCO₃ and extracted with DCM, the organic layer was dried over Na₂SO₄ and concentrated under reduced pressure to furnish the title compound (2.3 g) as a light yellow liquid. ¹H NMR (300 MHz, CDCl₃): 1.19-1.24 (t, 3H); 1.48-1.58 (m, 2H); 2.14-2.18 (m, 2H); 2.64-2.73 (m, 2H); 2.86 (s, 2H); 3.01-3.07 (m, 4H); 4.10-4.17 (m, 2H); 7.07-7.10 (m, 2H); 7.24-7.30 (m, 3H); ES Mass: 186 (100%), [M+1].

Intermediate 22

Synthesis of 4-ethylpiperidine-4-carboxylic acid

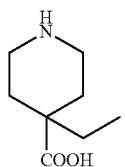

Step 1: Synthesis of 1-(tert-butoxycarbonyl)-4-ethylpiperidine-4-carboxylic acid

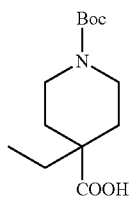

To a stirred solution of 1-tert-butyl 4-ethyl 4-ethylpiperidine-1,4-dicarboxylate (Intermediate 21-step 2, 10.0 g, 63.69. mmol) in 50 ml ethanol was added potassium hydroxide (8.0 g, 95.5 mmol) and the contents were refluxed for 16 hours. Upon completion of the reaction (monitored by TLC), the reaction mixture was diluted with water, acidified with 5% HCl and extracted with DCM. The organic layer was dried over $Na_2SO_4$ and concentrated under reduced pressure to furnish the title compound (8.2 g) as a light yellow liquid. $^1$H NMR (300 MHz, $CDCl_3$): 1.44 (s, 9H); 2.07-2.11 (m, 2H); 2.28 (s, 1H); 2.82 (s, 2H); 2.92-2.95 (m, 1H); 3.46-3.52 (m, 3H); ES Mass: 280 (100%), [M+Na].

Step 2: Synthesis of 4-ethylpiperidine-4-carboxylic acid

To a stirred solution of 1-(tert-butoxycarbonyl)-4-ethylpiperidine-4-carboxylic acid (above step 1, 4.5 g, 12.96 mmol) in DCM (50 ml) was cooled to 0° C. After ten minutes, trifluoro acetic acid (6.0 g) was added and stirred the reaction at room temperature for about 6 hours. Upon completion of the reaction (monitored by TLC), the reaction mixture was neutralized with saturated $NaHCO_3$ and extracted with DCM. The organic layer was dried over $Na_2SO_4$ and concentrated under reduced pressure to furnish the title compound (2.3 g) as a light yellow liquid. $^1$H NMR (300 MHz, $CDCl_3$): 1.48-1.58 (m, 2H); 2.14-2.18 (m, 2H); 2.64-2.73 (m, 2H); 2.86 (s, 2H); 3.01-3.07 (m, 4H); ES Mass: 158 (100%), [M+1].

Intermediate 23

Synthesis of ((1R,3S)-3-amino-2,2-dimethylcyclobutyl)(4-ethylpiperazin-1-yl)methanone

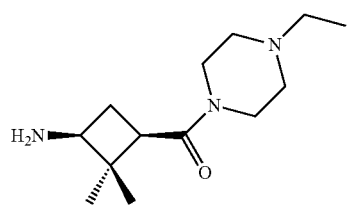

Step-1: Synthesis of benzyl (1S,3R)-3-(4-ethylpiperazine-1-carbonyl)-2,2-dimethylcyclobutylcarbamate

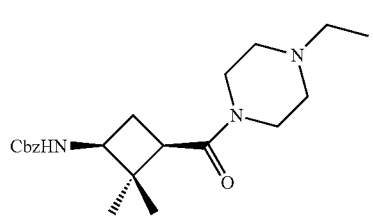

To a stirred solution of (1R,3S)-3-(benzyloxycarbonylamino)-2,2-dimethylcyclobutanecarboxylic acid (1.0 g) in DCM (30 ml) at 0° C. EDCI (800 mg) and HOBt (700 mg) were added, after 10 minutes N-Ethylpiperazine (800 mg) and $Et_3N$ (3 ml) were added drop wise and the reaction mass was allowed to stir at room temperature for 8 hours. After completion of the reaction (monitored by TLC), the reaction mixture was diluted with DCM and washed with water, saturated $NaHCO_3$ solution, water, 1N HCl, water and saturated brine. The organic layer was concentrated under reduced pressure then the resulting crude was purified by silica gel column (100-200 mesh, elution 90% EtOAC in hexane) to afford the title compound as a syrup. Wt: 780 mg; Yield: 57.9%. $^1$H NMR and Mass complies with the required product.

Step 2: Synthesis of ((1R,3S)-3-amino-2,2-dimethylcyclobutyl)(4-ethylpiperazin-1-yl)methanone To a stirred solution of benzyl (1S,3R)-3-(4-ethylpiperazine-1-carbonyl)-2,2-dimethylcyclobutylcarbamate (above step 1, 780 mg) in EtOAc (20 ml) 10% Pd/C (catalytic amount) was added at room temperature and the reaction mixture was stirred under $H_2$ gas atmosphere for 12 hours. After completion of the reaction (monitored by TLC), the reaction mixture was filtered through a celite bed and the obtained filtrate concentrated under reduced pressure to afford the title compound as a liquid which was proceeded as such for next reaction without characterization. Yield has been calculated as 100%.

Intermediate 24

Synthesis of ((1S,3R)-3-amino-2,2-dimethylcyclobutyl)(4-ethylpiperazin-1-yl)methanone, trifluoro acetic acid

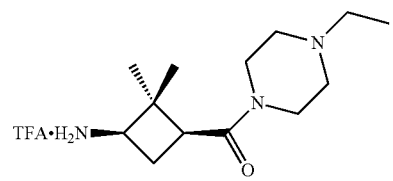

Step 1: Synthesis of tert-butyl (1R,3S)-3-(4-ethylpiperazine-1-carbonyl)-2,2-dimethylcyclobutylcarbamate

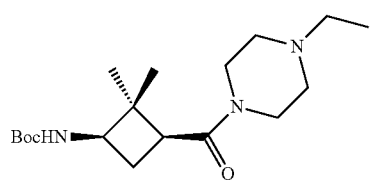

To a stirred solution of (1S,3R)-3-(tert-butoxycarbonylamino)-2,2-dimethylcyclobutanecarboxylic acid (2 g, 8.23 mmol) in DCM (50 ml) EDCI (946 mg, 9.876 mmol) and HOBt (756 mg, 9.876 mmol) were added at 0° C., after 10 minutes N-Ethyl piperazine (939 mg, 16.46 mmol) and $Et_3N$ (3 mL, 41.15 mmol) were added drop wise and the reaction mass was allowed to stir at room temperature for 12 hours. After completion of the reaction (monitored by TLC), the reaction mixture was diluted with DCM and washed with water, saturated $NaHCO_3$ solution, water, 1N HCl, water and saturated brine and the organic layer was concentrated under reduced pressure. The resulting crude residue was stirred in hexane and obtained solid was filtered. Wt: 1.6 g; Yield: 70%. ¹H NMR (300 MHz, CDCl₃): δ 4.77 (d, 1H, J=8.4 Hz), 3.89-3.78 (m, 1H), 3.6-3.46 (m, 3H), 2.80 (m, 1H), 2.60-2.40 (m, 8H), 1.80 (m, 1H), 1.43 (s, 9H), 1.12 (s, 3H), 1.2 (t, 3H), 0.87 (s, 3H); Mass: [M+1]⁺ 340 (25%), [M+Na]⁺ 362 (100%).

Step-2: Synthesis of ((1S,3R)-3-amino-2,2-dimethylcyclobutyl)(4-ethylpiperazin-1-yl)methanone, trifluoro acetic acid A solution of tert-butyl (1R,3S)-3-(4-ethylpiperazine-1-carbonyl)-2,2-dimethylcyclobutylcarbamate (1.6 g, 4.7 mmol) in TFA:DCM (1:2) (50 mL) stirred at room temperature for 1 hour. After completion of the reaction (monitored by TLC), the solvent was evaporated, the crude dissolved in DCM and basified with Et₃N (20 ml) then the resulting solution as such used for the next reaction.

Intermediate 25

Synthesis of ethyl 1-((1R,3S)-3-amino-2,2-dimethylcyclobutanecarbonyl)piperidine-4-carboxylate

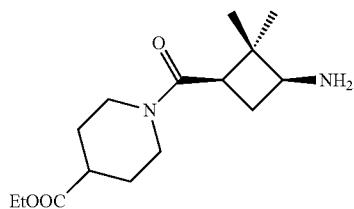

Step 1: Synthesis of ethyl 1-((1R,3S)-3-(benzyloxycarbonylamino)-2,2-dimethylcyclobutanecarbonyl)piperidine-4-carboxylate

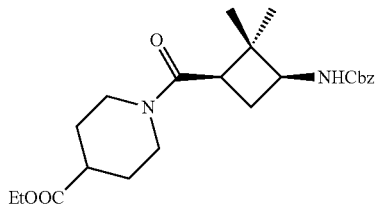

To a stirred solution of (1R,3S)-3-(benzyloxycarbonylamino)-2,2-dimethylcyclobutanecarboxylic acid (1.5 g, 5.415 mmol) in DCM (20 ml) EDCI (1.55 g, 8.122 mmol) and HOBt (1.24 g, 8.122 mmol) were added at 0° C. after 10 minutes, 4-ethylpiperidinecarboxylate (1.0 g, 6.498 mmol) and Et₃N (3.75 ml, 27.075 mmol) were added drop wise and the reaction mass was allowed to stir at room temperature for 12 hours. After completion of the reaction (monitored by TLC), the reaction mixture was diluted with DCM and washed with water, saturated NaHCO₃ solution, water, 1N HCl, water and saturated brine and the organic layer was concentrated under reduced pressure, the resulting crude residue was stirred in hexane, and the obtained solid was filtered and dried under vacuum. Wt: 1.3 g; Yield: 57.7%. ¹H NMR (300 MHz, CDCl₃): δ 7.35 (5H, s), 5.194-5.058 (3H, m), 4.506-4.3 (1H, m), 4.19-4.11 (2H, m), 3.98-3.78 (2H, m), 3.15-3.00 (1H, m), 2.9-2.7 (2H, m), 2.6-2.2 (3H, m), 2.0-1.8 (2H, m), 1.741.5 (2H, m), 1.26 (3H, s), 1.2 (3H, m), 0.85 (3H, s); Mass: [M+1]⁺ 417 (10%), [M+Na]⁺ 439 (100%).

Step 2: Synthesis of ethyl 1-((1R,3S)-3-amino-2,2-dimethylcyclobutanecarbonyl)piperidine-4-carboxylate To a solution of ethyl 1-((1R,3S)-3-(benzyloxycarbonylamino)-2,2-dimethylcyclobutanecarbonyl)piperidine-4-carboxylate (step 1, 1.30 g) in ethyl acetate (50 ml), Pd/C (100 mg) was added carefully under argon atmosphere. Then the reaction mixture was stirred for overnight under hydrogen conditions. After completion of the reaction (monitored by TLC), diluted with ethyl acetate, filtered on celite, washed with ethyl acetate. The combined organic extracts were concentrated under reduced pressure to give crude product which was preceded for next step without further purification and analysis.

EXAMPLES

Example 1

Preparation of (1R,3aS,5aR,5bR,7aR,9S,11aR,11bR,13aR,13bR)-9-acetoxy-5a,5b,8,8,11a-pentamethyl-1-(prop-1-en-2-yl)icosahydro-1H-cyclopenta[a]chrysene-3a-carboxylic acid

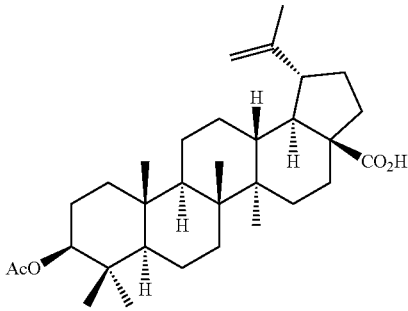

Ac₂O (about 0.93 ml, 9.87 mmol) was added to a stirred solution of (1R,3aS,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysene-3a-carboxylic acid (Betulinic acid, about 0.3 g, 0.657 mmol) and DMAP (about 0.167 g, 1.32 mmol) in pyridine (about 15 ml) at about 0° C. then the reaction mixture was slowly warmed to room temperature and refluxed for about 24 hours. After completion of the reaction (monitored by TLC), the reaction mixture poured in to ice water and extracted with EtOAc and washed with water, brine and dried over Na₂SO₄, the solvent was evaporated and purified by silica gel column (100-200, elution 10% EtOAc in hexane) to afford title compound as a off white solid. Wt: 0.196 g; Yield: 59.8%; ¹H NMR (300 MHZ, CDCl₃): δ 4.74 (s, 1H), 4.61 (s, 1H), 4.50-4.44 (m, 1H), 3.02-2.97 (m, 1H), 3.01-2.12 (m, 2H), 2.04 (s, 3H), 1.99-1.92 (m, 2H), 1.69 (s, 3H), 1.68-1.57 (m, 6H), 1.56-1.32 (m, 10H), 1.31-1.01 (m, 5H), 0.97, 0.93 (2s, 6H), 0.85 (Brs, 9H); Mass: [M−1] 497 (100%); IR (KBr, cm⁻¹): 3296, 2945, 1736, 1694, 1464, 1368, 1247, 1196, 1161, 1024, 980, 884, 777, 543; M.R: 283.7° C.-290.1° C.; HPLC: 97.17%.

Example 2

Preparation of (1S,3R)-benzyl 3-((1R,3aS,5aR,5bR, 7aR,9S,11aR,11bR,13aR,13bR)-9-acetoxy-5a,5b,8, 8,11a-pentamethyl-1-(prop-1-en-2-yl)icosahydro-1H-cyclopenta[a]chrysene-3a-carboxamido)-2,2-dimethylcyclobutanecarboxylate

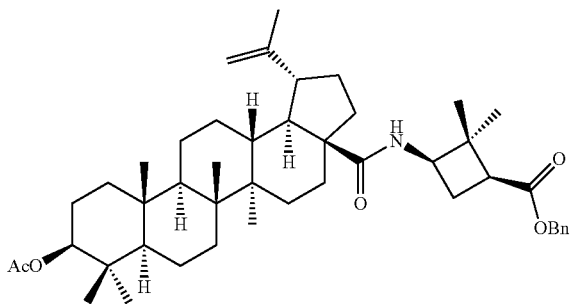

2M solution of (COCl)₂ in DCM was added to (1R,3aS, 5aR,5bR,7aR,9S,11aR,11bR,13aR,13bR)-9-acetoxy-5a,5b, 8,8,11a-pentamethyl-1-(prop-1-en-2-yl)icosahydro-1H-cyclopenta[a]chrysene-3a-carboxylic acid (Example 1, about 0.150 g, 0.301 mmol) at about 0° C. and the reaction mixture was stirred at about 15-20° C. for about 2 hours. After completion of the reaction (monitored by TLC), the solvent was evaporated under nitrogen atmosphere and dissolved in DCM (3 ml). To this solution, solution of Intermediate 7 (about 0.140 g, 0.602 mmol) in DCM and Et₃N (about 0.2 ml, 0.904 mmol) were added slowly at about −5° C. and allowed to stir at room temperature for 16 hours. After completion of the reaction (monitored by TLC), the reaction mixture was diluted with DCM and washed with water, brine and dried over Na₂SO₄, the solvent was evaporated and purified by silica gel column (100-200 mesh, elution 10% EtOAc in hexane) to afford the title compound as an off white solid. Wt: 0.110 g; Yield: 51.4%; ¹H NMR (300 MHZ, CDCl₃): δ 7.38-7.32 (m, 5H), 5.65 (d, 1H, J=10.5 Hz), 5.13 (dd, 2H, J=12.3, 19.2 Hz), 4.72 (s, 1H), 4.58 (s, 1H), 4.51-4.42 (m, 1H), 4.12 (q, 1H, J=9.0 Hz), 3.16-3.13 (m, 1H), 2.72-2.68 (m, 1H), 2.52-2.41 (m, 1H), 2.38-2.29 (m, 1H), 2.04 (s, 3H), 1.95-1.88 (m, 2H), 1.77-1.48 (m, 14H), 1.46-1.32 (m, 7H), 1.31 (s, 3H), 1.29-1.22 (m, 3H), 1.18-1.13 (m, 1H), 0.95 (s, 3H), 0.92 (s, 3H), 0.85-0.82 (m, 12H); Mass: [M+1]⁺ 714 (100%); IR (KBr, cm⁻¹): 3406, 2950, 1734, 1664, 1456, 1369, 1247, 1172, 1079, 1023, 979, 884, 750, 698; M.R: 113.3° C.-119.8° C.; HPLC: 93.86%.

Example 3

Preparation of (1R,3aS,5aR,5bR,7aR,9S,11aR,11bR, 13aR,13bR)-9-((1R,3S)-3-(tert-butoxycarbonyl)-2,2-dimethylcyclobutanecarbonyloxy)-5a,5b,8,8,11a-pentamethyl-1-(prop-1-en-2-yl)icosahydro-1H-cyclopenta[a]chrysene-3a-carboxylic acid

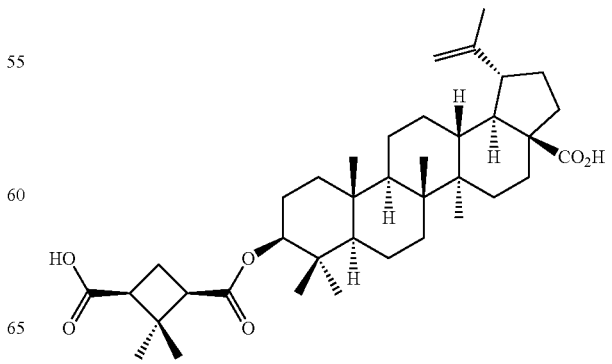

To a stirred solution of (1R,3aS,5aR,5bR,7aR,9S,11aR, 11bR,13aR,13bR)-9-hydroxy-5a,5b,8,8,11a-pentamethyl-1-(prop-1-en-2-yl)icosahydro-1H-cyclopenta[a]chrysene-3a-carboxylic acid (Betulinic acid, about 0.1 g, 0.22 mmol) in THF:Toluene (about 6 ml) (1R,3S)-3-(tert-butoxycarbonyl)-2,2-dimethylcyclobutanecarboxylic 2,4,6-trichlorobenzoic anhydride (Intermediate 10, about 0.955 g, 2.20 mmol) and DMAP (0.054 g, 0.44 mmol) were added and refluxed for about 12 hours and the solvent was evaporated then dry Pyridine (about 6 ml) was added and refluxed for about 16 hours. After completion of the reaction (monitored by TLC), the reaction mixture was diluted with DCM and washed with water, dried over Na₂SO₄ and concentrated under reduced pressure. The resulting crude was purified Silica gel column chromatography (100-200 Mesh, Elution: 5% EtOAc in Hexane) to afford the title compound as a white solid. Wt: 0.050 g; Yield: 34.2%; ¹H NMR (300 MHZ, CD₃OD): δ 4.74 (s, 1H), 4.61 (s, 1H), 4.47-4.43 (m, 1H), 3.03-2.97 (m, 1H), 2.77-2.64 (m, 2H), 2.58-2.54 (m, 1H), 2.29-2.24 (m, 2H), 2.03-1.94 (m, 3H), 1.69 (s, 5H), 1.64-1.50 (m, 9H), 1.44 (s, 12H), 1.38-1.21 (m, 8H), 1.00 (s, 3H), 0.97 (s, 3H), 0.93 (s, 3H), 0.84, 0.83 (2s, 9H), 0.80-0.77 (m, 1H); Mass: [M+Na]⁺ 689 (100%); IR (KBr, cm⁻¹): 2937, 2344, 1733, 1698, 1464, 1376, 1237, 1153, 1107, 982, 882; M. Range: 222.7-223.6° C.; HPLC: 95.04% % at RT 17.45 minutes.

Example 4

Preparation of (1R,3aS,5aR,5bR,7aR,9S,11aR,11bR, 13aR,13bR)-9-((1R,3S)-3-carboxy-2,2-dimethylcyclobutanecarbonyloxy)-5a,5b,8,8,11a-pentamethyl-1-(prop-1-en-2-yl)icosahydro-1H-cyclopenta[a]chrysene-3a-carboxylic acid To a stirred solution of (1R,3aS,5aR,5bR,7aR,9S,11aR, 11bR,13aR,13bR)-9-((1R,3S)-3-(tert-butoxycarbonyl)-2,2-dimethylcyclobutanecarbonyloxy)-5a,5b,8,8,11a-pentamethyl-1-(prop-1-en-2-yl)icosahydro-1H-cyclopenta[a]chrysene-3a-carboxylic acid (Example 3, about 0.160 g, 0.239 mmol) in 2M HCl in Dioxane (10 ml) was stirred at room temperature for about 12 hours. After completion of the reaction (monitored by TLC), the reaction mixture was diluted with EtOAc and washed with water, the organic layer dried over $Na_2SO_4$ and concentrated under reduced pressure. The resulting crude was purified by Silica gel column chromatography (100-200 Mesh, Elution: 20% EtOAc in Hexane) to afford the title compound as a white solid. Wt: 0.086 g; Yield: 59.0%; $^1$H NMR (300 MHZ, $CDCl_3$): δ 4.74 (s, 1H), 4.61 (s, 1H), 4.47-4.43 (m, 1H), 3.03-2.97 (m, 1H), 2.87-2.74 (m, 2H), 2.63-2.51 (m, 1H), 2.31-2.24 (m, 2H), 2.19-1.90 (m, 3H), 1.69 (s, 3H), 1.78-1.68 (m, 5H), 1.52-1.41 (m, 12H), 1.29-1.02 (m, 9H), 0.97 (s, 3H), 0.93 (s, 3H), 0.85 (s, 9H); Mass: $[M+Na]^+$ 633 (100%); IR (KBr, $cm^{-1}$): 3427, 2951, 1730, 1706, 1698, 1456, 1376, 1242, 1190, 1107, 1020, 885; M. Range: 282.5-289.3° C.; HPLC: 92.2% % at RT 8.76 minutes.

Example 5

Preparation of (1S,3R)-3-((1R,3aS,5aR,5bR,7aR,9S, 11aR,11bR,13aR,13bR)-9-hydroxy-5a,5b,8,8,11a-pentamethyl-1-(prop-1-en-2-yl)icosahydro-1H-cyclopenta[a]chrysene-3a-carboxamido)-2,2-dimethylcyclobutanecarboxylic acid

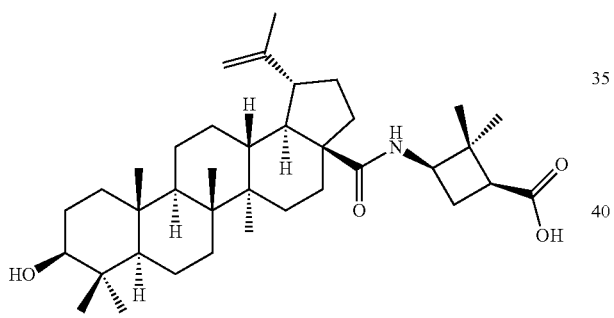

To a solution of (1S,3R)-benzyl 3-((1R,3aS,5aR,5bR,7aR, 9S,11aR,11bR,13aR,13bR)-9-acetoxy-5a,5b,8,8,11a-pentamethyl-1-(prop-1-en-2-yl)icosahydro-1H-cyclopenta[a]chrysene-3a-carboxamido)-2,2-dimethylcyclobutanecarboxylate (Example 2, about 0.140 g, 0.196 mmol) in MeOH:THF (2:1) (6 ml) at 0° C., 2N NaOH (2 ml) was added and allowed to stir at room temperature for about 6 hours. After completion of the reaction (monitored by TLC), the solvent was evaporated and acidified with 2N HCl, the aqueous layer was extracted with ethyl acetate and dried with $Na_2SO_4$. The solvent was evaporated and purified by silica gel column (100-200 mesh, elution 50% EtOAc in hexane) to afford the title compound as an off white solid. Wt: 0.105 g; Yield: 92%. $^1$H NMR (300 MHZ, $CDCl_3$): δ 5.64 (d, 1H, J=7.8 Hz), 4.72 (s, 1H), 4.58 (s, 1H), 4.15 (q, 1H, J=9.3 Hz), 3.18 (dd, 1H, J=5.1, 10.8 Hz), 3.14-3.08 (m, 1H), 2.71-2.64 (m, 1H), 2.52-2.41 (m, 1H), 2.40-2.28 (m, 1H), 2.10-1.88 (m, 4H), 1.78-1.64 (m, 9H), 1.62-1.51 (m, 3H), 1.49-1.41 (m, 4H), 1.39-1.32 (m, 7H), 1.28-1.22 (m, 4H), 0.98 (s, 3H), 0.97 (s, 3H), 0.96 (s, 3H), 0.93 (s, 3H), 0.81 (s, 3H), 0.75 (s, 3H); Mass: $[M+1]^+$ 582 (10%), $[M+Na]^+$ 604 (100%); IR (KBr, $cm^{-1}$): 3454, 3407, 2949, 2869, 1716, 1709, 1642, 1459, 1243, 1191, 1009, 885, 787; M.R: 174.6° C.-187.0° C.; HPLC: 90.33%.

Example 6

Preparation of (1R,2S,3aR,5aR,5bR,7aS,10R,12aR, 12bR)-2-(3-carboxy-3-methylbutanoyloxy)-3,3,5a, 5b,12b-pentamethyl-10-(prop-1-en-2-yl)icosahydrodicyclopenta[a,i]phenanthrene-1,7a-dicarboxylic acid

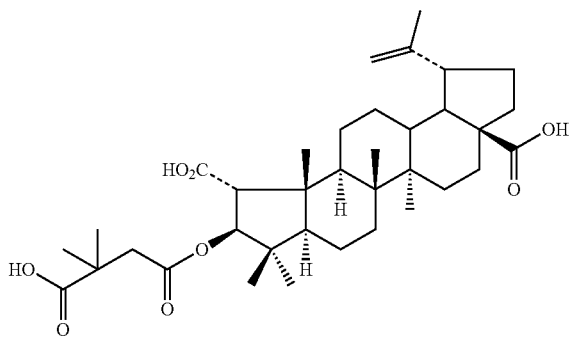

To a stirred solution of ceanotheic acid (about 0.22 mmol) in dry Pyridine (about 6 ml) dimethylsuccinic anhydride (about 3.30 mmol) and DMAP (0.44 mmol) were added and contents were refluxed for about 16 hours. After completion of the reaction (monitored by TLC), the reaction mixture was diluted with DCM and washed with water, the organic layer dried with $Na_2SO_4$ and concentrated under reduced pressure. The resulting crude was purified by Silica gel column chromatography (100-200 Mesh, Elution: 5% EtOAc in Hexane) to afford the title compound as a white solid. Wt: 0.050 g: Yield: 34.2%. $^1$H NMR (300 MHZ, $CDCl_3$): δ 5.08 (s, 1H), 4.62 (s, 1H), 4.48 (s, 1H), 2.92-2.87 (m, 1H), 0.9-1.9 (m, 44H); $[M+Na]^+$ 637.40 (100%).

Example 7

Preparation of (1R,3aS,5aR,5bR,7aR,9S,11aR,11bR, 13aR,13bR)-3a-((1S,3R)-2,2-dimethyl-3-(morpholine-4-carbonyl)cyclobutylcarbamoyl)-5a,5b,8,8,11a-pentamethyl-1-(prop-1-en-2-yl)icosahydro-1H-cyclopenta[a]chrysen-9-yl acetate

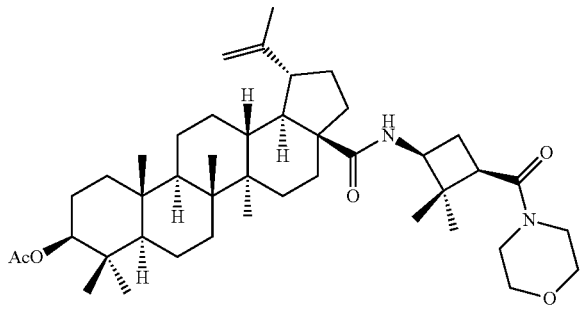

To a (1R,3aS,5aR,5bR,7aR,9S,11aR,11bR,13aR,13bR)-9-acetoxy-5a,5b,8,8,11a-pentamethyl-1-(prop-1-en-2-yl) icosahydro-1H-cyclopenta[a]chrysene-3a-carboxylic acid (0.4 g, 0.803 mmol) in DCM (1 ml) 2M solution of $(COCl)_2$ in DCM (4 ml, 8.03 mmol) was added at about 0° C. and the reaction mixture was stirred at room temperature for about 3 hours. After completion of the reaction (monitored by TLC) the solvent was evaporated under nitrogen atmosphere and dissolved in DCM (4 ml), which was added to a solution of ((1R,3S)-3-amino-2,2-dimethylcyclobutyl)(morpholino) methanone (Intermediate 11, 0.306 g, 1.45 mmol) in DCM (5 ml) and $Et_3N$ (0.22 ml, 1.61 mmol) at about 0° C. and allowed to stir at room temperature for about 16 hours. After completion of the reaction (monitored by TLC) the reaction mixture was diluted with DCM and washed with water, 1N HCl, water brine and dried with Na₂SO₄, the solvent was evaporated and purified by silica gel column (100-200 mesh, elution 10% EtOAc in hexane) to afford the title compound as an off white solid. Wt: 0.380 g: Yield: 68.4%; $^1$H NMR (300 MHz, CDCl$_3$): δ 5.88 (d, 1H), 4.73 (s, 1H), 4.58 (s, 1H), 4.51-4.42 (m, 1H), 4.17-4.06 (m, 1H), 3.80-3.41 (m, 7H), 3.17-3.08 (m, 1H), 2.93-2.84 (m, 1H), 2.50-2.29 (m, 2H), 2.05 (s, 3H), 1.99-1.86 (m, 3H), 1.80-1.02 (m, 22H), 0.95, 0.92 (s, 9H), 0.83 (s, 15H); Mass: [M+Na]⁺ 693 (100%); M.R: 144.8° C.-156.2° C.

Example 8

Preparation of (1R,3aS,5aR,5bR,7aR,9S,11aR,11bR,13aR,13bR)-N-((1S,3R)-2,2-dimethyl-3-(morpholine-4-carbonyl)cyclobutyl)-9-hydroxy-5a,5b,8,8,11a-pentamethyl-1-(prop-1-en-2-yl)icosahydro-1H-cyclopenta[a]chrysene-3a-carboxamide

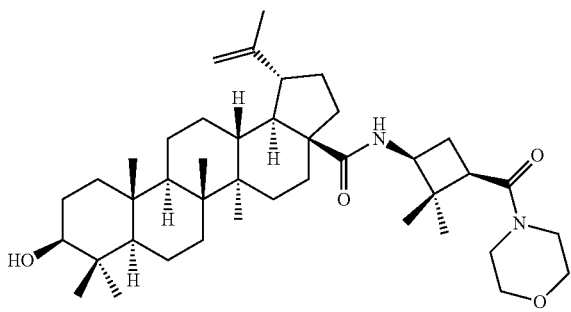

To a solution of (1R,3aS,5aR,5bR,7aR,9S,11aR,11bR,13aR,13bR)-3a-((1S,3R)-2,2-dimethyl-3-(morpholine-4-carbonyl)cyclobutylcarbamoyl)-5a,5b,8,8,11a-pentamethyl-1-(prop-1-en-2-yl)icosahydro-1H-cyclopenta[a]chrysen-9-yl acetate (Example 7, 0.380 g, 0.55 mmol) in MeOH:THF (2:1) (6 ml) NaOH (2N, 2 ml) was added at about 0° C. and allowed to stir at room temperature for about 16 hours. After completion of the reaction (monitored by TLC) the volatiles was evaporated and the aqueous layer was extracted with ethyl acetate and dried with Na₂SO₄. The solvent was evaporated and purified by silica gel column (100-200 mesh, elution 15% EtOAc in hexane) to afford the title compound as an off white solid. Wt: 0.320 g: Yield: 89.6%; $^1$H NMR (300 MHz, CDCl$_3$): δ 5.88 (d, 1H, J=8.1 Hz), 4.73 (s, 1H), 4.58 (s, 1H), 4.18-4.07 (m, 1H), 3.80-3.41 (m, 7H), 3.21-3.08 (m, 2H), 2.91-2.83 (m, 1H), 2.50-2.29 (m, 3H), 1.98-1.87 (m, 2H), 1.80-1.10 (m, 26H), 0.95-0.92 (s, 12H), 0.99-0.68 (s, 9H); Mass: [M+1]⁺ 651 (100%), [M+Na]⁺ 673 (70%); IR (KBr, cm⁻¹): 3367, 2856, 2926, 1714, 1634, 1493, 1463, 1375, 1270, 1241, 1115, 1040, 983, 884, 756, 665; M.R: 262.5° C.-267.8° C.; HPLC: 90.7%.

Example 9

Preparation of 4-((1R,3aS,5aR,5bR,7aR,9S,11aR,11bR,13aR,13bR)-3a-((1S,3R)-2,2-dimethyl-3-(morpholine-4-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid

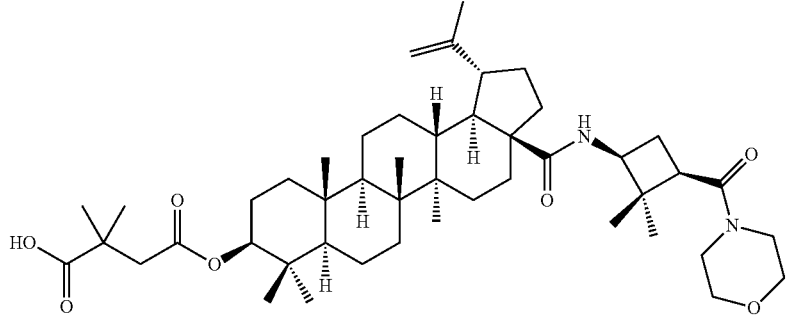

To a stirred solution of (1R,3aS,5aR,5bR,7aR,9S,11aR,11bR,13aR,13bR)-N-((1S,3R)-2,2-dimethyl-3-(morpholine-4-carbonyl)cyclobutyl)-9-hydroxy-5a,5b,8,8,11a-pentamethyl-1-(prop-1-en-2-yl)icosahydro-1H-cyclopenta[a]chrysene-3a-carboxamide (Example 8, 0.250 g, 0.385 mmol) 2,2-Dimethylsuccinic anhydride (0.26 ml, 2.31 mmol) and DMAP (0.094 g, 0.77 mmol) in pyridine (10 ml) were added at room temperature then the reaction mixture was refluxed for about 16 hours. After completion of the reaction (monitored by TLC) the reaction mixture was diluted with EtOAc, the organic layer was washed with water, 1N HCl, water, brine and dried with Na₂SO₄, the solvent was evaporated and purified by silica gel column (100-200, elution 35% EtOAc in hexane) to afford the title compound as a off white solid. Wt: 0.140 g: Yield: 46.8%; $^1$H NMR. (300 MHz, CDCl$_3$): δ 5.95 (d, 1H), 4.73 (s, 1H), 4.58 (s, 1H), 4.52-4.43 (m, 1H), 4.19-4.09 (m, 1H), 3.82-3.40 (m, 8H), 3.17-3.04 (m, 1H), 2.92-1.82 (m, 1H), 2.71-2.29 (m, 6H), 2.00-1.91 (m, 3H), 1.80-1.09 (m, 28H), 1.00-0.77 (m, 21H); Mass: [M+1]⁺ 779 (100%), [M+Na]⁺ 801 (15%); IR (KBr, cm⁻¹): 3419, 2952, 2867, 1757, 1733, 1729, 1638, 1631, 1460, 1452, 1376, 1243, 1180, 1117, 1067, 978, 879, 775; M.R: 248.7° C.-252.6° C.; HPLC: 87.7%

Example 10

Preparation of (1R,3aS,5aR,5bR,7aR,9S,11aR,11bR,13aR,13bR)-3a-((1S,3R)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yl acetate

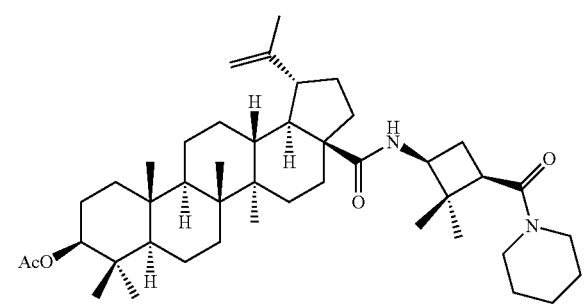

To a stirred solution of (1R,3aS,5aR,5bR,7aR,9S,11aR, 11bR,13aR,13bR)-9-acetoxy-5a,5b,8,8,11a-pentamethyl-1-(prop-1-en-2-yl)icosahydro-1H-cyclopenta[a]chrysene-3a-carboxylic acid (0.4 g, 0.803 mmol) in DCM (1 ml) (COCl)$_2$ (0.69 ml, 8.03 mmol) in DCM (4 ml) was added at about 0° C. and the reaction mixture was stirred at room temperature for about 3 hours. After completion of the reaction (monitored by TLC) the solvent was evaporated under nitrogen atmosphere and dissolved in DCM (4 ml), which was added to a stirred solution of ((1R,3S)-3-amino-2,2-dimethylcyclobutyl)(piperidin-1-yl)methanone (Intermediate 12, 0.306 g, 1.45 mmol) in DCM (5 ml) and Et$_3$N (0.22 ml, 1.61 mmol) at about 0° C. and allowed to stir at room temperature for about 16 hours. After completion of the reaction (monitored by TLC) the reaction mixture was diluted with DCM and washed with water, 1N HCl, water, brine and dried over Na$_2$SO$_4$, the solvent was evaporated and purified by silica gel column (100-200 mesh, elution 10% EtOAc in hexane) to afford the title compound as an off white solid. Wt: 0.380 g: Yield: 68.4%; δ 5.94 (d, 1H, J=7.8 Hz), 4.74 (s, 1H), 4.59 (s, 1H), 4.54-4.41 (m, 1H), 4.17-4.05 (m, 1H), 3.74-3.62 (m, 1H), 3.37 (brs, 2H), 3.18-3.07 (m, 1H), 2.89 (t, 1H, 7.8 Hz), 2.51-2.40 (m, 1H), 2.39-2.28 (m, 2H), 2.04 (s, 3H), 2.01-1.84 (m, 2H), 1.81-1.75 (m, 1H), 1.74-1.45 (m, 7H), 1.44-1.21 (m, 15H), 1.21-1.09 (m, 2H), 0.95, 0.93 (s, 9H), 0.83-0.82 (m, 12H); Mass: [M+Na]$^+$ 714 (100%); IR (KBr, cm$^{-1}$): 3372, 2943, 2864, 1736, 1730, 1652, 1636, 1623, 1501, 1459, 1444, 1369, 1248, 1192, 1024, 979, 881, 853.

1-carbonyl)cyclobutylcarbamoyl)-5a,5b,8,8,11a-pentamethyl-1-(prop-1-en-2-yl)icosahydro-1H-cyclopenta[a]chrysen-9-yl acetate (Example 10, 0.340 g, 0.492 mmol) in MeOH:THF (2:1) (6 ml) NaOH (2N, 2 ml) was added at about 0° C. and allowed to stir at room temperature for about 16 hours. After completion of the reaction (monitored by TLC) the volatiles were evaporated and the aqueous layer was extracted with ethyl acetate and the organic layer was washed with water, brine and dried with Na$_2$SO$_4$. The solvent was evaporated and purified by silica gel column (100-200 mesh, elution 15% EtOAc in hexane) to afford the title compound as an off white solid. Wt: 0.190 g: Yield: 59%; $^1$H NMR (300 MHz, CDCl$_3$): δ 5.94 (d, 1H, J=7.8 Hz), 4.73 (s, 1H), 4.58 (s, 1H), 4.17-4.13 (m, 1H), 3.73-3.59 (m, 1H), 3.54-3.41 (m, 1H), 3.40-3.30 (m, 2H), 3.22-3.04 (m, 2H), 2.93-2.83 (m, 1H), 2.52-2.23 (m, 3H), 2.00-1.82 (m, 2H), 1.79-1.42 (m, 15H), 1.41-1.11 (m, 17H), 0.96, 0.93 (s, 10H), 0.82, 0.80 (s, 6H), 0.75 (s, 3H). 0.71-0.62 (m, 1H); Mass: [M+1]$^+$ 649 (100%), [M+Na]$^+$ 671 (60%); IR (KBr, cm$^{-1}$): 3450, 2937, 2862, 2587, 2126, 1622, 1459, 1373, 1251, 1192, 1049, 1024, 882, 853; M.R: 110.0° C.-116.3° C.; HPLC: 97.2%.

Example 12

Preparation of 4-((1R,3aS,5aR,5bR,7aR,9S,11aR, 11bR,13aR,13bR)-3a-((1S,3R)-2,2-dimethyl-3-(piperidine-1-carbonyl)cyclobutylcarbamoyl)-5a,5b,8,8, 11a-pentamethyl-1-(prop-1-en-2-yl)icosahydro-1H-cyclopenta[a]chrysen-9-yloxy)-2,2-dimethyl-4-oxobutanoic acid

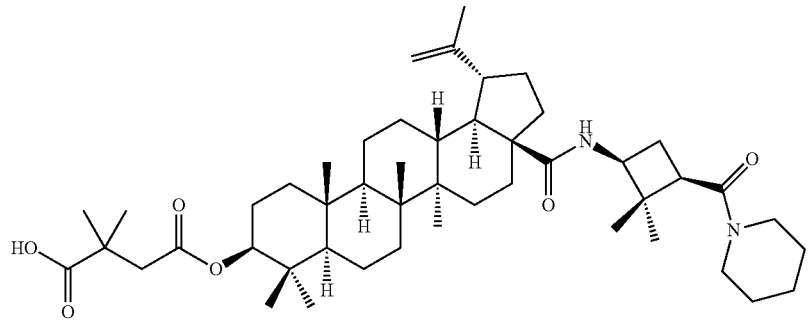

Example 11

Preparation of (1R,3aS,5aR,5bR,7aR,9S,11aR,11bR, 13aR,13bR)-N-((1S,3R)-2,2-dimethyl-3-(piperidine-1-carbonyl)cyclobutyl)-9-hydroxy-5a,5b,8,8,11a-pentamethyl-1-(prop-1-en-2-yl)icosahydro-1H-cyclopenta[a]chrysene-3a-carboxamide

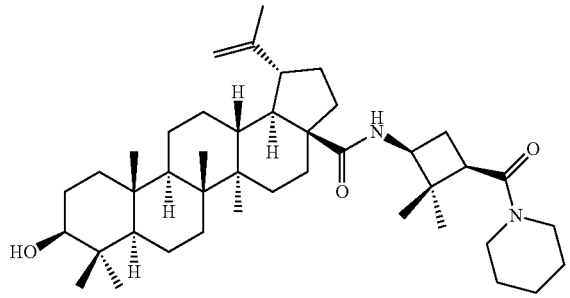

To a stirred solution of (1R,3aS,5aR,5bR,7aR,9S,11aR, 11bR,13aR,13bR)-3a-((1S,3R)-2,2-dimethyl-3-(piperidine- To a stirred solution of (1R,3aS,5aR,5bR,7aR,9S,11aR, 11bR,13aR,13bR)-N-((1S,3R)-2,2-dimethyl-3-(piperidine-1-carbonyl)cyclobutyl)-9-hydroxy-5a,5b,8,8,11a-pentamethyl-1-(prop-1-en-2-yl)icosahydro-1H-cyclopenta[a]chrysene-3a-carboxamide (Example 11, 0.110 g, 1.697 mmol) 2,2-Dimethylsuccinic anhydride (0.2 ml, 1.697 mmol) and DMAP (0.044 g, 0.338 mmol) in pyridine (5 ml) were added at room temperature then the reaction mixture was refluxed for about 16 hours. After completion of the reaction (monitored by TLC), the reaction mixture was diluted with EtOAc, washed with water, 1N HCl, water, brine and dried with Na$_2$SO$_4$, the solvent was evaporated and purified by silica gel column (100-200 mesh, elution 15% EtOAc in hexane) to afford the title compound as an off white solid. Wt: 0.080 g: Yield: 61%; $^1$H NMR (300 MHz, CDCl$_3$): δ 6.01 (d, 1H, J=8.4 Hz), 4.72 (s, 1H), 4.58 (s, 1H), 4.53-4.43 (m, 1H), 4.16-4.08 (m, 1H), 3.71-3.62 (m, 2H), 3.54-3.35 (m, 3H), 3.18-3.06 (m, 1H), 2.93-2.87 (m, 1H), 2.66 (d, 1H, J=15.9 Hz), 2.56 (d, 1H, J=15.9 Hz), 2.50-2.27 (m, 2H), 1.99-1.88 (m, 2H), 1.80-1.00 (m, 46H), 0.94, 0.92, 0.83 (s, 12H); Mass: [M+1]$^+$ 777 (100%), [M+Na]$^+$ 799 (80%); IR (KBr, cm$^{-1}$): 3411, 2944, 2867, 1733, 1730, 1625, 1467, 1445, 1368, 1253, 1220, 1192, 1022, 977, 884, 767; M.R: 139.5° C.-141.5° C.; HPLC: 96.7%.

Example 13

Preparation of (1R,3aS,5aR,5bR,7aR,9S,11aR,11bR, 13aR,13bR)-3a-((1S,3R)-2,2-dimethyl-3-(pyrrolidine-1-carbonyl)cyclobutylcarbamoyl)-5a,5b,8,8, 11a-pentamethyl-1-(prop-1-en-2-yl)icosahydro-1H-cyclopenta[a]chrysen-9-yl acetate

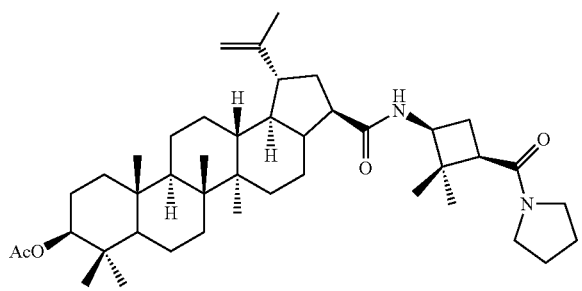

To a stirred solution of (1R,3aS,5aR,5bR,7aR,9S,11aR, 11bR,13aR,13bR)-9-acetoxy-5a,5b,8,8,11a-pentamethyl-1-(prop-1-en-2-yl)icosahydro-1H-cyclopenta[a]chrysene-3a-carboxylic acid (0.3 g, 0.602 mmol) in DCM (1 ml) a solution of (COCl)$_2$ (0.52 ml, 6.02 mmol) in DCM (4 ml) was added at about 0° C. and the reaction mixture was allowed to stir at room temperature for about 3 hours. After completion of the reaction (monitored by TLC), the solvent was evaporated under nitrogen atmosphere and dissolved in DCM (4 ml), which was added to a stirred solution of ((1R,3S)-3-amino-2,2-dimethylcyclobutyl)(pyrrolidin-1-yl)methanone (Intermediate 13, 0.288 g, 1.023 mmol) in DCM (5 ml) and Et$_3$N (0.16 ml, 1.204 mmol) at about 0° C. and allowed to stir at room temperature for about 16 hours. After completion of the reaction (monitored by TLC), the reaction mixture was diluted with DCM and washed with water, 1N HCl, water, brine and dried over Na$_2$SO$_4$, the solvent was evaporated and purified by silica gel column (100-200 mesh, elution 20% EtOAc in hexane) to afford the title compound as an off white solid. Wt: 0.230 g; Yield: 56.5%; $^1$H NMR (300 MHz, CDCl$_3$): δ 6.38 (d, 1H, J=8.4 Hz), 4.73 (s, 1H), 4.58 (s, 1H), 4.50-4.42 (m, 1H), 4.13-4.02 (m, 1H), 3.56-3.28 (m, 5H), 3.18-3.07 (m, 1H), 2.79 (t, 1H, J=7.2 Hz), 2.55-2.33 (m, 2H), 2.27-2.18 (m, 1H), 2.04 (s, 3H), 2.00-1.74 (m, 8H), 1.72-1.10 (m, 20H), 0.95, 0.92, 0.88, 0.83 (s, 22H); Mass: [M+Na]$^+$ 714 (100%); IR (KBr, cm$^{-1}$): 3372, 2943, 2864, 1736, 1730, 1652, 1636, 1623, 1501, 1459, 1444, 1369, 1248, 1192, 1024, 979, 881, 853; M.R: 125.4° C.-135.5° C.

Example 14

Preparation of (1R,3aS,5aR,5bR,7aR,9S,11aR,11bR, 13aR,13bR)-N-((1S,3R)-2,2-dimethyl-3-(pyrrolidine-1-carbonyl)cyclobutyl)-9-hydroxy-5a,5b,8,8, 11a-pentamethyl-1-(prop-1-en-2-yl)icosahydro-1H-cyclopenta[a]chrysene-3a-carboxamide

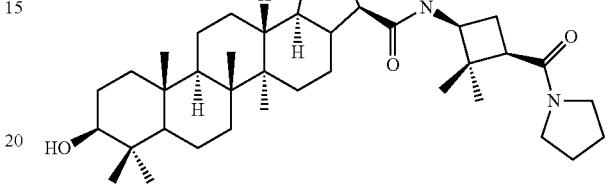

To a stirred solution of (1R,3aS,5aR,5bR,7aR,9S,11aR, 11bR,13aR,13bR)-3a-((1S,3R)-2,2-dimethyl-3-(pyrrolidine-1-carbonyl)cyclobutylcarbamoyl)-5a,5b,8,8,11a-pentamethyl-1-(prop-1-en-2-yl)icosahydro-1H-cyclopenta[a]chrysen-9-yl acetate (Example 13, 0.230 g, 0.340 mmol) in MeOH:THF (2:1) (9 ml) NaOH (2N, 3 ml) was added at about 0° C. and allowed to stir at room temperature for about 16 hours. After completion of the reaction (monitored by TLC), the volatiles were evaporated and the aqueous layer was extracted with ethyl acetate and the organic layer was washed with water, brine and dried with Na$_2$SO$_4$. The solvent was evaporated and purified by silica gel column (100-200 mesh, elution 15% EtOAc in hexane) to afford the title compound as an off white solid. Wt: 0.150 g; Yield: 69.5%; $^1$H NMR (300 MHz, CDCl$_3$): δ 6.39 (d, 1H, J=8.4 Hz), 4.73 (s, 1H), 4.57 (s, 1H), 4.13-4.03 (m, 1H), 3.58-3.28 (m, 4H), 3.21-3.07 (m, 2H), 2.79 (t, 1H, J=7.2 Hz), 2.57-2.33 (m, 2H), 2.27-2.18 (m, 1H), 2.04-1.72 (m, 8H), 1.70-1.10 (m, 23H), 0.95, 0.92, 0.88, 0.83, 0.80, 0.75 (s, 21H); Mass: [M+1]$^+$ 635 (100%), [M+Na]$^+$ 657 (90%); IR (KBr, cm$^{-1}$): 3489, 2947, 2869, 1637, 1615, 1441, 1376, 1357, 1250, 1194, 1050, 881, 717; M.R: 172.4° C.-173.8° C.; HPLC: 96.79%.

Example 15

Preparation of 4-((1R,3aS,5aR,5bR,7aR,9S,11aR, 11bR,13aR,13bR)-3a-((1S,3R)-2,2-dimethyl-3-(pyrrolidine-1-carbonyl)cyclobutylcarbamoyl)-5a,5b,8,8, 11a-pentamethyl-1-(prop-1-en-2-yl)icosahydro-1H-cyclopenta[a]chrysen-9-yloxy)-2,2-dimethyl-4-oxobutanoic acid

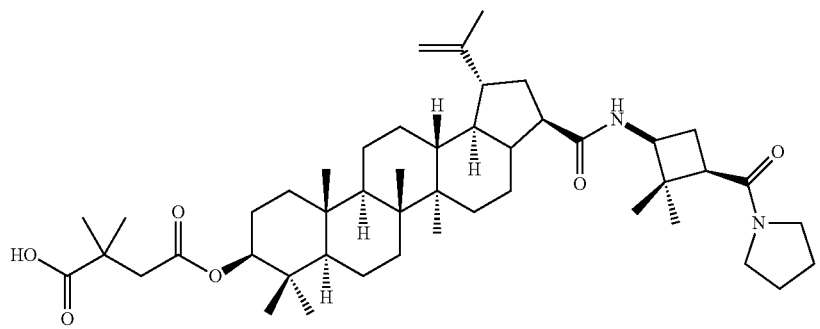

77

To a stirred solution of (1R,3aS,5aR,5bR,7aR,9S,11aR,11bR,13aR,13bR)-N-((1S,3R)-2,2-dimethyl-3-(pyrrolidine-1-carbonyl)cyclobutyl)-9-hydroxy-5a,5b,8,8,11a-pentamethyl-1-(prop-1-en-2-yl)icosahydro-1H-cyclopenta[a]chrysene-3a-carboxamide (Example 14, 0.15 g) in dry pyridine (5 ml) dimethyl succinamide (0.302 g) was added followed by DMAP (0.057 g) and the reaction mixture was refluxed for about 20 hours. After the completion of the reaction (monitored by TLC), the mixture was diluted with ethyl acetate, washed with water and brine solution. The combined organic layers were dried over $Na_2SO_4$, concentrated under reduced pressure to afford the title crude compound as a gummy solid. The crude compound was purified by silica-gel column chromatography using 100-200 mesh and hexane and ethyl acetate mixtures as mobile phase. $^1$H NMR (300 MHZ, $CDCl_3$): δ 6.42 (1H, d, J=8.1 Hz), 4.72 (1H, s), 4.5787 (1H, s), 4.51 (1H, m), 4.1 (1H, m), 3.42-3.5 (3H, m), 3.3-3.4 (1H, m), 3.08-3.15 (1H, m), 2.8 (1H, m), 2.2-2.7 (7H, m), 1.8-2.0 (11H, m), 1.2-1.78 (24H, m), 0.95 (6H, m), 0.8 (10H, m); IR (KBr, cm$^{-1}$): 3246, 2950, 2873, 2381, 1725, 1620, 1459, 1193, 1154, 909, 722; Mass: [M+H]$^+$ 763 (10%), 785 [M+Na]$^+$; Melting Range: 110-114° C.

Example 16

Preparation of (1R,3aS,5aR,5bR,7aR,9S,11aR,11bR,13aR,13bR)-3a-((1R,3S)-2,2-dimethyl-3-(morpholine-4-carbonyl)cyclobutylcarbamoyl)-5a,5b,8,8,11a-pentamethyl-1-(prop-1-en-2-yl)icosahydro-1H-cyclopenta[a]chrysen-9-yl acetate

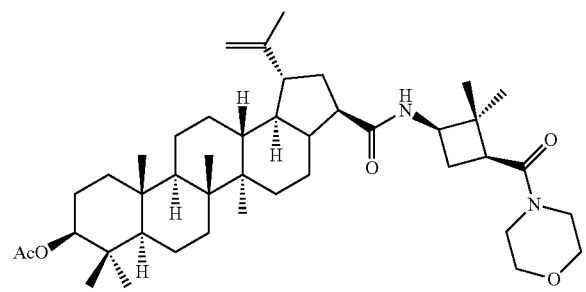

To a solution of (1R,3aS,5aR,5bR,7aR,9S,11aR,11bR,13aR,13bR)-9-acetoxy-5a,5b,8,8,11a-pentamethyl-1-(prop-1-en-2-yl)icosahydro-1H-cyclopenta[a]chrysene-3a-carboxylic acid (0.270 g, 0.542 mmol) in DCM (1 ml) 2M solution of $(COCl)_2$ in DCM (2.71 ml, 5.42 mmol) was added at about 0° C. and the reaction mixture was stirred at room temperature for about 3 hours. After completion of the reaction (monitored by TLC), the solvent was evaporated under nitrogen atmosphere and dissolved in DCM (4 ml), which was added to a solution of ((1S,3R)-3-amino-2,2-dimethylcyclobutyl)(morpholino)methanone (Intermediate 14, 0.172 g, 0.0813 mmol) in DCM at 0° C. and allowed to stir at room temperature for about 16 hours. After completion of the reaction (monitored by TLC), the reaction mixture was diluted with DCM and washed with water, 1N HCl, water, brine and dried over $Na_2SO_4$, the solvent was evaporated and purified by silica gel column (100-200 mesh, elution 15% EtOAc in hexane) to afford the title compound as an off white solid. Wt: 0.310 g: Yield: 82%; $^1$H NMR (300 MHz, $CDCl_3$): δ 5.83 (d, 1H, J=7.8 Hz), 4.72 (s, 1H), 4.58 (s, 1H), 4.51-4.40 (m, 1H), 4.19-4.08 (m, 1H), 3.81-3.40 (m, 8H), 3.18-3.05 (m, 1H), 2.90-2.82 (m, 1H), 2.54-2.21 (m, 3H), 2.04 (s, 3H), 1.99-1.83 (m, 2H), 1.80-1.12 (m, 27H), 1.08-1.70 (s, 18H); Mass: [M+1]$^+$ 693 (15%), [M+Na]$^+$ 715 (28%); JR (KBr, cm$^{-1}$): 3388, 2954, 2867, 1716, 1659, 1633, 1524, 1449, 1366, 1271, 1235, 1119, 1038, 980, 892; M.R: 71.6° C.-78.9° C.

Example 17

Preparation of (1R,3aS,5aR,5bR,7aR,9S,11aR,11bR,13aR,13bR)-N-((1R,3S)-2,2-dimethyl-3-(morpholine-4-carbonyl)cyclobutyl)-9-hydroxy-5a,5b,8,8,11a-pentamethyl-1-(prop-1-en-2-yl)icosahydro-1H-cyclopenta[a]chrysene-3a-carboxamide

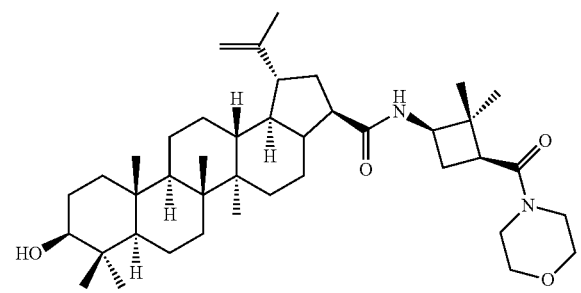

To a stirred solution of (1R,3aS,5aR,5bR,7aR,9S,11aR,11bR,13aR,13bR)-3a-((1R,3S)-2,2-dimethyl-3-(morpholine-4-carbonyl)cyclobutylcarbamoyl)-5a,5b,8,8,11a-pentamethyl-1-(prop-1-en-2-yl)icosahydro-1H-cyclopenta[a]chrysen-9-yl acetate (Example 16, 0.300 g, 0.43 mmol) in MeOH:THF (2:1) (15 ml), 2N NaOH (5 ml) was added at about 0° C. and allowed to stir at room temperature for about 16 hours. After completion of the reaction (monitored by TLC), the volatiles were evaporated and the aqueous layer was extracted with ethyl acetate and dried over $Na_2SO_4$. The solvent was evaporated and purified by silica gel column (100-200 mesh, elution 15% EtOAc in hexane) to afford the title compound as an off white solid. Wt: 0.230 g: Yield: 81.8%; $^1$H NMR (300 MHz, $CDCl_3$): δ 5.83 (d, 1H, J=7.8 Hz), 4.72 (s, 1H), 4.57 (s, 1H), 4.18-4.07 (m, 1H), 3.80-3.41 (m, 8H), 3.22-3.05 (m, 2H), 2.86 (t, 1H, J=8.1 Hz), 2.52-2.23 (m, 3H), 1.99-1.87 (m, 2H), 1.79-1.11 (m, 28H), 0.93, 0.89, 0.81, 0.74 (s, 18H); Mass: [M+1]$^+$ 673 (100); IR (KBr, cm$^{-1}$): 3419, 2951, 2864, 1624, 1527, 1459, 1374, 1271, 1249, 1112, 1068, 1044, 875, 861; M.R: 213.5° C.-216.5° C.; HPLC: 95.6%.

Example 18

Preparation of (1R,3aS,5aR,5bR,7aR,9S,11aR,11bR,13aR,13bR)-9-((1S,3R)-3-(benzyloxycarbonyl)-2,2-dimethylcyclobutanecarbonyloxy)-5a,5b,8,8,11a-pentamethyl-1-(prop-1-en-2-yl)icosahydro-1H-cyclopenta[a]chrysene-3a-carboxylic acid

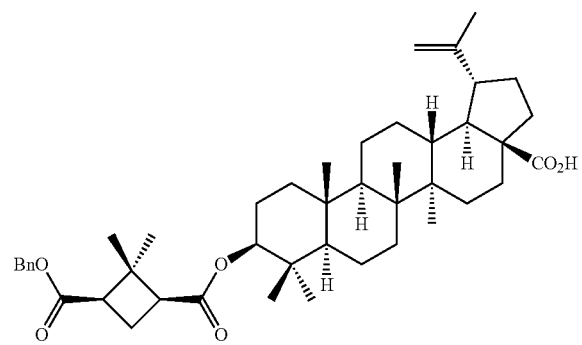

To a stirred solution of (1S,3R)-3-(benzyloxycarbonyl)-2,2-dimethylcyclobutanecarboxylic acid (Intermediate 15, 1.5 g) in THF (10 ml) DIPEA (2.215 g) was added under nitrogen atmosphere at about 0° C. then 2,4,6-trichlorobenzoyl chloride (1.346 g) was added and stirred the reaction mixture for about 3 hours. After completion of the reaction (anhydride formation), which was monitored by TLC, the reaction mixture was concentrated under reduced pressure and directly used for the next reaction.

To a stirred solution of (1R,3aS,5aR,5bR,7aR,9S,11aR, 11bR,13aR,13bR)-9-hydroxy-5a,5b,8,8,11a-pentamethyl-1-(prop-1-en-2-yl)icosahydro-1H-cyclopenta[a]chrysene-3a-carboxylic acid (1.3 g) in pyridine (10 ml) DMAP (0.57 g) was added followed by the crude reaction mixture (anhydride formation). The reaction mixture was stirred at reflux temperature for about 12 hours. After completion of the reaction (monitored by TLC), the mixture was cooled to room temperature, diluted with EtOAc, washed with dil HCl, water, followed by brine and dried over $Na_2SO_4$, and concentrated under reduced pressure. The crude reaction mixture was purified by column chromatography using hexane and ethyl acetate mixtures as an eluent to afford the title compound (300 mg, 15% yield). $^1H$ NMR (300 MHz, $CDCl_3$): δ 7.37-7.33 (5H, m), 5.16 (2H, m), 4.73 (1H, s), 4.61 (1H, s), 4.45-4.36 (1H, m), 3.65-3.6 (1H, m), 3.1-2.90 (1H, m), 2.85-2.6 (3H, m), 2.4 (1H, m), 2.3-1.9 (5H, m), 1.8-1.3 (17H, m), 1.26 (4H, m), 1.24 (3H, s), 1.22 (2H, m), 1.16 (3H, s), 1.14 (3H, s), 1.00 (2H, m), 0.8 (6H, s); Mass: [M+Na]$^+$ 723 (15%); IR (KBr, cm$^{-1}$): 3427, 2953, 17330, 1730, 1459, 1376, 1277, 1236, 1187, 1107, 1034, 940, 882.

Example 19

Preparation of (1R,3aS,5aR,5bR,7aR,9S,11aR,11bR, 13aR,13bR)-9-((1S,3R)-3-carboxy-2,2-dimethylcyclobutanecarbonyloxy)-5a,5b,8,8,11a-pentamethyl-1-(prop-1-en-2-yl)icosahydro-1H-cyclopenta[a]chrysene-3a-carboxylic acid

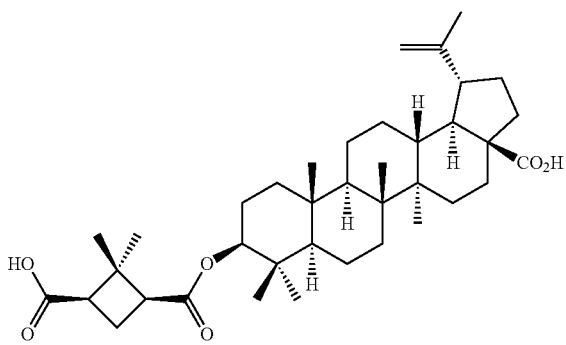

To a stirred solution of (1R,3aS,5aR,5bR,7aR,9S,11aR, 11bR,13aR,13bR)-9-((1S,3R)-3-(benzyloxycarbonyl)-2,2-dimethylcyclobutanecarbonyloxy)-5a,5b,8,8,11a-pentamethyl-1-(prop-1-en-2-yl)icosahydro-1H-cyclopenta[a]chrysene-3a-carboxylic acid (Example 18, 0.25 g) in dry DCM (10 ml) Et3N (5.77 ml) and Et3SiH (0.057 g) were added at about 0° C. then Pd(OAc)$_2$ (0.005 g) was added under nitrogen conditions and the reaction mixture was stirred at reflux temperatures for over night. After completion of the reaction (monitored by TLC), the reaction mixture was diluted with DCM, and concentrated under reduced pressure, purified by column chromatography to afford the title compound (80 mg, 36.86% Yield). $^1H$ NMR (300 MHz, $CDCl_3$): δ 4.73 (1H, s), 4.54 (1H, s), 4.4-4.36 (1H, m), 3.0-2.90 (1H, m), 2.80-2.65 (2H, m), 2.6 (2H, m), 2.3-2.1 (3H, m), 2.0-1.88 (4H, m), 1.64 (5H, m), 1.61 (2H, m), 1.6-1.4 (4H, m), 1.39-1.3 (4H, m), 1.32 (6H, s), 1.3-1.02 (4H, m), 1.00 (3H, s),0.91 (3H, s), 0.89 (3H, s), 0.809 (3H, s), 0.790 (3H, s), 0.751 (3H, s); Mass: [M+Na]$^+$ 633 (75%); 1R (KBr, cm$^{-1}$): 3400, 2949, 1732, 1703, 1459, 1389, 1364, 1264, 1211, 1139, 1126, 1106, 1020, 942, 889. Melting Range: 308-310° C.

Example 20

Preparation of (1R,3aS,5aR,5bR,7aR,9S,11aR,11bR, 13aR,13bR)-5a,5b,8,8,11a-pentamethyl-3a-((1R,3S)-3-morpholinomethyl)cyclopentylcarbamoyl)-1-(prop-1-en-2-yl)icosahydro-1H-cyclopenta[a]chrysen-9-yl acetate

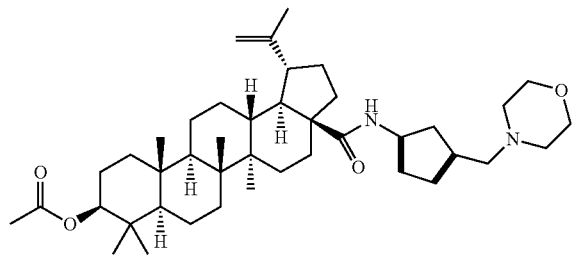

To a stirred solution of (1R,3aS,5aR,5bR,7aR,9S,11aR, 11bR,13aR,13bR)-9-acetoxy-5a,5b,8,8,11a-pentamethyl-1-(prop-1-en-2-yl)icosahydro-1H-cyclopenta[a]chrysene-3a-carboxylic acid (0.8 g, 1.6 mmol) (Prepared as described in J. Med. Chem. 2009. 52, 3248-3258) in 50 ml DCM was added Oxolyl chloride (2 ml, 15.87 mmol) and stirred at room temperature for about 6 hours and completion of the reaction was monitored by TLC. The reaction mixture was concentrated under reduced pressure and the residue was taken in DCM (15 ml) then kept under $N_2$ atmosphere.

To a stirred solution of (1R,3S)-3-(morpholinomethyl)cyclopentanamine (0.3 g, 19.8 mmol) in DCM (50 ml) triethyl amine (2 ml, 19.8 mmol) was added at about 0° C. and stirred for about 15 minutes then above prepared acid chloride was added and stirred continually at room temperature for about 8 hours and completion of reaction monitored by TLC. The reaction mixture was neutralized with saturated $NaHCO_3$ and extracted with DCM, the organic layer was dried over $Na_2SO_4$ and concentrated under reduced pressure. The residue was purified by silica gel column chromatography using 5% methanol in DCM as eluent to furnish the title compound (0.5 g) as a white solid. $^1H$ NMR (300 MHz, $CDCl_3$): 0.88-0.96 (m, 9H); 1.25-1.39 (m, 11H); 1.43-1.88 (m, 24H); 2.07 (s, 3H); 2.21-2.47 (m, 8H); 2.86-3.10 (m, 3H); 3.15-3.72 (m, 7H); 4.60 (s, 1H); 4.74 (s, 1H); ES Mass: 665 [M+1] (100%).

Example 21

Preparation of (1R,3aS,5aR,5bR,7aR,9S,11aR,11bR, 13aR,13bR)-5a,5b,8,8,11a-pentamethyl-3a-((1S,4R)-4-(morpholinomethyl)cyclopent-2-enylcarbamoyl)-1-(prop-1-en-2-yl)-icosahydro-1H-cyclopenta[a]chrysen-9-yl acetate

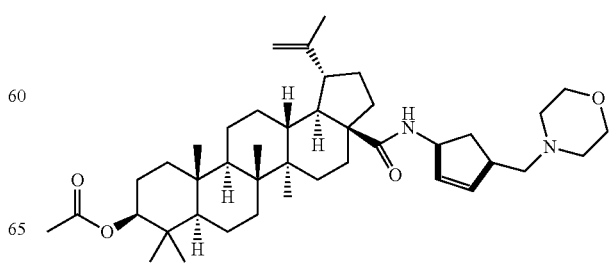

To a stirred solution of (1R,3aS,5aR,5bR,7aR,9S,11aR, 11bR,13aR,13bR)-9-acetoxy-5a,5b,8,8,11a-pentamethyl-1-(prop-1-en-2-yl)icosahydro-1H-cyclopenta[a]chrysene-3a-carboxylic acid (0.8 g, 1.6 mmol) in DCM (50 ml) oxalyl chloride (2 ml, 15.87 mmol) was added at room temperature and completion of the reaction monitored by TLC. The reaction mixture was concentrated under reduced pressure and the residue was taken in DCM (15 ml) then kept under N₂ atmosphere.

To a stirred solution of (1S,4R)-4-(morpholinomethyl)cyclopent-2-enamine (0.3 g, 19.8 mmol) in DCM (50 ml) triethyl amine (2 ml, 19.8 mmol) was added at about 0° C. and stirred for about 15 minutes then above prepared acid chloride was added and stirred continually at room temperature for about 8 hours and completion of reaction monitored by TLC. The reaction mixture was neutralized with saturated NaHCO₃ and extracted with DCM, the organic layer was dried over Na₂SO₄ and concentrated under reduced pressure. The residue was purified by silica gel column chromatography using 5% methanol in DCM as eluent to furnish the title compound (0.5 g) as a white solid. ¹H NMR (300 MHz, CDCl₃): 0.88-0.96 (m, 9H); 1.25-1.39 (m, 11H); 1.43-1.88 (m, 24H); 2.07 (s, 3H); 2.21-2.47 (m, 8H); 2.86-3.10 (m, 3H); 3.15-3.72 (m, 7H); 4.60 (s, 1H); 4.74 (s, 1H); 5.52-5.55 (m, 1H); 5.69-5.70 (m, 1H); 5.72-5.91 (m, 1H); ES Mass: 622 [M+Na] 645 (100%).

Example 22

Preparation of ((1R,5aR,5bR,7aR,9S,11aR,11bR, 13aR,13bR)-9-hydroxy-5a,5b,8,8,11a-pentamethyl-1-(prop-1-en-2-yl)icosahydro-1H-cyclopenta[a]chrysen-3a-yl)(3-(3-isopropyl-5-methyl-4H-1,2,4-triazol-4-yl)-8-azabicyclo[3.2.1]octan-8-yl)methanone

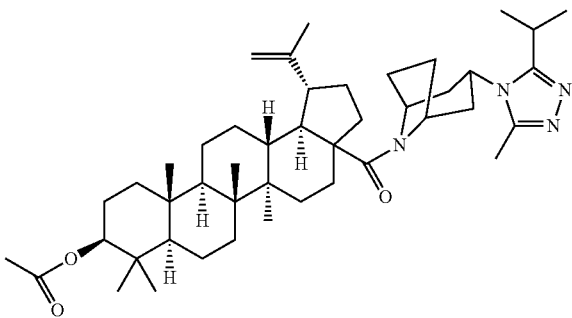

To a stirred solution of (1R,3aS,5aR,5bR,7aR,9S,11aR, 11bR,13aR,13bR)-9-acetoxy-5a,5b,8,8,11a-pentamethyl-1-(prop-1-en-2-yl)icosahydro-1H-cyclopenta[a]chrysene-3a-carboxylic acid ((0.8 g, 1.6 mmol) in DCM (50 ml) oxalyl chloride (2 ml, 15.87 mmol) was added at room temperature and completion of the reaction monitored by TLC. The reaction mixture was concentrated under reduced pressure and the residue was taken in DCM (15 ml) then kept under N₂ atmosphere.

To a stirred solution of 3-(3-isopropyl-5-methyl-4H-1,2,4-triazol-4-yl)-8-azabicyclo[3.2.1]octane (0.3 g, 19.8 mmol) in DCM (50 ml) triethyl amine (2 ml, 19.8 mmol) was added at about 0° C. and stirred for about 15 minutes then above prepared acid chloride was added and stirred continually at room temperature for about 8 hours and completion of reaction monitored by TLC. The reaction mixture was neutralized with saturated NaHCO₃ and extracted with DCM, the organic layer was dried over Na₂SO₄ and concentrated under reduced pressure. The residue was purified by silica gel column chromatography using 5% methanol in DCM as eluent to furnish the title compound (0.5 g) as a white solid. ¹H NMR (300 MHz, CDCl₃): 0.76-0.99 (m, 16H); 1.25-1.85 (m, 35H); 2.03-2.28 (m, 6H); 2.47 (s, 3H); 2.86-3.10 (m, 3H); 3.18 (s, 1H); 4.60 (s, 1H); 4.74 (s, 1H); ES Mass: 715 (100%), [M+1].

Example 23

Preparation of (1R,3aS,5aR,5bR,7aR,9S,11aR,11bR, 13aR,13bR)-9-hydroxy-5a,5b,8,8,11a-pentamethyl-N-((1R,3S)-3-(morpholinomethyl)cyclopentyl)-1-(prop-1-en-2-yl)icosahydro-1H-cyclopenta[a] chrysene-3a-carboxamide

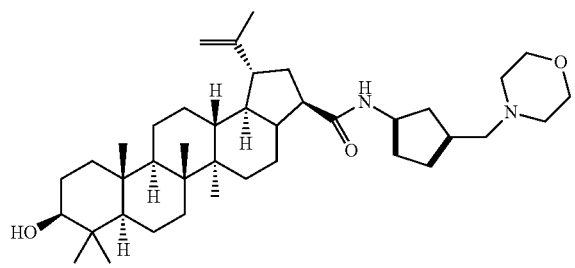

(1R,3aS,5aR,5bR,7aR,9S,11aR,11bR,13aR,13bR)-5a,5b, 8,8,11a-pentamethyl-3a-((1R,3S)-3-(morpholinomethyl)cyclopentylcarbamoyl)-1-(prop-1-en-2-yl)icosahydro-1H-cyclopenta[a]chrysen-9-yl acetate (Example 20, 0.22 g) in MeOH:THF (8:8 ml) and cooled the contents to 0° C. then sodium hydroxide (0.05 g in 4 ml water) was added and the contents were stirred for about 6 hours at room temperature then completion of the reaction was monitored by TLC. The reaction mixture was evaporated under reduced pressure, the residue was taken in water and extracted with DCM. The organic layer was dried over Na₂SO₄ and concentrated under reduced pressure. The residue was purified by silica gel column chromatography using 5% methanol in DCM as an eluent to furnish the title compound (0.14 g) as a white solid. ¹H NMR (300 MHz, CDCl₃): 0.88-0.96 (m, 9H); 1.25-1.39 (m, 11H); 1.43-1.88 (m, 24H) 2.21-2.47 (m, 8H); 2.86-3.10 (m, 3H); 3.15-3.72 (m, 7H); 4.60 (s, 1H); 4.74 (s, 1H); ES Mass: 622 (100%), [M+Na] 645; HPLC: 98.6%.

Example 24

Preparation of 2,2-dimethyl-4-oxo-4-((1R,3aS,5aR, 5bR,7aR,9S,11aR,11bR,13aR,13bR)-5a,5b,8,8,11a-pentamethyl-3a-((1R,3S)-3-(morpholinomethyl)cyclopentylcarbamoyl)-1-(prop-1-en-2-yl)icosahydro-1H-cyclopenta[a]chrysen-9-yloxy)butanoic acid To a stirred solution of (1R,3aS,5aR,5bR,7aR,9S,11aR, 11bR,13aR,13bR)-5a,5b,8,8,11a-pentamethyl-3a-((1R,3S)-3-(morpholinomethyl)cyclopentylcarbamoyl)-1-(prop-1-en-2-yl)icosahydro-1H-cyclopenta[a]chrysen-9-yl acetate (Example 23, 0.15 g, 0.24 mmol) in pyridine (5 ml) dimethyl amino pyridine (0.32 g, 0.48 mmol) and 3,3-dimethyldihydrofuran-2,5-dione (1.3 ml) were added and the contents were refluxed for about 16 hours and completion of the reaction monitored by TLC. The reaction mixture was diluted with ethyl acetate (30 ml). The organic layer was washed with 5% aqueous HCl, washed with water followed by brine solution, dried over Na₂SO₄ and concentrated under reduced pressure. The residue was purified by silica gel column chromatography using 5% MeOH in DCM as eluent to furnish the title compound (0.1 g) as a white solid. ¹H NMR (300 MHz, CDCl₃): 0.95-1.16 (m, 19H); 1.23-1.78 (m, 23H); 2.15-2.59

(m, 1H); 2.77-3.58 (m, 11H); 4.33-4.70 (m, 4H); 5.58-5.60 (s, 1H); 5.78-5.80 (s, 1H); 7.44-7.47 (s, 1H); ES Mass: [M+1] 750 (100%); HPLC: 98.08%.

Example 25

Preparation of ((1R,5aR,5bR,7aR,9S,11aR,11bR, 13aR,13bR)-9-hydroxy-5a,5b,8,8,11a-pentamethyl-1-(prop-1-en-2-yl)icosahydro-1H-cyclopenta[a]chrysen-3a-yl)(3-(3-isopropyl-5-methyl-4H-1,2,4-triazol-4-yl)-8-azabicyclo[3.2.1]octan-8-yl)methanone

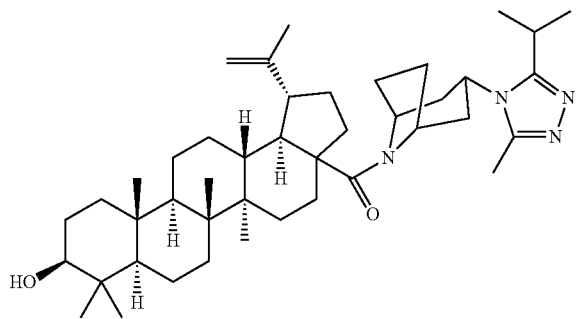

(1R,5aR,5bR,7aR,9S,11aR,11bR,13aR,13bR)-3a-(3-(3-isopropyl-5-methyl-4H-1,2,4-triazol-4-yl)-8-azabicyclo[3.2.1]octane-8-carbonyl)-5a,5b,8,8,11a-pentamethyl-1-(prop-1-en-2-yl)icosahydro-1H-cyclopenta[a]chrysen-9-yl acetate (Example 22, 0.2 g) in MeOH:THF (8:8 ml) and cooled the contents to 0° C. then sodium hydroxide (0.05 g in 4 ml water) was added and the contents were stirred for about for about 6 hours at room temperature and completion of the reaction was monitored by TLC. The reaction mixture was evaporated under reduced pressure, the residue was taken in water and extracted with DCM. The organic layer was dried over Na$_2$SO$_4$ and concentrated under reduced pressure. The residue was purified by silica gel column chromatography using 5% methanol in DCM as eluent to furnish the title compound (0.14 g) as a white solid. $^1$H NMR (300 MHz, CDCl$_3$): 0.76-0.99 (m, 16H); 1.25-1.85 (m, 35H); 2.03-2.28 (m, 6H); 2.47 (s, 3H); 2.86-3.10 (m, 3H); 3.18 (s, 1H); 4.60 (s, 1H); 4.74 (s, 1H); ES Mass: [M+] 672 (100%), [M+1] 673; HPLC: 95.5%.

Example 26

Preparation of (1R,3aS,5aR,5bR,7aR,9S,11aR,11bR, 13aR,13bR)-9-hydroxy-5a,5b,8,8,11a-pentamethyl-N-((1S,4R)-4-(morpholinomethyl)cyclopent-2-enyl)-1-(prop-1-en-2-yl)icosahydro-1H-cyclopenta[a]chrysene-3a-carboxamide

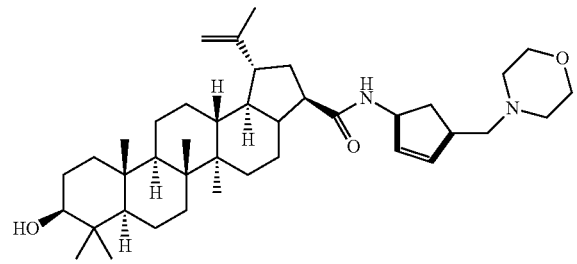

(1R,3aS,5aR,5bR,7aR,9S,11aR,11bR,13aR,13bR)-5a,5b,8,8,11a-pentamethyl-3a-((1S,4R)-4-(morpholinomethyl)cyclopent-2-enylcarbamoyl)-1-(prop-1-en-2-yl)icosahydro-1H-cyclopenta[a]chrysen-9-yl acetate (Example 21, 0.22 g) in MeOH:THF (8:8 ml) and cooled the contents to 0° C. then sodium hydroxide (0.05 g in 4 ml water) was added and the contents were stirred for about 6 hours at room temperature then completion of the reaction was monitored by TLC. The reaction mixture was evaporated under reduced pressure, the residue was taken in water and extracted with DCM. The organic layer was dried over Na$_2$SO$_4$ and concentrated under reduced pressure. The residue was purified by silica gel column chromatography using 5% methanol in DCM as eluent to furnish the title compound (0.14 g) as a white solid. $^1$H NMR (300 MHz, CDCl$_3$): 0.88-0.96 (m, 9H); 1.25-1.39 (m, 11H); 1.43-1.88 (m, 24H); 2.21-2.47 (m, 8H); 2.86-3.10 (m, 3H); 3.15-3.72 (m, 7H); 4.60 (s, 1H); 4.74 (s, 1H); 5.52-5.55 (m, 1H); 5.69-5.70 (m, 1H); 5.72-5.91 (m, 1H); ES Mass: 620 (100%), [M+1] 621; HPLC: 96.98%.

Example 27

Preparation of (1R,3aS,5aR,5bR,7aR,9S,11aR,11bR, 13aR,13bR)-3a-(4-(hydroxymethyl)cyclopent-2-enylcarbamoyl)-5a,5b,8,8,11a-pentamethyl-1-(prop-1-en-2-yl)icosahydro-1H-cyclopenta[a]chrysen-9-yl acetate

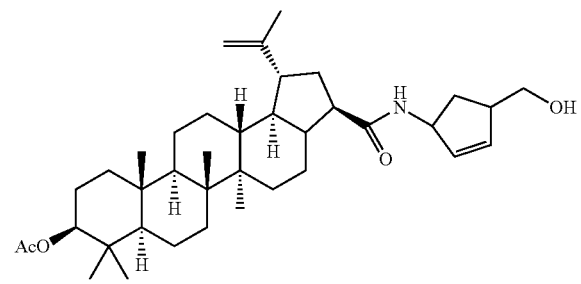

To a stirred solution of (1R,3aS,5aR,5bR,7aR,9S,11aR, 11bR,13aR,13bR)-9-acetoxy-5a,5b,8,8,11a-pentamethyl-1-(prop-1-en-2-yl)icosahydro-1H-cyclopenta[a]chrysene-3a-carboxylic acid (0.8 g, 1.6 mmol) in DCM (50 ml) oxalyl chloride (1.02 ml, 8.02 mmol) was added at room temperature and completion of the reaction monitored by TLC. The reaction mixture was concentrated under reduced pressure and the residue was taken in DCM (15 ml) then kept under N$_2$ atmosphere.

To a stirred solution of ((1R,4S)-4-aminocyclopent-2-enyl)methanol (0.22 g, 1.92 mmol) in DCM (50 ml) triethyl amine (2 ml, 19.8 mmol) was added at about 0° C. and stirred for about 15 minutes then above prepared acid chloride was added and stirred continually at room temperature for about 8 hours and completion of reaction monitored by TLC. The reaction mixture was neutralized with saturated NaHCO$_3$ and extracted with DCM, the organic layer was dried over Na$_2$SO$_4$ and concentrated under reduced pressure. The residue was purified by silica gel column chromatography using 5% methanol in DCM as eluent to furnish the title compound (0.56 g) as a white solid. $^1$H NMR (300 MHz, CDCl$_3$): 0.88-0.96 (m, 9H); 1.25-1.39 (m, 11H); 1.43-1.88 (m, 14H); 2.07 (s, 3H); 2.21-2.47 (m, 8H); 2.86-3.10 (m, 3H); 3.15-3.72 (m, 7H); 4.60 (s, 1H); 4.74 (s, 1H); 5.52-5.55 (m, 1H); 5.69-5.70 (m, 1H); 5.72-5.91 (m, 1H); ES Mass: 593 [M+Na] 616 (100%).

Example 28

Preparation of (1R,3aS,5aR,5bR,7aR,9S,11aR,11bR, 13aR,13bR)-9-hydroxy-N-(4-(hydroxymethyl)cyclopent-2-enyl)-5a,5b,8,8,11a-pentamethyl-1-(prop-1-en-2-yl)icosahydro-1H-cyclopenta[a]chrysene-3a-carboxamide

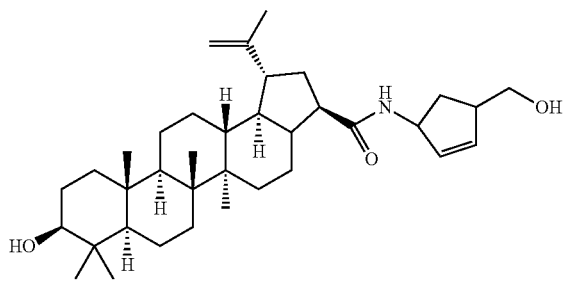

(1R,3aS,5aR,5bR,7aR,9S,11aR,11bR,13aR,13bR)-3a-(4-(hydroxymethyl)cyclopent-2-enylcarbamoyl)-5a,5b,8,8,11a-pentamethyl-1-(prop-1-en-2-yl)icosahydro-1H-cyclopenta[a]chrysen-9-yl acetate (Example 27, 0.22 g) in MeOH: THF (8:8 ml) and cooled the contents to 0° C. then sodium hydroxide (0.05 g in 4 ml water) was added and the contents were stirred for about 6 hours at room temperature then completion of the reaction was monitored by TLC. The reaction mixture was evaporated under reduced pressure, the residue was taken in water and extracted with DCM. The organic layer was dried over $Na_2SO_4$ and concentrated under reduced pressure. The residue was purified by silica gel column chromatography using 5% methanol in DCM as eluent to furnish the title compound (0.14 g) as a white solid. $^1$H NMR (300 MHz, CDCl$_3$): 0.76-0.99 (m, 16H); 1.25-1.85 (m, 35H); 2.03-2.28 (m, 6H); 2.47 (s, 3H); 2.86-3.10 (m, 3H); 3.18 (s, 1H); 4.60 (s, 1H); 4.74 (s, 1H); ES Mass: 551 (100%), [M+1] 551; HPLC: 96.94%.

Example 29

Preparation of (1R,3aS,5aR,5bR,7aR,9S,11aR,11bR, 13aR,13bR)-3a-((2S,3R)-4-((3S,4aS,8aS)-3-(tert-butylcarbamoyl)octahydroisoquinolin-2(1H)-yl)-3-hydroxy-1-phenylbutan-2-ylcarbamoyl)-5a,5b,8,8, 11a-pentamethyl-1-(prop-1-en-2-yl)icosahydro-1H-cyclopenta[a]chrysen-9-yl acetate To a stirred solution of (1R,3aS,5aR,5bR,7aR,9S,11aR, 11bR,13aR,13bR)-9-acetoxy-5a,5b,8,8,11a-pentamethyl-1-(prop-1-en-2-yl)icosahydro-1H-cyclopenta[a]chrysene-3a-carboxylic acid (0.5 g, 1.0 mmol) in DCM (50 ml) oxalyl chloride (1 ml, 7.93 mmol) was added at room temperature and completion of the reaction monitored by TLC. The reaction mixture was concentrated under reduced pressure and the residue was taken in DCM (15 ml) then kept under $N_2$ atmosphere.

To a stirred solution of (3S,4aS,8aS)-2-((2R,3S)-3-amino-2-hydroxy-4-phenylbutyl)-N-tert-butyldecahydroisoquinoline-3-carboxamide (0.44 g, 1.1 mmol) in DCM (50 ml) triethyl amine (0.4 ml, 3.01 mmol) was added at about 0° C. and stirred for about 15 minutes then above prepared acid chloride was added and stirred continually at room temperature for about 8 hours and completion of the reaction was monitored by TLC. The reaction mixture was neutralized with saturated $NaHCO_3$ and extracted with DCM, the organic layer was dried over $Na_2SO_4$ and concentrated under reduced pressure. The residue was purified by silica gel column chromatography using 5% methanol in DCM as eluent to furnish the title compound (0.68 g) as a white solid. $^1$H NMR (300 MHz, CDCl$_3$): 0.57-0.97 (m, 19H); 1.18-1.21 (m, 8H); 1.25-1.41 (m, 12H); 1.49-1.62 (m, 8H); 1.65-1.82 (m, 10H); 1.85-1.98 (m, 4H); 2.01 (s, 3H); 2.56-2.69 (m, 2H); 2.88-3.06 (m, 3H); 3.29-3.38 (m, 1H); 3.89-3.90 (m, 1H); 4.25-4.70 (m, 4H); 5.78 (s, 1H); 6.12-6.15 (d, J=9 Hz, 1H); 7.19-7.29 (m, 6H); ES Mass: 881 (100%), [M+1] 882.

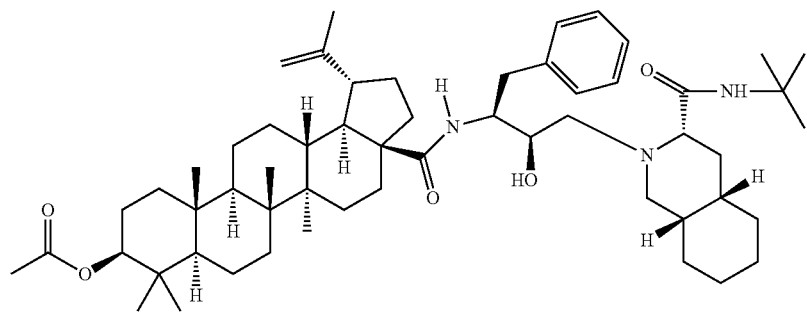

Example 30

Preparation of (3S,4aS,8aS)-N-tert-butyl-2-((2R,3S)-2-hydroxy-3-((1R,3aS,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysene-3a-carboxamido)-4-phenylbutyl)decahydroisoquinoline-3-carboxamide

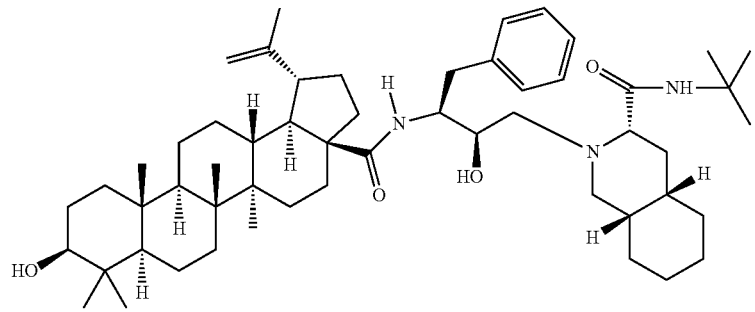

(1R,3aS,5aR,5bR,7aR,9S,11aR,11bR,13aR,13bR)-3a-((2S,3R)-4-((3S,4aS,8aS)-3-(tert-butylcarbamoyl)octahydroisoquinolin-2(1H)-yl)-3-hydroxy-1-phenylbutan-2-ylcarbamoyl)-5a,5b,8,8,11a-pentamethyl-1-(prop-1-en-2-yl)icosahydro-1H-cyclopenta[a]chrysen-9-yl acetate (Example 29, 0.5 g) in MeOH:THF (8:8 ml) and cooled the contents to 0° C. then sodium hydroxide (0.12 g in 4 ml water) was added and the contents were stirred for about 6 hours at room temperature, and the completion of the reaction was monitored by TLC. The reaction mixture was evaporated under reduced pressure, the residue was taken in water and extracted with DCM. The organic layer was dried over $Na_2SO_4$ and concentrated under reduced pressure. The residue was purified by silica gel column chromatography using 5% methanol in DCM as eluent to furnish the title compound (0.34 g) as a white solid. $^1$H NMR (300 MHz, $CDCl_3$): 0.57-0.97 (m, 19H); 1.18-1.21 (m, 8H); 1.25-1.41 (m, 12H); 1.49-1.62 (m, 8H); 1.65-1.82 (m, 10H); 1.85-1.98 (m, 4H); 2.56-2.69 (m, 2H); 2.88-3.06 (m, 3H); 3.29-3.38 (m, 1H); 3.89-3.90 (m, 1H); 4.25-4.70 (m, 4H); 5.78 (s, 1H); 6.12-6.15 (d, J=9 Hz, 1H); 7.19-7.29 (m, 6H); ES Mass: 839 (100%), [M+1] 840.

Example 31

Preparation of (1R,3aS,5aR,5bR,7aR,9S,11aR,11bR,13aR,13bR)-3a-((1R,3S)-3-((4-benzylpiperidin-1-yl)methyl)cyclopentylcarbamoyl)-5a,5b,8,8,11a-pentamethyl-1-(prop-1-en-2-yl)icosahydro-1H-cyclopenta[a]chrysen-9-yl acetate To a stirred solution of (1R,3aS,5aR,5bR,7aR,9S,11aR,11bR,13aR,13bR)-9-acetoxy-5a,5b,8,8,11a-pentamethyl-1-(prop-1-en-2-yl)icosahydro-1H-cyclopenta[a]chrysene-3a-carboxylic acid (0.5 g, 1.04 mmol) (Prepared as described in J. Med. Chem. 2009. 52, 3248-3258) in 50 ml DCM was added Oxolyl chloride (2 ml, 15.87 mmol) and stirred at room temperature for about 6 hours and completion of the reaction monitored by TLC. The reaction mixture was concentrated under reduced pressure and the residue was taken in DCM (15 ml) then kept under $N_2$ atmosphere.

To a stirred solution of (1R,3S)-3-((4-benzylpiperidin-1-yloxy)methyl)cyclopentanamine (0.43 g, 1.5 mmol) in DCM (50 ml) triethyl amine (0.3 ml, 3.12 mmol) was added at about 0° C. and stirred for about 15 minutes then the above prepared acid chloride was added and stirred continually at room temperature for about 8 hours and completion of the reaction was monitored by TLC. The reaction mixture was neutralized with saturated $NaHCO_3$ and extracted with DCM, the organic layer was dried over $Na_2SO_4$ and concentrated under reduced pressure. The residue was purified by silica gel column chromatography using 5% methanol in DCM as eluent to furnish the title compound (0.4 g) as a white solid. $^1$H NMR (300 MHz, $CDCl_3$): 0.57-0.97 (m, 19H); 1.18-1.21 (m, 8H); 1.25-1.41 (m, 12H); 1.49-1.62 (m, 8H); 1.65-1.82 (m, 10H); 1.85-1.98 (m, 4H); 2.56-2.69 (m, 2H); 2.88-3.06 (m, 3H); 3.29-3.38 (m, 1H); 3.89-3.90 (m, 1H); 4.25-4.70 (m, 4H); 5.78 (s, 1H); 6.12-6.15 (d, J=9 Hz, 1H); 7.19-7.29 (m, 6H); ES Mass: 753 (100%).

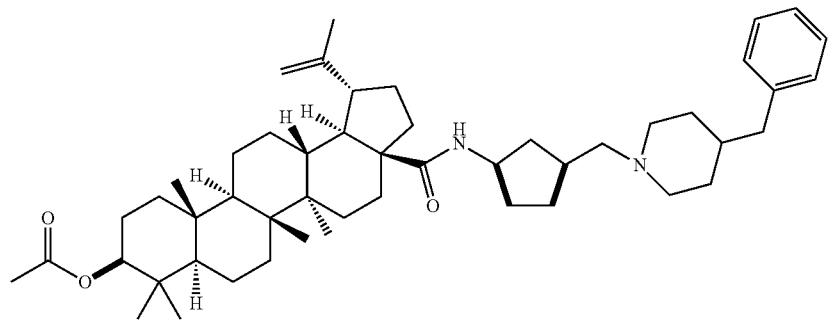

Example 32

Preparation of (1R,3aS,5aR,5bR,7aR,9S,11aR,11bR, 13aR,13bR)-N-((1R,3S)-3-((4-benzylpiperidin-1-yl) methyl)cyclopentyl)-9-hydroxy-5a,5b,8,8,11a-pentamethyl-1-(prop-1-en-2-yl)icosahydro-1H-cyclopenta[a]chrysene-3a-carboxamide

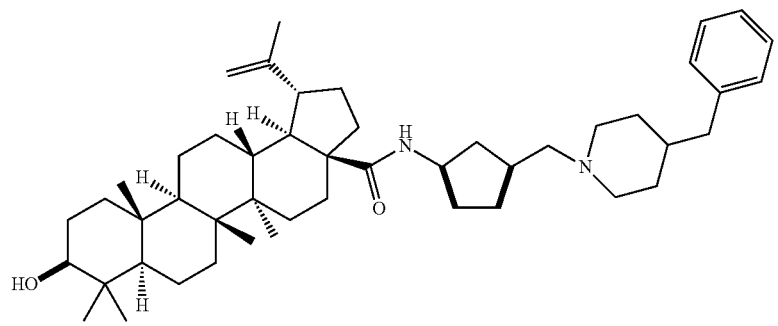

(2S,4aR,4bR,6aR,7R,8S,10aR,10bR,12aR)-8-((1R,3S)-3-((4-benzylpiperidin-1-yl)methyl)cyclopentylcarbamoyl)-1,1,4a,8,10a,10b-hexamethyl-7-(2-methylallyl)octadecahydrochrysen-2-yl acetate (Example 31, 0.5 g) in MeOH:THF (8:8 ml) and cooled the contents to 0° C. then sodium hydroxide (0.12 g in 4 ml water) was added and the contents were stirred for about 6 hours at room temperature then completion of the reaction was monitored by TLC. The reaction mixture was evaporated under reduced pressure, the residue was taken in water and extracted with DCM. The organic layer was dried over $Na_2SO_4$ and concentrated under reduced pressure. The residue was purified by silica gel column chromatography using 5% methanol in DCM as eluent to furnish the title compound (0.34 g) as a white solid. $^1$H NMR (300 MHz, CDCl$_3$): 0.57-0.97 (m, 19H); 1.18-1.21 (m, 8H); 1.25-1.41 (m, 12H); 1.49-1.62 (m, 8H); 1.65-1.82 (m, 10H); 1.85-1.98 (m, 4H); 2.56-2.69 (m, 2H); 2.88-3.06 (m, 3H); 3.29-3.38 (m, 1H); 3.89-3.90 (m, 1H); 4.25-4.70 (m, 4H); 5.78 (s, 1H); MASS: 711 (100%).

Example 33

Preparation of 5-((1R,3aS,5aR,5bR,7aR,9S,11aR, 11bR,13aR,13bR)-3a-((1R,3S)-3-((4-benzylpiperidin-1-yl)methyl)cyclopentylcarbamoyl)-5a,5b,8,8, 11a-pentamethyl-1-(prop-1-en-2-yl)icosahydro-1H-cyclopenta[a]chrysen-9-yloxy)-5-oxopentanoic acid To a stirred solution of (1R,3aS,5aR,5bR,7aR,9S,11aR, 11bR,13aR,13bR)-N-((1R,3S)-3-((4-benzylpiperidin-1-yl) methyl)cyclopentyl)-9-hydroxy-5a,5b,8,8,11a-pentamethyl-1-(prop-1-en-2-yl)icosahydro-1H-cyclopenta[a]chrysene-3a-carboxamide (Example 32, 0.24 mmol) in pyridine (5 ml) dimethyl amino pyridine (0.32 g, 0.48 mmol) and glutaric anhydride (1.3 ml) were added and the contents were refluxed for about 16 hours and completion of the reaction monitored by TLC. The reaction mixture was diluted with ethyl acetate (30 ml). The organic layer was washed with 5% aqueous HCl, washed with water followed by brine solution, dried over $Na_2SO_4$ and concentrated under reduced pressure. The residue was purified by silica gel column chromatography using 5% MeOH in DCM as eluent to furnish the title compound (0.1 g) as a white solid. $^1$H NMR (300 MHz, CDCl$_3$): 0.82-0.95 (m, 17H) 1.13-3.01 (m, 48H); 3.05-3.12 (m, 4H), 3.13-3.54 (m, 2H), 4.18-4.21 (m, 1H), 4.45-4.17 (m, 1H), 4.58 (s, 1H), 4.72 (s, 1H); 6.28-6.30 (m, 1H), 7.11-7.13 (m, 2H), 7.14-7.22 (m, 1H), 7.24-7.29 (m, 2H); ES Mass: [M+] 825 (100%); HPLC: 90%.

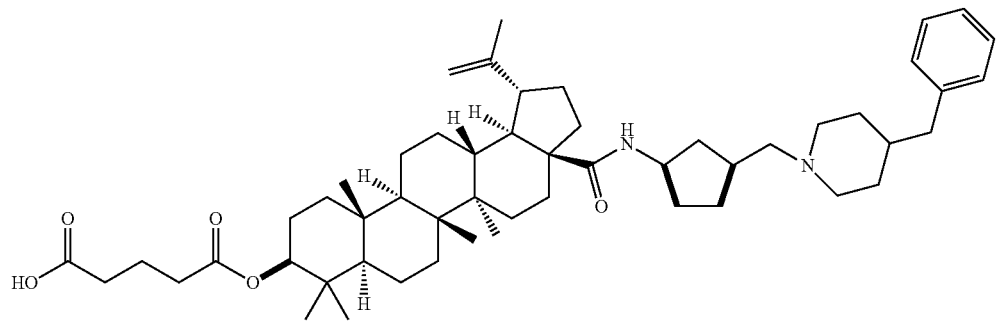

Example 34

Preparation of (1R,3aS,5aR,5bR,7aR,9S,11aR,11bR, 13aR,13bR)-3a-((1R,3S)-3-((4-ethylpiperazin-1-yl) methyl)cyclopentylcarbamoyl)-5a,5b,8,8,11a-pentamethyl-1-(prop-1-en-2-yl)icosahydro-1H-cyclopenta[a]chrysen-9-1 acetate

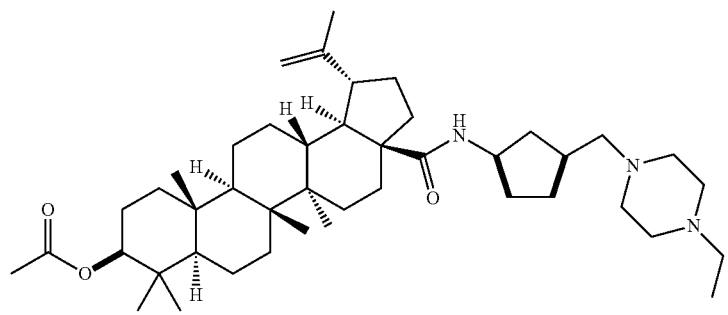

To a stirred solution of (1R,3aS,5aR,5bR,7aR,9S,11aR, 11bR,13aR,13bR)-9-acetoxy-5a,5b,8,8,11a-pentamethyl-1-(prop-1-en-2-yl)icosahydro-1H-cyclopenta[a]chrysene-3a-carboxylic acid (0.5 g, 1.04 mmol) (Prepared as described in J. Med. Chem. 2009, 52, 3248-3258) in 50 ml DCM was added Oxolyl chloride (2 ml, 15.87 mmol) and stirred at room temperature for about 6 hours and completion of the reaction monitored by TLC. The reaction mixture was concentrated under reduced pressure and the residue was taken in DCM (15 ml) then kept under $N_2$ atmosphere.

To a stirred solution of (1R,3S)-3-((4-ethylpiperazin-1-yl) methyl)cyclopentanamine (0.43 g, 1.5 mmol) in DCM (50 ml) triethyl amine (0.3 ml, 3.12 mmol) was added at about 0° C. and stirred for about 15 minutes then the above prepared acid chloride was added and stirred continually at room temperature for about 8 hours and completion of reaction monitored by TLC. The reaction mixture was neutralized with saturated $NaHCO_3$ and extracted with DCM, the organic layer was dried over $Na_2SO_4$ and concentrated under reduced pressure. The residue was purified by silica gel column chromatography using 5% methanol in DCM as eluent to furnish the title compound (0.56 g) as a white solid. $^1$H NMR (300 MHz, $CDCl_3$): 0.57-0.97 (m, 19H); 1.18-1.21 (m, 8H); 1.25-1.41 (m, 12H); 1.49-1.62 (m, 8H); 1.65-1.82 (m, 10H); 1.85-1.98 (m, 4H); 2.56-2.69 (m, 2H); 2.88-3.06 (m, 3H); 3.29-3.38 (m, 1H); 3.89-3.90 (m, 1H); 4.25-4.70 (m, 4H); 5.78 (s, 1H); 6.12-6.15 (d, J=9 Hz, 1H); 7.19-7.29 (m, 6H); MASS: 692 (100%).

Example 35

Preparation of (1R,3aS,5aR,5bR,7aR,9S,11aR,11bR, 13aR,13bR)-N-((1R,3S)-3-((4-ethylpiperazin-1-yl) methyl)cyclopentyl)-9-hydroxy-5a,5b,8,8,11a-pentamethyl-1-(prop-1-en-2-yl)icosahydro-1H-cyclopenta[a]chrysene-3a-carboxamide

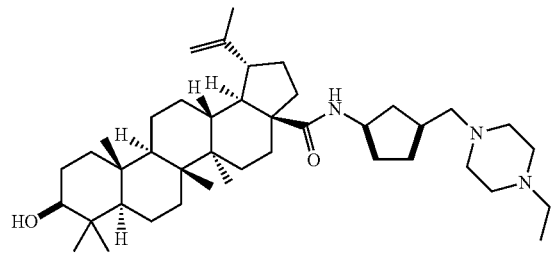

1R,3aS,5aR,5bR,7aR,9S,11aR,11bR,13aR,13bR)-3a-((1R,3S)-3-((4-ethylpiperazin-1-yl)methyl)cyclopentylcarbamoyl)-5a,5b,8,8,11a-pentamethyl-1-(prop-1-en-2-yl) icosahydro-1H-cyclopenta[a]chrysen-9-yl acetate (Example 34, 0.5 g) in MeOH:THF (8:8 ml) and cooled the contents to 0° C. then sodium hydroxide (0.12 g in 4 ml water) was added and the contents were stirred for about 6 hours at room temperature then completion of the reaction was monitored by TLC. The reaction mixture was evaporated under reduced pressure, the residue was taken in water and extracted with DCM. The organic layer was dried over $Na_2SO_4$ and concentrated under reduced pressure. The residue was purified by silica gel column chromatography using 5% methanol in DCM as eluent to furnish the title compound (0.34 g) as a white solid. $^1$H NMR (300 MHz, $CDCl_3$): 0.57-0.97 (m, 19H); 1.18-1.21 (m, 8H); 1.25-1.41 (m, 12H); 1.49-1.62 (m, 8H); 1.65-1.82 (m, 10H); 1.85-1.98 (m, 4H); 2.56-2.69 (m, 2H); 2.88-3.06 (m, 3H); 3.29-3.38 (m, 1H); 3.89-3.90 (m, 1H); 4.25-4.70 (m, 4H); 5.78 (s, 1H); MASS: 650 (100%).

Example 36

Preparation of 4-((1R,3aS,5aR,5bR,7aR,9S,11aR,11bR,13aR,13bR)-3a-((1R,3S)-3-((4-ethylpiperazin-1-yl)methyl)cyclopentylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid

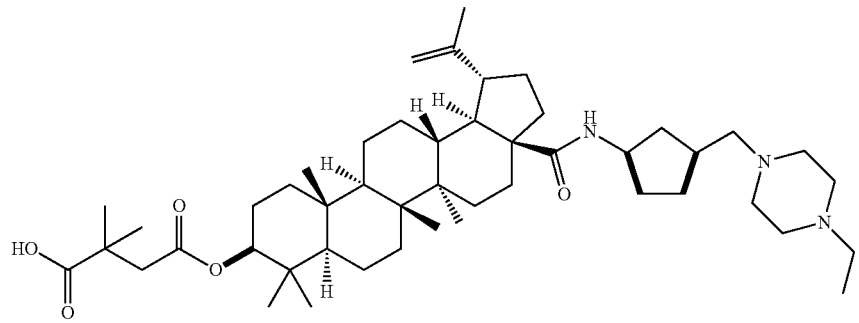

To a stirred solution of (1R,3aS,5aR,5bR,7aR,9S,11aR,11bR,13aR,13bR)-N-((1R,3S)-3-((4-ethylpiperazin-1-yl)methyl)cyclopentyl)-9-hydroxy-5a,5b,8,8,11a-pentamethyl-1-(prop-1-en-2-yl)icosahydro-1H-cyclopenta[a]chrysene-3a-carboxamide (Example 35, 0.24 mmol) in pyridine (5 ml) dimethyl amino pyridine (0.32 g, 0.48 mmol) and 3,3-dimethyldihydrofuran-2,5-dione (1.3 ml) were added and the contents were refluxed for about 16 hours and completion of the reaction was monitored by TLC. The reaction mixture was diluted with ethyl acetate (30 ml). The organic layer was washed with 5% aqueous HCl, washed with water followed by brine solution, dried over $Na_2SO_4$ and concentrated under reduced pressure. The residue was purified by silica gel column chromatography using 5% MeOH in DCM as eluent to furnish the title compound (0.1 g) as a white solid. $^1$H NMR (300 MHz, $CDCl_3$): 0.80-0.95 (m, 16H) 1.23-1.90 (m, 41H); 2.03-3.08 (m, 16H), 4.13-4.18 (m, 1H), 4.46 (s, 1H), 4.58 (s, 1H), 4.72 (s, 1H); 5.61-5.63 (m, 1H); ES Mass: [M+1] 778 (100%); HPLC: 78.4%.

Example 37

Preparation of methyl 3-((1S,3R)-3-((1R,3aS,5aR,5bR,7aR,9S,11aR,11bR,13aR,13bR)-9-acetoxy-5a,5b,8,8,11a-pentamethyl-1-(prop-1-en-2-yl)icosahydro-1H-cyclopenta[a]chrysene-3a-carboxamido)-2,2-dimethylcyclobutanecarboxamido)propanoate Step 1: Synthesis of methyl 3-((1S,3R)-3-(tert-butoxycarbonylamino)-2,2-dimethylcyclobutanecarboxamido)propanoate

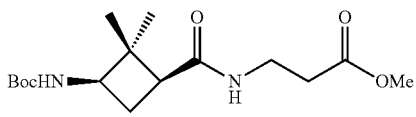

To a stirred solution of (1S,3R)-3-(tert-butoxycarbonylamino)-2,2-dimethylcyclobutanecarboxylic acid (0.3 g, 1.234 mmol) in DCM (5 ml) EDCI (0.284 g, 1.48 mmol) and HOBt (0.2 g, 1.48 mmol) were added at about 0° C., after 10 minutes methyl 3-aminopropanoate hydrochloride (0.254 g, 2.47 mmol) and $Et_3N$ (0.9 ml, 6.17 mmol) in DCM (5 ml) were added drop wise and the reaction mass was allowed to stir at room temperature for about 16 hours. After completion of the reaction (monitored by TLC), the reaction mixture was diluted with DCM and washed with water and saturated $NaHCO_3$ solution, then washed with aqueous 1N HCl, then washed with water and saturated brine, and the organic layer was concentrated under reduced pressure, the resulting crude was purified by silica gel column (100-200 mesh, elution 70% EtOAC in hexane) to afford the title compound as solid. Wt: 0.336 g; Yield: 88.9%; $^1$H NMR (300 MHz, $CDCl_3$): δ 5.89 (brs, 1H), 4.79 (d, 1H, J=8.1 Hz), 3.88-3.73 (m, 1H), 3.70 (s,

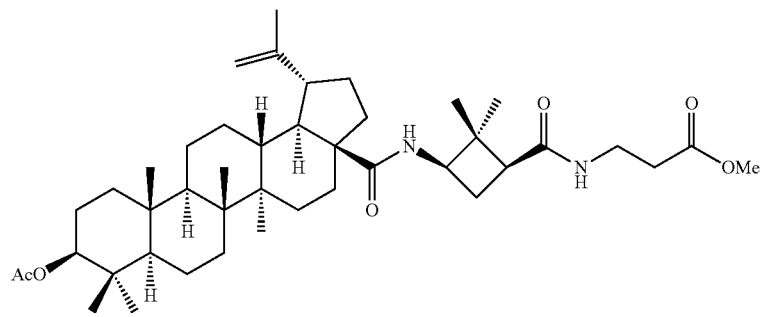

3H), 3.59-3.42 (m, 2H), 2.54-2.51 (m, 2H), 2.39-2.20 (m, 2H), 2.11-1.99 (m, 1H), 1.43 (s, 9H), 1.26 (s, 3H), 0.87 (s, 3H); Mass: [M+Na]$^+$ 351 (100%); IR (KBr, cm$^{-1}$): 3359, 3319, 2973, 1737, 1696, 1667, 1539, 1454, 1366, 1271, 1254, 1176, 1051, 1024, 782, 683; M.R: 98.6° C.-100.2° C.

Step 2: synthesis of methyl 3-((1S,3R)-3-amino-2,2-dimethylcyclobutanecarboxamido)propanoate

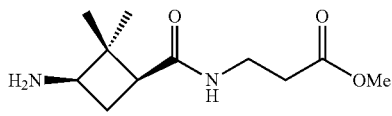

A stirred solution of methyl 3-((1S,3R)-3-(tert-butoxycarbonylamino)-2,2-dimethylcyclobutanecarboxamido)propanoate (step 1, 0.336 g, 1.024 mmol) in TFA:DCM (1:4) (4 ml) at 0° C.-room temperature for about 1 hour and after completion of the reaction, the solvent was evaporated and the crude dissolved in DCM and basified with Et$_3$N (0.87 ml, 6.29 mmol) then the resulting solution as such used for the next reaction. Wt: 0.233 g (Based on 100% yield calculated and proceeded for next reaction).

Step 3: Preparation of methyl 3-((1S,3R)-3-((1R,3aS, 5aR,5bR,7aR,9S,11aR,11bR,13aR,13bR)-9-acetoxy-5a,5b,8,8,11a-pentamethyl-1-(prop-1-en-2-yl) icosahydro-1H-cyclopenta[a]chrysene-3a-carboxamido)-2,2-dimethylcyclobutanecarboxamido)propanoate To a stirred solution of (1R,3aS,5aR,5bR,7aR,9S,11aR, 11bR,13aR,13bR)-9-acetoxy-5a,5b,8,8,11a-pentamethyl-1-(prop-1-en-2-yl)icosahydro-1H-cyclopenta[a]chrysene-3a-carboxylic acid (0.25 g, 0.502 mmol) (Prepared as described in J. Med. Chem. 2009. 52, 3248-3258) in DCM (1 ml) Oxolyl chloride (2 M) in DCM (2.5 ml, 5.02 mmol) was added and stirred at room temperature for about 3 hours and completion of the reaction was monitored by TLC then the solvent was evaporated under a nitrogen atmosphere and dissolved in DCM (4 ml), which was added to a solution of methyl 3-((1S,3R)-3-amino-2,2-dimethylcyclobutanecarboxamido) propanoate (step 2) in DCM (5 ml) at about 0° C. and allowed to stir at room temperature for 16 hours. After completion of the reaction (monitored by TLC), the reaction mixture was diluted with DCM and washed with water, 1N HCl, water brine and dried over Na$_2$SO$_4$, the solvent was evaporated and purified by silica gel column (100-200 mesh, elution 25% EtOAc in hexane) to afford the compound as a off white solid. Wt: 0.150 g: Yield: 35.2%; $^1$H NMR (300 MHz, CDCl$_3$): δ 5.99 (d, 1H, J=8.1 Hz), 5.90 (t, 1H, J=6.0 Hz), 4.73 (s, 1H), 4.58 (s, 1H), 4.50-4.41 (m, 1H), 4.14-4.04 (m, 1H), 3.70 (s, 3H), 3.59-3.43 (m, 3H), 3.17-3.08 (m, 1H), 2.59-2.22 (m, 6H), 2.19-2.06 (m, 1H), 2.04 (s, 3H), 1.99-1.87 (m, 2H), 1.80-1.12 (m, 25H), 0.96-0.73 (s, 18H); Mass: [M+Na]$^+$ 731 (100%); IR (KBr, cm$^{-1}$): 3375, 2952, 1736, 1656, 1516, 1439, 1369, 1247, 1178, 1074, 1027, 980, 885; M.R: 87.9° C.-90.7° C.

Example 38

Preparation of 3-((1S,3R)-3-((1R,3aS,5aR,5bR,7aR, 9S,11aR,11bR,13aR,13bR)-9-hydroxy-5a,5b,8,8, 11a-pentamethyl-1-(prop-1-en-2-yl)icosahydro-1H-cyclopenta[a]chrysene-3a-carboxamido)-2,2-dimethylcyclobutanecarboxamido)propanoic acid

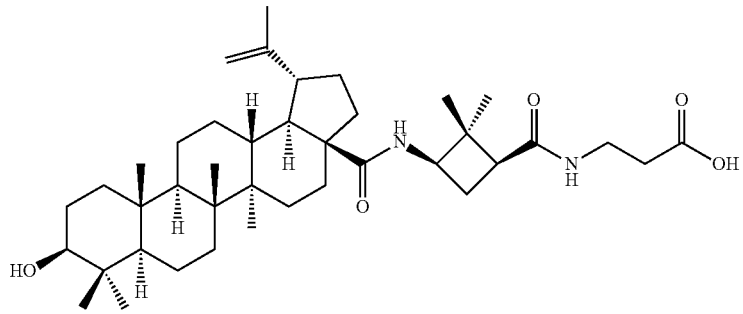

To a stirred solution of methyl 3-((1S,3R)-3-((1R,3aS,5aR, 5bR,7aR,9S,11aR,11bR,13aR,13bR)-9-acetoxy-5a,5b,8,8, 11a-pentamethyl-1-(prop-1-en-2-yl)icosahydro-1H-cyclopenta[a]chrysene-3a-carboxamido)-2,2-dimethylcyclobutanecarboxamido)propanoate (Example 37, 0.150 g, 0.211 mmol) in MeOH:THF (2:1) (7.5 ml), 2N NaOH (2.5 ml) was added at about 0° C. and allowed to stir at room temperature for about 16 hours. After completion of the reaction (monitored by TLC), the volatile was evaporated. The reaction mixture was acidified with 1N HCl, filtered, washed with water and dried under vacuum to afford the title compound as an off white solid. Wt: 0.030 g: Yield: 21.7%; $^1$H NMR (300 MHz, DMSO-d6): δ 7.61 (brm, 1H), 7.54 (d, 1H, J=7.2 Hz), 4.63 (s, 1H), 4.52 (s, 1H), 2.90-2.80 (m, 1H), 3.20-3.08 (m, 3H), 3.00-2.89 (m, 3H), 2.68-2.54 (m, 2H), 2.40-2.18 (m, 5H), 1.90-1.74 (m, 2H), 1.70-1.00 (m, 28H), 0.90, 0.86, 0.84, 0.75, 0.72, 0.64 (s, 15H); Mass: [M+1]$^+$ 653 (2%), [M+Na]$^+$ 675 (100%); IR (KBr, cm$^{-1}$): 3408, 2947, 2868, 1724, 1652, 1636, 1523, 1376, 1250, 1194, 1108, 1074, 1033, 983, 881, 730; M.R: 188.6° C.-200.1° C.; HPLC: 99.35%.

Example 39

Preparation of (S)-methyl 2-((1S,3R)-3-((1R,3aS, 5aR,5bR,7aR,9S,11aR,11bR,13aR,13bR)-9-acetoxy-5a,5b,8,8,11a-pentamethyl-1-(prop-1-en-2-yl) icosahydro-1H-cyclopenta[a]chrysene-3a-carboxamido)-2,2-dimethylcyclobutanecarboxamido)-3-methylbutanoate

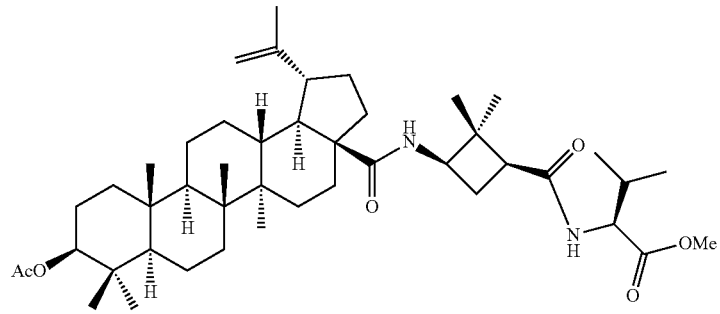

Step 1: Synthesis of (S)-methyl 2-((1S,3R)-3-(tert-butoxycarbonylamino)-2,2-dimethylcyclobutanecarboxamido)-3-methylbutanoate

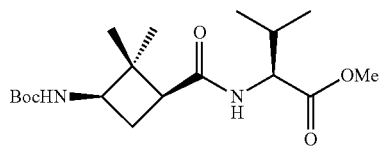

To a stirred solution of (1S,3R)-3-(tert-butoxycarbonylamino)-2,2-dimethylcyclobutanecarboxylic acid (0.350 g, 1.44 mmol) in DCM (5 ml) EDCI (0.331 g, 1.73 mmol) and HOBt (0.234 g, 1.73 mmol) were added at about 0° C. After 10 minutes, (S)-methyl 2-amino-3-methylbutanoate hydrochloride (0.720, 8.64 mmol) and Et$_3$N (1.2 ml, 6.17 mmol) in DCM (5 ml) were added drop wise and the reaction mass was allowed to stir at room temperature for about 16 hours. After completion of the reaction (monitored by TLC), the reaction mixture was diluted with DCM and washed with water and saturated NaHCO$_3$ solution, then washed with aqueous 1N HCl, then washed with water and saturated brine, and the organic layer was concentrated under reduced pressure, the resulting crude was purified by silica gel column (100-200 mesh, elution 70% EtOAC in hexane) to afford the title compound as a solid. Wt: 0.440 g; Yield: 85.9%; $^1$H NMR (300 MHz, CDCl$_3$): δ 5.62 (d, 1H, J=8.4 Hz), 4.77 (d, 1H, J=8.4 Hz), 4.70-4.60 (m, 1H), 4.89-4.71 (m, 1H), 3.72 (s, 3H), 2.46-2.21 (m, 2H), 2.18-1.99 (m, 1H), 1.70-1.50 (m, 1H), 1.42 (s, 9H), 1.31 (s, 3H), 0.94-0.90 (s, 9H); Mass: The related mass peak was not observed; IR (KBr, cm$^{-1}$): 3345, 3314, 2960, 1753, 1690, 1664, 1529, 1456, 1366, 1271, 1172, 1049, 1028, 986, 873.

Step 2: Synthesis of (S)-methyl 2-((1S,3R)-3-amino-2,2-dimethylcyclobutanecarboxamido)-3-methylbutanoate

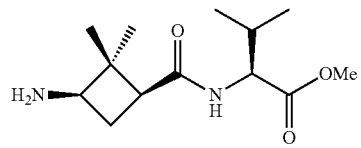

A stirred solution of (S)-methyl 2-((1S,3R)-3-(tert-butoxycarbonylamino)-2,2-dimethylcyclobutanecarboxamido)-3-methylbutanoate (step 1, 0.430 g, 1.21 mmol) in TFA:DCM (1:4) (4 ml) at 0° C.-room temperature for about 1 hour. After completion of the reaction, the solvent was evaporated and the crude was dissolved in DCM and basified with Et$_3$N (1.0 ml, 7.25 mmol) then the resulting solution as such used for next reaction immediately. Wt: 0.309 g (Based on 100% yield calculated and proceeded for next reaction).

Step 3: Preparation of (S)-methyl 2-((1S,3R)-3-((1R, 3aS,5aR,5bR,7aR,9S,11aR,11bR,13aR,13bR)-9-acetoxy-5a,5b,8,8,11a-pentamethyl-1-(prop-1-en-2-yl)icosahydro-1H-cyclopenta[a]chrysene-3a-carboxamido)-2,2-dimethylcyclobutanecarboxamido)-3-methylbutanoate To a stirred solution of (1R,3aS,5aR,5bR,7aR,9S,11aR,11bR,13aR,13bR)-9-acetoxy-5a,5b,8,8,11a-pentamethyl-1-(prop-1-en-2-yl)icosahydro-1H-cyclopenta[a]chrysene-3a-carboxylic acid (0.350 g, 0.702 mmol) (Prepared as described in J. Med. Chem. 2009. 52, 3248-3258) in DCM (1 ml) Oxolyl chloride (2 M) in DCM (3.51 ml, 0.702 mmol) was added at 0° C. and stirred at room temperature for about 3 hours and completion of the reaction monitored by TLC then the solvent was evaporated under nitrogen atmosphere and dissolved in DCM (4 ml), which was added to a solution of (S)-methyl 2-((1S,3R)-3-amino-2,2-dimethylcyclobutanecarboxamido)-3-methylbutanoate (Step 2, 0.27 g) in DCM (5 ml) at 0° C. and allowed to stir at room temperature for about 16 hours. After completion of the reaction (monitored by TLC), the reaction mixture was diluted with DCM and washed with aqueous 1N HCl, then water and brine, and dried over Na$_2$SO$_4$, the solvent was evaporated and purified by silica gel column (100-200 mesh, elution 30% EtOAc in hexane) to afford the title compound as an off white solid. Wt: 0.300 g: Yield: 35.2%; $^1$H NMR (300 MHz, CDCl$_3$): δ 5.87 (d, 1H, J=8.1 Hz), 5.56 (d, 1H, J=8.1 Hz), 4.72 (s, 1H), 4.61 (s, 1H), 4.50-4.40 (m, 1H), 4.18-4.08 (m, 1H), 3.74 (s, 3H), 3.17-3.07 (m, 1H), 2.53-2.40 (m, 2H), 2.38-2.24 (m, 1H), 2.19-2.04 (m, 1H), 2.03 (s, 3H), 1.99-1.84 (m, 2H), 1.79-1.11 (m, 21H), 1.09-0.74 (m, 32H); Mass: [M+Na]$^+$ 759 (100%).

Example 40

Preparation of (S)-2-((1S,3R)-3-((1R,3aS,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysene-3a-carboxamido)-2,2-dimethylcyclobutanecarboxamido)-3-methylbutanoic acid

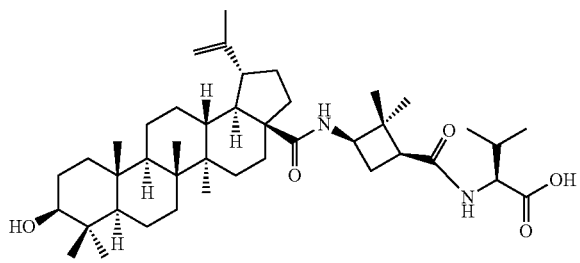

To a stirred solution of (S)-methyl 2-((1S,3R)-3-((1R,3aS,5aR,5bR,7aR,9S,11aR,11bR,13aR,13bR)-9-acetoxy-5a,5b,8,8,11a-pentamethyl-1-(prop-1-en-2-yl)icosahydro-1H-cyclopenta[a]chrysene-3a-carboxamido)-2,2-dimethylcyclobutanecarboxamido)-3-methylbutanoate (Example 39, 0.300 g, 0.407 mmol) in MeOH:THF (2:1) (7.5 ml) 2N NaOH (2.5 ml) was added at 0° C. and allowed to stir at room temperature for about 16 hours. After completion of the reaction (monitored by TLC), the volatile was evaporated and the reaction mixture was acidified with 1N HCl, filtered, washed with water and dried under vacuum to afford the title compound as an off white solid. Wt: 0.180 g: Yield: 64.9%; $^1$H NMR (300 MHz, DMSO-d6): δ 7.55 (d, 2H, J=6.6 Hz), 4.62 (s, 1H), 4.51 (s, 1H), 4.20-4.11 (m, 1H), 3.91-3.82 (m, 1H), 3.00-2.98 (m, 2H), 2.71-2.56 (m, 1H), 2.48-2.39 (m, 1H), 2.37-2.18 (m, 2H), 1.92-1.76 (m, 2H), 1.69-1.15 (m, 32H), 0.93-0.76 (m, 15H), 0.85 (s, 3H), 0.84 (s, 3H); Mass: [M+Na]$^+$ 703 (100); IR (KBr, cm$^{-1}$): 3321, 2951, 1713, 1631, 1532, 1460, 1386, 1252, 1169, 1108, 1044, 983, 882; M.R: 203.9° C.-205.0° C.; HPLC: 97.3%.

Example 41

Preparation of (S)-methyl 2-((1S,3R)-3-((1R,3aS,5aR,5bR,7aR,9S,11aR,11bR,13aR,13bR)-9-acetoxy-5a,5b,8,8,11a-pentamethyl-1-(prop-1-en-2-yl)icosahydro-1H-cyclopenta[a]chrysene-3a-carboxamido)-2,2-dimethylcyclobutanecarboxamido)-4-methylpentanoate

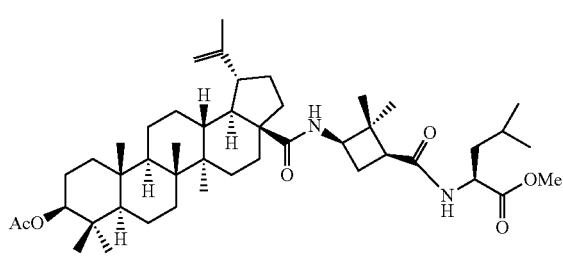

Step 1: Synthesis of (S)-methyl 2-((1S,3R)-3-(tert-butoxycarbonylamino)-2,2-dimethylcyclobutanecarboxamido)-4-methylpentanoate

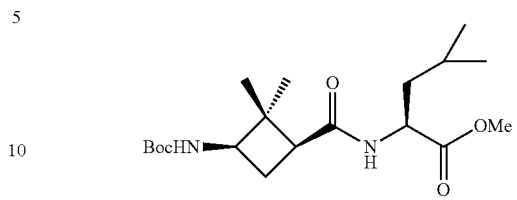

To a stirred solution of (1S,3R)-3-(tert-butoxycarbonylamino)-2,2-dimethylcyclobutanecarboxylic acid (0.350 g, 1.44 mmol) in DCM (5 ml) EDCI (0.331 g, 1.73 mmol) and HOBt (0.234 g, 1.73 mmol) were added at 0° C. After 10 minutes, (S)-methyl 2-amino-4-methylpentanoate hydrochloride (0.780, 4.32 mmol) and Et$_3$N (1.2 ml, 8.64 mmol) in DCM (5 ml) were added drop wise and the reaction mass was allowed to stir at room temperature for about 16 hours. After completion of the reaction (monitored by TLC), the reaction mixture was diluted with DCM and washed with water, sat. NaHCO$_3$ solution, water, 1N HCl, water and saturated brine and the organic layer was concentrated under reduced pressure, the resulting crude was purified by silica gel column (100-200 mesh, elution 65% EtOAC in hexane) to afford the title compound as a solid. Wt: 0.210 g; Yield: 39.4%; $^1$H NMR (300 MHz, CDCl$_3$): δ 5.56 (d, 1H), 4.75 (d, 1H, J=9 Hz), 4.70-4.60 (m, 1H), 3.88-3.79 (m, 1H), 3.73 (s, 3H), 2.48-2.25 (m, 2H), 2.14-1.99 (m, 1H), 1.70-1.48 (m, 3H), 1.43 (s, 9H), 1.32 (s, 3H), 0.95-0.91 (m, 9H); Mass: [M+Na]$^+$ 393 (100%); IR (KBr, cm$^{-1}$): 3344, 2960, 2873, 1743, 1689, 1664, 1531, 1458, 1366, 1271, 1174, 1050, 1028, 873, 827, 744; M.R: 100.5° C.-103.9° C.

Step 2: Synthesis of (S)-methyl 2-((1S,3R)-3-amino-2,2-dimethylcyclobutanecarboxamido)-4-methylpentanoate

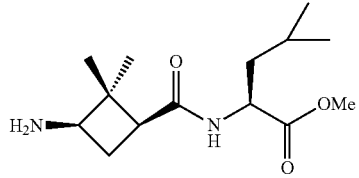

A stirred solution of (S)-methyl 2-((1S,3R)-3-(tert-butoxycarbonylamino)-2,2-dimethylcyclobutanecarboxamido)-4-methylpentanoate (step 1, 0.200 g, 0.54 mmol) in TFA:DCM (1:4) (4 ml) at 0° C.-room temperature for about 1 hour. After completion of the reaction, the solvent was evaporated and the crude was dissolved in DCM and basified with Et$_3$N (0.5 ml, 3.24 mmol) then the resulting solution as such used for next reaction immediately. Wt: 0.145 g (Based on 100% yield calculated and proceeded for next reaction).

Step 3: Preparation of (S)-methyl 2-((1S,3R)-3-((1R,3aS,5aR,5bR,7aR,9S,11aR,11bR,13aR,13bR)-9-acetoxy-5a,5b,8,8,11a-pentamethyl-1-(prop-1-en-2-yl)icosahydro-1H-cyclopenta[a]chrysene-3a-carboxamido)-2,2-dimethylcyclobutanecarboxamido)-4-methylpentanoate To a stirred solution of (1R,3aS,5aR,5bR,7aR,9S,11aR,11bR,13aR,13bR)-9-acetoxy-5a,5b,8,8,11a-pentamethyl-1-(prop-1-en-2-yl)icosahydro-1H-cyclopenta[a]chrysene-3a-carboxylic acid (0.200 g, 0.401 mmol) (Prepared as described in J. Med. Chem. 2009. 52, 3248-3258) in DCM (1 ml) Oxolyl chloride (2 M) in DCM (2.0 ml, 4.016 mmol) was added at 0° C. and stirred at room temperature for about 3 hours and completion of the reaction monitored by TLC then the solvent was evaporated under nitrogen atmosphere and dissolved in DCM (4 ml), which was added to a solution of the above (S)-methyl 2-((1S,3R)-3-amino-2,2-dimethylcyclobutane carboxamido)-4-methylpentanoate (step 2, 0.16 g) in DCM (5 ml) at 0° C. and allowed to stir at room temperature for about 16 hours. After completion of the reaction (monitored by TLC), the reaction mixture was diluted with DCM and washed with water, 1N HCl, water, brine and dried over Na$_2$SO$_4$, the solvent was evaporated and purified by silica gel column (100-200 mesh, elution 25% EtOAc in hexane) to afford the title compound as an off white solid. Wt: 0.195 g: Yield: 64.7%; $^1$H NMR (300 MHz, CDCl$_3$): δ 5.88 (d, 1H, J=8.1 Hz), 5.68 (d, 1H, J=8.7 Hz) 4.72 (s, 1H), 4.57 (s, 1H), 4.50-4.42 (m, 1H), 4.18-4.09 (m, 1H), 3.75 (s, 3H), 3.17-3.05 (m, 1H), 2.57-2.43 (m, 2H), 2.38-2.29 (m, 1H), 2.20-2.08 (m, 2H), 2.04 (s, 3H), 1.99-1.88 (m, 2H), 1.79-1.09 (m, 30H), 0.98-0.78 (m, 24H).

Example 42

Preparation of (S)-2-((1S,3R)-3-((1R,3aS,5aR,5bR, 7aR,9S,11aR,11bR,13aR,13bR)-9-hydroxy-5a,5b,8, 8,11a-pentamethyl-1-(prop-1-en-2-yl)icosahydro-1H-cyclopenta[a]chrysene-3a-carboxamido)-2,2-dimethylcyclobutanecarboxamido)-4-methylpentanoic acid

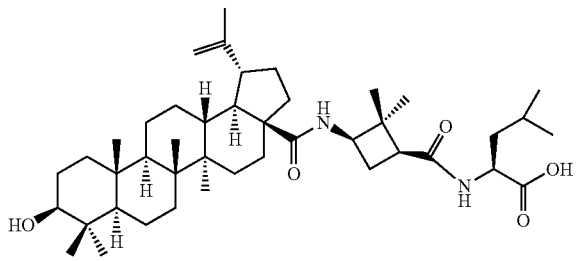

To a stirred solution of (S)-methyl 2-((1S,3R)-3-((1R,3aS, 5aR,5bR,7aR,9S,11aR,11bR,13aR,13bR)-9-acetoxy-5a,5b, 8,8,11a-pentamethyl-1-(prop-1-en-2-yl)icosahydro-1H-cyclopenta[a]chrysene-3a-carboxamido)-2,2-dimethylcyclobutanecarboxamido)-4-methylpentanoate (Example 41, 0.190 g, 0.253 mmol) in MeOH:THF (2:1) (7.5 ml) 2N NaOH (2.5 ml) was added at 0° C. and allowed to stir at room temperature for about 16 hours. After completion of the reaction (monitored by TLC), the volatiles were evaporated and the reaction mixture was acidified with 1N HCl, extracted with EtOAc, dried over Na$_2$SO$_4$ then the organic layer was concentrated and dried under vacuum to afford the title compound as an off white solid. Wt: 0.100 g: Yield: 56.7%; $^1$H NMR (300 MHz, DMSO-d6): δ 7.69 (d, 1H, J=8.1 Hz), 7.54 (d, 1H, J=6.6 Hz), 4.62 (s, 1H), 4.51 (s, 1H), 4.29-4.18 (m, 2H), 3.95-3.84 (m, 1H), 3.01-2.88 (m, 2H), 2.34-2.18 (m, 3H), 1.91-1.72 (m, 3H), 1.69-1.10 (m, 31H), 0.96-0.58 (m, 23H); Mass: [M+1]+694 (10%), [M+Na]$^+$ 717 (100%); IR (KBr, cm$^{-1}$): 3454, 2950, 1726, 1634, 1523, 1466, 1369, 1266, 1207, 1195, 1157, 1044, 1009, 922, 882, 722; M.R: 192.4° C.-213.8° C.; HPLC: 95.97%.

Example 43

Preparation of (1R,3aS,5aR,5bR,7aR,9S,11aR,11bR, 13aR,13bR)-3a-((1R,3S)-2,2-dimethyl-3-(pyrrolidine-1-carbonyl)cyclobutylcarbamoyl)-5a,5b,8,8, 11a-pentamethyl-1-(prop-1-en-2-yl)icosahydro-1H-cyclopenta[a]chrysen-9-yl acetate

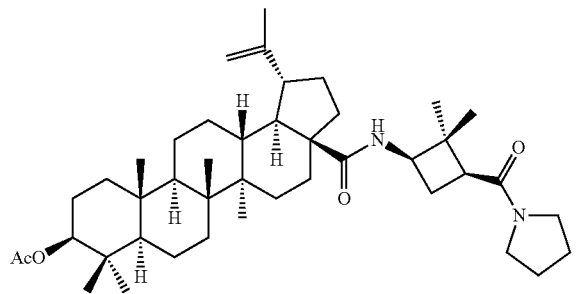

Step 1: Synthesis of tert-butyl (1R,3S)-2,2-dimethyl-3-(pyrrolidine-1-carbonyl)cyclobutylcarbamate

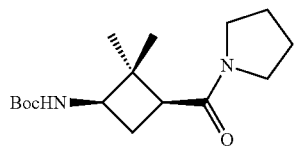

To a stirred solution of (1S,3R)-3-(tert-butoxycarbonylamino)-2,2-dimethylcyclobutanecarboxylic acid (0.700 g, 2.88 mmol) in DCM (20 ml) EDCI (0.660 g, 3.456 mmol) and HOBt (0.529 g, 3.456 mmol) were added at about 0° C. and after 10 minutes, pyrrolidine (0.47 ml, 5.761 mmol) and Et$_3$N (1.42 ml, 14.403 mmol) were added drop wise and the reaction mass was allowed to stir at room temperature for about 12 hours. After completion of the reaction (monitored by TLC), the reaction mixture was diluted with DCM and washed with water and saturated NaHCO$_3$ solution, then washed with aqueous 1N HCl, then water and saturated brine, and the organic layer was concentrated under reduced pressure, the resulting crude residue was stirred in hexane and the resulting solid was obtained which was filtered and dried under vacuum. Wt: 0.400 g; Yield: 46.9%; $^1$H NMR (300 MHz, CDCl$_3$): δ 5.00 (d, 1H, J=7.5 Hz), 3.89-3.77 (m, 1H), 3.57-3.29 (m, 4H), 2.78-2.68 (m, 1H), 2.31-2.22 (m, 2H), 1.98-1.78 (m, 4H), 1.43 (s, 9H), 1.35 (s, 3H), 0.89 (s, 31-1); Mass: [M+1]$^+$ 297 (40%), [M+Na]$^+$ 319 (100%); 1R (KBr, cm$^{-1}$): 3312, 2977, 2956, 1709, 1621, 1606, 1526, 1442, 1365, 1348, 1283, 1267, 1176, 1106, 1046, 1009, 912, 877; M.R: 164.8° C.-165.5° C.

Step 2: Synthesis of ((1S,3R)-3-amino-2,2-dimethylcyclobutyl)(pyrrolidin-1-yl)methanone

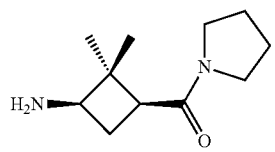

A solution of tert-butyl (1R,3S)-2,2-dimethyl-3-(pyrrolidine-1-carbonyl)cyclobutylcarbamate (step 1, 0.400 g, 1.351 mmol) in TFA:DCM (1:2) (3 ml) stirred at 0° C.-room temperature for about 1 hour. After completion of the reaction, the solvent was evaporated and the crude was dissolved in DCM and basified with Et₃N (1.124 ml, 8.108 mmol) the resulting solution as such used for next reaction immediately. Wt: 0.264 g (Based on 100% yield calculated and proceeded for next reaction).

Step 3: Preparation of (1R,3aS,5aR,5bR,7aR,9S, 11aR,11bR,13aR,13bR)-3a-(1R,3S)-2,2-dimethyl-3-(pyrrolidine-1-carbonyl)cyclobutylcarbamoyl)-5a,5b, 8,8,11a-pentamethyl-1-(prop-1-en-2-yl)icosahydro-1H-cyclopenta[a]chrysen-9-yl acetate To a stirred solution of (1R,3aS,5aR,5bR,7aR,9S,11aR, 11bR,13aR,13bR)-9-acetoxy-5a,5b,8,8,11a-pentamethyl-1-(prop-1-en-2-yl)icosahydro-1H-cyclopenta[a]chrysene-3a-carboxylic acid (0.336 g, 0.674 mmol) (Prepared as described in J. Med. Chem. 2009. 52, 3248-3258) in DCM (1 ml) Oxolyl chloride (0.58 ml, 6.746 mmol) in DCM (3.15 ml) was added at 0° C. and stirred at room temperature for about 3 hours and completion of the reaction monitored by TLC then the solvent was evaporated under nitrogen atmosphere and dissolved in DCM (4 ml), which was added to the above stirred solution of ((1S,3R)-3-amino-2,2-dimethylcyclobutyl)(pyrrolidin-1-yl)methanone (step 2, 0.264 g, 1.349 mmol) at 0° C. and allowed to stir at room temperature for about 16 hours. After completion of the reaction (monitored by TLC), the reaction mixture was diluted with DCM and washed with aqueous 1N HCl, then washed with water and brine, and dried over Na₂SO₄, the solvent was evaporated and purified by silica gel column (100-200 mesh, elution 15% EtOAc in hexane) to afford the title compound as an off white solid. Wt: 0.350 g: Yield: 76.7%; ¹H NMR (300 MHz, CDCl₃): δ 6.28 (d, 1H), 4.72 (s, 1H), 4.58 (s, 1H), 4.51-4.06 (m, 2H), 3.56-3.27 (m, 8H), 3.18-3.08 (m, 1H), 2.91-2.74 (m, 2H), 2.60-2.46 (m, 2H), 2.37-2.20 (m, 3H), 2.08 (s, 3H), 1.99-1.11 (m, 26H), 1.00-0.75 (s, 18H); Mass: [M+Na]⁺ 699 (100%); IR (KBr, cm⁻¹): 3268, 3077, 2955, 2873, 1734, 1716, 1618, 1549, 1455, 1452, 1371, 1344, 1242, 1180, 1150, 1033, 980, 869; M.R: 94.9° C.-101.2° C.

Example 44

Preparation of (1R,3aS,5aR,5bR,7aR,9S,11aR,11bR, 13aR,13bR)-N-((1R,3S)-2,2-dimethyl-3-(pyrrolidine-1-carbonyl)cyclobutyl)-9-hydroxy-5a,5b,8,8, 11a-pentamethyl-1-(prop-1-en-2-yl)icosahydro-1H-cyclopenta[a]chrysene-3a-carboxamide

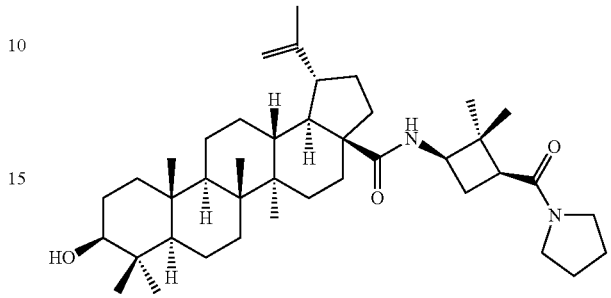

To a stirred solution of (1R,3aS,5aR,5bR,7aR,9S,11aR, 11bR,13aR,13bR)-3a-((1R,3S)-2,2-dimethyl-3-(pyrrolidine-1-carbonyl)cyclobutylcarbamoyl)-5a,5b,8,8,11a-pentamethyl-1-(prop-1-en-2-yl)icosahydro-1H-cyclopenta[a]chrysen-9-yl acetate (Example 43, 0.350 g, 0.517 mmol) in MeOH:THF (2:1) (30 ml) 2N NaOH (10 ml) was added at 0° C. and allowed to stir at room temperature for about 16 hours. After completion of the reaction (monitored by TLC), the volatile was evaporated and the aqueous layer was extracted with ethyl acetate and the organic layer was washed with water, brine and dried over Na₂SO₄ then the solvent was evaporated and the resulting crude was stirred in hexane and the resulting solid was obtained which was filtered and dried under vacuum to afford the title compound. Wt: 0.220 g: Yield: 67%; ¹H NMR (300 MHz, CDCl₃): δ 6.27 (d, 1H, J=8.1 Hz), 4.72 (s, 1H), 4.57 (s, 1H), 4.17-4.07 (m, 1H), 3.56-3.11 (m, 4H), 3.19-3.09 (m, 2H), 2.82-2.76 (m, 1H), 2.57-2.43 (m, 1H), 2.39-2.18 (m, 2H), 2.01-1.72 (m, 7H), 1.67 (s, 3H), 1.61-1.11 (m, 22H), 0.96, 0.93, 0.87, 0.81, 0.74 (s, 18H); Mass: [M+1]⁺ 635 (5%), [M+Na]⁺ 657 (100%); IR (KBr, cm⁻¹): 3390, 3071, 2947, 2869, 1617, 1455, 1369, 1341, 1250, 1194, 1168, 1108, 1034, 921, 880; M.R: 176.3° C.-180.9° C.; HPLC: 98.9%.

Example 45

Preparation of 4-((1R,3aS,5aR,5bR,7aR,9S,11aR, 11bR,13aR,13bR)-3a-((1R,3S)-2,2-dimethyl-3-(pyrrolidine-1-carbonyl)cyclobutylcarbamoyl)-5a,5b,8,8, 11a-pentamethyl-1-(prop-1-en-2-yl)icosahydro-1H-cyclopenta[a]chrysen-9-yloxy-2,2-dimethyl-4-oxobutanoic acid

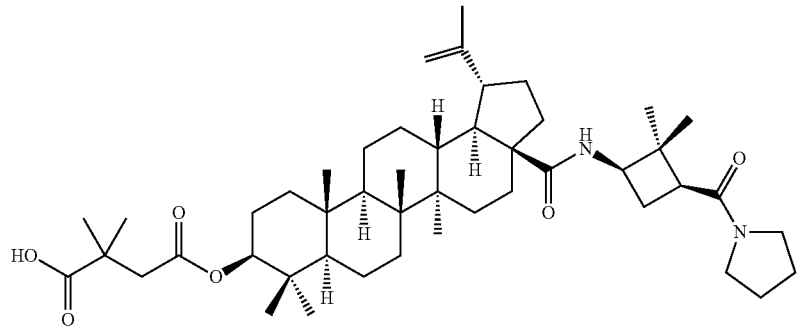

2,2-Dimethylsuccinic anhydride (0.303 g, 2.365 mmol) was added to a stirred solution of (1R,3aS,5aR,5bR,7aR,9S,11aR,11bR,13aR,13bR)-N-((1R,3S)-2,2-dimethyl-3-(pyrrolidine-1-carbonyl)cyclobutyl)-9-hydroxy-5a,5b,8,8,11a-pentamethyl-1-(prop-1-en-2-yl)icosahydro-1H-cyclopenta[a]chrysene-3a-carboxamide (Example 44, 0.150 g, 0.236 mmol) and DMAP (0.057 g, 0.473 mmol) in pyridine (10 ml) at room temperature and refluxed for about 24 hours. After completion of the reaction (monitored by TLC), the reaction mixture was diluted with EtOAc, washed with aqueous 1N HCl, them washed with water and brine, and dried over $Na_2SO_4$, the solvent was evaporated and purified by silica gel column (100-200 mesh, elution 20% EtOAc in hexane) to afford the title compound as an off white solid. Wt: 0.045 g: Yield: 24.4%; $^1$H NMR (300 MHz, $CDCl_3$): δ 6.33 (d, 1H, J=7.8 Hz), 4.73 (s, 1H), 4.57 (s, 1H), 4.53-4.46 (m, 1H), 4.16-4.07 (m, 1H), 3.54-3.30 (m, 4H), 3.18-3.08 (m, 1H), 2.82-2.42 (m, 6H), 2.34-2.27 (m, 2H), 2.08-1.78 (m, 8H), 1.78-1.10 (m, 30H), 098-0.71 (s, 18H); Mass: [M+1]$^+$ 763 (30%), [M+Na]$^+$ 785 (100%); IR (KBr, cm$^{-1}$): 3407, 2951, 2346, 2273, 1726, 1619, 1453, 1192, 1019, 879; HPLC: 96.0%; M.R: 134.8° C.-145.0° C.

Example 46

Preparation of (1R,3aS,5aR,5bR,7aR,9S,11aR,11bR,13aR,13bR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yl acetate

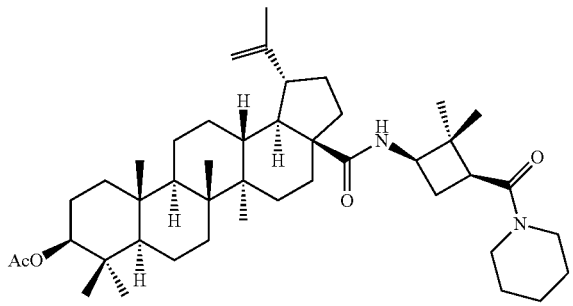

Step 1: Synthesis of tert-butyl (1R,3S)-2,2-dimethyl-3-(piperidine-1-carbonyl)cyclobutylcarbamate

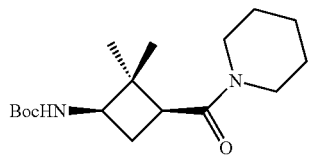

To a stirred solution of (1S,3R)-3-(tert-butoxycarbonylamino)-2,2-dimethylcyclobutanecarboxylic acid (0.500 g, 2.057 mmol) in DCM (20 ml) EDCI (0.472 g, 2.469 mmol) and HOBt (0.378 g, 2.469 mmol) were added at 0° C. and after 10 minutes, piperidine (0.4 ml, 4.115 mmol) and $Et_3N$ (1.42 ml, 10.288 mmol) were added drop wise and the reaction mass was allowed to stir at room temperature for about 12 hours. After completion of the reaction (monitored by TLC), the reaction mixture was diluted with DCM and washed with water, sat. $NaHCO_3$ solution, water, 1N HCl, water, saturated brine and the organic layer was concentrated under reduced pressure, the resulting crude residue was stirred in hexane and the resulting solid was obtained which was filtered and dried under vacuum to afford the title compound. Wt: 0.400 g; Yield: 62.79%; $^1$H NMR (300 MHz, $CDCl_3$): δ 4.77 (d, 1H, J=8.4 Hz), 3.89-3.78 (m, 1H), 3.77-3.67 (m, 1H), 3.49-3.28 (m, 3H), 2.87-2.76 (m, 1H), 2.40-2.18 (m, 2H), 1.70-1.46 (m, 6H), 1.43 (s, 9H), 1.33 (s, 3H), 0.87 (s, 3H); Mass: [M+1]$^+$ 311 (35%), [M+Na]$^+$ 333 (100%); IR (KBr, cm$^{-1}$): 3337, 2939, 1712, 1628, 1522, 1456, 1445, 1388, 1353, 1366, 1288, 1264, 1254, 1217, 1172, 1047, 1026, 1013, 976; M.R: 176.0° C.-178.0° C.

Step 2: Synthesis of ((1S,3R)-3-amino-2,2-dimethyl-cyclobutyl)(piperidin-1-yl)methanone

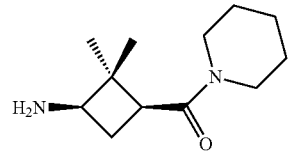

A solution of tert-butyl (1R,3S)-2,2-dimethyl-3-(piperidine-1-carbonyl)cyclobutylcarbamate (step 1, 0.500 g, 1.612 mmol) in TFA:DCM (1:2) (3 ml) stirred at 0° C.-room temperature for about 1 hour. After completion of the reaction (monitored by TLC), the solvent was evaporated and the crude was dissolved in DCM and basified with $Et_3N$ (1.34 ml, 9.677 mmol) then the resulting solution as such used for the next reaction. Wt: 0.338 g (Based on 100% yield calculated and proceeded for next reaction).

Step 3: Preparation of (1R,3aS,5aR,5bR,7aR,9S,11aR,11bR,13aR,13bR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yl acetate To a stirred solution of (1R,3aS,5aR,5bR,7aR,9S,11aR,11bR,13aR,13bR)-9-acetoxy-5a,5b,8,8,11a-pentamethyl-1-(prop-1-en-2-yl)icosahydro-1H-cyclopenta[a]chrysene-3a-carboxylic acid (0.410 g, 0.823 mmol) (Prepared as described in J. Med. Chem. 2009. 52, 3248-3258) in DCM (1 ml) Oxolyl chloride (0.71 ml, 8.232 mmol) in DCM (3.42 ml) was added at 0° C. and stirred at room temperature for about 3 hours and completion of the reaction was monitored by TLC, then the solvent was evaporated under nitrogen atmosphere and dissolved in DCM (4 ml), which was added to a stirred solution of ((1S,3R)-3-amino-2,2-dimethylcyclobutyl)(piperidin-1-yl)methanone (step 2, 0.328 g, 1.56 mmol) at 0° C. and allowed to stir at room temperature for about 16 hours. After completion of the reaction (monitored by TLC), the reaction mixture was diluted with DCM and washed with aqueous 1N HCl, then washed with water and brine, and dried over $Na_2SO_4$ then the solvent was evaporated and purified by silica gel column (100-200 mesh, elution 15% EtOAc in hexane) to afford the title compound as an off white solid. Wt: 0.400 g; Yield: 71.9%; $^1$H NMR (300 MHz, $CDCl_3$): δ 5.85 (d, 1H), 4.72 (s, 1H), 4.58 (s, 1H), 4.50-4.41 (m, 1H), 4.18-4.07 (m, 1H), 3.78-3.67 (m, 1H), 2.50-2.30 (m, 3H), 3.19-3.07 (m, 1H), 2.88 (t, 1H, J=8.1 Hz), 2.54-2.13 (m, 3H), 2.04 (s, 3H), 2.00-1.86 (m, 2H), 1.80-1.11 (m, 33H), 0.95, 0.93, 0.87, 0.83, 0.81 (s, 18H); Mass: [M+H]$^+$ 691 (100%), [M+Na]$^+$ 713 (25%); IR (KBr, cm$^{-1}$): 3395, 2943, 2864, 1736, 1734, 1624, 1444, 1370, 1248, 1192, 1154, 1024, 979, 884; M.R: 140.2° C.-145.8° C.

Example 47

Preparation of (1R,3aS,5aR,5bR,7aR,9S,11aR,11bR, 13aR,13bR)-N-((1R,3S)-2,2-dimethyl-3-(piperidine-1-carbonyl)cyclobutyl)-9-hydroxy-5a,5b,8,8,11a-pentamethyl-1-(prop-1-en-2-yl)icosahydro-1H-cyclopenta[a]chrysene-3a-carboxamide

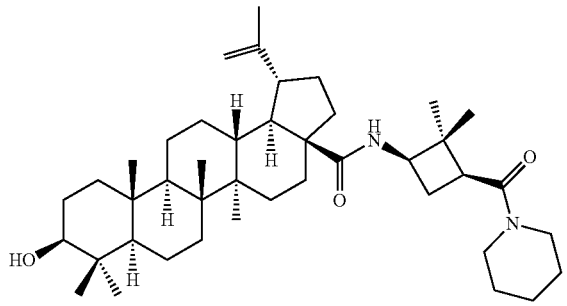

To a stirred solution of (1R,3aS,5aR,5bR,7aR,9S,11aR, 11bR,13aR,13bR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yl acetate (Example 46, 0.400 g, 0.579 mmol) in MeOH:THF (2:1) (30 ml) 2N NaOH (10 ml) was added at 0° C. and allowed to stir at room temperature for about 16 hours. After completion of the reaction (monitored by TLC), the volatile was evaporated and the aqueous layer was extracted with ethyl acetate and the organic layer was washed with water, brine and dried over $Na_2SO_4$ then the solvent was evaporated and the resulting crude stirred in hexane and the resulting solid was obtained which was filtered and dried under vacuum to afford the title compound. Wt: 0.280 g; Yield: 74.6%; $^1$H NMR (300 MHz, CDCl$_3$): δ 5.86 (d, 1H, J=8.1 Hz), 4.72 (s, 1H), 4.57 (s, 1H), 4.18-4.06 (m, 1H), 3.78-3.68 (m, 1H), 3.52-3.30 (m, 3H), 3.23-3.08 (m, 2H), 2.92-2.86 (m, 1H), 2.52-2.20 (m, 3H), 2.01-1.88 (m, 2H), 1.80-1.12 (m, 33H), 0.96, 0.93, 0.87, 0.81, 0.74 (s, 18H); Mass: [M+1]$^+$ 649 (5%), [M+Na]$^+$ 671 (100%); IR (KBr, cm$^{-1}$): 3353, 2937, 2858, 1635, 1618, 1533, 1459, 1390, 1262, 1250, 1148, 1048, 1033, 1020, 983, 883; M.R: 177° C.-188.7° C.; HPLC: 95.72%.

Example 48

Preparation of 4-((1R,3aS,5aR,5bR,7aR,9S,11aR, 11bR,13aR,13bR)-3a-((1R,3S)-2,2-dimethyl-3-(piperidine-1-carbonyl)cyclobutylcarbamoyl)-5a,5b,8,8, 11a-pentamethyl-1-(prop-1-en-2-yl)icosahydro-1H-cyclopenta[a]chrysen-9-yloxy)-2,2-dimethyl-4-oxobutanoic acid

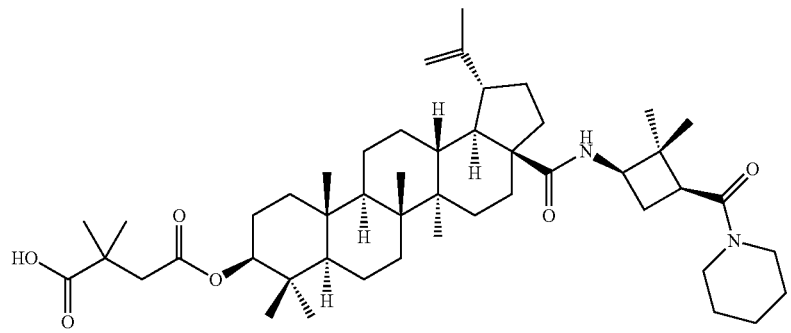

To a stirred solution of (1R,3aS,5aR,5bR,7aR,9S,11aR, 11bR,13aR,13bR)-N-((1R,3S)-2,2-dimethyl-3-(piperidine-1-carbonyl)cyclobutyl)-9-hydroxy-5a,5b,8,8,11a-pentamethyl-1-(prop-1-en-2-yl)icosahydro-1H-cyclopenta[a] chrysene-3a-carboxamide (Example 47, 0.190 g, 0.293 mmol) 2,2-Dimethylsuccinic anhydride (0.375 g, 2.932 mmol) and DMAP (0.071 g, 0.586 mmol) in pyridine (10 ml) were added at room temperature and refluxed for about 24 hours. After completion of the reaction (monitored by TLC), the reaction mixture was diluted with EtOAc, washed with aqueous 1N HCl, then water and brine, and dried over $Na_2SO_4$ then the solvent was evaporated and purified by silica gel column (100-200 mesh, elution 20% EtOAc in hexane) to afford the title compound as an off white solid. Wt: 0.090 g; Yield: 39.6%; $^1$H NMR (300 MHz, CDCl$_3$): δ 5.96 (d, 1H, J=8.1 Hz), 4.72 (s, 1H), 4.58 (s, 1H), 4.52-4.44 (m, 1H), 4.16-4.07 (m, 1H), 3.79-3.58 (m, 1H), 3.50-3.31 (m, 3H), 3.18-3.07 (m, 1H), 2.91-2.87 (m, 1H), 2.71-2.56 (m, 2H), 2.56-2.37 (m, 2H), 2.30-2.19 (m, 1H), 2.01-1.81 (m, 3H), 1.80-1.10 (m, 35H), 0.95, 0.93, 0.88, 0.87 (s, 21H); Mass: [M+1]$^+$ 777 (30%), [M+Na]$^+$ 799 (100%); IR (KBr, cm$^{-1}$): 3400, 2947, 2868, 1733, 1622, 1456, 1390, 1369, 1320, 1252, 1231, 1192, 1150, 1021, 978, 881; HPLC: 97.37%; M.R: 168.5° C.-176.9° C.

Example 49

Preparation of (1R,3aS,5aR,5bR,7aR,9S,11aR,11bR, 13aR,13bR)-5a,5b,8,8,11a-pentamethyl-3a-((1R,3S)-3-((3-methylpiperidin-1-yl)methyl)cyclopentylcarbamoyl)-1-(prop-1-en-2-yl)icosahydro-1H-cyclopenta[a]chrysen-9-yl acetate

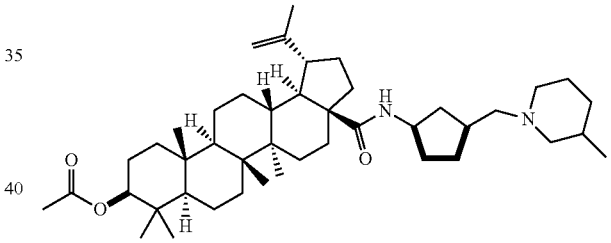

To a stirred solution of (1R,3aS,5aR,5bR,7aR,9S,11aR, 11bR,13aR,13bR)-9-acetoxy-5a,5b,8,8,11a-pentamethyl-1-(prop-1-en-2-yl)icosahydro-1H-cyclopenta[a]chrysene-3a-carboxylic acid (0.5 g, 1.04 mmol) (Prepared as described in J. Med. Chem. 2009. 52, 3248-3258) in 50 ml DCM, Oxallyl chloride (2 ml, 15.87 mmol) was added and stirred at room temperature for about 6 hours. Completion of the reaction was monitored by TLC. The reaction mixture was concentrated under reduced pressure. The residue was taken in DCM (15 ml) then kept under N₂ atmosphere. (1R,3S)-3-((3-methylpiperidin-1-yl)methyl)cyclopentanamine (Intermediate 10, 0.21 g) in DCM, triethyl amine (0.3 ml, 3.12 mmol) was added at 0° C. and stirred for about 15 minutes followed by above prepared acid chloride was added and stirred at room temperature for about 8 hours. Completion of the reaction was monitored by TLC. The reaction mixture was neutralized with sat. NaHCO₃ and extracted with DCM, the organic layer was dried over Na₂SO₄ and concentrated under reduced pressure. The residue was purified by silica gel column chromatography using 50% ethyl acetate in hexane as eluent to furnish the title compound as a white solid. ¹H NMR (300 MHz, CDCl₃): 0.57-0.97 (m, 19H); 1.18-1.21 (m, 8H); 1.25-1.41 (m, 12H); 1.49-1.62 (m, 8H); 1.65-1.82 (m, 10H); 1.85-1.98 (m, 4H); 2.56-2.69 (m, 2H); 2.88-3.06 (m, 3H); 3.29-3.38 (m, 1H); 3.89-3.90 (m, 1H); 4.25-4.70 (m, 4H); 5.78 (s, 1H); 6.12-6.15 (m, 1H); MASS: 763 (100%).

Example 50

Preparation of (1R,3aS,5aR,5bR,7aR,9S,11aR,11bR,13aR,13bR)-9-hydroxy-5a,5b,8,8,11a-pentamethyl-N-((1R,3S)-3-((3-methylpiperidin-1-yl)methyl)cyclopentyl)-1-(prop-1-en-2-yl)icosahydro-1H-cyclopenta[a]chrysene-3a-carboxamide

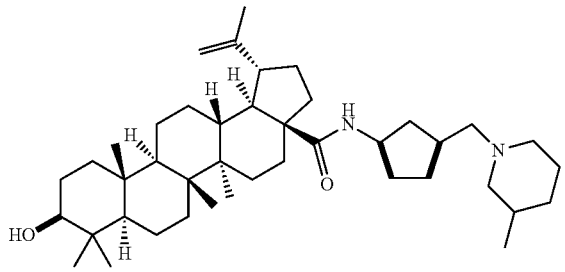

(1R,3aS,5aR,5bR,7aR,9S,11aR,11bR,13aR,13bR)-5a,5b,8,8,11a-pentamethyl-3a-((1R,3S)-3-((3-methylpiperidin-1-yl)methyl)cyclopentylcarbamoyl)-1-(prop-1-en-2-yl) icosahydro-1H-cyclopenta[a]chrysen-9-yl acetate (Example 49, 0.5 g) in MeoH:THF (8:8 ml) and cooled the contents to 0° C. then sodium hydroxide (0.12 g in 4 ml water) was added and stirred for about 6 hours at room temperature. Completion of the reaction (monitored by TLC), the reaction mixture was evaporated under reduced pressure and the residue was taken in water, and extracted with DCM, the organic layer was dried over Na₂SO₄ and concentrated under reduced pressure. The residue was purified by silica gel column chromatography using 5% methanol in DCM as eluent to furnish the title compound (0.31 g) as a white solid. ¹H NMR (300 MHz, CDCl₃): 0.57-0.97 (m, 19H); 1.18-1.21 (m, 8H); 1.25-1.41 (m, 12H); 1.49-1.62 (m, 8H); 1.65-1.82 (m, 10H); 1.85-1.98 (m, 4H); 2.56-2.69 (m, 2H); 3.29-3.38 (m, 1H); 3.89-3.90 (m, 1H); 4.25-4.70 (m, 4H); 5.78 (s, 1H); MASS: 635 (100%).

Example 51

Preparation of 2,2-dimethyl-4-oxo-4-((1R,3aS,5aR,5bR,7aR,9S,11aR,11bR,13aR,13bR)-5a,5b,8,8,11a-pentamethyl-3a-((1R,3S)-3-((3-methylpiperidin-1-yl)methyl)cyclopentylcarbamoyl)-1-(prop-1-en-2-yl) icosahydro-1H-cyclopenta[a]chrysen-9-yloxy) butanoic acid

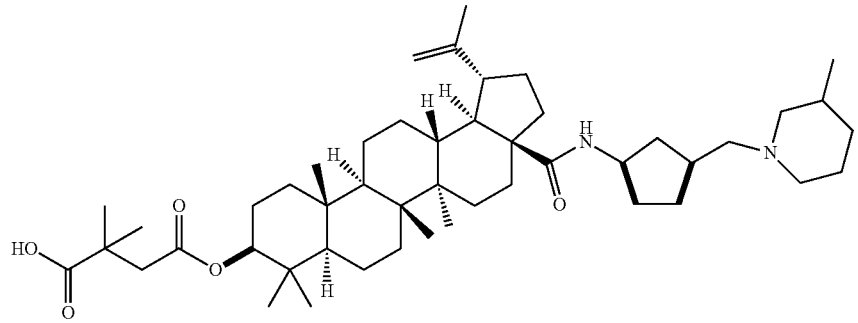

To a stirred solution of (1R,3aS,5aR,5bR,7aR,9S,11aR,11bR,13aR,13bR)-9-hydroxy-5a,5b,8,8,11a-pentamethyl-N-((1R,3S)-3-((3-methylpiperidin-1-yl)methyl)cyclopentyl)-1-(prop-1-en-2-yl)icosahydro-1H-cyclopenta[a]chrysene-3a-carboxamide (Example –50, 0.24 mmol) in pyridine (5 ml) dimethyl amino pyridine (0.32 g, 0.48 mmol) and 3,3-dimethyldihydrofuran-2,5-dione (1.3 ml) were added and the contents were refluxed for about 16 hours and completion of the reaction monitored by TLC. The reaction mixture was diluted with ethyl acetate (30 ml). The organic layer was washed with 5% aqueous HCl, washed with water followed by brine solution, dried over Na₂SO₄ and concentrated under reduced pressure. The residue was purified by silica gel column chromatography using 5% MeOH in DCM as eluent to furnish the title compound (0.1 g) as a white solid. ¹H NMR (300 MHz, CDCl₃): 0.80-0.95 (m, 16H) 1.23-1.90 (m, 41H); 2.03-3.08 (m, 16H), 4.13-4.18 (m, 1H), 4.46 (s, 1H), 4.58 (s, 1H), 4.72 (s, 1H); 5.61-5.63 (m, 1H); ES Mass: [M+1] 778 (100%); HPLC: 78.4%.

Example 52

Preparation of (1R,3aS,5aR,5bR,7aR,9S,11aR,11bR,13aR,13bR)-3a-(4-ethylpiperazine-1-carbonyl)-5a,5b,8,8,11a-pentamethyl-1-(prop-1-en-2-yl)icosahydro-1H-cyclopenta[a]chrysen-9-yl acetate

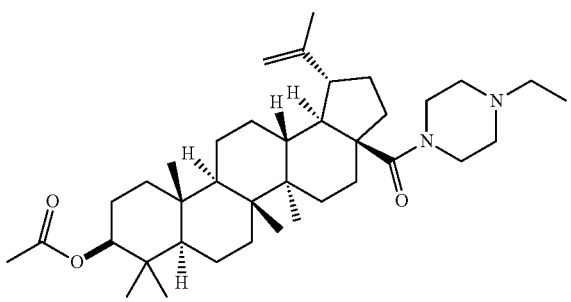 [SMILES: C=C(C)[C@@H]1CC[C@]2(C(=O)N3CCN(CC)CC3)CC[C@]3(C)[C@H](CC[C@@H]4[C@@]5(C)CC[C@H](OC(C)=O)C(C)(C)[C@@H]5CC[C@]43C)[C@@H]12]

To a stirred solution of (1R,3aS,5aR,5bR,7aR,9S,11aR,11bR,13aR,13bR)-9-acetoxy-5a,5b,8,8,11a-pentamethyl-1-

(prop-1-en-2-yl)icosahydro-1H-cyclopenta[a]chrysene-3a-carboxylic acid (0.5 g, 1.04 mmol) (Prepared as described in J. Med. Chem. 2009. 52, 3248-3258) in 50 ml DCM, Oxallyl chloride (2 ml, 15.87 mmol) was added and stirred at room temperature for about 6 hours and completion of the reaction monitored by TLC. The reaction mixture was concentrated under reduced pressure and the residue was taken in DCM (15 ml) then kept under $N_2$ atmosphere.

1-ethylpiperazine (0.23 g, 1.24 mmol) in DCM (50 ml) triethyl amine (0.3 ml, 3.12 mmol) was added at 0° C. and stirred for about 15 minutes followed by above prepared acid chloride was added and stirred at room temperature for about 8 hours. Upon completion of the reaction (monitored by TLC), the reaction mixture was neutralized with sat. NaHCO₃ and extracted with DCM, the organic layer was dried over Na₂SO₄ and concentrated under reduced pressure. The residue was purified by silica gel column chromatography using 50% ethyl acetate in hexane as eluent to furnish the title compound. ¹H NMR (300 MHz, CDCl₃): 0.57-0.97 (m, 11H); 1.18-1.21 (m, 8H); 1.25-1.41 (m, 10H); 1.49-1.62 (m, 8H); 1.65-1.82 (m, 10H); 1.85-1.98 (m, 4H); 2.56-2.69 (m, 2H); 2.88-3.06 (m, 3H); 3.89-3.90 (m, 1H); 4.25-4.70 (m, 4H); 5.78 (s, 1H); 6.12-6.15 (m, 1H); ES Mass: 595 (100%) [M+1].

Example 53

Preparation of 4-ethylpiperazin-1-yl)((1R,3aS,5aR, 5bR,7aR,9S,11aR,11bR,13aR,13bR)-9-hydroxy-5a, 5b,8,8,11a-pentamethyl-1-(prop-1-en-2-yl)icosahydro-1H-cyclopenta[a]chrysen-3a-yl)methanone

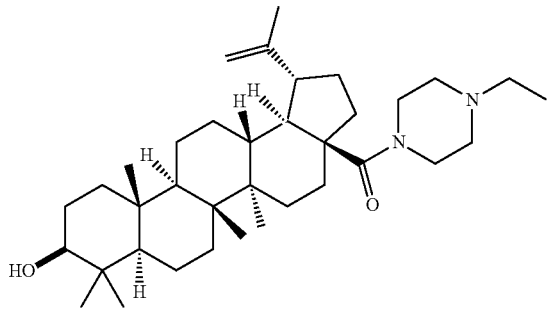

(1R,3aS,5aR,5bR,7aR,9S,11aR,11bR,13aR,13bR)-3a-(4-ethylpiperazine-1-carbonyl)-5a,5b,8,8,11a-pentamethyl-1-(prop-1-en-2-yl)icosahydro-1H-cyclopenta[a]chrysen-9-yl acetate (Example 52, 0.5 g) in MeOH:THF (8:8 ml) and cooled the contents to 0° C., then sodium hydroxide (0.16 g in 4 ml water) was added and stirred for about 6 hours at room temperature. Completion of the reaction was monitored by TLC, the reaction mixture was evaporated under reduced pressure and the residue was taken in water, and extracted with DCM. The organic layer was dried over Na₂SO₄ and concentrated under reduced pressure. The residue was purified by silica gel column chromatography using 5% methanol in DCM as eluent to furnish the title compound (0.31 g) as a white solid. ¹H NMR (300 MHz, CDCl₃): 0.57-0.97 (m, 12H); 1.18-1.21 (m, 8H); 1.25-1.41 (m, 10H); 1.49-1.62 (m, 8H); 1.65-1.82 (m, 10H); 1.85-1.98 (m, 4H); 2.56-2.69 (m, 2H); 3.29-3.38 (m, 1H); 3.89-3.90 (m, 1H); 4.25-4.70 (m, 4H); 5.78 (s, 1H); MASS 552 (100%).

Example 54

Preparation of 3-(((1R,3aS,5aR,5bR,7aR,9S,11aR, 11bR,13aR,13bR)-3a-(4-ethylpiperazine-1-carbonyl)-5a,5b,8,8,11a-pentamethyl-1-(prop-1-en-2-yl) icosahydro-1H-cyclopenta[a]chrysen-9-yloxy) carbonyl)-2,2-dimethylcyclobutanecarboxylic acid

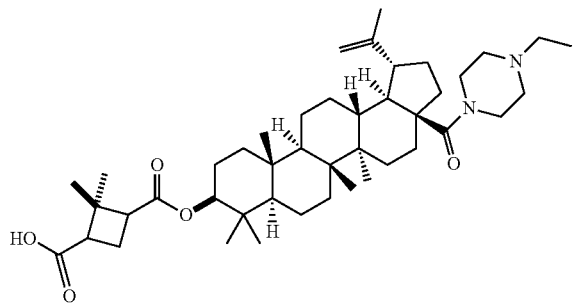

To a stirred solution of 3-(tert-butoxycarbonyl)-2,2-dimethylcyclobutanecarboxylic acid (0.5 g, 0.24 mmol) in THF (15 ml) Diisopropylethylamine (0.32 g 0.48, mmol) was added and cool the contents to 0° C. then 2,4,6-trichloro benzoyl chloride (1.3 ml) was added and stirred at room temperature for about 4 hours. Completion of the reaction was monitored by TLC. The reaction mixture was concentrated under reduced pressure. The residue was taken in pyridine (15 ml) under N2 atmosphere which was added to 4-ethylpiperazin-1-yl)((1R,3aS,5aR,5bR,7aR,9S,11aR,11bR, 13aR,13bR)-9-hydroxy-5a,5b,8,8,11a-pentamethyl-1-(prop-1-en-2-yl)icosahydro-1H-cyclopenta[a]chrysen-3a-yl)methanone (Example 47, 0.25 g. 15 mmol) and dimethyl amino pyridine (0.02 g, 22 mmol). The contents were refluxed for about 16 hours. Completion of the reaction was monitored by TLC, the reaction mixture was diluted with 30 ml ethyl acetate. The organic layer was washed with 5% aqueous HCl, washed with water followed by brine sol, dried over Na₂SO₄ and concentrated under reduced pressure. The residue was purified by silica gel column chromatography using 5% MeOH in DCM as eluent to furnish the title compound as white solid (0.12 g). ¹H NMR (300 MHz, CDCl₃): 0.95-1.16 (m, 17H); 1.21-1.86 (m, 19H); 2.25-2.48 (m, 11H); 2.77-3.58 (m, 16H); 4.33-4.70 (m, 4H); 5.58-5.60 (s, 1H); 5.78-5.80 (s, 1H); 7.44-7.47 (s, 1H); ES Mass: 707 (100%).

Example 55

Preparation of ethyl 4-((1R,3aS,5aR,5bR,7aR,9S, 11aR,11bR,13aR,13bR)-9-acetoxy-5a,5b,8,8,11a-pentamethyl-1-(prop-1-en-2-yl)icosahydro-1H-cyclopenta[a]chrysene-3a-carbonyl)-1-benzylcyclohexanecarboxylate

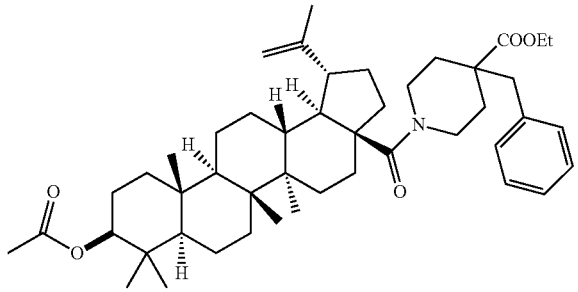 [SMILES: C=C(C)[C@@H]1CC[C@]2(C(=O)N3CCC(Cc4ccccc4)(C(=O)OCC)CC3)CC[C@]3(C)[C@H](CC[C@@H]4[C@@]5(C)CC[C@H](OC(C)=O)C(C)(C)[C@@H]5CC[C@]43C)[C@@H]12]

Step 1: Synthesis of 1-tert-butyl 4-ethyl piperidine-1,4-dicarboxylate

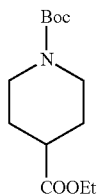

To a stirred solution of ethyl piperidine-4-carboxylate (10.0 g, 63.69 mmol) in THF (50 ml) Sodium bicarbonate (8.0 g, 95.5 mmol) was added at room temperature and cooled to 0° C. After ten minutes, di-tert-butyl dicarbonate (15.27 g, 70.05 mmol) was added and stirred the reaction mixture at room temperature for about 14 hours. After completion of the reaction (monitored by TLC), the reaction mixture was diluted with water, extracted with DCM and the organic layer was dried over $Na_2SO_4$ then concentrated under reduced pressure to furnish the title compound (11.4 g) as a light yellow liquid. $^1$H NMR (300 MHz, $CDCl_3$): 1.23-1.28 (t, 3H); 1.45 (s, 9H); 1.60-1.68 (m, 3H); 1.85-1.90 (d, J=15 Htz, 2H); 2.41-2.46 (m, 1H); 2.83-2.87 (m, 2H); 4.04-4.17 (m, 3H); ES Mass: 258 (100%) [M+1].

Step 2: Synthesis of 1-tert-butyl 4-ethyl 4-benzylpiperidine-1,4-dicarboxylate

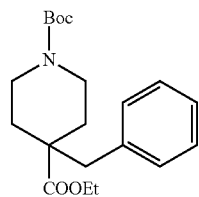 [SMILES: CCOC(=O)C1(Cc2ccccc2)CCN(C(=O)OC(C)(C)C)CC1]

Diisopropyl ethylamine (6.5 ml) in dry THF (25 ml) cooled the contents to about −10° C. then N-butyl lithium (1.6 M, 23 ml) was added drop wise under nitrogen atmosphere and maintain the same temperature for about 45 minutes and cooled to about −75° C. for about 15 minutes then 1-tert-butyl 4-ethyl piperidine-1,4-dicarboxylate (step 1, 5 g) in THF (30 ml) was added and stirred for about 30 minutes then increase the reaction temperature to −35° C. and stirred for about 45 minutes and again cooled to −75° C. then benzyl bromide (3.5 g in 20 ml THF) was added drop wise and slowly allowed the reaction to room temperature and stirred the reaction for about 12 hours. After completion of the reaction (monitored by TLC), the reaction mixture was quenched with saturated ammonium chloride and extracted with ethyl acetate. The organic layer was washed with sat. $NaHCO_3$ followed by brine, dried over $Na_2SO_4$ and concentrated under reduced pressure. The residue was purified by silica gel column chromatography using 3% ethyl acetate in hexane as eluent to furnish the title compound as a light yellow colour liquid. $^1$H NMR (300 MHz, $CDCl_3$): 1.16-1.18 (t, 3H); 1.44 (s, 9H); 2.07-2.11 (m, 2H); 2.28 (s, 1H); 2.82 (s, 2H); 2.92-2.95 (m, 1H); 3.46-3.52 (m, 3H); 4.09-4.11 (m, 2H); 7.03-7.06 (m, 2H); 7.23-7.24 (m, 3H); ES Mass: 370 (100%) [M+Na].

Step 3: Synthesis of ethyl 4-benzylpiperidine-4-carboxylate

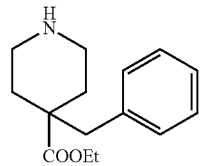 [SMILES: CCOC(=O)C1(Cc2ccccc2)CCNCC1]

A solution of 1-tert-butyl 4-ethyl 4-benzylpiperidine-1,4-dicarboxylate (step 2, 4.5 g, 12.96 mmol) in DCM (50 ml) was cooled to 0° C. After ten minutes, trifluoroacetic acid (6.0 g) was added and stirred the reaction at room temperature for about 6 hours. After completion of the reaction (monitored by TLC), the reaction mixture was neutralized with sat. $NaHCO_3$, extracted with DCM, dried over $Na_2SO_4$ and concentrated under reduced pressure to furnish the title compound (2.3 g) as a light yellow liquid. $^1$H NMR (300 MHz, $CDCl_3$): 1.19-1.24 (t, 3H); 1.48-1.58 (m, 2H); 2.14-2.18 (m, 2H); 2.64-2.73 (m, 2H); 2.86 (s, 2H); 3.01-3.07 (m, 4H); 4.10-4.17 (m, 2H); 7.07-7.10 (m, 2H); 7.24-7.30 (m, 3H); ES Mass: 248 (100%) [M+1].

Step 4: Preparation of ethyl 4-((1R,3aS,5aR,5bR,7aR,9S,11aR,11bR,13aR,13bR)-9-acetoxy-5a,5b,8,8,11a-pentamethyl-1-(prop-1-en-2-yl)icosahydro-1H-cyclopenta[a]chrysene-3a-carbonyl)-1-benzylcyclohexanecarboxylate To a stirred solution of (1R,3aS,5aR,5bR,7aR,9S,11aR,11bR,13aR,13bR)-9-acetoxy-5a,5b,8,8,11a-pentamethyl-1-(prop-1-en-2-yl)icosahydro-1H-cyclopenta[a]chrysene-3a-carboxylic acid (1.0 g, 2.08 mmol) (Prepared as described in J. Med. Chem. 2009. 52, 3248-3258) in 50 ml DCM Oxolyl chloride (2 ml, 15.87 mmol) was added and stirred at room temperature for about 6 hours and completion of the reaction was monitored by TLC. The reaction mixture was concentrated under reduced pressure and the residue was taken in DCM (15 ml) and then kept under $N_2$ atmosphere.

Ethyl 4-benzylpiperidine-4-carboxylate (step 3, 0.49 g, 2.08 mmol) in DCM (50 triethyl amine (0.3 ml, 3.12 mmol) was added at 0° C. and stirred for about 15 minutes, followed by above prepared acid chloride. Reaction was continued at room temperature for about 8 hours. Completion of the reaction was monitored by TLC. The reaction mixture was neutralized with sat. $NaHCO_3$ and extracted with DCM, dried over $Na_2SO_4$ and concentrated under reduced pressure. The residue was purified by silica gel column chromatography using 50% ethyl acetate in hexane as eluent to furnish the title compound as a white solid (0.9 g). $^1$H NMR (300 MHz, $CDCl_3$): 0.57-0.97 (m, 19H); 1.18-1.21 (m, 8H); 1.25-1.41 (m, 12H); 1.49-1.62 (m, 8H); 1.65-1.82 (m, 10H); 1.85-1.98 (m, 4H); 2.56-2.69 (m, 2H); 2.88-3.06 (m, 3H); 3.29-3.38 (m, 1H); 3.89-3.90 (m, 1H); 4.12-4.23 (m, 2H); 4.44-4.47 (m, 1H); 4.56 (s, 1H); 4.71 (s, 1H); 7.03-7.05 (m, 2H); 7.23-7.25 (m, 3H); ES Mass: 728 (100%) [M+1].

Example 56

Preparation of Ethyl 1-benzyl-4-((1R,3aS,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysene-3a-carbonyl)cyclohexanecarboxylate

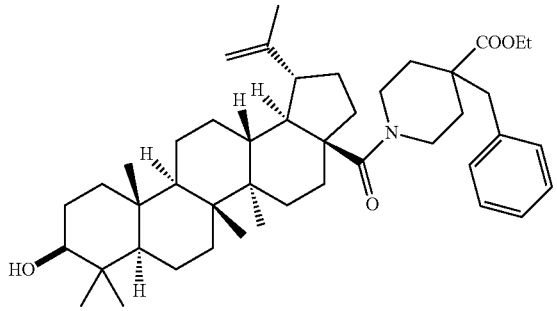 [SMILES: C=C(C)[C@@H]1CC[C@]2(C(=O)N3CCC(Cc4ccccc4)(C(=O)OCC)CC3)CC[C@]3(C)[C@H](CC[C@@H]4[C@@]5(C)CC[C@H](O)C(C)(C)[C@@H]5CC[C@]43C)[C@@H]12]

Ethyl 4-((1R,3aS,5aR,5bR,7aR,9S,11aR,11bR,13aR,13bR)-9-acetoxy-5a,5b,8,8,11a-pentamethyl-1-(prop-1-en-2-yl)icosahydro-1H-cyclopenta[a]chrysene-3a-carbonyl)-1-benzylcyclohexanecarboxylate (Example 55, 0.9 g) was taken in MeOH:THF (8:8 ml) and cooled the contents to 0° C. then sodium hydroxide (0.28 g in 4 ml water) was added and stirred for about 6 hours at room temperature. Completion of the reaction was monitored by TLC. The reaction mixture was evaporated under reduced pressure and the residue was taken in water, extracted with DCM, dried over $Na_2SO_4$ and concentrated under reduced pressure. The residue was purified by silica gel column chromatography using 5% methanol in DCM as eluent to furnish the title compound (0.45 g) as a white solid. $^1$H NMR (300 MHz, $CDCl_3$): 0.57-0.97 (m, 19H); 1.18-1.21 (m, 8H); 1.25-1.41 (m, 12H); 1.49-1.62 (m, 8H); 1.65-1.82 (m, 10H); 1.85-1.98 (m, 4H); 2.56-2.69 (m, 2H); 3.29-3.38 (m, 1H); 3.89-3.90 (m, 1H); 4.12-4.23 (m, 2H) 4.56 (s, 1H); 4.71 (s, 1H); 7.03-7.05 (m, 2H); 7.23-7.25 (m, 3H); MASS: 685 (100%).

Example 57

Preparation of 4-((1R,3aS,5aR,5bR,7aR,9S,11aR,11bR,13aR,13bR)-3a-(4-benzyl-4-(ethoxycarbonyl)piperidine-1-carbonyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid

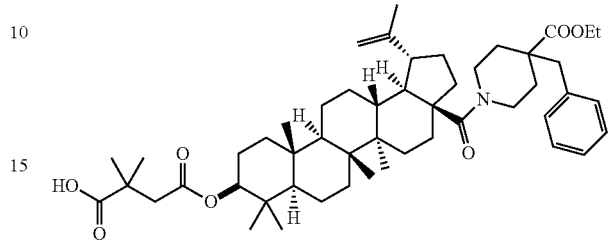

To a stirred solution of Ethyl 1-benzyl-4-((1R,3aS,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysene-3a-carbonyl)cyclohexanecarboxylate (Example 56, 0.25 g, 0.36 mmol), 2,2-dimethylsuccinic anhydride (0.375 g, 2.932 mmol) and DMAP (0.071 g, 0.586 mmol) in pyridine (10 ml) were added at room temperature and refluxed for about 24 hours. After completion of the reaction (monitored by TLC), the reaction mixture was diluted with EtOAc, washed with water, 1N HCl, water, brine and dried over $Na_2SO_4$ then the solvent was evaporated and purified by silica gel column (100-200 mesh, elution 20% EtOAc in hexane) to afford the title compound as a white solid. Wt: 0.26 g; $^1$H NMR (300 MHz, $CDCl_3$): 0.57-0.97 (m, 16H); 1.18-1.21 (m, 14H); 1.25-1.41 (m, 12H); 1.49-1.62 (m, 8H); 1.65-1.82 (m, 10H); 1.85-1.98 (m, 4H); 2.56-2.69 (m, 4H); 3.29-3.38 (m, 1H); 3.89-3.90 (m, 1H); 4.12-4.23 (m, 2H); 4.56 (s, 1H); 4.71 (s, 1H); 7.03-7.05 (m, 2H); 7.23-7.25 (m, 3H); ES Mass: 814 (100%) [M+1].

Example 58

Preparation of (1S,3R)-1-tert-butyl 3-((1R,3aS,5aR,5bR,7aR,9S,11aR,11bR,13aR,13bR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yl)2,2-dimethylcyclobutane-1,3-dicarboxylate

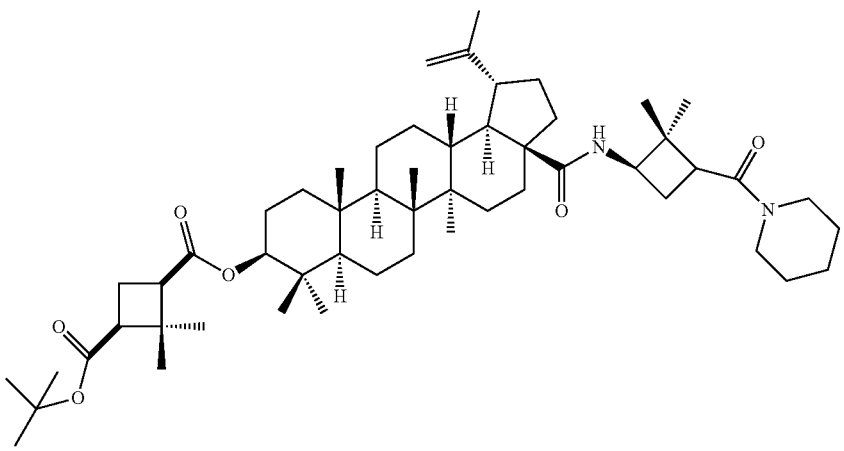

To a solution of (1R,3S)-3-(tert-butoxycarbonyl)-2,2-dimethylcyclobutanecarboxylic 2,4,6-trichlorobenzoic anhydride (1.117 g) in pyridine (20 ml) (1R,3aS,5aR,5bR,7aR,9S,11aR,11bR,13aR,13bR)-N-((1R,3S)-2,2-dimethyl-3-(piperidine-1-carbonyl)cyclobutyl)-9-hydroxy-5a,5b,8,8,11a-pentamethyl-1-(prop-1-en-2-yl)icosahydro-1H-cyclopenta[a]chrysene-3a-carboxamide (Example 47, 1.0 g) in pyridine was added, followed by DMAP (376 mg). Thus obtained reaction mixture was stirred at reflux temperature for about 12 hours. After completion of the reaction (monitored by TLC), water (20 mL) was added and extracted with ethyl acetate. The combined organic layers were washed with 1N HCl, brine, and water, dried over sodium sulfate, concentrated under reduced pressure to give crude compound. The so obtained crude product was purified by column chromatography to give title compound as a white solid. Wt: 800 mg: Yield: 61%. $^1$H NMR (300 MHz, CDCl$_3$): δ 5.94 (d, 1H, J=8.1 Hz), 4.729 (s, 1H), 4.580 (s, 1H), 4.434 (m, 1H), 4.154 (m, 1H), 3.70 (m, 3H), 3.44 (m, 4H), 3.1 (m, 1H), 2.93-2.2 (m, 11H), 2.00 (m, 4H), 1.80-1.10 (m, 38H), 0.95 (s, 6H), 0.93 (3H), 0.89 (s, 9H), 0.82 (m, 1H); Mass: [M+H$^+$]$^+$ 860.45 (100%).

11bR,13aR,13bR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yl)2,2-dimethylcyclobutane-1,3-dicarboxylate (Example 58, 800 mg) was added and allowed to warm to room temperature. Stirred at room temperature for about 12 hours and check the TLC. After completion of the reaction (monitored by TLC) water was added and extracted with EtOAc. The combined organic layers were dried over sodium sulfate, evaporated under reduced pressure, purified over silica-gel column chromatography to yield the title compound as a white solid. Wt: 0.200 g: Yield: 30%. $^1$H NMR (300 MHz, CDCl$_3$): δ 5.98 (d, 1H, J=8.1 Hz), 4.725 (s, 1H), 4.582 (s, 1H), 4.44 (m, 1H), 4.11 (m, 1H), 3.70-3.00 (m, 6H), 2.902-2.76 (m, 4H), 2.60-1.85 (m, 10H), 1.81-1.10 (m, 34H), 0.96 (s, 3H), 0.93 (s, 6H), 0.87 (s, 9H), 0.82 (m, 1H); Mass: [M+H$^+$]$^+$ 803.25 (20%), 825.5 (100%) [M+Na$^+$]$^+$; IR (KBr, cm$^{-1}$): 3400, 2949, 2866, 1734, 1638, 1625, 1500, 1463, 1369, 1251, 1233, 1191, 1107, 1088, 977, 882, 542; M.R: 186.2-238.1° C.; HPLC: 95.25%.

Example 59

Preparation of (1S,3R)-3-(((1R,3aS,5aR,5bR,7aR,9S,11aR,11bR,13aR,13bR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)carbonyl)-2,2-dimethylcyclobutanecarboxylic acid Example 60

Preparation of (1S,3R)-1-tert-butyl 3-((1R,3aS,5aR,5bR,7aR,9S,11aR,11bR,13aR,13bR)-3a-((1S,3R)-2,2-dimethyl-3-(morpholine-4-carbonyl)cyclobutylcarbamoyl)-5a,5b,8,8,11a-pentamethyl-1-(prop-1-en-2-yl)icosahydro-1H-cyclopenta[a]chrysen-9-yl)2,2-dimethylcyclobutane-1,3-dicarboxylate

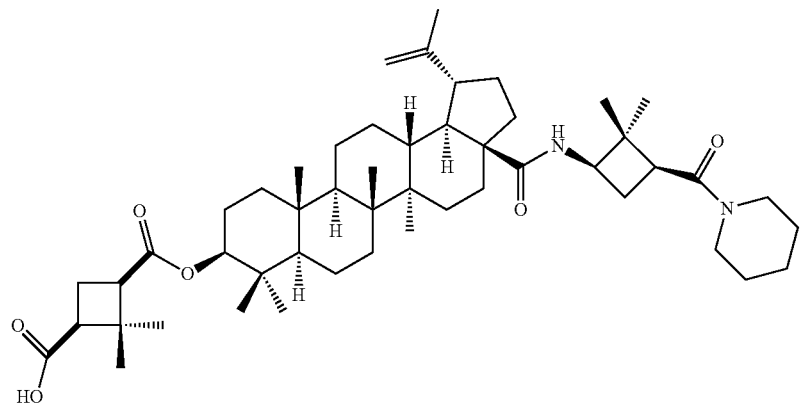

To a cooled (0° C.) HCl in 1,4-dioxane solution (10 mL) (1S,3R)-1-tert-butyl 3-((1R,3aS,5aR,5bR,7aR,9S,11aR,

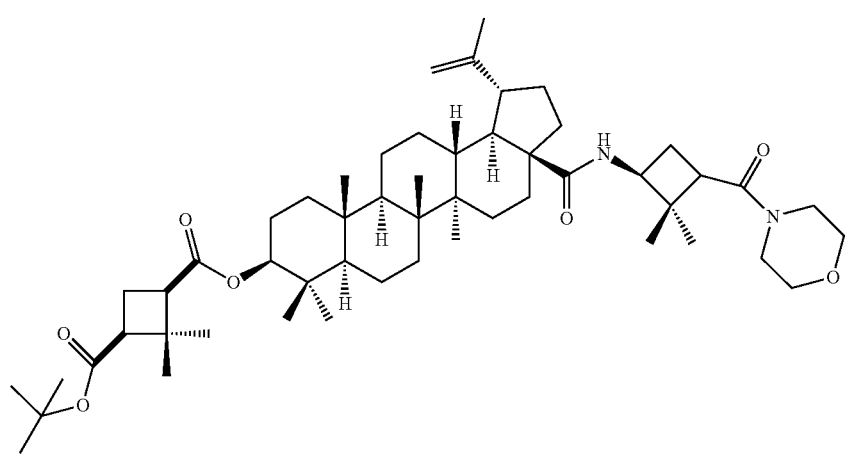

To a solution of (1R,3S)-3-(tert-butoxycarbonyl)-2,2-dimethylcyclobutanecarboxylic 2,4,6-trichlorobenzoic anhydride (1.115 g) in pyridine (1R,3aS,5aR,5bR,7aR,9S,11aR,11bR,13aR,13bR)-N-((1S,3R)-2,2-dimethyl-3-(morpholine-4-carbonyl)cyclobutyl)-9-hydroxy-5a,5b,8,8,11a-pentamethyl-1-(prop-1-en-2-yl)icosahydro-1H-cyclopenta[a]chrysene-3a-carboxamide (Example 8, 1.0 gr) in pyridine was added, followed by DMAP (375 mg). Thus obtained reaction mixture was stirred at reflux temperature for about 12 hours. After completion of the reaction (monitored by TLC), water (20 mL) was added and extracted with ethyl acetate. The combined organic layers were washed with aqueous 1N HCl, then brine and water, then dried over sodium sulfate, concentrated under reduced pressure to give crude compound. The so obtained crude product was purified by column chromatography to give the title compound as a white solid. Wt: 0.800 g: Yield: 61%. $^1$H NMR (300 MHz, CDCl$_3$): δ 5.9 (d, 1H, J=8.1 Hz), 4.7356 (s, 1H), 4.590 (s, 1H), 4.43 (m, 1H), 4.15 (m, 1H), 3.80-3.44 (m, 9H), 3.11 (m, 1H), 2.87 (m, 1H), 2.8-2.3 (m, 6H), 2.0-1.80 (m, 3H), 1.80-1.10 (m, 34H), 0.98 (s, 3H), 0.95 (s, 6H), 0.8 (s, 9H), 0.78 (m, 2H); Mass: [M+H$^+$]$^+$ 861.45 (100%), [M+Na]$^+$ 884.6 (30%).

2,2-dimethylcyclobutane-1,3-dicarboxylate (Example 60, 900 mg) was added and allowed to warm to room temperature. Stirred at room temperature for about 12 hours and check the TLC. After completion of the reaction (monitored by TLC), water was added and extracted with EtOAc. The combined organic layers were dried over sodium sulfate, evaporated under reduced pressure, purified over silica-gel column chromatography to yield the title compound as a white solid. Wt: 0.220 g: Yield: 30%. $^1$H NMR (300 MHz, CDCl$_3$): δ 5.988 (d, 1H, J=7.8 Hz), 4.736 (s, 1H), 4.586 (s, 1H), 4.43 (m, 1H), 4.15 (m, 1H), 3.80-3.44 (m, 8H), 3.12 (m, 1H), 2.902-2.76 (m, 4H), 2.650-2.3 (m, 8H), 2.1-1.80 (m, 3H), 1.80-1.10 (m, 28H), 0.98 (s, 3H), 0.95 (s, 6H), 0.8 (s, 9H), 0.78 (m, 1H); Mass: [M+H$^+$]$^+$ 806.5 (100%); IR (KBr, cm$^{-1}$): 3447, 2953, 2869, 1736, 1723, 1645, 1626, 1500, 1463, 1369, 1271, 1239, 1191, 1117, 1038, 975, 882, 722, 573; M.R: 255.5° C.-266.5° C.; HPLC: 92.86%.

Example 61

Preparation of (1S,3R)-3-(((1R,3aS,5aR,5bR,7aR,9S,11aR,11bR,13aR,13bR)-3a-((1S,3R)-2,2-dimethyl-3-(morpholine-4-carbonyl)cyclobutylcarbamoyl)-5a,5b,8,8,11a-pentamethyl-1-(prop-1-en-2-yl)icosahydro-1H-cyclopenta[a]chrysen-9-yloxy)carbonyl)-2,2-dimethylcyclobutanecarboxylic acid Example 62

Preparation of 4-((1R,3aS,5aR,5bR,7aR,9S,11aR,11bR,13aR,13bR)-3a-((1S,3R)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-4-oxobutanoic acid

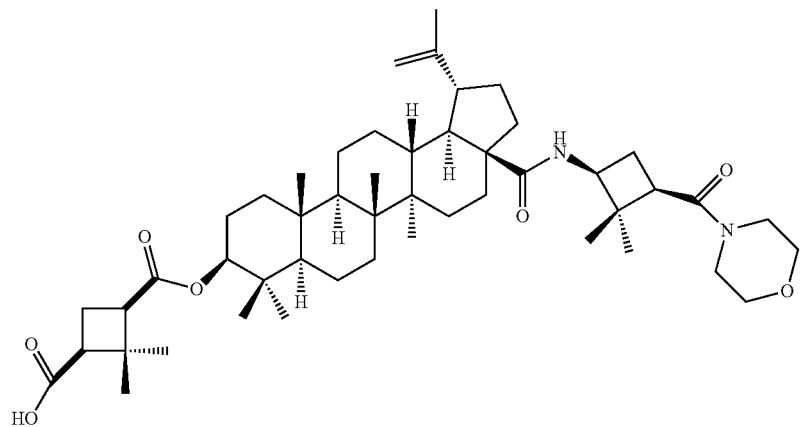

To a cooled (0° C.) HCl in 1,4-dioxane solution (1S,3R)-1-tert-butyl 3-((1R,3aS,5aR,5bR,7aR,9S,11aR,11bR,13aR,13bR)-3a-((1S,3R)-2,2-dimethyl-3-(morpholine-4-carbonyl)cyclobutylcarbamoyl)-5a,5b,8,8,11a-pentamethyl-1-(prop-1-en-2-yl)icosahydro-1H-cyclopenta[a]chrysen-9-yl)

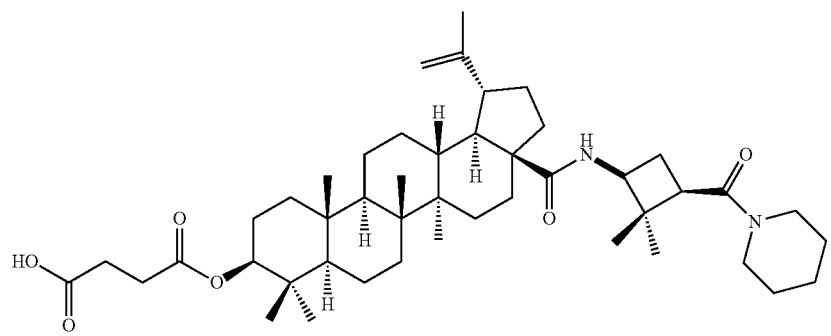

To a stirred solution of (1R,3aS,5aR,5bR,7aR,9S,11aR, 11bR,13aR,13bR)-N-((1S,3R)-2,2-dimethyl-3-(piperidine-1-carbonyl)cyclobutyl)-9-hydroxy-5a,5b,8,8,11a-pentamethyl-1-(prop-1-en-2-yl)icosahydro-1H-cyclopenta[a]chrysene-3a-carboxamide (Example 11, 500 mg) in dry pyridine (10 mL) succinic anhydride (771.6 mg) was added followed by DMAP (188.53 mg). Reflux the reaction mixture for 20 hours, after completing the reaction (monitored by TLC), diluted with ethyl acetate, and washed with water and brine solutions. The combined organic layers were dried over Na$_2$SO$_4$, concentrated under reduced pressure to afford title compound as a gummy solid. The crude compound was purified by silica-gel column chromatography using 100-200 mesh and hexane and ethyl acetate mixtures as a mobile phase to give 250 mg (43.5% yield) of title compound with 5.95% purity by HPLC. $^1$H NMR (300 MHZ, CDCl$_3$): δ 6.027 (1H, d, J=8.1 Hz), 4.738 (1H, s), 4.585 (1H, s), 4.52 (1H, m), 4.13 (1H, m), 3.66 (1H, m), 3.512 (1H, m), 3.38 (2H, m), 3.12 (1H, m), 2.95 (2H, m), 2.55-2.7 (7H, m), 2.25-2.54 (5H, m), 1.9 (3H, m), 1.2-1.8 (28H, m), 0.953 (3H, s), 0.924 (3H, s), 0.827 (9H, m), 0.754 (2H, m); IR (KBr, cm$^{-1}$): 3403, 2946, 2867, 1802, 1733, 1619, 1449, 1370, 1293, 1253, 1228, 1162, 1110, 991, 934, 880, 826; Mass: [M+H]$^+$ 749.55 (40%), 771.55 [M+Na]$^+$ (100%).

(piperidine-1-carbonyl)cyclobutyl)-9-hydroxy-5a,5b,8,8, 11a-pentamethyl-1-(prop-1-en-2-yl)icosahydro-1H-cyclopenta[a]chrysene-3a-carboxamide (Example 11, 1 g) in pyridine was added followed by DMAP (375 mg). Thus obtained reaction mixture was stirred at reflux temperature for 12 hours. After completion of the reaction (monitored by TLC), water (20 mL) was added and extracted with ethyl acetate. The combined organic layers were washed with aqueous 1N HCl, then brine, and water, and subsequently dried over sodium sulfate, concentrated under reduced pressure to give crude compound. The so obtained crude product was purified by column chromatography to give the title compound as a white solid. $^1$H NMR (300 MHZ, CDCl$_3$): δ 6.02 (1H, d, J=8.1 Hz), 4.74 (1H, s), 4.59 (1H, s), 4.42 (1H, m), 4.11 (1H, m), 3.66 (1H, m), 3.5 (1H, m), 3.4 (2H, m), 3.1 (1H, m), 2.95-2.75 (4H, m), 2.6-2.3 (5H, m), 1.9 (2H, m), 1.8 (1H, m), 1.68 (3H, s), 1.64-1.12 (28H, m), 1.11 (12H, s), 1.05 (6H, s), 0.83 (12H, s), 0.75 (1H, m); Mass: [M+H]$^+$ 787.2 (100%).

Example 63

Preparation of (1S,3R)-1-tert-butyl 3-((1R,3aS,5aR, 5bR,7aR,9S,11aR,11bR,13aR,13bR)-3a-((1S,3R)-2, 2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yl)2,2-dimethylcyclobutane-1,3-dicarboxylate Example 64

Preparation of (1S,3R)-3-(((1R,3aS,5aR,5bR,7aR, 9S,11aR,11bR,13aR,13bR)-3a-((1S,3R)-2,2-dimethyl-3-(piperidine-1-carbonyl)cyclobutylcarbamoyl)-5a,5b,8,8,11a-pentamethyl-1-(prop-1-en-2-yl) icosahydro-1H-cyclopenta[a]chrysen-9-yloxy) carbonyl)-2,2-dimethylcyclobutanecarboxylic acid

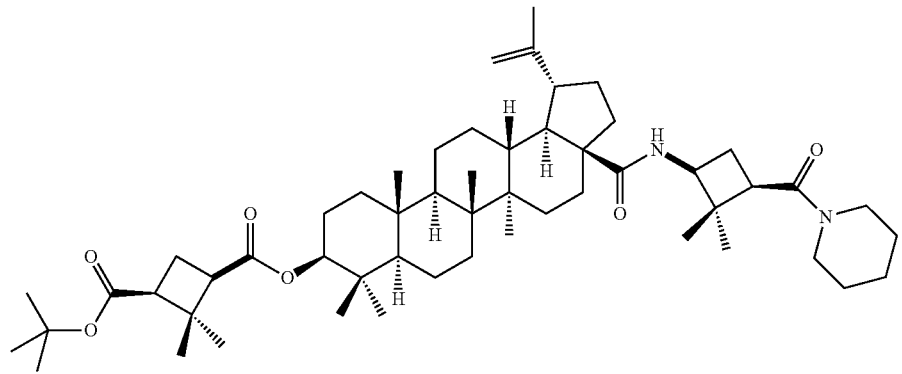

To a solution of (1R,3S)-3-(tert-butoxycarbonyl)-2,2-dimethylcyclobutanecarboxylic 2,4,6-trichlorobenzoic anhydride (1.34 g)) in pyridine (20 mL) (1R,3aS,5aR,5bR,7aR, 9S,11aR,11bR,13aR,13bR)-N-((1S,3R)-2,2-dimethyl-3-

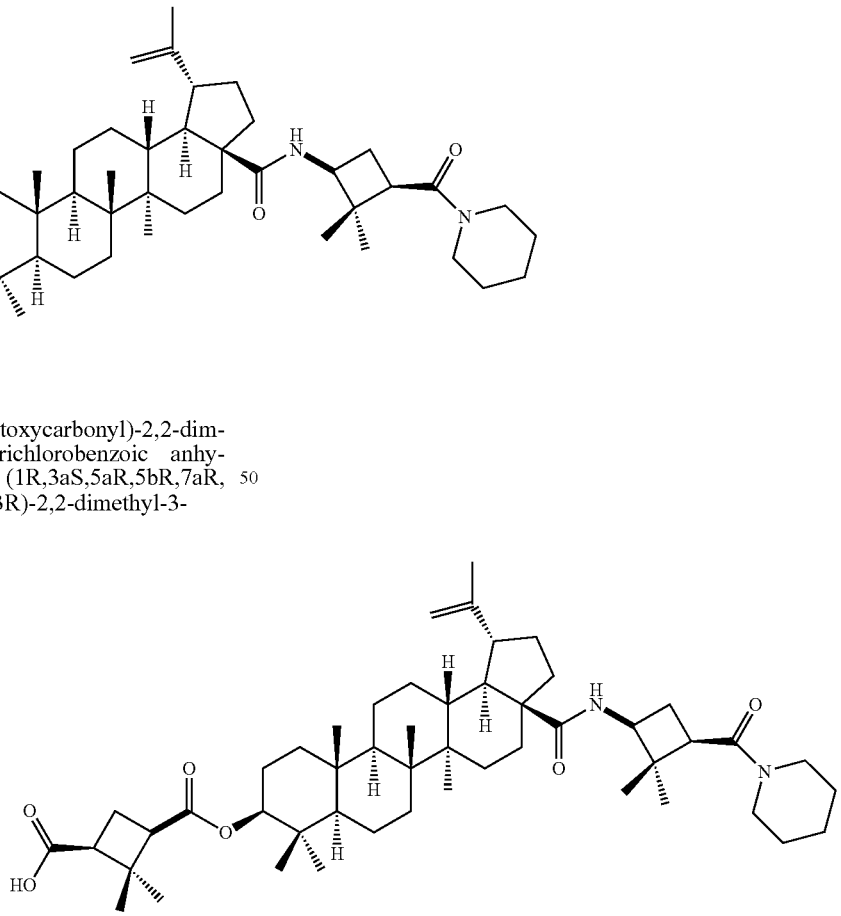

To a cooled HCl in 1,4-dioxane solution (15 mL) (1S,3R)-1-tert-butyl 3-((1R,3aS,5aR,5bR,7aR,9S,11aR,11bR,13aR,13bR)-3a-((1S,3R)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yl)2,2-dimethylcyclobutane-1,3-dicarboxylate (Example 63, 800 mg) was added and allowed to warm to room temperature. Stirred at room temperature for 12 hours and check the TLC. After completion of the reaction (monitored by TLC), water was added and extracted with EtOAc. The combined organic layers were dried over sodium sulfate, evaporated under reduced pressure, purified over silica-gel column chromatography to yield the title compound (350 mg) as a white solid. $^1$H NMR (300 MHZ, CDCl$_3$): δ 6.02 (1H, d, J=8.1 Hz), 4.734 (1H, s), 4.587 (1H, s), 4.44 (1H, m), 4.14 (1H, m), 3.66 (1H, m), 3.5 (1H, m), 3.4 (2H, m), 3.1 (1H, m), 2.95-2.75 (3H, m), 2.6-2.3 (5H, m), 1.9 (2H, m), 1.8 (1H, m), 1.68 (3H, s), 1.64-1.12 (35H, m), 1.05 (6H, s), 0.83 (12H, s), 0.75 (1H, m); Mass: [M+H]$^+$ 803.7 (100%), 825.7 (50) [M+Na]$^+$; IR (KBr, cm$^{-1}$): 3426, 2947, 2866, 2346, 1734, 1625, 1466, 1369, 1252, 1232, 1190, 1107, 1022, 983, 883 and 651 cm$^{-1}$; M.P. 257.7-269° C.

Example 65

Preparation of 5-((1R,3aS,5aR,5bR,7aR,9S,11aR,11bR,13aR,13bR)-3a-((1S,3R)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-5-oxopentanoic acid

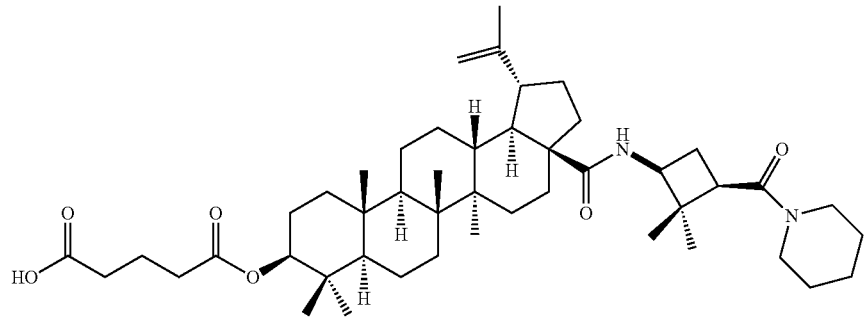

To a stirred solution of 5-((1R,3aS,5aR,5bR,7aR,9S,11aR,11bR,13aR,13bR)-3a-((1S,3R)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-5-oxopentanoic acid (Example 11, 500 mg) in dry pyridine (10 mL) glutaric anhydride (880.14 mg) was added followed by DMAP (188.53 mg). Reflux the reaction mixture for 20 hours. After completing the reaction as monitored by TLC, diluted with ethyl acetate, washed with water and brine solutions. The combined organic layers were dried over Na$_2$SO$_4$, concentrated under reduced pressure to afford crude title compound as a gummy solid. The crude compound was purified by silica-gel column chromatography using 100-200 mesh and hexane and ethyl acetate mixtures as mobile phase to give 350 mg (59.5% yield) of title compound with 91.4% purity by HPLC. $^1$H NMR (300 MHZ, CDCl$_3$): δ 6.07 (1H, d, J=8.1 Hz), 4.729 (1H, s), 4.58 (1H, s), 4.50 (1H, m), 4.132 (1H, m), 3.71 (2H, m), 3.5 (1H, m), 3.4 (2H, m), 3.147 (1H, m), 2.90 (1H, m), 2.3-2.55 (10H, m), 2.0 (6H, m), 1.2-1.8 (29H, m), 0.94 (3H, s), 0.92 (3H, s), 0.85 (10H, m), 0.75 (1H, m); IR (KBr, cm$^{-1}$): 3395, 2950, 2868, 1712, 1603, 1509, 1517, 1445, 1412, 1390, 1375, 1304, 1253, 1206, 1065, 977, 920, 784; Mass: [M+H]$^+$ 763.55 (50%), 785.6 [M+Na]$^+$ (100%).

Example 66

Preparation of (1R,3aS,5aR,5bR,7aR,9S,11aR,11bR,13aR,13bR)-3a-((1S,3R)-3-(4-ethylpiperazine-1-carbonyl)-2,2-dimethylcyclobutylcarbamoyl)-5a,5b,8,8,11a-pentamethyl-1-(prop-1-en-2-yl)icosahydro-1H-cyclopenta[a]chrysen-9-yl acetate

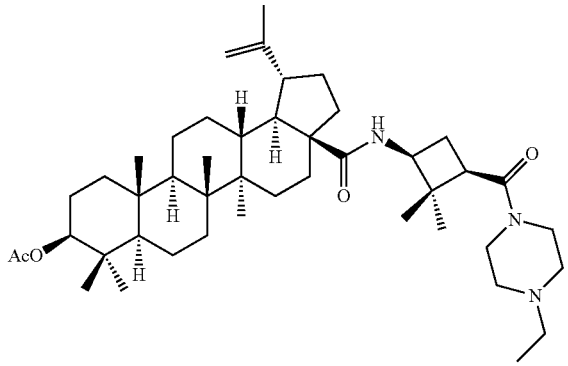

Oxallyl chloride was added To a cooled solution of (1R,3aS,5aR,5bR,7aR,9S,11aR,11bR,13aR,13bR)-9-acetoxy-5a,5b,8,8,11a-pentamethyl-1-(prop-1-en-2-yl)icosahydro-1H-cyclopenta[a]chrysene-3a-carboxylic acid (835 mg) in DCM (20 mL) at 0° C. and the reaction mass was allowed to stir at room temperature for about 6 hours. After completion of the reaction (monitored by TLC) the solvent was evaporated under nitrogen atmosphere and dissolved in DCM, which was added to a solution of ((1R,3S)-3-amino-2,2-dimethylcyclobutyl)(4-ethylpiperazin-1-yl)methanone (500 mg) in DCM and Et$_3$N (6 mL) at 0° C. and allowed to stir at room temperature for about 12 hours. After completion of the reaction (monitored by TLC), the reaction mixture was diluted with DCM and washed with water, 1N HCl, water brine and dried with Na$_2$SO$_4$, the solvent was evaporated and purified by silica-gel column (100-200 mesh, elution 10% EtOAc in hexane) to afford the title compound as an off white solid. Wt: 760 mg; Yield: 67.3%. $^1$H NMR (300 MHz, CDCl$_3$): δ 5.88 (d, J=8.1 Hz, 1H), 4.737 (d, J=1.5 Hz, 1H), 4.58 (d, J=1.5 Hz, 1H), 4.49-4.438 (m, 1H), 4.10 (m, 1H), 3.80-3.41 (m, 4H), 3.17-3.08 (m, 1H), 2.9 (m, 1H), 2.60-2.295 (m, 9H), 2.04 (s, 3H), 1.90 (m, 2H), 1.80-1.02 (m, 30H), 0.95, 0.92 (s, 6H), 0.83 (s, 12H); Mass: [M+H$^+$]$^+$ 720 (100%).

Example 67

Preparation of (1R,3aS,5aR,5bR,7aR,9S,11aR,11bR, 13aR,13bR)-N-((1S,3R)-3-(4-ethylpiperazine-1-carbonyl)-2,2-dimethylcyclobutyl)-9-hydroxy-5a,5b, 8,8,11a-pentamethyl-1-(prop-1-en-2-yl)icosahydro-1H-cyclopenta[a]chrysene-3a-carboxamide

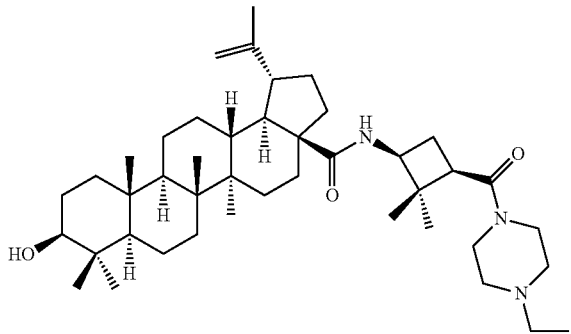

A solution of (1R,3aS,5aR,5bR,7aR,9S,11aR,11bR,13aR, 13bR)-3a-((1S,3R)-3-(4-ethylpiperazine-1-carbonyl)-2,2-dimethylcyclobutylcarbamoyl)-5a,5b,8,8,11a-pentamethyl-1-(prop-1-en-2-yl)icosahydro-1H-cyclopenta[a]chrysen-9-yl acetate (Example 66, 0.760 g) in MeOH:THF (2:1) (45 ml) at 0° C., 2N NaOH (15 ml) were added and allowed to stir at room temperature for about 16 hours. After completion of the reaction (monitored by TLC), the volatiles were evaporated, the aqueous layer extracted with ethyl acetate and dried with $Na_2SO_4$. The solvent was evaporated and purified by silica gel column (100-200 mesh, elution 15% EtOAc in hexane) to afford the title compound as a white solid. Wt: 0.500 g: Yield: 69.9%; $^1$H NMR (300 MHz, CDCl$_3$): δ 5.90 (d, J=8.1 Hz, 1H), 4.728 (s, 1H), 4.57 (s, 1H), 4.10 (m, 1H), 3.80-3.41 (m, 4H), 3.20-3.10 (m, 2H), 2.9 (m, 1H), 2.60-2.295 (m, 9H), 2.1 (m, 2H), 1.90 (m, 1H), 1.80-1.02 (m, 22H), 0.95, 0.92 (s, 6H), 0.83 (s, 3H), 0.80 (s, 3H). Mass: [M+H$^+$]$^+$ 679 (100%); IR (KBr, cm$^{-1}$): 3445, 2946, 2867, 1634, 1459, 1463, 1376, 1270, 1242, 1126, 1043, 983, 883, 768, 656; M.R: 122.0° C.-155.1° C.; HPLC: 94.8%.

Example 68

Preparation of 4-((1R,3aS,5aR,5bR,7aR,9S,11aR, 11bR,13aR,13bR)-3a-((1S,3R)-3-(4-ethylpiperazine-1-carbonyl)-2,2-dimethylcyclobutylcarbamoyl)-5a, 5b,8,8,11a-pentamethyl-1-(prop-1-en-2-yl) icosahydro-1H-cyclopenta[a]chrysen-9-yloxy)-2,2-dimethyl-4-oxobutanoic acid

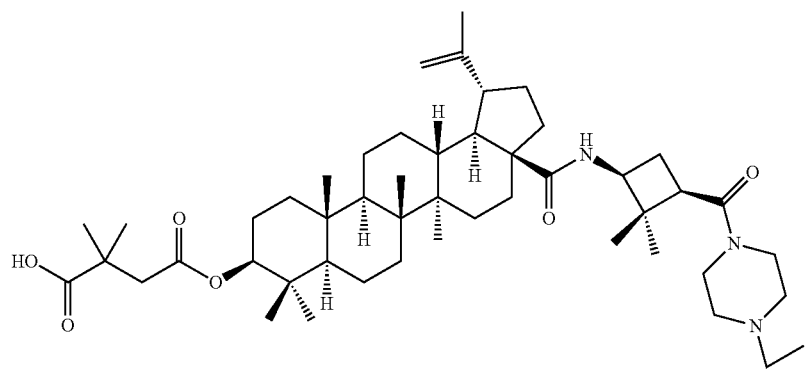

2,2-Dimethylsuccinic anhydride (238 mg) was added to a stirred solution of (1R,3aS,5aR,5bR,7aR,9S,11aR,11bR, 13aR,13bR)-N-((1S,3R)-3-(4-ethylpiperazine-1-carbonyl)-2,2-dimethylcyclobutyl)-9-hydroxy-5a,5b,8,8,11a-pentamethyl-1-(prop-1-en-2-yl)icosahydro-1H-cyclopenta[a]chrysene-3a-carboxamide (Example 67, 125 mg) and DMAP (45 mg) in dry pyridine (10 mL) at room temperature. After addition, the reaction mixture was refluxed for 14 hours. After completion of the reaction (monitored by TLC), it was diluted with EtOAc, the organic layer was washed with aqueous 1N HCl, then washed with water and brine, and dried with $Na_2SO_4$. The solvent was evaporated and purified by silica gel column (100-200, elution 35% EtOAc in hexane) to afford 90 mg of title compound (60.8% yield) as an off white solid with 81.67% HPLC purity. $^1$H-NMR (300 MHz, CDCl$_3$): δ 5.92 (d, J=7.8 Hz, 1H), 4.73 (s, 1H), 4.58 (s, 1H), 4.52-4.44 (m, 1H), 4.19-4.09 (m, 1H), 3.90 (m, 2H), 3.7 (m, 2H), 3.15-3.04 (m, 1H), 2.87-2.82 (m, 6H), 2.60 (m, 3H), 2.5-2.3 (m, 3H), 2.00-1.91 (m, 3H), 1.75-1.10 (m, 36H), 0.947, 0.914, 0.900 (s, 18H); Mass: [M+1]$^+$ 806 (100%); IR (KBr, cm$^{-1}$): 3394, 2957, 2873, 1724, 1623, 1455, 1374, 1367, 1244, 1188, 1146, 980, 883, 765; M.R: 63.8° C.-122.5° C.

Example 69

Preparation of (1R,3aS,5aR,5bR,7aR,9S,11aR,11bR, 13aR,13bR)-3a-((1R,3S)-3-(4-ethylpiperazine-1-carbonyl)-2,2-dimethylcyclobutylcarbamoyl)-5a,5b, 8,8,11a-pentamethyl-1-(prop-1-en-2-yl)icosahydro-1H-cyclopenta[a]chrysen-9-yl acetate

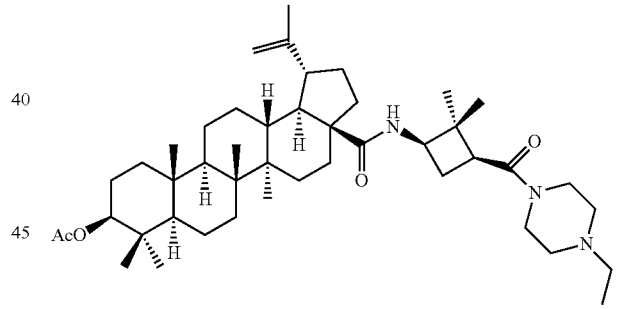

A solution of (COCl)$_2$ in DCM was added to a stirred solution of (1R,3aS,5aR,5bR,7aR,9S,11aR,11bR,13aR, 13bR)-9-acetoxy-5a,5b,8,8,11a-pentamethyl-1-(prop-1-en-2-yl)icosahydro-1H-cyclopenta[a]chrysene-3a-carboxylic acid (651 mg) in DCM (10 mL) at 0° C. and the reaction mass was allowed to stir at room temperature for about 3 hours. After completion of the reaction (monitored by TLC), the solvent was evaporated under nitrogen atmosphere and dissolved in DCM, which was added to a stirred solution of ((1S,3R)-3-amino-2,2-dimethylcyclobutyl)(4-ethylpiperazin-1-yl)methanone itrifluoro acetic acid salt (900 mg) at 0° C. and allowed to stir at room temperature for about 16 hours. After completion of the reaction (monitored by TLC), the reaction mixture was diluted with DCM and washed with aqueous 1N HCl, then washed with water and brine, and then dried with $Na_2SO_4$, the solvent was evaporated and purified by silica gel column (100-200 mesh, elution 15% EtOAc in hexane) to afford the title compound as an off white solid. Wt: 550 mg. $^1$H NMR (300 MHz, $CDCl_3$): δ 5.80 (d, J=6.5 Hz, 1H), 4.73 (s, 1H), 4.58 (s, 1H), 4.50-4.41 (m, 1H), 4.2-4.10 (m, 1H), 3.78-3.67 (m, 3H), 3.6-3.50 (m, 4H), 3.5-3.4 (m, 7H), 3.1 (m, 1H), 3.0 (m, 2H), 2.9 (m, 1H), 2.60-2.40 (m, 6H), 2.0 (3H, s), 1.9-1.86 (m, 2H), 1.80-1.2 (m, 18H), 0.95, 0.93, 0.87, 0.83, 0.81, (s, 24H).

Example 70

Preparation of (1R,3aS,5aR,5bR,7aR,9S,11aR,11bR,13aR,13bR)-N-((1R,3S)-3-(4-ethylpiperazine-1-carbonyl)-2,2-dimethylcyclobutyl)-9-hydroxy-5a,5b,8,8,11a-pentamethyl-1-(prop-1-en-2-yl)icosahydro-1H-cyclopenta[a]chrysene-3a-carboxamide To a stirred solution of (1R,3aS,5aR,5bR,7aR,9S,11aR,11bR,13aR,13bR)-3a-((1R,3S)-3-(4-ethylpiperazine-1-carbonyl)-2,2-dimethylcyclobutylcarbamoyl)-5a,5b,8,8,11a-pentamethyl-1-(prop-1-en-2-yl)icosahydro-1H-cyclopenta[a]chrysen-9-yl acetate (Example 69, 550 mg) in MeOH:THF (2:1) at 0° C. temperature 2N NaOH (4 mL) was added and allowed to stir at room temperature for about 16 hours. After completion of the reaction (monitored by TLC), the volatiles was evaporated, the aqueous layer was extracted with ethyl acetate and the organic layer was washed with water, brine and dried with $Na_2SO_4$. The solvent was evaporated and the resulting crude was stirred in hexane to get crude solid. The solid crude was purified over silica-gel column chromatography to afford the title compound. Wt: 200 mg, Yield: 93.3%. $^1$H NMR (300 MHz, $CDCl_3$): δ 5.86 (d, 1H, J=8.1 Hz), 4.72 (s, 1H), 4.57 (s, 1H), 4.18-4.06 (m, 1H), 3.78-3.68 (m, 1H), 3.52-3.30 (m, 3H), 3.23-3.08 (m, 2H), 2.92-2.86 (m, 1H), 2.52-2.20 (m, 3H), 2.01-1.88 (m, 2H), 1.80-1.12 (m, 33H), 0.96, 0.93, 0.87, 0.81, 0.74 (s, 18H); Mass: $[M+1]^+$ 649 (5%), $[M+Na]^+$ 671 (100%); IR (KBr, $cm^{-1}$): 3353, 2937, 2858, 1635, 1618, 1533, 1459, 1390, 1262, 1250, 1148, 1048, 1033, 1020, 983, 883; M.R: 177° C.-188.7° C.; HPLC: 95.72%.

Example 71

Preparation of 4-((1R,3aS,5aR,5bR,7aR,9S,11aR,11bR,13aR,13bR)-3a-((1R,3S)-3-(4-ethylpiperazine-1-carbonyl)-2,2-dimethylcyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid: (Prepared as described in above procedure)

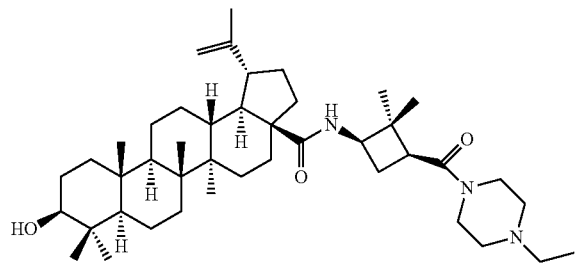

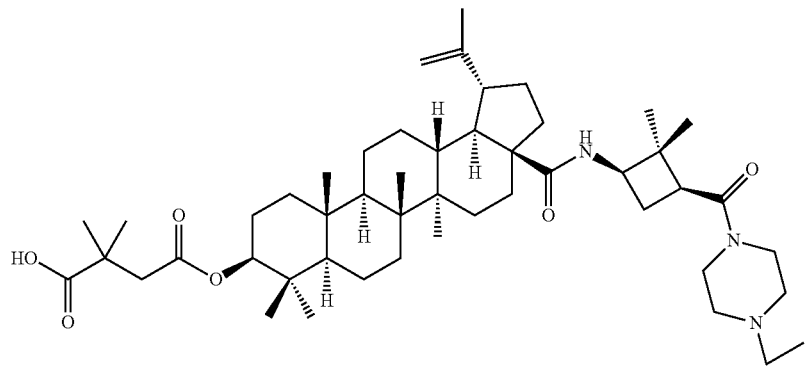

$^1$H-NMR (300 MHz, CDCl$_3$): δ 5.91 (d, J=7.8 Hz, 1H), 4.73 (s, 1H), 4.58 (s, 1H), 4.53-4.44 (m, 1H), 4.19-4.10 (m, 1H), 3.90 (m, 2H), 3.7 (m, 2H), 3.15-3.04 (m, 1H), 2.87-2.82 (m, 6H), 2.60 (m, 3H), 2.5-2.3 (m, 3H), 2.00-1.91 (m, 3H), 1.75-1.10 (m, 36H), 0.947, 0.914, 0.900 (s, 18H); Mass: [M+1]$^+$ 806 (100%); IR (KBr, cm$^{-1}$): 3390, 2956, 2873, 1724, 1623, 1458, 1374, 1367, 1244, 1188, 1146, 980, 883, 765.

Example 72

Preparation of ethyl 1-((1R,3aS,5aR,5bR,7aR,9S,11aR,11bR,13aR,13bR)-9-acetoxy-5a,5b,8,8,11a-pentamethyl-1-(prop-1-en-2-yl)icosahydro-1H-cyclopenta[a]chrysene-3a-carbonyl)-4-ethylpiperidine-4-carboxylate

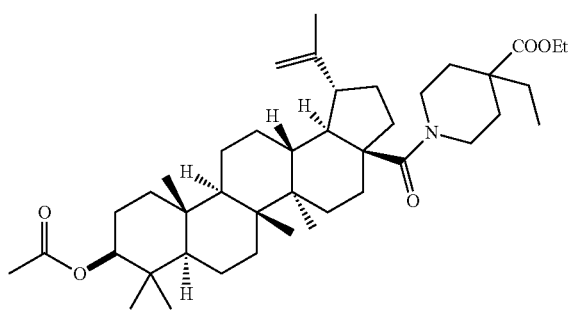 [SMILES: C=C(C)[C@@H]1CC[C@]2(C(=O)N3CCC(CC)(C(=O)OCC)CC3)CC[C@]3(C)[C@H](CC[C@@H]4[C@@]5(C)CC[C@H](OC(C)=O)C(C)(C)[C@@H]5CC[C@]43C)[C@@H]12]

To a stirred solution of (1R,5aR,5bR,7aR,9S,11aR,11bR,13aR,13bR)-9-acetoxy-5a,5b,8,8,11a-pentamethyl-1-(prop-1-en-2-yl)icosahydro-1H-cyclopenta[a]chrysene-3a-carboxylic acid (2.0 g, 4.01 mmol) in DCM (50 ml) oxalyl chloride (4 ml, 15.87 mmol) was added at room temperature. Completion of the reaction as shown on TLC, reaction mixture was concentrated under reduced pressure. The residue was taken in DCM (15 ml) and kept under N2 atmosphere.

Ethyl 4-benzylpiperidine-4-carboxylate (0.74 g, 4.01 mmol) in DCM (50 ml) triethyl amine (1 ml) was added at 0° C. and stirred for about 15 minutes followed by above prepared acid chloride and the reaction was continued at room temperature for about 8 hours. After completion of the reaction (monitored by TLC), the reaction mixture was neutralized with saturated NaHCO$_3$ and extracted with DCM, the organic layer was dried over Na$_2$SO$_4$ and concentrated under reduced pressure. The residue was purified by silica gel column chromatography using 50% ethyl acetate in hexane as an eluent to furnish the title compound as a white solid (1.8 g). $^1$H NMR (300 MHz, CDCl$_3$): 0.57-0.97 (m, 19H); 1.18-1.21 (m, 8H); 1.25-1.41 (m, 12H); 1.49-1.62 (m, 8H); 1.65-1.82 (m, 10H); 1.85-1.98 (m, 4H); 2.56-2.69 (m, 2H); 2.88-3.06 (m, 3H); 3.29-3.38 (m, 1H); 3.89-3.90 (m, 1H); 4.12-4.23 (m, 2H); 4.44-4.47 (m, 1H); 4.56 (s, 1H); 4.71 (s, 1H); 7.03-7.05 (m, 2H); 7.23-7.25 (m, 3H); ES Mass: 666 (100%), [M+1].

Example 73

Preparation of ethyl 4-ethyl-1-((1R,3aS,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysene-3a-carbonyl)piperidine-4-carboxylate

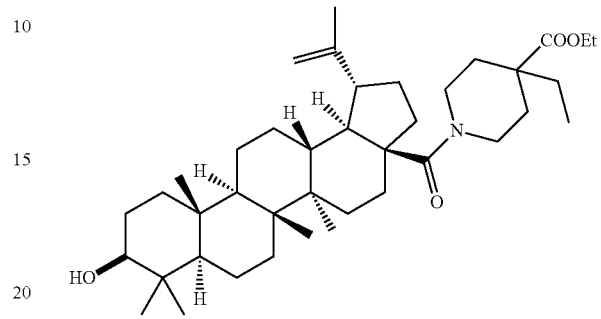

Ethyl 1-((1R,3aS,5aR,5bR,7aR,9S,11aR,11bR,13aR,13bR)-9-acetoxy-5a,5b,8,8,11a-pentamethyl-1-(prop-1-en-2-yl)icosahydro-1H-cyclopenta[a]chrysene-3a-carbonyl)-4-ethylpiperidine-4-carboxylate (Example 72, 2.0 g) was taken in MeOH:THF (8:8 ml) and cooled the contents to 0° C. then sodium hydroxide (1.5 g in 4 ml water) was added and the contents were stirred for about 6 hours at room temperature. After completion of the reaction (monitored by TLC), the reaction mixture was evaporated under reduced pressure. The residue was taken in water and extracted with DCM; the organic layer was dried over Na$_2$SO$_4$ and concentrated under reduced pressure. The residue was purified by silica gel column chromatography using 5% methanol in DCM as eluent to furnish the title compound (1.45 g) as a white solid. $^1$H NMR (300 MHz, CDCl$_3$): 0.57-0.97 (m, 19H); 1.18-1.21 (m, 8H); 1.25-1.41 (m, 12H); 1.49-1.62 (m, 10H); 1.65-1.82 (m, 10H); 1.85-1.98 (m, 4H); 2.56-2.69 (m, 2H); 3.29-3.38 (m, 1H); 3.89-3.90 (m, 1H); 4.15-4.18 (m, 2H); 4.56 (s, 1H); 4.71 (s, 1H); MASS: 624 (100%).

Example 74

Preparation of 4-((1R,3aS,5aR,5bR,7aR,9S,11aR,11bR,13aR,13bR)-3a-(4-(ethoxycarbonyl)-4-ethylpiperidine-1-carbonyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid

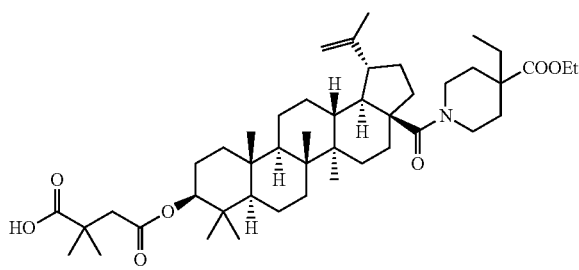

To a stirred solution of ethyl 4-ethyl-1-((1R,3aS,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysene-3a-carbonyl)piperidine-4-carboxylate (Example 73, 0.5 g, 0.80 mmol) in pyridine (5 ml) dimethyl amino pyridine (0.2 g, 1.6 mmol) was added then 3,3-dimethyldihydrofuran-2,5-dione (0.82 ml) was added and the contents were refluxed for about 16 hours. Completion of the reaction was monitored by TLC, the reaction mixture was diluted with ethyl acetate (30 ml) and the organic layer was washed with 5% aqueous HCl, washed with water followed by brine, dried over $Na_2SO_4$ and concentrated under reduced pressure. The residue was purified by silica gel column chromatography using 5% MeOH in DCM as eluent to furnish the title compound (0.25 g) as a white solid. $^1$H NMR (300 MHz, $CDCl_3$): 0.95-1.16 (m, 19H); 1.23-1.78 (m, 23H); 2.15-2.59 (m, 11H); 2.77-3.58 (m, 16H); 4.33-4.70 (m, 4H); 5.58-5.60 (s, 1H); 5.78-5.80 (s, 1H); 7.44-7.47 (s, 1H); ES Mass: 753; (100%), [M+1].

Example 75

Preparation of (1R,3aS,5aR,5bR,7aR,9S,11aR,11bR,13aR,13bR)-3a-(4-cyano-4-phenylpiperidine-1-carbonyl)-5a,5b,8,8,11a-pentamethyl-1-(prop-1-en-2-yl)icosahydro-1H-cyclopenta[a]chrysen-9-yl acetate

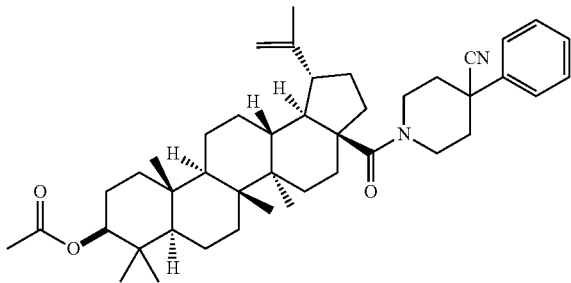 [SMILES: C=C(C)[C@@H]1CC[C@]2(C(=O)N3CCC(C#N)(c4ccccc4)CC3)CC[C@]3(C)[C@H](CC[C@@H]4[C@@]5(C)CC[C@H](OC(C)=O)C(C)(C)[C@@H]5CC[C@]43C)[C@@H]12]

To a stirred solution of (1R,5aR,5bR,7aR,9S,11aR,11bR,13aR,13bR)-9-acetoxy-5a,5b,8,8,11a-pentamethyl-1-(prop-1-en-2-yl)icosahydro-1H-cyclopenta[a]chrysene-3a-carboxylic acid (1.0 g, 2.08 mmol) in DCM (50 ml) oxalyl chloride (4 ml, 15.87 mmol) was added at room temperature. Upon completion of the reaction as shown on TLC, the reaction mixture was concentrated under reduced pressure. The residue was taken in DCM (15 ml) and kept under $N_2$ atmosphere.

4-phenylpiperidine-4-carbonitrile (0.49 g, 2.08 mmol) in DCM (50 ml) triethyl amine (0.3 ml, 3.12 mmol) was added at 0° C. and stirred for about 15 minutes then the above prepared acid chloride was added and reaction was continued at room temperature for about 8 hours. Upon completion of the reaction (monitored by TLC), the reaction mixture was neutralized with saturated $NaHCO_3$ and extracted with DCM, the organic layer was dried over $Na_2SO_4$ and concentrated under reduced pressure. The residue was purified by silica gel column chromatography using 50% ethyl acetate in hexane as eluent to furnish the title compound (0.9 g). $^1$H NMR (300 MHz, $CDCl_3$): 0.57-0.97 (m, 19H); 1.18-1.21 (m, 8H); 1.25-1.41 (m, 12H); 1.49-1.62 (m, 8H); 1.65-1.82 (m, 10H); 1.85-1.98 (m, 4H); 2.56-2.69 (m, 2H); 2.88-3.06 (m, 3H); 3.29-3.38 (m, 1H); 3.89-3.90 (m, 1H); 4.12-4.23 (m, 2H) 4.44-4.47 (m, 1H); 4.56 (s, 1H); 4.71 (s, 1H); 7.03-7.05 (m, 2H); 7.23-7.25 (m, 3H); ES Mass: 667 (100%), [M+1].

Example 76

Preparation of 1-((1R,3aS,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysene-3a-carbonyl)-4-phenylpiperidine-4-carbonitrile

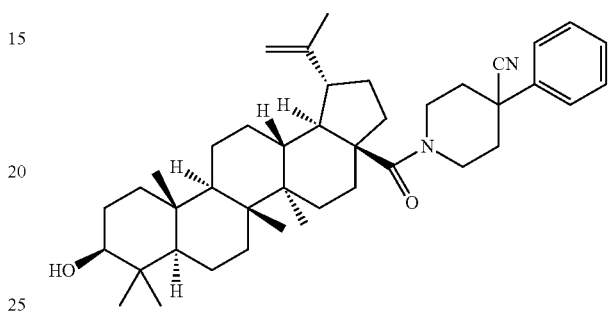

(1R,3aS,5aR,5bR,7aR,9S,11aR,11bR,13aR,13bR)-3a-(4-cyano-4-phenylpiperidine-1-carbonyl)-5a,5b,8,8,11a-pentamethyl-1-(prop-1-en-2-yl)icosahydro-1H-cyclopenta[a]chrysen-9-yl acetate (Example 75, 2.0 g) was taken in MeOH:THF (8:8 ml) and cooled the contents to 0° C. then sodium hydroxide (1.5 g in 4 ml water) was added and the contents were stirred for about 6 hours at room temperature. After completion of the reaction (monitored by TLC), the reaction mixture was evaporated under reduced pressure and the residue was taken in water and extracted with DCM, the organic layer was dried over $Na_2SO_4$ and concentrated under reduced pressure. The residue was purified by silica gel column chromatography using 5% methanol in DCM as eluent to furnish the title compound (1.45 g) as a white solid. $^1$H NMR (300 MHz, $CDCl_3$): 0.57-0.97 (m, 19H); 1.18-1.21 (m, 8H); 1.25-1.41 (m, 12H); 1.49-1.62 (m, 10H); 1.65-1.82 (m, 10H); 1.85-1.98 (m, 4H); 2.56-2.69 (m, 2H); 3.29-3.38 (m, 1H); 3.89-3.90 (m, 1H); 4.15-4.18 (m, 2H); 4.56 (s, 1H); 4.71 (s, 1H); MASS: 624 (100%).

Example 77

Preparation of 4-((1R,3aS,5aR,5bR,7aR,9S,11aR,11bR,13aR,13bR)-3a-(4-cyano-4-phenylpiperidine-1-carbonyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid

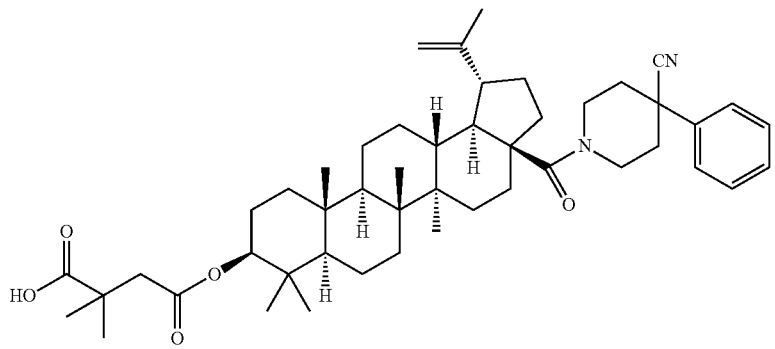

To a stirred solution of ((1R,3aS,5aR,5bR,7aR,9S,11aR, 11bR,13aR,13bR)-9-hydroxy-5a,5b,8,8,11a-pentamethyl-1-(prop-1-en-2-yl)icosahydro-1H-cyclopenta[a]chrysene-3a-carbonyl)-4-phenylpiperidine-4-carbonitrile (Example 76, 0.5 g, 0.80 mmol) in pyridine (5 ml) dimethyl amino pyridine (0.2 g, 1.6 mmol) was added then 3,3-dimethyldihydrofuran-2,5-dione (0.82 ml) was added and the contents were refluxed for about 16 hours. Upon completion of the reaction (monitored by TLC), the reaction mixture was diluted with ethyl acetate (30 ml). The organic layer was washed with 5% aqueous HCl, washed with water followed by brine, dried over $Na_2SO_4$ and concentrated under reduced pressure. The residue was purified by silica gel column chromatography using 5% MeOH in DCM as eluent to furnish the title compound (0.25 g) as a white solid. $^1$H NMR (300 MHz, $CDCl_3$): 0.95-1.16 (m, 19H); 1.23-1.78 (m, 23H); 2.15-2.59 (m, 11H); 2.77-3.58 (m, 16H); 4.33-4.70 (m, 4H); 5.58-5.60 (s, 1H); 5.78-5.80 (s, 1H); 7.44-7.47 (s, 1H); ES Mass: 753 (100%), [M+1].

Example 78

Preparation of tert-butyl 2-(6-(2-((1R,3aS,5aR,5bR, 7aR,9S,11aR,11bR,13aR,13bR)-9-acetoxy-5a,5b,8, 8,11a-pentamethyl-1-(prop-1-en-2-yl)icosahydro-1H-cyclopenta[a]chrysene-3a-carboxamido)ethyl)-2, 2-dimethyl-1,3-dioxan-4-yl)acetate mixture was concentrated under reduced pressure. The residue was taken in DCM (15 ml) and kept under $N_2$ atmosphere.

Tert-butyl 2-(6-(2-aminoethyl)-2,2-dimethyl-1,3-dioxan-4-yl)acetate (0.49 g, 2.08 mmol) in DCM (50 ml) triethyl amine (0.3 ml, 3.12 mmol) was added at 0° C. and stirred for about 15 minutes, then the above prepared acid chloride was added and the reaction was continued at room temperature for about 8 hours. Completion of the reaction was monitored by TLC, and the reaction mixture was neutralized with saturated $NaHCO_3$ and extracted with DCM, and the organic layer was dried over $Na_2SO_4$ and concentrated under reduced pressure. The residue was purified by silica gel column chromatography using 50% ethyl acetate in hexane as eluent to furnish the title compound (0.9 g). $^1$H NMR (300 MHz, $CDCl_3$): 0.57-0.97 (m, 19H); 1.18-1.21 (m, 8H); 1.25-1.41 (m, 12H); 1.49-1.62 (m, 8H); 1.65-1.82 (m, 10H); 1.85-1.98 (m, 4H); 2.56-2.69 (m, 2H); 2.88-3.06 (m, 3H); 3.29-3.38 (m, 1H); 3.89-3.90 (m, 1H); 4.12-4.23 (m, 4H) 4.44-4.47 (m, 1H); 4.56 (s, 1H); 4.71 (s, 1H); ES Mass: 754; (100%), [M+1].

Example 79

Preparation of tert-butyl 2-(6-(2-((1R,3aS,5aR,5bR, 7aR,9S,11aR,11bR,13aR,13bR)-9-hydroxy-5a,5b,8, 8,11a-pentamethyl-1-(prop-1-en-2-yl)icosahydro-1H-cyclopenta[a]chrysene-3a-carboxamido)ethyl)-2, 2-dimethyl-1,3-dioxan-4-yl)acetate

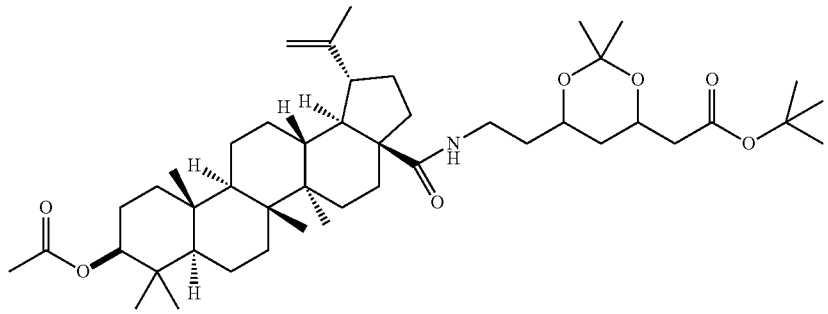 [SMILES: C=C(C)[C@@H]1CC[C@]2(C(=O)NCCC3CC(CC(=O)OC(C)(C)C)OC(C)(C)O3)CC[C@]3(C)[C@H](CC[C@@H]4[C@@]5(C)CC[C@H](OC(C)=O)C(C)(C)[C@@H]5CC[C@]43C)[C@@H]12]

To a stirred solution of (1R,5aR,5bR,7aR,9S,11aR,11bR, 13aR,13bR)-9-acetoxy-5a,5b,8,8,11a-pentamethyl-1-(prop-1-en-2-yl)icosahydro-1H-cyclopenta[a]chrysene-3a-carboxylic acid (1.0 g, 2.08 mmol) in DCM (50 ml) oxalyl chloride (4 ml, 15.87 mmol) was added at room temperature. Completion of the reaction as shown on TLC, the reaction

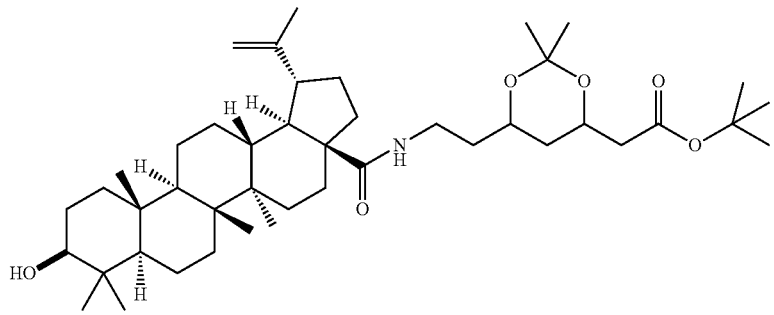 [SMILES: C=C(C)[C@@H]1CC[C@]2(C(=O)NCCC3CC(CC(=O)OC(C)(C)C)OC(C)(C)O3)CC[C@]3(C)[C@H](CC[C@@H]4[C@@]5(C)CC[C@H](O)C(C)(C)[C@@H]5CC[C@]43C)[C@@H]12]

Tert-butyl 2-(6-(2-((1R,3aS,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysene-3a-carboxamido)ethyl)-2,2-dimethyl-1,3-dioxan-4-yl)acetate (Example 78, 2.0 g) was taken in MeOH:THF (8:8 ml) and cooled the contents to 0° C. then sodium hydroxide (1.5 g in 4 ml water) was added and contents were stirred for 6 hours at room temperature. Completion of the reaction was monitored by TLC, reaction mixture was evaporated under reduced pressure and the residue was taken in water and extracted with DCM, the organic layer was dried over $Na_2SO_4$ and concentrated under reduced pressure. The residue was purified by silica gel column chromatography using 5% methanol in DCM as eluent to furnish the title compound (1.45 g) as a white solid. $^1$H NMR (300 MHz, $CDCl_3$): 0.57-0.97 (m, 19H); 1.18-1.21 (m, 8H); 1.25-1.41 (m, 12H); 1.49-1.62 (m, 10H); 1.65-1.82 (m, 10H); 1.85-1.98 (m, 4H); 2.56-2.69 (m, 2H); 3.29-3.38 (m, 1H); 3.89-3.90 (m, 1H); 4.15-4.18 (m, 2H); 4.56 (s, 1H); 4.71 (s, 1H); MASS: 712 (100%).

Example 80

Preparation of 4-((1R,3aS,5aR,5bR,7aR,9S,11aR,11bR,13aR,13bR)-3a-(2-(6-(2-tert-butoxy-2-oxoethyl)-2,2-dimethyl-1,3-dioxan-4-yl)ethylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid dioxan-4-yl)acetate (Example 79, 0.5 g, 0.80 mmol) in pyridine (5 ml), dimethyl amino pyridine (0.2 g, 1.6 mmol) and 3,3-dimethyldihydrofuran-2,5-dione (0.82 ml) were added. Contents were refluxed for about 16 hours. After completion of the reaction, the reaction mixture was diluted with ethyl acetate (30 ml). The organic layer was washed with 5% aqueous HCl, water followed by brine, dried over $Na_2SO_4$ and concentrated under reduced pressure. The residue was purified by silica gel column chromatography using 5% MeOH in DCM as eluent to furnish the title compound (0.25 g) as a white solid. $^1$H NMR (300 MHz, $CDCl_3$): 0.95-1.16 (m, 19H); 1.23-1.78 (m, 23H); 2.15-2.59 (m, 11H); 2.77-3.58 (m, 16H); 4.33-4.70 (m, 4H); 5.58-5.60 (s, 1H); 5.78-5.80 (s, 1H); 7.44-7.47 (s, 1H); ES Mass: 806 [M+Na].

Example 81

Preparation of 7-((1R,3aS,5aR,5bR,7aR,9S,11aR,11bR,13aR,13bR)-9-(3-carboxy-3-methylbutanoyloxy)-5a,5b,8,8,11a-pentamethyl-1-(prop-1-en-2-yl)icosahydro-1H-cyclopenta[a]chrysene-3a-carboxamido)-3,5-dihydroxyheptanoic acid

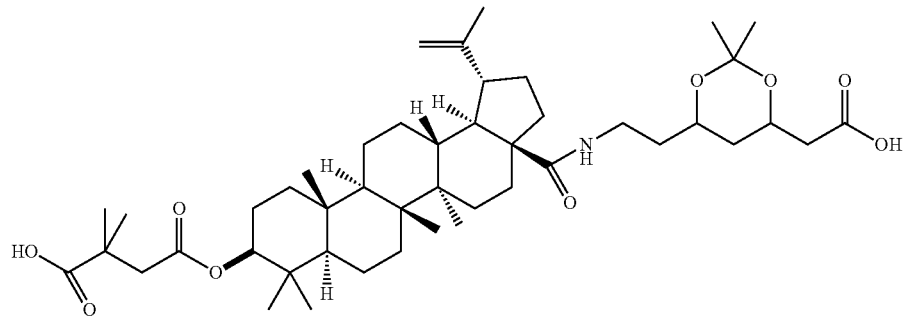 [SMILES: C=C(C)[C@@H]1CC[C@]2(C(=O)NCCC3CC(CC(=O)O)OC(C)(C)O3)CC[C@]3(C)[C@H](CC[C@@H]4[C@@]5(C)CC[C@H](OC(=O)CC(C)(C)C(=O)O)C(C)(C)[C@@H]5CC[C@]43C)[C@@H]12]

To a stirred solution of tert-butyl 2-(6-(2-((1R,3aS,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysene-3a-carboxamido)ethyl)-2,2-dimethyl-1,3-

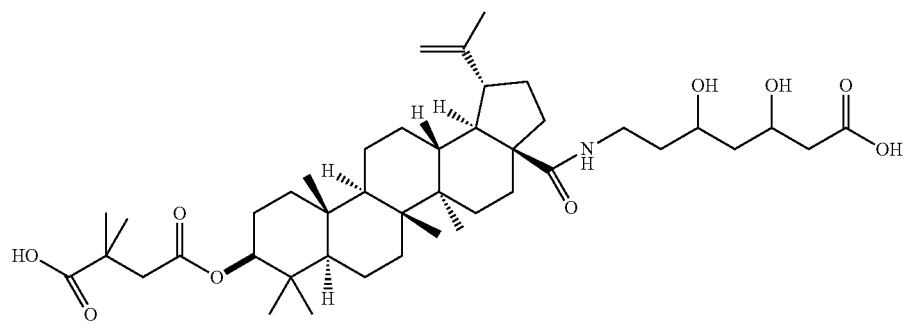 [SMILES: C=C(C)[C@@H]1CC[C@]2(C(=O)NCCC(O)CC(O)CC(=O)O)CC[C@]3(C)[C@H](CC[C@@H]4[C@@]5(C)CC[C@H](OC(=O)CC(C)(C)C(=O)O)C(C)(C)[C@@H]5CC[C@]43C)[C@@H]12]

4-((1R,3aS,5aR,5bR,7aR,9S,11aR,11bR,13aR,13bR)-3a-(2-(6-(carboxymethyl)-2,2-dimethyl-1,3-dioxan-4-yl)ethylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid (Example 80, 0.3 g) was taken in MeOH (3 ml) and cooled the contents to 0° C. then Aq HCl (0.5 ml) was added and the contents were stirred for 6 hours at room temperature. After completion of the reaction (monitored by TLC), the reaction mixture was evaporated under reduced pressure. The residue was taken in water and extracted with DCM, the organic layer was dried over Na$_2$SO$_4$ and concentrated under reduced pressure. The residue was purified by silica gel column chromatography using 5% methanol in DCM as eluent to furnish the title compound (0.08 g) as a white solid. $^1$H NMR (300 MHz, CDCl$_3$): 0.57-0.97 (m, 19H); 1.18-1.21 (m, 8H); 1.25-1.41 (m, 12H); 1.49-1.62 (m, 8H); 1.65-1.82 (m, 10H); 1.85-1.98 (m, 4H); 2.56-2.69 (m, 2H); 2.88-3.06 (m, 3H); 3.29-3.38 (m, 1H); 3.89-3.90 (m, 1H); 4.44-4.47 (m, 1H); 4.56 (s, 1H); 4.71 (s, 1H); Mass: 744 [M+1].

Example 82

Preparation of 5-((1R,3aS,5aR,5bR,7aR,9S,11aR,11bR,13aR,13bR)-3a-((1R,3S)-3-((4-benzylpiperidin-1-yl)methyl)cyclopentylcarbamoyl)-5a,5b,8,8,11a-pentamethyl-1-(prop-1-en-2-yl)icosahydro-1H-cyclopenta[a]chrysen-9-yloxy)-3,3-dimethyl-5-oxopentanoic acid

Example 83

Preparation of ((1R,3aS,5aR,5bR,7aR,9S,11aR,11bR,13aR,13bR)-9-acetoxy-5a,5b,8,8,11a-pentamethyl-1-(prop-1-en-2-yl)icosahydro-1H-cyclopenta[a]chrysene-3a-carbonyl)-4-ethylpiperidine-4-carboxylic acid

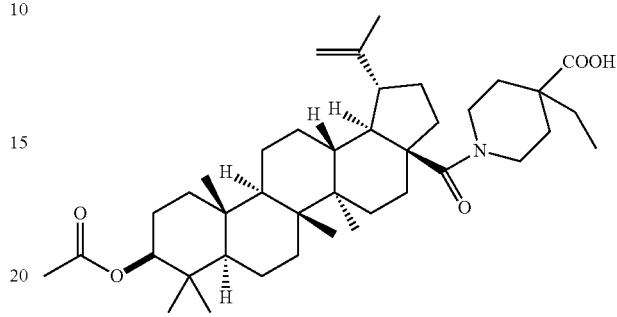

To a stirred solution of (1R,5aR,5bR,7aR,9S,11aR,11bR,13aR,13bR)-9-acetoxy-5a,5b,8,8,11a-pentamethyl-1-(prop-1-en-2-yl)icosahydro-1H-cyclopenta[a]chrysene-3a-carboxylic acid (2.0 g, 4.01 mmol) in DCM (50 ml) oxallyl chloride (4 ml, 15.87 mmol) was added at room temperature. Upon completion of the reaction as shown on TLC, the reac-

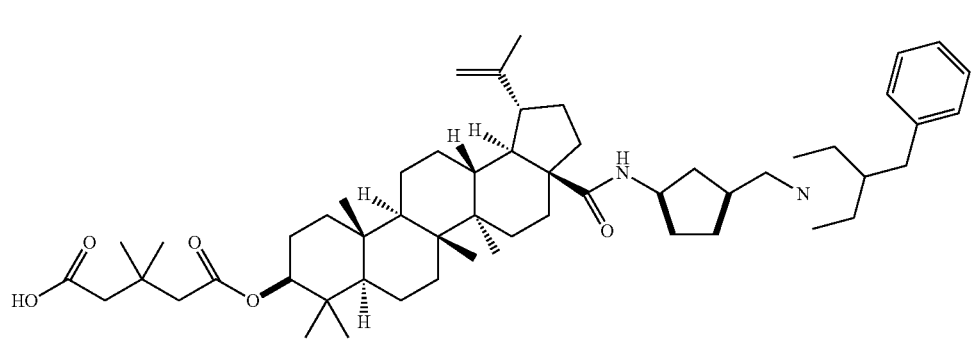

To a stirred solution of (1R,3aS,5aR,5bR,7aR,9S,11aR,11bR,13aR,13bR)-N-((1R,3S)-3-((4-benzylpiperidin-1-yl)methyl)cyclopentyl)-9-hydroxy-5a,5b,8,8,11a-pentamethyl-1-(prop-1-en-2-yl)icosahydro-1H-cyclopenta[a]chrysene-3a-carboxamide (Example 32, 0.5 g, 0.80 mmol) in pyridine (5 ml), dimethyl amino pyridine (0.2 g, 1.6 mmol) was added, followed by 4,4-dimethyldihydro-2H-pyran-2,6(3H)-dione (0.82 ml) was added. The contents were refluxed for 16 hours. After completion of the reaction (monitored by TLC), the reaction mixture was diluted with ethyl acetate (30 ml). The organic layer was washed with 5% aqueous HCl, water followed by brine, dried over Na$_2$SO$_4$ and concentrated under reduced pressure. The residue was purified by silica gel column chromatography using 5% MeOH in DCM as eluent to furnish the title compound (0.25 g) as a white solid. $^1$H NMR (300 MHz, CDCl$_3$): 0.80-0.95 (m, 17H); 1.14-1.67 (m, 23H); 1.82-2.02 (m, 15H); 2.23-3.50 (m, 15H); 4.21-4.45 (m, 2H); 4.57 (s, 1H); 4.72 (s, 1H); 6.28-6.30 (m, 1H); 7.11-7.13 (m, 2H); 7.14-7.22 (m, 1H); 7.24-7.29 (m, 2H); ES Mass: 841 (100%), [M+1].

tion mixture was concentrated under reduced pressure. The residue was taken in DCM (15 ml) and kept under N$_2$ atmosphere.

4-ethylpiperidine-4-carboxylic acid (0.74 g, 4.01 mmol) in DCM (50 ml) triethyl amine (1 ml) was added at 0° C. and stirred for 15 minutes followed by above prepared acid chloride and the reaction was continued at room temperature for about 8 hours. After completion of reaction monitored by TLC, the reaction mixture was neutralized with saturated NaHCO$_3$ and extracted with DCM. The organic layer was dried over Na$_2$SO$_4$ and concentrated under reduced pressure. The residue was purified by silica gel column chromatography using 50% ethyl acetate in hexane as eluent to furnish the title compound (1.8 g). $^1$H NMR (300 MHz, CDCl$_3$): 0.57-0.97 (m, 19H); 1.18-1.21 (m, 8H); 1.25-1.41 (m, 12H); 1.49-1.62 (m, 8H); 1.65-1.82 (m, 10H); 1.85-1.98 (m, 4H); 2.56-2.69 (m, 2H); 2.88-3.06 (m, 3H); 3.29-3.38 (m, 1H); 3.89-3.90 (m, 1H); 4.12-4.23 (m, 2H); 4.44-4.47 (m, 1H); 4.56 (s, 1H); 4.71 (s, 1H); 7.03-7.05 (m, 2H); 7.23-7.25 (m, 3H); ES Mass: 660 (100%), [M+Na].

Example 84

Preparation of 4-ethyl-1-((1R,3aS,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysene-3a-carbonyl)piperidine-4-carboxylic acid

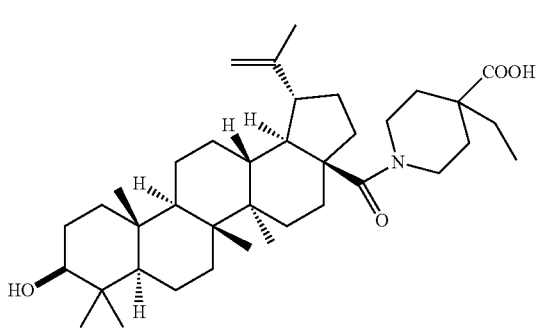 [SMILES: C=C(C)[C@@H]1CC[C@]2(C(=O)N3CCC(CC)(C(=O)O)CC3)CC[C@]3(C)[C@H](CC[C@@H]4[C@@]5(C)CC[C@H](O)C(C)(C)[C@@H]5CC[C@]43C)[C@@H]12]

1-((1R,3aS,5aR,5bR,7aR,9S,11aR,11bR,13aR,13bR)-9-acetoxy-5a,5b,8,8,11a-pentamethyl-1-(prop-1-en-2-yl)icosahydro-1H-cyclopenta[a]chrysene-3a-carbonyl)-4-ethylpiperidine-4-carboxylic acid (Example 83, 2.0 g) was taken in MeOH:THF (8:8 ml) and cooled the contents to 0° C. then sodium hydroxide (1.5 g in 4 ml water) was added and the contents were stirred for 6 hours at room temperature. Completion of the reaction was monitored by TLC. The reaction mixture was evaporated under reduced pressure and the residue was taken in water and extracted with DCM, the organic layer was dried over $Na_2SO_4$ and concentrated under reduced pressure. The residue was purified by silica gel column chromatography using 5% methanol in DCM as eluent to furnish the title compound (1.45 g) as a white solid. $^1$H NMR (300 MHz, CDCl$_3$): 0.57-0.97 (m, 19H); 1.18-1.21 (m, 8H); 1.25-1.41 (m, 12H); 1.49-1.62 (m, 10H); 1.65-1.82 (m, 10H); 1.85-1.98 (m, 4H); 2.56-2.69 (m, 2H); 3.29-3.38 (m, 1H); 3.89-3.90 (m, 1H); 4.15-4.18 (m, 2H); 4.56 (s, 1H); 4.71 (s, 1H); MASS: 595 (100%).

Example 85

Preparation of 1-((1R,3aS,5aR,5bR,7aR,9S,11aR,11bR,13aR,13bR)-9-(3-carboxy-3-methylbutanoyloxy)-5a,5b,8,8,11a-pentamethyl-1-(prop-1-en-2-yl)icosahydro-1H-cyclopenta[a]chrysene-3a-carbonyl)-4-ethylpiperidine-4-carboxylic acid

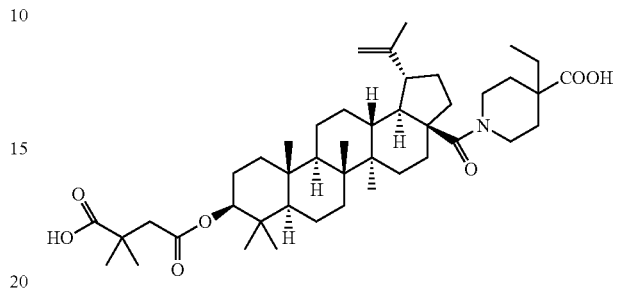

To a stirred solution of 4-ethyl-1-((1R,3aS,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysene-3a-carbonyl)piperidine-4-carboxylic acid (Example 84, 0.5 g, 0.80 mmol) in pyridine (5 ml) dimethyl amino pyridine (0.2 g, 1.6 mmol) and 3,3-dimethyldihydrofuran-2,5-dione (0.82 ml) were added. The contents were refluxed for about 16 hours. After completion of the reaction (monitored by TLC), the reaction mixture was diluted with ethyl acetate (30 ml). The organic layer was washed with 5% aqueous HCl, water followed by brine then dried over $Na_2SO_4$ and concentrated under reduced pressure. The residue was purified by silica gel column chromatography using 5% MeOH in DCM as eluent to furnish the title compound (0.25 g) as a white solid. $^1$H NMR (300 MHz, CDCl$_3$): 0.95-1.16 (m, 19H); 1.23-1.78 (m, 23H); 2.15-2.59 (m, 11H); 2.77-3.58 (m, 16H); 4.33-4.70 (m, 4H); 5.58-5.60 (s, 1H); 5.78-5.80 (s, 1H); 7.44-7.47 (s, 1H); ES Mass: 725 (100%), [M+1].

Example 86

Preparation of 1-(((1S,3R)-3-((1R,3aS,5aR,5bR,7aR,9S,11aR,11bR,13aR,13bR)-9-(3-carboxy-3-methylbutanoyloxy)-5a,5b,8,8,11a-pentamethyl-1-(prop-1-en-2-yl)icosahydro-1H-cyclopenta[a]chrysene-3a-carbonyl)cyclopentyl)methyl)piperidine-4-carboxylic acid

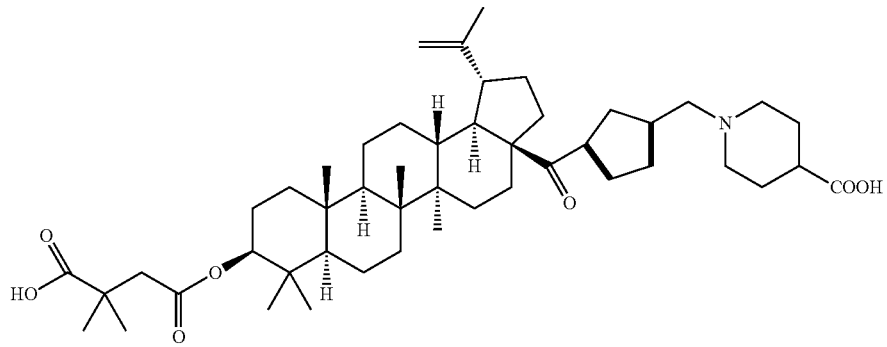

To a stirred solution of 1-(((1S,3R)-3-((1R,3aS,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysene-3a-carbonyl)cyclopentyl)methyl)piperidine-4-carboxylic acid (0.5 g, 0.80 mmol) in pyridine (5 ml) dimethyl amino pyridine (0.2 g, 1.6 mmol) and 3,3-dimethyldihydrofuran-2,5-dione (0.82 ml) were added and the contents were refluxed for about 16 hours. After completion of the reaction (monitored by TLC), the reaction mixture was diluted with ethyl acetate (30 ml), the organic layer was washed with 5% aqueous HCl, then water followed by brine, dried over $Na_2SO_4$ and concentrated under reduced pressure. The residue was purified by silica gel column chromatography using 5% MeOH in DCM as eluent to furnish the title compound (0.25 g) as a white solid. $^1$H NMR (300 MHz, $CDCl_3$): 0.95-1.16 (m, 19H); 1.23-1.78 (m, 23H); 2.15-2.59 (m, 11H); 2.77-3.58 (m, 16H); 4.33-4.70 (m, 4H); 5.58-5.60 (s, 1H); 5.78-5.80 (s, 1H); 7.44-7.47 (s, 1H); ES Mass: 778 (100%), [M+1].

Example 87

Preparation of 4-((1R,3aS,5aR,5bR,7aR,9S,11aR,11bR,13aR,13bR)-3a-((1R,3S)-3-(benzyloxycarbonyl)-2,2-dimethylcyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid

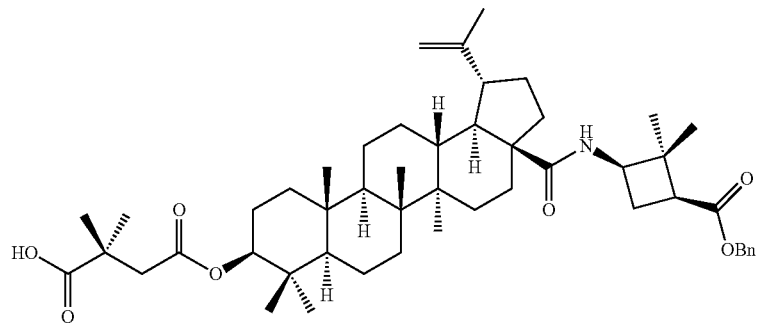

Step 1: synthesis of (1S,3R)-benzyl 34(1R,3aS,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysene-3a-carboxamido)-2,2-dimethylcyclobutanecarboxylate

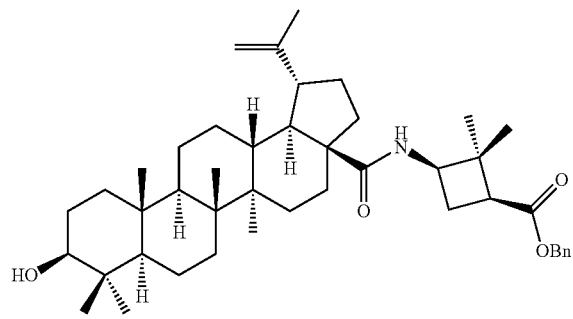

A stirred solution of (1S,3R)-3-((1R,3aS,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysene-3a-carboxamido)-2,2-dimethylcyclobutanecarboxylic acid (Example 5, 2.0 g, 3.844 mmol) in DMF (15 ml) $Cs_2CO_3$ (1.45 g, 4.473 mmol) and benzyl bromide (0.51 ml, 3.843 mmol) were added slowly portion wise at 0° C. After addition, the reaction was stirred at room temperature for 2 hours. After completion of the reaction (monitored by TLC), the reaction mixture was diluted with EtOAc (100 ml) and washed with water (50 ml), brine (50 ml) and dried over $Na_2SO_4$ then the solvent was evaporated and purified by silica gel column (60-120, elution 4% EtOAc in hexane) to afford the title compound as a white solid. $^1$H NMR and Mass complies with the product structure and forwarded to next step.

Step 2: Preparation of 4-((1R,3aS,5aR,5bR,7aR,9S,11aR,11bR,13aR,13bR)-3a-((1R,3S)-3-(benzyloxycarbonyl)-2,2-dimethylcyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid To a stirred solution of (1S,3R)-benzyl 3-((1R,3aS,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysene-3a-carboxamido)-2,2-dimethylcyclobutanecarboxylate (above step 1, 500 mg) in dry pyridine (10 ml) dimethyl Succinic anhydride (953 mg) was added followed by DMAP 181 mg) then reflux the reaction mixture for 20 hours. After completing the reaction (monitored by TLC), diluted with ethyl acetate and washed with water and brine. The combined organic layers were dried over $Na_2SO_4$, concentrated under reduced pressure to afford the crude compound as a gummy solid. The crude compound was purified by silica-gel column chromatography using 100-200 mesh and hexane and ethyl acetate mixtures as mobile phase to get the title compound. Wt: 400 mg, Yield: 67.1%. $^1$H NMR (300 MHZ, $CDCl_3$): δ 7.36 (5H, s), 5.70 (1H, d, J=7.8 Hz), 5.136 (2H, d, J=5.7 Hz), 4.723 (1H, s), 4.58 (1H, s), 4.57-4.47 (1H, m), 4.14-4.11 (1H, m), 3.10-3.09 (1H, m), 2.71-2.60 (4H, m), 2.52-2.31 (2H, m), 2.15-2.00 (1H, m), 1.93-1.89 (2H, m), 1.80-1.17 (31H, m), 0.95 (6H, m), 0.91 (3H, s), 0.882 (3H, s), 0.856 (3H, s), 0.820 (3H, s), 0.786 (1H, m); IR (KBr, $cm^{-1}$): 3406, 3069, 2951, 1734, 1664, 1642, 1509, 1499, 1474, 1456, 1391, 1234, 1184, 1150, 977, 881, 697; Mass: $[M+H]^+$ 800.6 (10%), 822.65 $[M+Na]^+$; Melting Range: 64.7-100.4° C.

Example 88

Preparation of (1S,3R)-3-((1S,3aS,5aR,5bR,7aR,9S,11aR,11bR,13aR,13bR)-9-(3-carboxy-3-methylbutanoyloxy)-1-isopropyl-5a,5b,8,8,11a-pentamethylicosahydro-1H-cyclopenta[a]chrysene-3a-carboxamido)-2,2-dimethylcyclobutanecarboxylic acid

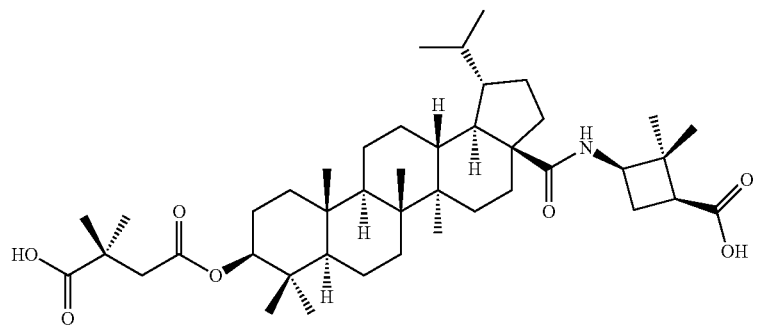

To a stirred solution of 4-((1R,3aS,5aR,5bR,7aR,9S,11aR,11bR,13aR,13bR)-3a-((1R,3S)-3-(benzyloxycarbonyl)-2,2-dimethylcyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid (Example 87, 200 mg) in EtOAc (20 ml) at room temperature 10% Pd/C (catalytic amount) were added and the reaction mixture was stirred under $H_2$ gas atmosphere at room temperature for 12 hours. After completion of the reaction (monitored by TLC), the reaction mixture was filtered through a celite bed and the obtained filtrate was concentrated under reduced pressure to afford the debenzylated title compound as a white solid. Wt: 0.100 g; Yield: 56.2%. $^1$H NMR (300 MHz, CDCl$_3$): δ 5.77 (d, J=7.8 Hz, 1H), 4.54-4.507 (m, 1H), 4.157-4.13 (m, 1H), 2.9-2.80 (m, 1H), 2.7-2.61 (m, 3H), 2.60-2.20 (m, 5H), 2.00-1.93 (m, 1H), 1.80-1.10 (m, 30H), 0.95 (s, 6H), 0.941 (s, 3H), 0.88 (s, 6H), 0.84 (d, J=7.6 Hz, 6H), 0.832 (s, 3H), 0.823 (s, 3H); IR (KBr, cm$^{-1}$): 3403, 2956, 2620, 1710, 1652, 1648, 1509, 1474, 1367, 1245, 1194, 1148, 1000, 978, 877, 620, 509; M.R: 150.1° C.-282.9° C.

Example 89

Preparation of (1R,3S)-1-benzyl 3-((1R,3aS,5aR,5bR,7aR,9S,11aR,11bR,13aR,13bR)-3a-((1S,3R)-3-(4-(ethoxycarbonyl)piperidine-1-carbonyl)-2,2-dimethylcyclobutylcarbamoyl)-5a,5b,8,8,11a-pentamethyl-1-(prop-1-en-2-yl)icosahydro-1H-cyclopenta[a]chrysen-9-yl)2,2-dimethylcyclobutane-1,3-dicarboxylate

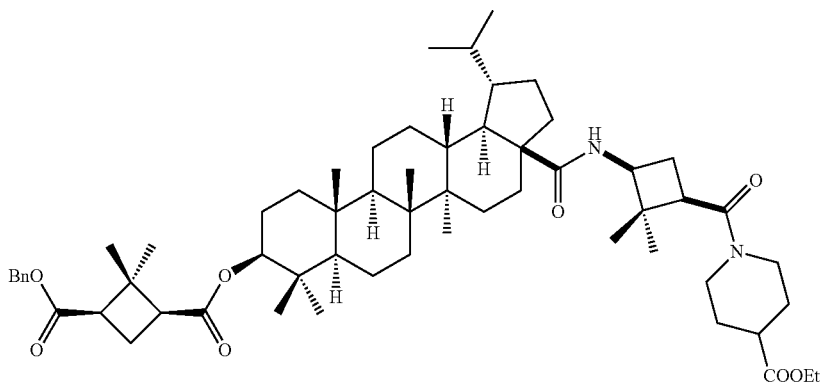

To a cooled solution of (1R,3aS,5aR,5bR,7aR,9S,11aR,11bR,13aR,13bR)-9-((1S,3R)-3-(benzyloxycarbonyl)-2,2-dimethylcyclobutanecarbonyloxy)-5a,5b,8,8,11a-pentamethyl-1-(prop-1-en-2-yl)icosahydro-1H-cyclopenta[a]chrysene-3a-carboxylic acid (Example 18, 1.0 g) in dry DCM (15 ml) oxallyl chloride (1.24 ml) was added drop wise to the reaction mixture under nitrogen and stirred for 2 hours. After completion of the reaction (monitored by TLC), the solvent was evaporated under reduced pressure to get crude compound as a white solid. This crude acid chloride was dissolved in dry DCM and was added to a mixture of ethyl 1-((1R,3S)-3-amino-2,2-dimethylcyclobutanecarbonyl)piperidine-4-carboxylate (678 mg) and triethyl amine (0.5 ml). The reaction mixture was stirred at room temperature for over night. After completion of the reaction, the mixture was diluted with DCM, washed with water, brine and dried over $Na_2SO_4$, concentrated under reduced pressure, purified over silica-gel column chromatography to afford the title compound (700 mg). Yield: 51%. $^1$H NMR (300 MHZ, CDCl$_3$): δ 7.353 (5H, m), 5.958-5.80 (1H, m), 5.12 (2H, d, J=3.90 Hz), 4.73 (1H, m), 4.586 (1H, s), 4.5-4.35 (2H, m), 4.20-4.11 (2H, m), 3.80 (1H, m), 3.20-3.02 (2H, m), 2.898-2.75 (4H, m), 2.70-2.6 (1H, m), 2.59-2.40 (2H, m), 2.38-2.28 (2H, m), 1.96-1.80 (5H, m), 1.79-1.10 (32H, m), 0.961 (6H, s), 0.952 (6H, s), 0.926 (6H, s), 0.840 (3H, s), 0.829 (3H, s), 0.728 (1H, m); FAB Mass: 988 [M+Na]$^+$; IR (KBr, cm$^{-1}$): 3403, 2952, 1733, 1656, 1652, 1639, 1509, 1497, 1463, 1455, 1375, 1263, 1235, 1184, 1108, 1021, 983, 882, 750 and 697; M.R: 138.1° C.-154.2° C.; HPLC: 91.21%.

Example 90

Preparation of (1R,3S)-3-(((1R,3aS,5aR,5bR,7aR,9S,11aR,11bR,13aR,13bR)-3a-((1S,3R)-3-(4-(ethoxycarbonyl)piperidine-1-carbonyl)-2,2-dimethylcyclobutylcarbamoyl)-5a,5b,8,8,11a-pentamethyl-1-(prop-1-en-2-yl)icosahydro-1H-cyclopenta[a]chrysen-9-yloxy)carbonyl)-2,2-dimethylcyclobutanecarboxylic acid To a stirred solution of (1R,3S)-1-benzyl 3-((1R,3aS,5aR,5bR,7aR,9S,11aR,11bR,13aR,13bR)-3a-((1S,3R)-3-(4-(ethoxycarbonyl)piperidine-1-carbonyl)-2,2-dimethylcyclobutylcarbamoyl)-5a,5b,8,8,11a-pentamethyl-1-(prop-1-en-2-yl)icosahydro-1H-cyclopenta[a]chrysen-9-yl)2,2-dimethylcyclobutane-1,3-dicarboxylate (Example 89, 200 mg) in dry DCM (10 ml) triethyl amine (0.1 ml) and Et$_3$SiH (48.1 mg) were added at 0° C. then Pd(OAc)$_2$ (5 mg) was added under nitrogen conditions. The reaction mixture was stirred at reflux temperatures for over night. After completion of the reaction (monitored by TLC), diluted with DCM and concentrated under reduced pressure then purified by column chromatography to get the title compound (150 mg, 83.3% Yield). $^1$H NMR (300 MHz, CDCl$_3$): δ 6.152-6.09 (1H, m), 4.736 (1H, s), 4.58 (1H, s), 4.52-4.35 (2H, m), 4.19-4.12 (3H, m), 3.85-3.80 (1H, m), 3.18-3.08 (2H, m) 2.95-2.86 (4H, m), 2.66-2.20 (7H, m), 2.10 (1H, m), 2.05-1.89 (7H, m), 1.80-1.14 (31H, m), 1.059 (3H, s), 0.955 (3H, s), 0.930 (3H, s), 0.918-0.884 (11H, m), 0.846 (1H, m). Mass (ESI): 897.70 [M+Na] (50%); JR (KBr, cm$^{-1}$): 3403, 2954, 2869, 1733, 1603, 1456, 1459, 1376, 1236, 1185, 1041, 983, 943 and 883; MR: 78° C.-125.2° C.; HPLC: 93.94%.

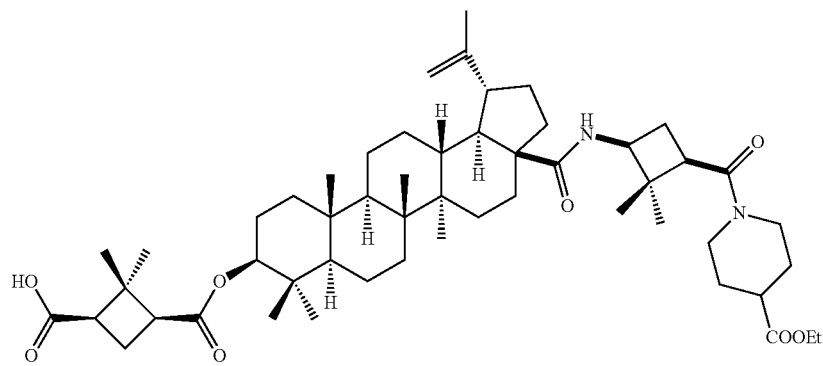

Example 91

Preparation of (1R,3S)-1-benzyl 3-((1R,3aS,5aR, 5bR,7aR,9S,11aR,11bR,13aR,13bR)-3a-((1R,3S)-3-(benzyloxycarbonyl)-2,2-dimethylcyclobutylcarbamoyl)-5a,5b,8,8,11a-pentamethyl-1-(prop-1-en-2-yl) icosahydro-1H-cyclopenta[a]chrysen-9-yl)2,2-dimethylcyclobutane-1,3-dicarboxylate

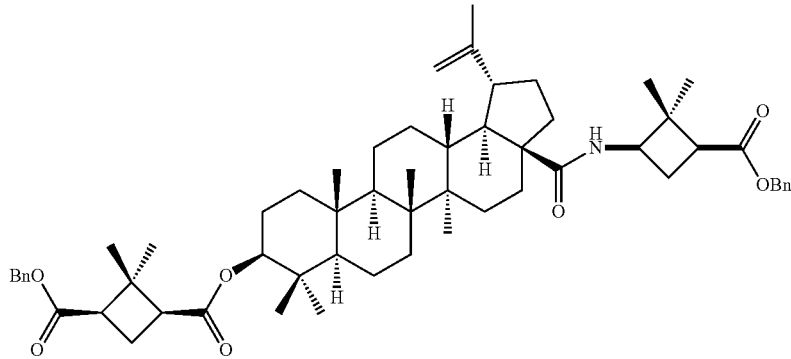

To a stirred solution of (1S,3R)-3-(benzyloxycarbonyl)-2,2-dimethylcyclobutanecarboxylic acid (525 mg, 2.003 mmol) and diisopropyl ethyl amine (1.027 ml, 6.0 mmol) in THF (10 ml) 2,4,6-trichloro benzoyl chloride (0.313 ml, 2.00 mmol) was added at 0° C. temperature and the reaction mixture was allowed to stir at room temperature for 6 hours, After completion of the reaction (monitored by TLC), the solvent was evaporated and crude anhydride was dissolved in dry pyridine (10 ml) then (1S,3R)-benzyl 3-((1R,3aS,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysene-3a-carboxamido)-2,2-dimethylcyclobutanecarboxylate (Example 87-step 1, 0.7 g, 1.641 mmol) in pyridine (10 ml) was added followed by DMAP (catalytic) and refluxed for 12 hours and the solvent was evaporated. The reaction mixture was diluted with DCM and washed with water, the organic layer was dried with $Na_2SO_4$ and concentrated under reduced pressure. The resulting crude purified by silica gel column chromatography (100-200 Mesh, Elution: 5% EtOAc in Hexane) to afford the title compound as a white solid. $^1$H NMR (300 MHZ, $CD_3OD$): δ 7.35 (10H, s), 5.65 (1H, d, J=8.1 Hz), 5.13 (4H, d, J=3.6 Hz), 4.72 (1H, s), 4.57 (1H, s), 4.47-4.43 (1H, m), 4.2-4.09 (1H, m), 3.2-3.0 (1H, m), 2.81-2.61 (5H, m), 2.46-2.317 (3H, m), 1.877 (3H, s), 1.713-1.14 (25H, m), 0.954 (6H, s), 0.95 (3H, s), 0.914 (3H, s), 0.892 (3H, s), 0.880 (3H, s), 0.851 (3H, s), 0.782 (1H, m); FAB Mass: [M+Na]$^+$ 940 (100%); IR (KBr, cm$^{-1}$): 3410, 2954, 2869, 1733, 1664, 1498, 1459, 1456, 1234, 1184, 1020, 883, 697; M. Range: 71.9-111.3° C.

Example 92

Preparation of (1S,3R)-3-((1R,3aS,5aR,5bR,7aR,9S,11aR,11bR,13aR,13bR)-9-((1S,3R)-3-carboxy-2,2-dimethylcyclobutanecarbonyloxy)-5a,5b,8,8,11a-pentamethyl-1-(prop-1-en-2-yl)icosahydro-1H-cyclopenta[a]chrysene-3a-carboxamido)-2,2-dimethylcyclobutanecarboxylic acid

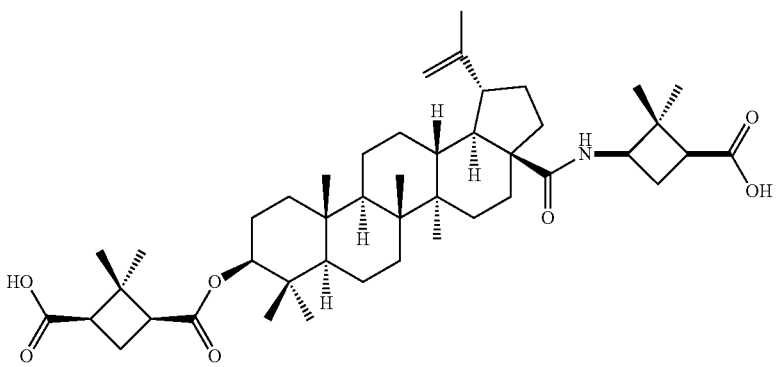

To a stirred solution of (1R,3S)-1-benzyl 3-((1R,3aS,5aR,5bR,7aR,9S,11aR,11bR,13aR,13bR)-3a-((1R,3S)-3-(benzyloxycarbonyl)-2,2-dimethylcyclobutylcarbamoyl)-5a,5b,8,8,11a-pentamethyl-1-(prop-1-en-2-yl)icosahydro-1H-cyclopenta[a]chrysen-9-yl)2,2-dimethylcyclobutane-1,3-dicarboxylate (Example 91, 350 mg) in dry DCM (10 ml) triethyl amine (0.1 ml) and Et₃SiH (88.5 mg) were added at 0° C. then Pd (OAc)₂ (5 mg) was added under nitrogen conditions and the reaction mixture was stirred at reflux temperatures for over night. After completion of the reaction (monitored by TLC), diluted with DCM and concentrated under reduced pressure then purified by column chromatography to get the title compound as a white solid. ¹H NMR (300 MHZ, CD₃OD): δ 5.86 (1H, d, J=8.1 Hz), 4.732 (1H, s), 4.585 (1H, s), 4.54-4.43 (1H, m), 4.2-4.09 (1H, m), 3.2-3.0 (2H, m), 2.80-2.71 (2H, m), 2.46-2.3 (5H, m), 2.00-1.87 (3H, m), 1.83-1.134 (30H, m), 0.978 (6H, s), 0.948 (3H, s), 0.914 (3H, s), 0.884 (3H, s), 0.880 (3H, s), 0.851 (3H, s), 0.782 (1H, m); FAB Mass: [M+Na]⁺ 759 (100%); IR (KBr, cm⁻¹): 3405, 2955, 2870, 1726, 1658, 1652, 1638, 1463, 1390, 1234, 1192, 1019, 879, 727, 621; M. Range: 102.3-158.2° C.

Example 93

Preparation of (1R,3S)-1-benzyl 3-((1R,3aS,5aR,5bR,7 aR,9S,11aR,11bR,13aR,13bR)-3a-(4-(ethoxycarbonyl)piperidine-1-carbonyl)-5a,5b,8,8,11a-pentamethyl-1-(prop-1-en-2-yl)icosahydro-1H-cyclopenta[a]chrysen-9-yl)2,2-dimethylcyclobutane-1,3-dicarboxylate completion of the reaction (monitored by TLC), the solvent was evaporated under nitrogen atmosphere and dissolved in DCM (10 ml), which was added to a stirred solution of 4-ethylpiperidinecarboxylate (0.179 g, 1.142 mmol) at 0° C. and allowed to stir at room temperature for 16 hours. After completion of the reaction (monitored by TLC), the reaction mixture was diluted with DCM and washed with water, 1N HCl, water brine and dried with Na₂SO₄, the solvent was evaporated and purified by silica gel column (100-200 mesh, elution 15% EtOAc in hexane) to afford the title compound as an off white solid. Wt: 0.400 g: Yield: 83.5%. ¹H NMR (300 MHz, CDCl₃): δ 7.363-7.34 (5H, m), 5.12 (2H, d, J=3.9 Hz), 4.72 (1H, d, J=1.5 Hz), 4.51 (1H, d, J=1.5 Hz), 4.44 (1H, m), 4.25 (1H, m), 4.2 (2H, m), 2.98-2.73 (5H, m), 2.63 (1H, m), 2.51 (1H, m) 2.1-2.0 (2H, m), 2.09-1.8 (6H, m), 1.65-1.10 (30H, m), 0.959 (6H, s), 0.949 (3H, s), 0.928 (9H, s), 0.838 (1H, m); Mass (ESI): 862.70 [M+Na] (20%); IR (KBr, cm⁻¹): 3434, 2950, 2867, 2366, 1734, 1631, 1456, 1411, 1390, 1376, 1319, 1264, 1234, 1182, 1168, 1039, 916, 881, 748, 697 cm−1; MR: 57.9° C.-92.9° C.; HPLC: 94.30%.

The following compounds have been prepared by above procedures and the starting C₃—OH compounds have been taken from above compounds.

Example 94

5-((1R,3aS,5aR,5bR,7aR,9S,11aR,11bR,13aR,13bR)-3a-((1R,3S)-3-((4-benzylpiperidin-1-yl)methyl)cyclopentylcarbamoyl)-5a,5b,8,8,11a-pentamethyl-1-(prop-1-en-2-yl)icosahydro-1H-cyclopenta[a]chrysen-9-yloxy)-3,3-dimethyl-5-oxopentanoic acid

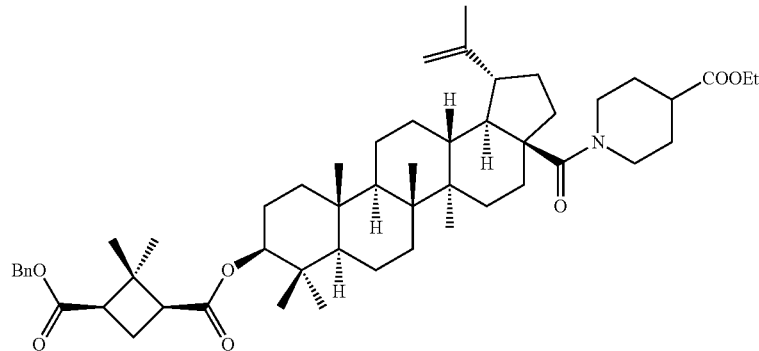

A solution of (COCl)₂ (0.493 ml, 5.71 mmol) in DCM (5 ml) was added to a stirred solution of (1R,3aS,5aR,5bR,7aR,9S,11aR,11bR,13aR,13bR)-9-((1S,3R)-3-(benzyloxycarbonyl)-2,2-dimethylcyclobutanecarbonyloxy)-5a,5b,8,8,11a-pentamethyl-1-(prop-1-en-2-yl)icosahydro-1H-cyclopenta[a]chrysene-3a-carboxylic acid (Example 18, 0.400 g, 0.0.571 mmol) in DCM (10 ml) at 0° C. The reaction mass was allowed to stir at room temperature for 3 hours. After

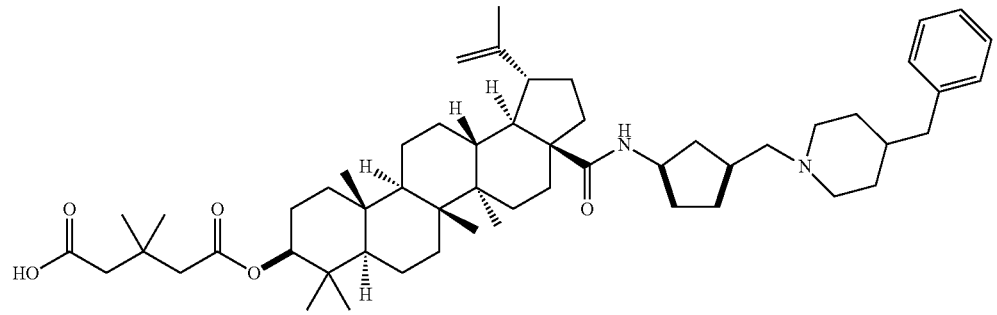

¹H NMR (300 MHz, CDCl₃): δ7.24-7.29 (2H, m), 7.14-7.22 (1H, m), 7.11-7.13 (2H, m), 6.28-6.30 (1H, m), 4.72 (1H, s), 4.57 (1H, s), 4.21-4.45 (2H, m), 2.23-2.50 (15H, m), 1.82-2.02 (15H, m), 1.14-1.67 (23H, m), 0.80-095 (17H, m); Mass (ESI): 854 [M+1] (100%); IR (KBr, cm⁻¹): 3423, 3066, 2947, 1724, 1656, 1639, 1509, 1375, 1232, 1151, MR: 112-160° C.; HPLC: 97.36%.

Example 95

2,2-dimethyl-4-oxo-4-((1R,3aS,5aR,5bR,7aR,9S,11aR,11bR,13aR,13bR)-5a,5b,8,8,11a-pentamethyl-3a-((1S,4R)-4-(morpholinomethyl)cyclopent-2-enyl-carbamoyl)-1-(prop-1-en-2-yl)icosahydro-1H-cyclopenta[a]chrysen-9-yloxy)butanoic acid

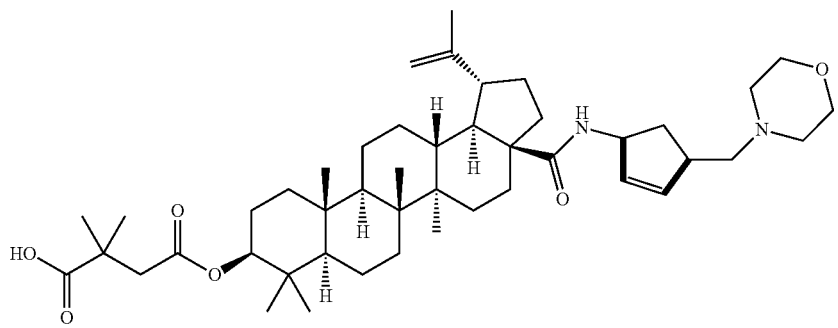

¹H NMR (300 MHz, CDCl₃): δ 0.95-1.16 (m, 19H), 1.23-1.78 (m, 23H), 2.15-2.59 (m, 11H), 2.77-3.58 (m, 11H), 4.33-4.70 (m, 4H), 5.58-5.60 (s, 1H), 5.78-5.80 (s, 1H), 7.44-7.47 (s, 1H); ES Mass: 749 (100%); HPLC: 99.6%.

Example 96

4-oxo-4-((1R,3aS,5aR,5bR,7aR,9S,11aR,11bR,13aR,13bR)-5a,5b,8,8,11a-pentamethyl-3a-(3-(piperidin-1-ylmethyl)cyclopentylcarbamoyl)-1-(prop-1-en-2-yl)icosahydro-1H-cyclopenta[a]chrysen-9-yloxy)butanoic acid

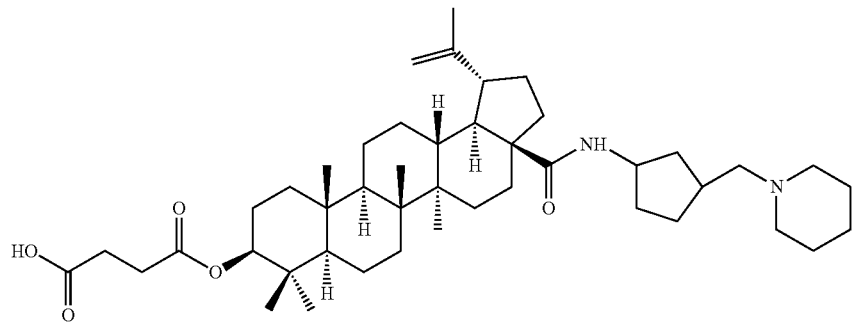

H1NMR (300 MHz, CDCl$_3$): 0.95-1.16 (m, 19H), 1.23-1.78 (m, 23H), 2.15-2.59 (m, 11H), 2.77-3.58 (m, 16H), 4.33-4.70 (m, 4H), 5.58-5.60 (s, 1H), 5.78-5.80 (s, 1H); IRcm$^{-1}$: 3391, 2951, 2866, 2731, 2556, 1726, 1630, 1356, 1244, 1185, 1137, 1004; Mass: 749 [M+1] (100%); HPLC: 90%.

Example 97

(1R,3aS,5aR,5bR,7aR,9S,11aR,11bR,13aR,13bR)-N-(2,2-dimethyl-3-(3-morpholino-3-oxopropylcarbamoyl)cyclobutyl)-9-hydroxy-5a,5b,8,8,11a-pentamethyl-1-(prop-1-en-2-yl)icosahydro-1H-cyclopenta[a]chrysene-3a-carboxamide

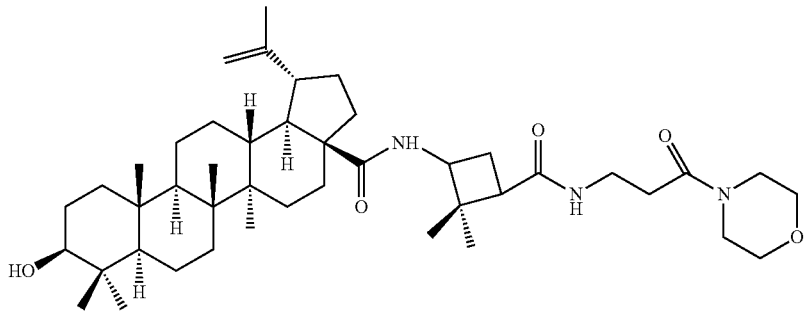

H1NMR (300 MHz, CDCl$_3$): 0.87-0.96 (m, 20H), 1.22-1.89 (m, 23H), 1.89-2.08 (m, 8H), 2.34-2.52 (m, 4H), 3.12-3.16 (m, 2H), 3.40-3.43 (m, 2H), 3.55-3.66 (m, 8H), 4.09 (m, 1H), 4.58 (s, 1H), 4.73 (s, 1H), 6.072-6.10 (d, 1H, J=8.4 Hz), 6.21-6.24 (m, 1H); IRcm$^{-1}$: 3372, 2945, 2865, 1656, 1652, 1646, 1509, 1375, 1271, 1235, 1161, 1034, 754; Mass: 744 [M+Na] (100%); HPLC: 89%

Example 98

(1R,3aS,5aR,5bR,7aR,9S,11aR,11bR,13aR,13bR)-N-(2,2-dimethyl-3-(3-oxo-3-(pyrrolidin-1-yl)propylcarbamoyl)cyclobutyl)-9-hydroxy-5a,5b,8,8,11a-pentamethyl-1-(prop-1-en-2-yl)icosahydro-1H-cyclopenta[a]chrysene-3a-carboxamide

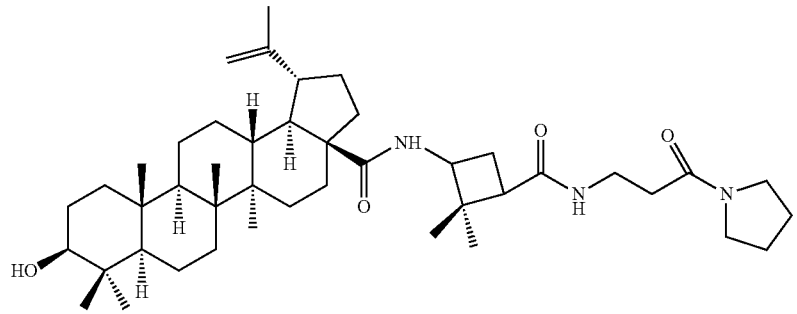

H1NMR (300 MHz, CDCl$_3$): 0.74-0.95 (m, 23H), 1.22-1.38 (m, 12H), 1.49-1.67 (m, 13H), 1.84-2.37 (m, 7H), 2.37-2.47 (m, 5H), 3.12-3.60 (m, 6H), 4.05-4.08 (m, 1H), 4.58 (s, 1H), 4.72 (s, 1H), 6.13-6.15 (d, 1H, J=8.4 Hz), 6.44-6.48 (m, 1H); IRcm$^{-1}$: 3355, 2948, 2869, 1638, 1513, 1452, 1376, 1250, 1046, 881, 752; Mass: 728 [M+Na] (100%); HPLC: 84%.

Example 99

4-((1R,3aS,5aR,5bR,7aR,9S,11aR,11bR,13aR,13bR)-3a-((1R,3S)-3-((4-benzylpiperidin-1-yl)methyl)cyclopentylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid

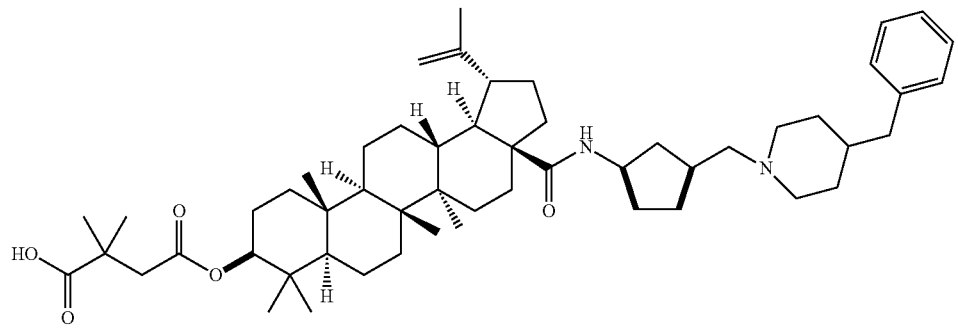

H1NMR (300 MHz, CDCl$_3$): 0.80-0.95 (m, 17H), 1.14-1.67 (m, 23H), 1.82-2.02 (m, 15H), 2.23-3.50 (m, 15H), 4.21-4.45 (m, 2H), 4.57 (s, 1H), 4.72 (s, 11H), 6.28-6.30 (m, 1H), 7.11-7.13 (m, 2H), 7.14-7.22 (m, 1H), 7.24-7.29 (m, 2H); IRcm$^{-1}$: 3416, 2944, 2869, 2179, 1733, 1729, 1640, 1466, 1365, 1033, 1055, 977; Mass: 840 [M+1] (100%); HPLC: 83.13%.

Pharmacological Activity

The compounds described herein can be tested for their activity for antiviral following any procedures known to a person of ordinary skill in the art. For example, the following protocols may be employed for testing the compounds. These protocols are illustrative and do not limit to the scope of the invention.

Example 100

Evaluation of Compounds Cytotoxicity on Sup-T1 Cells

Reduction of 3-(4,5-dimethylthiozol-2-yl)-2,5-diphenyltetrazolium bromide (MTT, sigma) is chosen as an optimal end point of cell viability measurement (Mosmann, 1983; Cole, 1986; Alley et al., 1988) T$^1$ Cells (0.2×10$^6$ cells per well) are seeded in 96-well plates. Increasing concentrations of compound are added to the cells and incubated at 37° C. for about 14 hours in a CO$_2$ Incubator with 5% CO$_2$. The media is replaced with a fresh growth medium along with 20 µL of 5 mg/ml 3-(4,5-dimethylthiazol-2-yl)-2,5-diphenyltetrazolium bromide (MTT, Sigma). After incubation for about 4 hours in a humidified atmosphere, the media is removed and 200 µL of 0.1 N acidic isopropyl alcohol is added to the wells to dissolve the MTT-formazan crystals. The absorbance is recorded at 570 nm, immediately after the development of purple colour. Each experiment is conducted in triplicate and the data are represented as average, with standard deviation. Percent viability of the cells is computed with reference to the absorbance of reduced MTT in the experiments conducted in absence of any compound.

Cell line: Sup-T1
Results:

|  | Percent Viability | |
| --- | --- | --- |
| Concentration | Example 4 | Example 6 |
| 1 mM | 26.18 | 23.15 |
| 100 µM | 38.99 | 88.79 |

-continued

|  | Percent Viability | |
| --- | --- | --- |
| Concentration | Example 4 | Example 6 |
| 1 µM | 85.16 | 88.63 |
| 100 nM | 86.84 | 82.71 |
| 1 nM | 85.81 | 86.88 |

Example 101

Evaluation of Compounds Cytotoxicity on Molt-4 Cells 10 mM stock solution of the test compound was made in DMSO and stored at −20° C. for further use. During the day of the experiment working stocks were made by serial dilution with DMSO. The final concentration of DMSO in the test media is 1%.

MTT assay was performed in a 96 well format using Molt-4 cell line (Human acute T lymphoblastic leukemia)—a suspension culture maintained in RPMI with 10% FBS media.

Approximately 0.03 million cells are seeded/well and the plate was incubated for 16 hours. Following incubation, cells are treated with a test compound at a defined concentration in triplicates and incubation was continued for another 24 hours. At the end of the incubation, MTT reagent was added (10 µl, 5 mg/ml stock) to the plate and continued incubation for additional 4 hours. Reaction was terminated by addition of 200 µl 0.1N acidic propanol. The colour developed was measured by a plate reader using 590 nM filters. The percent viability was calculated by comparing mean absorbance value of sample with the control (Vehicle alone).

Cell line: Molt-4

Results:

|  | Percent Viability | |
| --- | --- | --- |
| Concentration | Example 4 | Example 6 |
| 0.1 µM | 101.26 | 102.89 |
| 1 µM | 98.74 | 98.99 |
| 10 µM | 102.26 | 82.79 |
| 100 µM | 7.03 | 7.27 |

Example 102

P24 assay for Anti-HIV Activity

Viral p24 is measured after about 72 hours of post infection in presence of drugs using an ABL p24 ELISA kit. 0.5 million cells/well are taken into the 24 well plates and added increasing concentrations of drugs. 1 ng/ml of HIV-1 virus was added to each well and incubated for overnight at 37° C. (37° C. and 5% $CO_2$). After about 16 hours incubation the media was changed and fresh media was added and cultured for about 72 hours. P24 was quantified at the $4^{th}$ day of post-infection using an ABL kit according to manufacturer's instructions.

Results:

Percent Inhibition of HIV-193IN 101 Replication in Sup-T1 Cells

|  | Percent Viability | |
| --- | --- | --- |
| Concentration | Example 4 | Example 6 |
| 100 µM | 87.54 | 34.87 |
| 1 µM | 42.44 | 32.08 |
| 100 nM | 23.54 | 21.15 |
| 1 nM | 17.66 | 15.16 |
| 100 pM | 13.03 | 17.47 |

Example 103

Determining the Anti HIV-1($IC_{50}$) and Cytotoxicity Against Infectious HIV-1 strain (92-HT 599)

MT2 cells were infected with the HIV-1 strain 92-HT599 (10TCID50/30000 cells). The infected cells are plated at the concentration of 30000 cells per well in a 96 well assay micro plate. A test compound was added to the micro plate in a defined format with the final concentration of DMSO (vehicle) being not more than 1%. Incubation was carried out in a $CO_2$ incubator for 96 hours for viral infection. At the end of incubation period an aliquot from each well was taken for p24 estimation. The quantitation of p24 is an index for antiviral activity of the compound. Percent inhibition was calculated with reference to control values (vehicle).

P24 estimation was carried out using an Advance Biosciences kit as per the procedure as detailed by supplier.

Compound Preparation:

10 mm stock was made by dissolving test compound in DMSO. Subsequent dilutions were made with DMSO to make necessary working stocks (100×).

Results:

| Example | IC50 (µM) |
| --- | --- |
| 96 | 0.0001 |
| 51 | 0.001 |
| 59 | 0.006 |
| 61 | 0.007 |
| AZT | 3.1 |

| Example | concentration | Percent inhibition |
| --- | --- | --- |
| 23 | 1 µM | 37 |
|  | 0.1 µM | 11 |
| 14 | 1 µM | 32 |
|  | 0.1 µM | 71 |
| 40 | 1 µM | 42 |
|  | 0.1 µM | 13 |
| 44 | 1 µM | 43 |
|  | 0.1 µM | 15 |
| 25 | 1 µM | 25 |
|  | 0.1 µM | 33 |
| 15 | 1 µM | 98 |
|  | 0.1 µM | 86 |
| 97 | 1 µM | 67 |
|  | 0.1 µM | 37 |
| 98 | 1 µM | 50 |
|  | 0.1 µM | 1 |
| 26 | 1 µM | 53 |
|  | 0.1 µM | 52 |
| 99 | 1 µM | 97 |
|  | 0.1 µM | 89 |

Example 104

Evaluation of Compounds for their Anti-HIV-1 $IC_{50}$s and Cytotoxicities ($CC_{50}$) Using Three Infectious HIV-1 Strains (NL4-3, IIIB and CNHN24) in MT2 Cells Assay Procedures:

Compound Preparation:

Compound was dissolved in DMSO to make 30 mM stock. Then the 30 mM stock is further diluted to 4 mM using DMSO. The 4 mM stock was used as the top concentration to carry out an 11-point, 3-fold dilution scheme using DMSO in a 96-well plate to make the compound dose plate. Compounds in the dose plate were transferred to a new 96-well plate (working plate) containing PBS with 0.05% pluronic acid. From this working plate, the compound solution was transferred to the 384-well assay plates.

Control compounds used in compound control wells were prepared and added to assay plates individually.

Assay Methods:

MT2 cells were mixed with HIV-1 strain NL4-3 (or IIIB, or CNHN24) and the cell/virus mixture was added to the aforementioned antivirus assay plates. After incubation in a 37° C., 5% $CO_2$ incubator, the supernatant from the assay plate was transferred to a new 384-well plate containing the indicator cells with a fire fly luciferase gene under HIV-1 LTR control. The expression level of luciferase was related to HIV-1 infectivity and was measured by Bright-Glo kit (Promega).

For cytotoxicity assay the same amount of MT2 cells as in antivirus assay but without HIV-1 virus were added to the cytotoxicity plates. The cytotoxicity was measured by Cell Titer-Glo cell viability assay (Promega).

Therapeutic index (TI) was determined by taking ratio of $CC_{50}/IC_{50}$

Results:

| Viral strain | Example 9 | | | Example 12 | | | Example 48 | | |
|---|---|---|---|---|---|---|---|---|---|
| | IC50 (μM) | CC50 (μM) | TI | IC50 (μM) | CC50 (μM) | Safety Index | IC50 (μM) | CC50 (μM) | Safety Index |
| NL4-3 | 0.005 | >20 | 3579 | 0.021 | >20 | 316 | 0.009 | >20 | 2072 |
| II B | 0.007 (0.034) | >20 | 2658 | 0.029 | >20 | 227 | 0.018 | >20 | 1061 |
| CNHN24 | 0.008 (0.051) | >20 | 2429 | 0.017 | >20 | 383 | 0.011 | >20 | 1691 |

| Viral strain | Example 57 | | | Example 54 | | | Example 94 | | |
|---|---|---|---|---|---|---|---|---|---|
| | IC50 (μM) | CC50 (μM) | TI | IC50 (μM) | CC50 (μM) | Safety Index | IC50 (μM) | CC50 (μM) | Safety Index |
| NL4-3 | 0.857 | >20 | 23 | 0.013 | >20 | 1538 | 0.023 | 4 | 173 |
| II B | 0.590 | >20 | 33 | 0.005 | >20 | 4000 | 0.019 | 4 | 210 |
| CNHN24 | 1.068 | >20 | 20 | 0.024 | >20 | 833 | 0.026 | 4 | 153 |

| Viral strain | Example 74 | | | Example 54 | | | Example 4 | | |
|---|---|---|---|---|---|---|---|---|---|
| | IC50 (μM) | CC50 (μM) | TI | IC50 (μM) | CC50 (μM) | Safety Index | IC50 (μM) | CC50 (μM) | Safety Index |
| NL4-3 | 0.165 | 7.76 | 47 | 0.013 | >20 | 1538 | 0.201 | 20 | 91 |
| II B | 0.086 | 7.76 | 90 | 0.005 | >20 | 4000 | 0.364 | 20 | 54 |
| CNHN24 | 0.163 | 7.76 | 47 | 0.024 | >20 | 833 | 0.218 | 20 | 91 |

| Viral strain | Example 8 | | | Example 11 | | | Example 48 | | |
|---|---|---|---|---|---|---|---|---|---|
| | IC50 (μM) | CC50 (μM) | TI | IC50 (μM) | CC50 (μM) | Safety Index | IC50 (μM) | CC50 (μM) | Safety Index |
| NL4-3 | 2.197 | 20 | 9 | 4.250 | >20 | 4.7 | 0.017 | 20 | 1176 |
| II B | 3.136 | 20 | 6 | 5.666 | >20 | 3.5 | 0.025 | 20 | 800 |
| CNHN24 | 2.828 | 20 | 7 | 5.880 | >20 | 3.4 | 0.021 | 20 | 800 |

| Viral strain | Example 19 | | | Example 95 | | | Example 33 | | |
|---|---|---|---|---|---|---|---|---|---|
| | IC50 (μM) | CC50 (μM) | TI | IC50 (μM) | CC50 (μM) | Safety Index | IC50 (μM) | CC50 (μM) | Safety Index |
| NL4-3 | 0.072 | 20 | 277 | 0.004 | >20 | 5000 | 6.700 | 20 | 2.98 |
| II B | 0.021 | 20 | 952 | 0.001 | >20 | 20000 | 6.700 | 20 | 2.98 |
| CNHN24 | 0.026 | 20 | 769 | 0.003 | >20 | 6666 | 6.700 | 20 | 2.98 |

| Viral strain | Example 45 | | | Example 36 | | |
|---|---|---|---|---|---|---|
| | IC50 (μM) | CC50 (μM) | TI | IC50 (μM) | CC50 (μM) | Safety Index |
| NL4-3 | 0.017 | 20 | 1177 | 0.005 | >20 | 4000 |
| II B | 0.025 | 20 | 800 | 0.004 | >20 | 5000 |
| CNHN24 | 0.022 | 20 | 800 | 0.005 | >20 | 4000 |

Example 105

Evaluation of Compounds for their Anti-HIV-1 $IC_{50}$s and Cytotoxicities ($CC_{50}$) Using Three Infectious HIV-1 Strains (NL4-3, IIIB and CNHN24) in PBMC Cells Compound Preparation:
Compound was dissolved in DMSO to make 30 mM stock. Then the 30 mM stock was further diluted to 4 mM using DMSO. The 4 mM stock was used as the top concentration to carry out an 11-point, 3-fold dilution scheme using DMSO in a 96-well plate to make the compound dose plate. Compounds in the dose plate were transferred to a new 96-well plate (working plate) containing PBS with 0.05% pluronic acid. From this working plate the compound solution was transferred to the 384-well assay plates.

Control compounds for cpd control wells were prepared and added to assay plates individually.

Assay Method:

PBMC cells were isolated from human whole blood using Histopaque-1077 (Sigma, #10771) and frozen down and kept in liquid nitrogen tank. Two days before the assay PBMC was recovered and cultured in medium containing PHA-P (Sigma, #L1668). On the day of assay PBMC cells were pelleted down and resuspended in medium containing IL-2 (Sigma, #I7908), then the cells were mixed with HIV-1 strain NL4-3, MOI=0.01 (or IIIB, or CNHN24) and the cell/virus mixture was added to the aforementioned antivirus assay plates. After incubation in a 37° C., 5% $CO_2$ incubator, the supernatant from the assay plate was transferred to a new 384-well plate containing the indicator cells with a fire fly luciferase gene under HIV-1 LTR control. The expression level of luciferase was related to HIV-1 infectivity and was measured by Bright-Glo kit (Promega).

For the cytotoxicity assay, the same amount of PBMC cells as in the antivirus assay but without the HIV-1 virus, was added to the cytotoxicity plates. The cytotoxicity was measured by a CellTiter-Glo cell viability assay (Promega).

Results:

| | Example 45 | | |
|---|---|---|---|
| Viral strain | IC50 (μM) | CC50 (μM) | Safety Index |
| NL4-3 | 0.017 | >20 | 1146 |
| II B | 0.025 | >20 | 793 |
| CNHN24 | 0.022 | >20 | 921 |

REFERENCES

1. Mosmann T, December 1983, *Journal of immunological methods,* 65 (1-2), 55-63.
2. *SPC Cole, cancer chemotherapy and Pharmacology,* 1986, 17, 259-263.
3. *Antiviral methods and protocols* (Eds: D. Kinchington and R F Schinazi), Humana press Inc, 2000]
4. *HIV protocols* (Eds: N L Michael and J H Kin), Humana press Inc, 1999]
5. *DAIDS virology manual for HIV laboratories,* publication NIH-97-38-38, 1997
6. *HIV-1 p24 antigen capture assay, enzyme immuno assay for deduction of HIV-1 p24 in tissue culture media*—Advance bioscience laboratories Inc., kit procedure.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as described above.

All publications and patent applications cited in this application are herein incorporated by reference to the same extent as if each individual publication or patent application was specifically and individually indicated to be incorporated herein by reference.

We claim:

1. A compound of the formula (I):

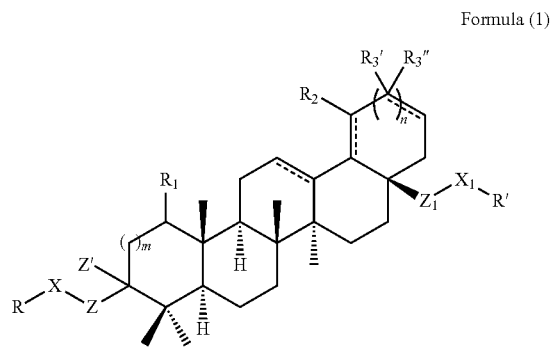

Formula (1)

wherein,

R is H, substituted or unsubstituted alkyl, substituted or unsubstituted aryl, substituted or unsubstituted cycloalkyl, or substituted or unsubstituted heterocyclyl;

R' is H, substituted or unsubstituted alkyl, substituted or unsubstituted aryl, substituted or unsubstituted cycloalkyl, substituted or unsubstituted cycloalkenyl, substituted or unsubstituted heterocyclyl, substituted or unsubstituted alkyloxy, or substituted or unsubstituted aryloxy;

X and $X_1$ are independently selected from a bond, —O—, —NR"—, —C(O)—, —C(O)$_2$—, —(CH$_2$)$_n$—, or —C(O)NR"—;

Z and $Z_1$ are independently selected from a bond, —(CH$_2$)$_n$—, —C(O)—, —O—, —S—, —SO$_2$—, or —NR"—;

Z' is H, substituted or unsubstituted alkyl, or Z and Z' are together with the attached carbon to form oxo (C=O) and when Z and Z' together with the attached carbon form oxo (C=O) then X and R are absent;

n is an integer 0-2;

m is an integer 0-2;

" $=\!=\!=$ " is single bond or double bond;

$R_1$ is H, C(O)$_2$R", or substituted or unsubstituted alkyl;

$R_2$ is H, substituted or unsubstituted alkyl, substituted or unsubstituted alkenyl, substituted or unsubstituted alkynyl, or substituted or unsubstituted cycloalkyl;

$R_3$' and $R_3$" are independently selected from H, or substituted or unsubstituted alkyl and when " $=\!=\!=$ " is a double bond then one of $R_3$' or $R_3$" is absent; and each R" is independently selected from H, substituted or unsubstituted alkyl, substituted or unsubstituted amino, substituted or unsubstituted aryl, substituted or unsubstituted cycloalkyl, or substituted or unsubstituted heterocyclyl; and a proviso that one of the R or R' is substituted or unsubstituted 4 or 5 membered cycloalkyl group, and if R or R' is 4 membered cycloalkyl group then at least one of the carbon atom of the 4 membered cycloalkyl group must be substituted by two identical groups and which are selected from alkyl or halogen, and if R' is 5 membered cycloalkyl group it is substituted by substituted or unsubstituted heterocyclylalkyl, a pharmaceutically acceptable salt thereof, a tautomer thereof, a regioisomer thereof, or a stereoisomer thereof.

2. The compound according to claim 1, which is a compound of the formula (IA):

Formula (1A)

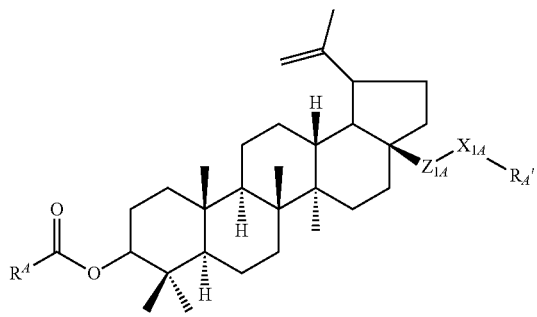

wherein,
R$^A$ is substituted or unsubstituted alkyl or substituted or unsubstituted cycloalkyl; wherein cycloalkyl is a 4 or 5 membered ring system and substituents in each occurrence is independently selected from H, halo, C$_1$-C$_4$ alkyl, CO—O—R$_b$, —CH$_2$—O—R$_b$, CO—NHR$_b$, or CON(R$_b$)$_2$;

R$_A$' is H, substituted or unsubstituted alkyl, substituted or unsubstituted aryl, substituted or unsubstituted cycloalkyl;

X$_{1A}$ is a bond, —O—, —NR"—, —C(O)—, —C(O)$_2$—, or —C(O)NR"—;

Z$_{1A}$ is a bond, —C(O)—, —O—, —S—, —SO$_2$—, or —NR"—;

R$_b$ is H, or substituted or unsubstituted alkyl; and each R" is independently selected from H, substituted or unsubstituted alkyl, substituted or unsubstituted amino, substituted or unsubstituted aryl, substituted or unsubstituted cycloalkyl, or substituted or unsubstituted heterocyclyl; and a proviso that one of the R$^A$ or R$_A$' is substituted or unsubstituted 4 or 5 membered cycloalkyl group, and if R$^A$ or R$_A$' is 4 membered cycloalkyl group then at least one of the carbon atom of the 4 membered cycloalkyl group must be substituted by two identical groups and which are selected from alkyl or halogen, and if R$_A$' is 5 membered cycloalkyl group it is substituted by substituted or unsubstituted heterocyclylalkyl, a pharmaceutically acceptable salt thereof, a tautomer thereof, a regioisomer thereof, or a stereoisomer thereof.

3. The compound according to claim 1, which is a compound of the formula (2):

Formula (2)

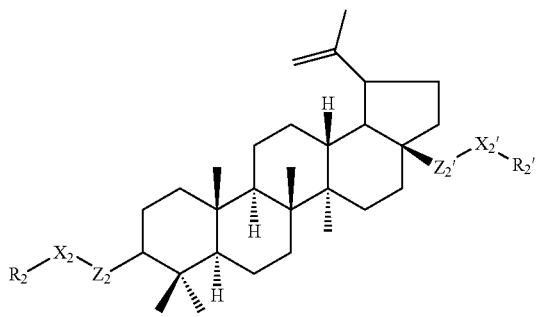

wherein,
R$_2$ is H, substituted or unsubstituted alkyl, substituted or unsubstituted aryl, or substituted or unsubstituted cycloalkyl;

R$_2$' is H, substituted or unsubstituted alkyl, substituted or unsubstituted aryl, substituted or unsubstituted cycloalkyl, substituted or unsubstituted heterocyclyl, substituted or unsubstituted alkyloxy, or substituted or unsubstituted aryloxy;

X$_2$ and X$_2$' are independently selected from a bond, —O—, —NR"—, —C(O)—, —C(O)$_2$—, —(CH$_2$)$_n$—, or —C(O)NR"—;

n is 0-3;

Z$_2$ and Z$_2$' are independently selected from a bond, —C(O)—, —O—, or —NR"—;

each R" is independently selected from H, —[CH(R''')]$_p$C(O)$_2$R''', substituted or unsubstituted alkyl, substituted or unsubstituted amino, substituted or unsubstituted aryl, substituted or unsubstituted cycloalkyl, or substituted or unsubstituted hetero cyclyl;

p is 0-3; and each R''' is independently selected from H, substituted or unsubstituted alkyl, or substituted or unsubstituted cycloalkyl; and a proviso that one of the R$_2$ or R$_2$' is substituted or unsubstituted 4 or 5 membered cycloalkyl group, and if R$_2$ or R$_2$' is 4 membered cycloalkyl group then at least one of the carbon atom of the 4 membered cycloalkyl group must be substituted by two identical groups and which are selected from alkyl or halogen, and if R$_2$' is 5 membered cycloalkyl group it is substituted by substituted or unsubstituted heterocyclylalkyl, a pharmaceutically acceptable salt thereof, a tautomer thereof, a regioisomer thereof, or a stereoisomer thereof.

4. A compound of the formula (2A):

Formula (2A)

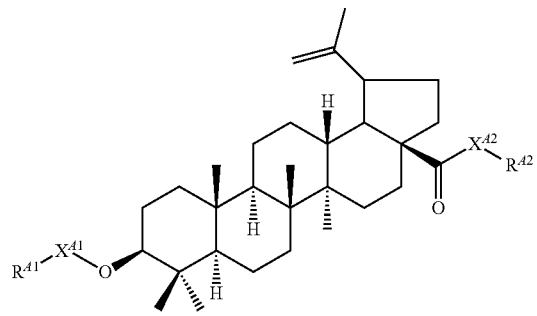

wherein,
X$^{41}$ is a bond, or —C(O)—;
X$^{42}$ is a NH;
R$^{41}$ is H, substituted or unsubstituted alkyl, substituted or unsubstituted aryl,

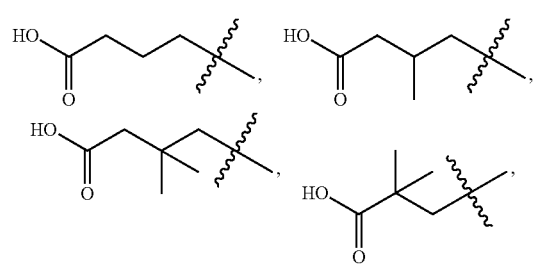

165
-continued

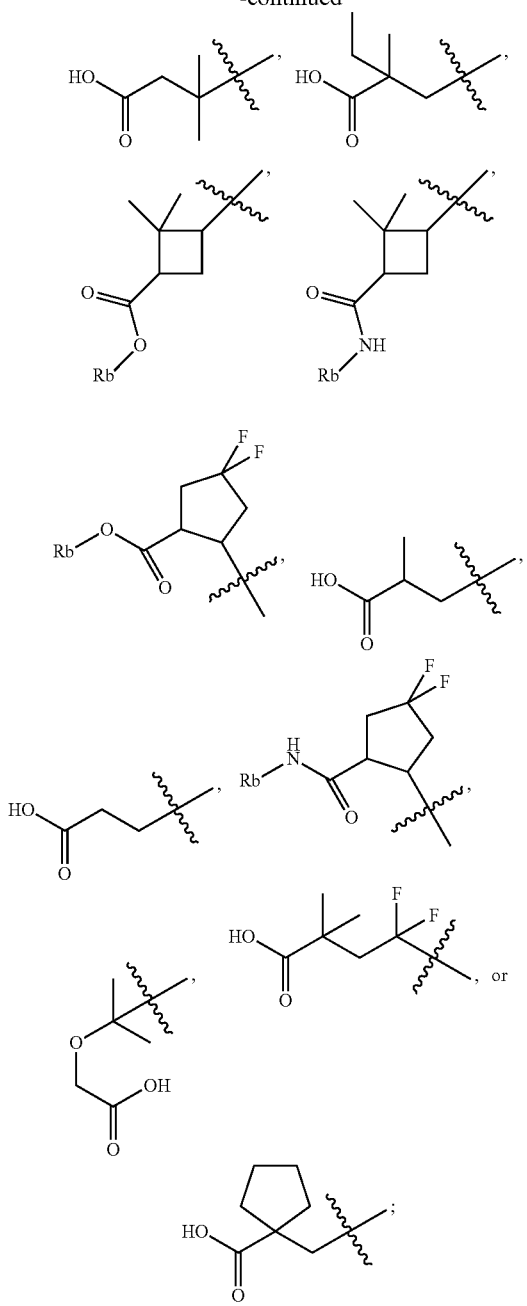

Rb is H, or substituted or unsubstituted alkyl;

R$^{A2}$ is H, substituted or unsubstituted alkyl, substituted or unsubstituted amino, substituted or unsubstituted cycloalkyl, substituted or unsubstituted cycloalkenyl, substituted or unsubstituted heterocyclyl, or substituted or unsubstituted aryl and when substituted, R$^{A2}$ is substituted by R'''; and each R''' is substituted or unsubstituted alkyl, substituted or unsubstituted heterocyclyl, wherein heterocycle is nitrogen containing heterocycle and is bonded through nitrogen atom, substituted or unsubstituted N contained heterocyclylalkyl (wherein alkyl is bonded to ring nitrogen atom of heterocycle), substituted or unsubstituted aralkyl or substituted or unsubstituted phenyl,

166 when X$^{A2}$ is NH, then R$^{A2}$ is

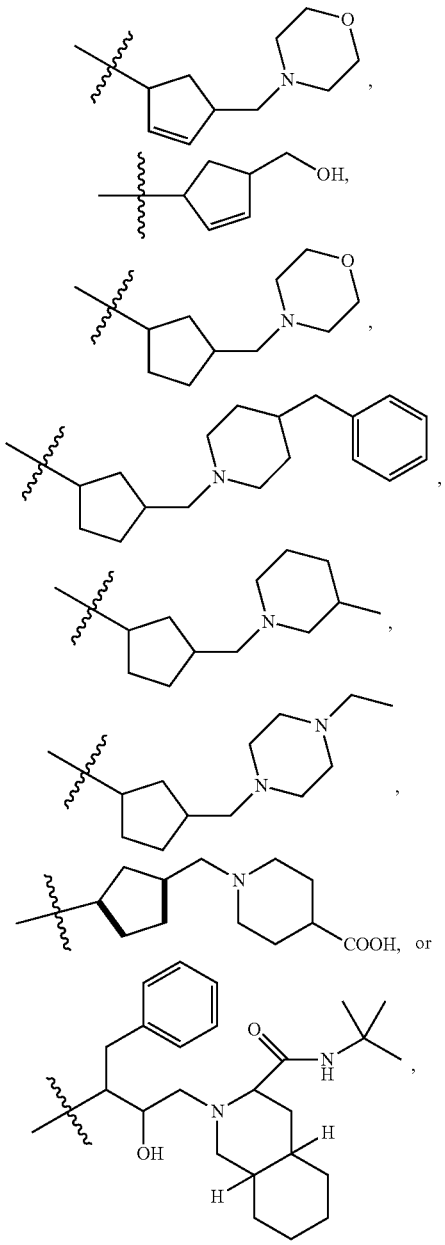

a pharmaceutically acceptable salt thereof, a tautomer thereof, a regioisomer thereof, or a stereo isomer thereof.

5. A compound selected from the group consisting of:
(1S,3R)-benzyl 3-((1R,3aS,5aR,5bR,7aR,9S,11aR,11bR, 13aR,13bR)-9-acetoxy-5a,5b, 8,8,11a-pentamethyl-1-(prop-1-en-2-yl)icosahydro-1H-cyclopenta[a]chrysene-3a-carboxamido)-2,2-dimethylcyclobutanecarboxylate,
(1R,3aS,5aR,5bR,7aR,9S,11aR,11bR,13aR,13bR)-9-((1R,3S)-3-(tert-butoxycarbonyl)-2,2-dimethylcyclobutanecarbonyloxy)-5a,5b,8,8,11a-pentamethyl-1-(prop-1-en-2-yl)icosahydro-1H-cyclopenta[a]chrysene-3a-carboxylic acid,
(1R,3aS,5aR,5bR,7aR,9S,11aR,11bR,13aR,13bR)-9-((1R,3S)-3-carboxy-2,2-dimethylcyclobutanecarbonyloxy)-5a,5b,8,8,11a-pentamethyl-1-(prop-1-en-2-yl) icosahydro-1H-cyclopenta[a]chrysene-3a-carboxylic acid, (1S,3R)-3-((1R,3aS,5aR,5bR,7aR,9S,11aR,11bR,13aR, 13bR)-9-hydroxy-5a,5b,8,8,11a-pentamethyl-1-(prop-1-en-2-yl)icosahydro-1H-cyclopenta[a]chrysene-3a-carboxamido)-2,2-dimethylcyclobutanecarboxylic acid, (1R,2S,3aR,5aR,5bR,7aS,10R,12aR,12bR)-2-(3-carboxy-3-methylbutanoyloxy)-3,3,5a,5b,12b-pentamethyl-10-(prop-1-en-2-yl)icosahydrodicyclopenta[a]phenanthrene-1,7a-dicarboxylic acid, (1R,3aS,5aR,5bR,7aR,9S,11aR,11bR,13aR,13bR)-3a-((1S,3R)-2,2-dimethyl-3-(morpholine-4-carbonyl)cyclobutylcarbamoyl)-5a,5b,8,8,11a-pentamethyl-1-(prop-1-en-2-yl)icosahydro-1H-cyclopenta[a]chrysen-9-yl acetate, (1R,3aS,5aR,5bR,7aR,9S,11aR,11bR,13aR,13bR)-N-((1S,3R)-2,2-dimethyl-3-(morpholine-4-carbonyl)cyclobutyl)-9-hydroxy-5a,5b, 8,8,11a-pentamethyl-1-(prop-1-en-2-yl)icosahydro-1H-cyclopenta[a]chrysene-3a-carboxamide, 4-((1R,3aS,5aR,5bR,7aR,9S,11aR,11bR,13aR,13bR)-3a-((1S,3R)-2,2-dimethyl-3-(morpholine-4-carbonyl)cyclobutylcarbamoyl)-5a, 5b,8,8,11a-pentamethyl-1-(prop-1-en-2-yl)icosahydro-1H-cyclopenta[a]chrysen-9-yloxy)-2,2-dimethyl-4-oxobutanoic acid, (1R,3aS,5aR,5bR,7aR,9S,11aR,11bR,13aR,13bR)-3a-((1S,3R)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yl acetate, (1R,3aS,5aR,5bR,7aR,9S,11aR,11bR,13aR,13bR)-N-((1S,3R)-2,2-dimethyl-3-(piperidine-1-carbonyl)cyclobutyl)-9-hydroxy-5a,5b,8,8,11a-pentamethyl-1-(prop-1-en-2-yl)icosahydro-1H-cyclopenta[a]chrysene-3a-carboxamide, 4-((1R,3aS,5aR,5bR,7aR,9S,11aR,11bR,13aR,13bR)-3a-((1S,3R)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid, (1R,3aS,5aR,5bR,7aR,9S,11aR,11bR,13aR,13bR)-3a-((1S,3R)-2,2-dimethyl-3-(pyrrolidine-1-carbonyl)cyclobutylcarbamoyl)-5a,5b,8,8,11a-pentamethyl-1-(prop-1-en-2-yl)icosahydro-1H-cyclopenta[a]chrysen-9-yl acetate, (1R,3aS,5aR,5bR,7aR,9S,11aR,11bR,13aR,13bR)-N-((1S,3R)-2,2-dimethyl-3-(pyrrolidine-1-carbonyl)cyclobutyl)-9-hydroxy-5a,5b,8,8,11a-pentamethyl-1-(prop-1-en-2-yl)icosahydro-1H-cyclopenta[a]chrysene-3a-carboxamide, 4-((1R,3aS,5aR,5bR,7aR,9S,11aR,11bR,13aR,13bR)-3a-((1S,3R)-2,2-dimethyl-3-(pyrrolidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid, (1R,3aS,5aR,5bR,7aR,9S,11aR,11bR,13aR,13bR)-3a-((1R,3S)-2,2-dimethyl-3-(morpholine-4-carbonyl)cyclobutylcarbamoyl)-5a,5b,8,8,11a-pentamethyl-1-(prop-1-en-2-yl)icosahydro-1H-cyclopenta[a]chrysen-9-yl acetate, (1R,3aS,5aR,5bR,7aR,9S,11aR,11bR,13aR,13bR)-N-((1S,3R)-2,2-dimethyl-3-(morpholine-4-carbonyl)cyclobutyl)-9-hydroxy-5a,5b,8,8,11a-pentamethyl-1-(prop-1-en-2-yl)icosahydro-1H-cyclopenta[a]chrysene-3a-carboxamide, (1R,3aS,5aR,5bR,7aR,9S,11aR,11bR,13aR,13bR)-9-((1S,3R)-3-(benzyloxycarbonyl)-2,2-dimethylcyclobutanecarbonyloxy)-5a,5b,8,8,11a-pentamethyl-1-(prop-1-en-2-yl)icosahydro-1H-cyclopenta[a]chrysene-3a-carboxylic acid, (1R,3aS,5aR,5bR,7aR,9S,11aR,11bR,13aR,13bR)-9-((1S,3R)-3-carboxy-2,2-dimethylcyclobutanecarbonyloxy)-5a,5b,8,8,11a-pentamethyl-1-(prop-1-en-2-yl)icosahydro-1H-cyclopenta[a]chrysene-3a-carboxylic acid, (1R,3aS,5aR,5bR,7aR,9S,11aR,11bR,13aR,13bR)-5a,5b,8,8,11a-pentamethyl-3a-((1R,3S)-3-morpholinomethyl)cyclopentylcarbamoyl)-1-(prop-1-en-2-yl)icosahydro-1H-cyclopenta[a]chrysen-9-yl acetate, (1R,3aS,5aR,5bR,7aR,9S,11aR,11bR,13aR,13bR)-5a,5b,8,8,11a-pentamethyl-3a-((1S,4R)-4-(morpholinomethyl)cyclopent-2-enylcarbamoyl)-1-(prop-1-en-2-yl)-icosahydro-1H-cyclopenta[a]chrysen-9-yl acetate, ((1R,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysen-3a-yl)(3-(3-isopropyl-5-methyl-4H-1,2,4-triazol-4-yl)-8-azabicyclo[3.2.1]octan-8-yl)methanone, (1R,3aS,5aR,5bR,7aR,9S,11aR,11bR,13aR,13bR)-9-hydroxy-5a,5b,8,8,11a-pentamethyl-N-((1R,3S)-3-(morpholinomethyl)cyclopentyl)-1-(prop-1-en-2-yl)icosahydro-1H-cyclopenta[a]chrysene-3a-carboxamide, 2,2-dimethyl-4-oxo-4-((1R,3aS,5aR,5bR,7aR,9S,11aR,11bR,13aR,13bR)-5a,5b,8,8,11a-pentamethyl-3a-((1R,3S)-3-(morpholinomethyl)cyclopentylcarbamoyl)-1-(prop-1-en-2-yl)icosahydro-1H-cyclopenta[a]chrysen-9-yl oxy)butanoic acid, ((1R,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysen-3a-yl)(3-(3-isopropyl-5-methyl-4H-1,2,4-triazol-4-yl)-8-azabicyclo[3.2.1]octan-8-yl)methanone, (1R,3aS,5aR,5bR,7aR,9S,11aR,11bR,13aR,13bR)-9-hydroxy-5a,5b,8,8,11a-pentamethyl-N-((1S,4R)-4-(morpholinomethyl)cyclopent-2-enyl)-1-(prop-1-en-2-yl)icosahydro-1H-cyclopenta[a]chrysene-3a-carboxamide, (1R,3aS,5aR,5bR,7aR,9S,11aR,11bR,13aR,13bR)-3a-(4-(hydroxymethyl)cyclopent-2-enylcarbamoyl)-5a,5b,8,8,11a-pentamethyl-1-(prop-1-en-2-yl)icosahydro-1H-cyclopenta[a]chrysen-9-yl acetate, (1R,3aS,5aR,5bR,7aR,9S,11aR,11bR,13aR,13bR)-9-hydroxy-N-(4-(hydroxymethyl)cyclopent-2-enyl)-5a,5b,8,8,11a-pentamethyl-1-(prop-1-en-2-yl)icosahydro-1H-cyclopenta[a]chrysene-3a-carboxamide, (1R,3aS,5aR,5bR,7aR,9S,11aR,11bR,13aR,13bR)-3a-((2S,3R)-4-((3S,4aS,8aS)-3-(tert-butylcarbamoyl)octahydroisoquinolin-2(1H)-yl)-3-hydroxy-1-phenylbutan-2-ylcarbamoyl)-5a,5b,8,8,11a-pentamethyl-1-(prop-1-en-2-yl)icosahydro-1H-cyclopenta[a]chrysen-9-yl acetate, (3S,4aS,8aS)-N-tert-butyl-2-((2R,3S)-2-hydroxy-3-((1R,3aS,5aR,5bR,7aR,9S,11aR,11bR,13aR,13bR)-9-hydroxy-5a,5b,8,8,11a-penta methyl-1-(prop-1-en-2-yl)icosahydro-1H-cyclopenta[a]chrysene-3a-carboxamido)-4-phenylbutyl)decahydroisoquinoline-3-carboxamide, (1R,3aS,5aR,5bR,7aR,9S,11aR,11bR,13aR,13bR)-3a-((1R,3S)-3-((4-benzylpiperidin-1-yl)methyl)cyclopentylcarbamoyl)-5a,5b,8,8,11a-pentamethyl-1-(prop-1-en-2-yl)icosahydro-1H-cyclopenta[a]chrysen-9-yl acetate, (1R,3aS,5aR,5bR,7aR,9S,11aR,11bR,13aR,13bR)-N-((1R,3S)-3-((4-benzylpiperidin-1-yl)methyl)cyclopentyl)-9-hydroxy-5a,5b,8,8,11a-pentamethyl-1-(prop-1-en-2-yl)icosahydro-1H-cyclopenta[a]chrysene-3a-carboxamide, 5-((1R,3aS,5aR,5bR,7aR,9S,11aR,11bR,13aR,13bR)-3a-((1R,3S)-3-((4-benzylpiperidin-1-yl)methyl)cyclopentylcarbamoyl)-5a,5b,8,8,11a-pentamethyl-1-(prop-1-en-2-yl)icosahydro-1H-cyclopenta[a]chrysen-9-yloxy)-5-oxopentanoic acid, (1R,3aS,5aR,5bR,7aR,9S,11aR,11bR,13aR,13bR)-3a-((1R,3S)-3-((4-ethylpiperazin-1-yl)methyl)cyclopentylcarbamoyl)-5a,5b,8,8,11a-pentamethyl-1-(prop-1-en-2-yl)icosahydro-1H-cyclopenta[a]chrysen-9-yl acetate, (1R,3aS,5aR,5bR,7aR,9S,11aR,11bR,13aR,13bR)-N-((1R,3S)-3-((4-ethylpiperazin-1-yl)methyl)cyclopentyl)-9-hydroxy-5a,5b,8,8,11a-pentamethyl-1-(prop-1-en-2-yl)icosahydro-1H-cyclopenta[a]chrysene-3a-carboxamide, 4-((1R,3aS,5aR,5bR,7aR,9S,11aR,11bR,13aR,13bR)-3a-((1R,3S)-3-((4-ethylpiperazin-1-yl)methyl)cyclopentylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid, Methyl 3-((1S,3R)-3-((1R,3aS,5aR,5bR,7aR,9S,11aR,11bR,13aR,13bR)-9-acetoxy-5a,5b,8,8,11a-pentamethyl-1-(prop-1-en-2-yl)icosahydro-1H-cyclopenta[a]chrysene-3a-carboxamido)-2,2-dimethylcyclobutanecarboxamido) propanoate, 3-((1S,3R)-3-((1R,3aS,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysene-3a-carboxamido)-2,2-dimethylcyclobutanecarboxamido)propanoic acid, (S)-methyl 2-((1S,3R)-3-((1R,3aS,5aR,5bR,7aR,9S,11aR,11bR,13aR,13bR)-9-acetoxy-5a,5b,8,8,11a-pentamethyl-1-(prop-1-en-2-yl)icosahydro-1H-cyclopenta[a]chrysene-3a-carboxamido)-2,2-dimethylcyclobutanecarboxamido)-3-methylbutanoate, (S)-2-((1S,3R)-3-((1R,3aS,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysene-3a-carboxamido)-2,2-dimethylcyclobutanecarboxamido)-3-methylbutanoic acid, (S)-methyl 2-(1S,3R)-3-((1R,3aS,5aR,5bR,7aR,9S,11aR,11bR,13aR,13bR)-9-acetoxy-5a,5b,8,8,11a-pentamethyl-1-(prop-1-en-2-yl)icosahydro-1H-cyclopenta[a]chrysene-3a-carboxamido)-2,2-dimethylcyclobutanecarboxamido)-4-methyl pentanoate, (S)-2-((1S,3R)-3-((1R,3aS,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysene-3a-carboxamido)-2,2-dimethylcyclobutanecarboxamido)-4-methylpentanoic acid, (1R,3aS,5aR,5bR,7aR,9S,11aR,11bR,13aR,13bR)-3a-((1R,3S)-2,2-dimethyl-3-(pyrrolidine-1-carbonyl)cyclobutylcarbamoyl)-5a,5b,8,8,11a-pentamethyl-1-(prop-1-en-2-yl)icosahydro-1H-cyclopenta[a]chrysen-9-yl acetate, (1R,3aS,5aR,5bR,7aR,9S,11aR,11bR,13aR,13bR)-N-((1R,3S)-2,2-dimethyl-3-(pyrrolidine-1-carbonyl)cyclobutyl)-9-hydroxy-5a,5b,8,8,11a-pentamethyl-1-(prop-1-en-2-yl)icosahydro-1H-cyclopenta[a]chrysene-3a-carboxamide, 4-((1R,3aS,5aR,5bR,7aR,9S,11aR,11bR,13aR,13bR)-3a-((1R,3S)-2,2-dimethyl-3-(pyrrolidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid, (1R,3aS,5aR,5bR,7aR,9S,11aR,11bR,13aR,13bR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yl acetate, (1R,3aS,5aR,5bR,7aR,9S,11aR,11bR,13aR,13bR)-N-((1R,3S)-2,2-dimethyl-3-(piperidine-1-carbonyl)cyclobutyl)-9-hydroxy-5a,5b,8,8,11a-pentamethyl-1-(prop-1-en-2-yl)icosahydro-1H-cyclopenta[a]chrysene-3a-carboxamide, 4-((1R,3aS,5aR,5bR,7aR,9S,11aR,11bR,13aR,13bR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid, (1R,3aS,5aR,5bR,7aR,9S,11aR,11bR,13aR,13bR)-5a,5b,8,8,11a-pentamethyl-3a-((1R,3S)-3-((3-methylpiperidin-1-yl)methyl)cyclopentylcarbamoyl)-1-(prop-1-en-2-yl)icosahydro-1H-cyclopenta[a]chrysen-9-yl acetate, (1R,3aS,5aR,5bR,7aR,9S,11aR,11bR,13aR,13bR)-9-hydroxy-5a,5b,8,8,11a-pentamethyl-N-((1R,3S)-3-((3-methylpiperidin-1-yl)methyl)cyclopentyl)-1-(prop-1-en-2-yl)icosahydro-1H-cyclopenta[a]chrysene-3a-carboxamide, 2,2-dimethyl-4-oxo-4-((1R,3aS,5aR,5bR,7aR,9S,11aR,11bR,13aR,13bR)-5a,5b,8,8,11a-pentamethyl-3a-((1R,3S)-3-((3-methylpiperidin-1-yl)methyl)cyclopentylcarbamoyl)-1-(prop-1-en-2-yl)icosahydro-1H-cyclopenta[a]chrysen-9-yloxy)butanoic acid, (1R,3aS,5aR,5bR,7aR,9S,11aR,11bR,13aR,13bR)-3a-(4-ethylpiperazine-1-carbonyl)-5a,5b,8,8,11a-pentamethyl-1-(prop-1-en-2-yl)icosahydro-1H-cyclopenta[a]chrysen-9-yl acetate, 4-ethylpiperazin-1-yl)((1R,3aS,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysen-3a-yl)methanone, 3-(((1R,3aS,5aR,5bR,7aR,9S,11aR,11bR,13aR,13bR)-3a-(4-ethylpiperazine-1-carbonyl)-5a,5b,8,8,11a-pentamethyl-1-(prop-1-en-2-yl)icosahydro-1H-cyclopenta[a]chrysen-9-yloxy)carbonyl)-2,2-dimethylcyclobutanecarboxylic acid, Ethyl 4-((1R,3aS,5aR,5bR,7aR,9S,11aR,11bR,13aR,13bR)-9-acetoxy-5a,5b,8,8,11a-pentamethyl-1-(prop-1-en-2-yl)icosahydro-1H-cyclopenta[a]chrysene-3a-carbonyl)-1-benzylcyclohexanecarboxylate, Ethyl 1-benzyl-4-((1R,3aS,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysene-3a-carbonyl)cyclohexanecarboxylate, 4-((1R,3aS,5aR,5bR,7aR,9S,11aR,11bR,13aR,13bR)-3a-(4-benzyl-4-(ethoxycarbonyl)piperidine-1-carbonyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid, (1S,3R)-1-tert-butyl 3-((1R,3aS,5aR,5bR,7aR,9S,11aR,11bR,13aR,13bR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yl)2,2-dimethylcyclobutane-1,3-dicarboxylate, (1S,3R)-3-(((1R,3aS,5aR,5bR,7aR,9S,11aR,11bR,13aR,13bR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)carbonyl)-2,2-dimethylcyclobutanecarboxylic acid, (1S,3R)-1-tert-butyl 3-((1R,3aS,5aR,5bR,7aR,9S,11aR,11bR,13aR,13bR)-3a-((1S,3R)-2,2-dimethyl-3-(morpholine-4-carbonyl)cyclobutylcarbamoyl)-5a,5b,8,8,11a-pentamethyl-1-(prop-1-en-2-yl)icosahydro-1H-cyclopenta[a]chrysen-9-yl)2,2-dimethylcyclobutane-1,3-dicarboxylate, (1S,3R)-3-(((1R,3aS,5aR,5bR,7aR,9S,11aR,11bR,13aR,13bR)-3a-((1S,3R)-2,2-dimethyl-3-(morpholine-4-carbonyl)cyclobutylcarbamoyl)-5a,5b,8,8,11a-pentamethyl-1-(prop-1-en-2-yl)icosahydro-1H-cyclopenta[a]chrysen-9-yloxy)carbonyl)-2,2-dimethylcyclobutanecarboxylic acid, 4-((1R,3aS,5aR,5bR,7aR,9S,11aR,11bR,13aR,13bR)-3a-((1S,3R)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-4-oxobutanoic acid, (1S,3R)-1-tert-butyl 3-((1R,3aS,5aR,5bR,7aR,9S,11aR,11bR,13aR,13bR)-3a-((1S,3R)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yl)2,2-dimethylcyclobutane-1,3-dicarboxylate, (1S,3R)-3-(((1R,3aS,5aR,5bR,7aR,9S,11aR,11bR,13aR,13bR)-3a-((1S,3R)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)carbonyl)-2,2-dimethylcyclobutanecarboxylic acid, 5-((1R,3aS,5aR,5bR,7aR,9S,11aR,11bR,13aR,13bR)-3a-((1S,3R)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-5-oxopentanoic acid, (1R,3aS,5aR,5bR,7aR,9S,11aR,11bR,13aR,13bR)-3a-((1S,3R)-3-(4-ethylpiperazine-1-carbonyl)-2,2-dimethylcyclobutylcarbamoyl)-5a,5b,8,8,11a-pentamethyl-1-(prop-1-en-2-yl)icosahydro-1H-cyclopenta[a]chrysen-9-yl acetate, (1R,3aS,5aR,5bR,7aR,9S,11aR,11bR,13aR,13bR)-N-((1S,3R)-3-(4-ethylpiperazine-1-carbonyl)-2,2-dimethylcyclobutyl)-9-hydroxy-5a,5b,8,8,11a-pentamethyl-1-(prop-1-en-2-yl)icosahydro-1H-cyclopenta[a]chrysene-3a-carboxamide, 4-((1R,3aS,5aR,5bR,7aR,9S,11aR,11bR,13aR,13bR)-3a-((1S,3R)-3-(4-ethylpiperazine-1-carbonyl)-2,2-dimethylcyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid, (1R,3aS,5aR,5bR,7aR,9S,11aR,11bR,13aR,13bR)-3a-((1R,3S)-3-(4-ethylpiperazine-1-carbonyl)-2,2-dimethylcyclobutylcarbamoyl)-5a,5b,8,8,11a-pentamethyl-1-(prop-1-en-2-yl)icosahydro-1H-cyclopenta[a]chrysen-9-yl acetate, (1R,3 aS,5aR,5bR,7aR,9S,11aR,11bR,13aR,13bR)-N-((1R,3S)-3-(4-ethylpiperazine-1-carbonyl)-2,2-dimethylcyclobutyl)-9-hydroxy-5a,5b,8,8,11a-pentamethyl-1-(prop-1-en-2-yl)icosahydro-1H-cyclopenta[a]chrysene-3a-carboxamide, 4-((1R,3aS,5aR,5bR,7aR,9S,11aR,11bR,13aR,13bR)-3a-((1R,3S)-3-(4-ethylpiperazine-1-carbonyl)-2,2-dimethylcyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid, Ethyl 1-((1R,3aS,5aR,5bR,7aR,9S,11aR,11bR,13aR,13bR)-9-acetoxy-5a,5b,8,8,11a-pentamethyl-1-(prop-1-en-2-yl)icosahydro-1H-cyclopenta[a]chrysene-3a-carbonyl)-4-ethylpiperidine-4-carboxylate, Ethyl 4-ethyl-1-((1 R,3aS,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysene-3a-carbonyl)piperidine-4-carboxylate, 4-((1R,3 aS,5aR,5bR,7aR,9S,11aR,11bR,13aR,13bR)-3a-(4-(ethoxycarbonyl)-4-ethylpiperidine-1-carbonyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid, (1R,3aS,5aR,5bR,7aR,9S,11aR,11bR,13aR,13bR)-3a-(4-cyano-4-phenylpiperidine-1-carbonyl)-5a,5b,8,8,11a-pentamethyl-1-(prop-1-en-2-yl)icosahydro-1H-cyclopenta[a]chrysen-9-yl acetate, 1-((1R,3aS,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysene-3a-carbonyl)-4-phenylpiperidine-4-carbonitrile, 4-((1R,3 aS,5aR,5bR,7aR,9 S,11aR,11bR,13aR,13bR)-3a-(4-cyano-4-phenylpiperidine-1-carbonyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid, Tert-butyl 2-(6-(2-((1R,3aS,5aR,5bR,7aR,9S,11aR,11bR,13aR,13bR)-9-acetoxy-5a,5b,8,8,11a-pentamethyl-1-(prop-1-en-2-yl)icosahydro-1H-cyclopenta[a]chrysene-3a-carboxamido)ethyl)-2,2-dimethyl-1,3-dioxan-4-yl)acetate, Tert-butyl 2-(6-(2-((1R,3aS,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysene-3a-carboxamido)ethyl)-2,2-dimethyl-1,3-dioxan-4-yl)acetate, 4-((1R,3aS,5aR,5bR,7aR,9S,11aR,11bR,13aR,13bR)-3a-(2-(6-(2-tert-butoxy-2-oxo ethyl)-2,2-dimethyl-1,3-dioxan-4-yl)ethylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid, 7-((1R,3aS,5aR,5bR,7aR,9S,11aR,11bR,13aR,13bR)-9-(3-carboxy-3-methylbutanoyl oxy)-5a,5b,8,8,11a-pentamethyl-1-(prop-1-en-2-yl)icosahydro-1H-cyclopenta[a]chrysene-3a-carboxamido)-3,5-dihydroxyheptanoic acid, 5-((1R,3aS,5aR,5bR,7aR,9S,11aR,11bR,13aR,13bR)-3a-((1R,3S)-3-((4-benzylpiperidin-1-yl)methyl)cyclopentylcarbamoyl)-5a,5b,8,8,11a-pentamethyl-1-(prop-1-en-2-yl)icosahydro-1H-cyclopenta[a]chrysen-9-yloxy)-3,3-dimethyl-5-oxopentanoic acid, ((1R,3aS,5aR,5bR,7aR,9S,11aR,11bR,13aR,13bR)-9-acetoxy-5a,5b,8,8,11a-pentamethyl-1-(prop-1-en-2-yl)icosahydro-1H-cyclopenta[a]chrysene-3a-carbonyl)-4-ethylpiperidine-4-carboxylic acid, 4-ethyl-1-((1R,3aS,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysene-3a-carbonyl)piperidine-4-carboxylic acid, 1-((1R,3aS,5aR,5bR,7aR,9S,11aR,11bR,13aR,13bR)-9-(3-carboxy-3-methylbutanoyl oxy)-5a,5b,8,8,11a-pentamethyl-1-(prop-1-en-2-yl)icosahydro-1H-cyclopenta[a]chrysene-3a-carbonyl)-4-ethylpiperidine-4-carboxylic acid, 1-(((1S,3R)-3-((1R,3aS,5aR,5bR,7aR,9S,11aR,11bR,13aR,13bR)-9-(3-carboxy-3-methylbutanoyloxy)-5a,5b,8,8,11a-pentamethyl-1-(prop-1-en-2-yl)icosahydro-1H-cyclopenta[a]chrysene-3a-carbonyl)cyclopentyl)methyl)piperidine-4-carboxylic acid, 4-((1R,3aS,5aR,5bR,7aR,9S,11aR,11bR,13aR,13bR)-3a-((1R,3S)-3-(benzyloxycarbonyl)-2,2-dimethylcyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid, (1S,3R)-3-((1 S,3aS,5aR,5bR,7aR,9S,11aR,11bR,13aR,13bR)-9-(3-carboxy-3-methyl butanoyloxy)-1-isopropyl-5a,5b,8,8,11a-pentamethylicosahydro-1H-cyclopenta[a]chrysene-3a-carboxamido)-2,2-dimethylcyclobutanecarboxylic acid, (1R,3S)-1-benzyl 3-((1R,3aS,5aR,5bR,7aR,9S,11aR,11bR,13aR,13bR)-3a-((1S,3R)-3-(4-(ethoxycarbonyl)piperidine-1-carbonyl)-2,2-dimethylcyclobutylcarbamoyl)-5a,5b,8,8,11a-pentamethyl-1-(prop-1-en-2-yl)icosahydro-1H-cyclopenta[a]chrysen-9-yl)2,2-dimethylcyclobutane-1,3-dicarboxylate, (1R,3S)-3-((1R,3aS,5aR,5bR,7aR,9S,11aR,11bR,13aR,13bR)-3a-((1S,3R)-3-(4-(ethoxycarbonyl)piperidine-1-carbonyl)-2,2-dimethylcyclobutylcarbamoyl)-5a,5b,8,8,11a-pentamethyl-1-(prop-1-en-2-yl)icosahydro-1H-cyclopenta[a]chrysen-9-yloxy)carbonyl)-2,2-dimethylcyclobutanecarboxylic acid, (1R,3S)-1-benzyl 3-((1R,3aS,5aR,5bR,7aR,9S,11aR,11bR,13aR,13bR)-3a-((1R,3S)-3-(benzyloxycarbonyl)-2,2-dimethylcyclobutylcarbamoyl)-5a,5b,8,8,11a-pentamethyl-1-(prop-1-en-2-yl)icosahydro-1H-cyclopenta[a]chrysen-9-yl)2,2-dimethylcyclobutane-1,3-dicarboxylate, (1S,3R)-3-((1R,3aS,5aR,5bR,7aR,9S,11aR,11bR,13aR,13bR)-9-((1S,3R)-3-carboxy-2,2-dimethylcyclobutanecarbonyloxy)-5a,5b,8,8,11a-pentamethyl-1-(prop-1-en-2-yl)icosahydro-1H-cyclopenta[a]chrysene-3a-carboxamido)-2,2-dimethylcyclobutanecarboxylic acid, (1R,3S)-1-benzyl 3-((1R,3aS,5aR,5bR,7aR,9S,11aR,11bR,13aR,13bR)-3a-(4-(ethoxycarbonyl)piperidine-1-carbonyl)-5a,5b,8,8,11a-pentamethyl-1-(prop-1-en-2-yl)icosahydro-1H-cyclopenta[a]chrysen-9-yl)2,2-dimethylcyclobutane-1,3-dicarboxylate, 5-((1R,3aS,5aR,5bR,7aR,9S,11aR,11bR,13aR,13bR)-3a-((1R,3S)-3-((4-benzylpiperidin-1-yl)methyl)cyclopentylcarbamoyl)-5a,5b,8,8,11a-pentamethyl-1-(prop-1-en-2-yl)icosahydro-1H-cyclopenta[a]chrysen-9-yloxy)-3,3-dimethyl-5-oxopentanoic acid, 2,2-dimethyl-4-oxo-4-((1R,3aS,5aR,5bR,7aR,9S,11aR,11bR,13aR,13bR)-5a,5b,8,8,11a-pentamethyl-3a-((1S,4R)-4-(morpholinomethyl)cyclopent-2-enylcarbamoyl)-1-(prop-1-en-2-yl)icosahydro-1H-cyclopenta[a]chrysen-9-yloxy)butanoic acid, 4-oxo-4-((1R,3aS,5aR,5bR,7aR,9S,11aR,11bR,13aR,13bR)-5a,5b,8,8,11a-pentamethyl-3a-(3-(piperidin-1-ylmethyl)cyclopentylcarbamoyl)-1-(prop-1-en-2-yl)icosahydro-1H-cyclopenta[a]chrysen-9-yloxy)butanoic acid, (1R,3aS,5aR,5bR,7aR,9S,11aR,11bR,13aR,13bR)-N-(2,2-dimethyl-3-(3-morpholino-3-oxopropylcarbamoyl)cyclobutyl)-9-hydroxy-5a,5b,8,8,11a-pentamethyl-1-(prop-1-en-2-yl)icosahydro-1H-cyclopenta[a]chrysene-3a-carboxamide, (1R,3aS,5aR,5bR,7aR,9S,11aR,11bR,13aR,13bR)-N-(2,2-dimethyl-3-(3-oxo-3-(pyrrolidin-1-yl)propylcarbamoyl)cyclobutyl)-9-hydroxy-5a,5b,8,8,11a-pentamethyl-1-(prop-1-en-2-yl)icosahydro-1H-cyclopenta[a]chrysene-3a-carboxamide, 4-((1R,3aS,5aR,5bR,7aR,9S,11aR,11bR,13aR,13bR)-3a-((1R,3S)-3-((4-benzylpiperidin-1-yl)methyl)cyclopentylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid, (1R,3aS,5aR,5bR,7aR,9S,11aR,11bR)-9-((3R)-3-(benzyloxycarbonyl)-2,2-dimethylcyclobutanecarbonyloxy)-5a,5b,8,8,11a-pentamethyl-1-(prop-1-en-2-yl)icosahydro-1H-cyclopenta[a]chrysene-3a-carboxylic acid, (1R,3aS,5aR,5bR,7aR,9S,11aR,11bR)-9-((3R)-3-(tert-butylcarbamoyl)-2,2-dimethylcyclobutanecarbonyloxy)-5a,5b,8,8,11a-pentamethyl-1-(prop-1-en-2-yl)icosahydro-1H-cyclopenta[a]chrysene-3a-carboxylic acid, (1R,3aS,5aR,5bR,7aR,9S,11aR,11bR)-9-((3R)-3-(tert-butoxycarbonylamino)-2,2-dimethylcyclobutanecarbonyloxy)-5a,5b,8,8,11a-pentamethyl-1-(prop-1-en-2-yl)icosahydro-1H-cyclopenta[a]chrysene-3a-carboxylic acid, (1R,3aS,5aR,5bR,7aR,9S,11aR,11bR)-9-((3R)-3-(ethoxycarbonylamino)-2,2-dimethylcyclobutanecarbonyloxy)-5a,5b,8,8,11a-pentamethyl-1-(prop-1-en-2-yl)icosahydro-1H-cyclopenta[a]chrysene-3a-carboxylic acid, (1R)-3-(((1R,3 aS,5aR,5bR,7aR,9S,11aR,11bR)-3a-(carboxymethylcarbamoyl)-5a,5b,8,8,11a-pentamethyl-1-(prop-1-en-2-yl)icosahydro-1H-cyclopenta[a]chrysen-9-yloxy)carbonyl)-2,2-dimethylcyclobutanecarboxylic acid, (1R)-3-(((1R,3 aS,5aR,5bR,7aR,9S,11aR,11bR)-3a-(1-carboxy-3-methylbutylcarbamoyl)-5a,5b,8,8,11a-pentamethyl-1-(prop-1-en-2-yl)icosahydro-1H-cyclopenta[a]chrysen-9-yloxy)carbonyl)-2,2-dimethylcyclobutanecarboxylic acid, (1R,3aS,5aR,5bR,7aR,9S,11aR,11bR)-9-((3R)-3-(1,1-difluoroethyl)-2,2-dimethylcyclobutanecarbonyloxy)-5a,5b,8,8,11a-pentamethyl-1-(prop-1-en-2-yl)icosahydro-1H-cyclopenta[a]chrysene-3a-carboxylic acid, (1R)-3-(((1R,3 aS,5aR,5bR,7aR,9S,11aR,11bR)-3a-(1-carboxyethylcarbamoyl)-5a,5b,8,8,11a-pentamethyl-1-(prop-1-en-2-yl)icosahydro-1H-cyclopenta[a]chrysen-9-yloxy)carbonyl)-2,2-dimethylcyclobutanecarboxylic acid, (1R)-3-(((1R,3aS,5aR,5bR,7aR,9S,11aR,11bR)-3a-(1-carboxy-2,2-dimethylpropylcarbamoyl)-5a,5b,8,8,11a-pentamethyl-1-(prop-1-en-2-yl)icosahydro-1 H-cyclopenta[a]chrysen-9-yloxy)carbonyl)-2,2-dimethylcyclobutanecarboxylic acid, 4-((1R,3aS,5aR,5bR,7aR,9S,11aR,11bR)-9-(3-carboxy-2,2-dimethylpropanoyloxy)-5a,5b,8,8,11a-pentamethyl-1-(prop-1-en-2-yl)icosahydro-1H-cyclopenta[a]chrysene-3a-carboxamido)-3,3-difluorocyclopentanecarboxylic acid, (1R)-3-(((1R,3 aS,5aR,5bR,7aR,9S,11aR,11bR)-3a-(4-(2-carboxyethyl)piperidine-1-carbonyl)-5a,5b,8,8,11a-pentamethyl-1-(prop-1-en-2-yl)icosahydro-1H-cyclopenta[a]chrysen-9-yloxy)carbonyl)-2,2-dimethylcyclobutanecarboxylic acid, 4-((1R,3 aS,5aR,5bR,7aR,9S,11aR,11bR)-9-(3-carboxy-3-methylbutanoyloxy)-5a,5b,8,8,11a-pentamethyl-1-(prop-1-en-2-yl)icosahydro-1H-cyclopenta[a]chrysene-3a-carboxamido)-3,3-difluorocyclopentanecarboxylic acid, (1R,2S,3aR,5aR,5bR,7aS,10R,12aR,12bR)-7a-(1-carboxy-2,2-dimethylpropylcarbamoyl)-2-(3-carboxy-3-methylbutanoyloxy)-3,3,5a,5b,12b-pentamethyl-10-(prop-1-en-2-yl)icosahydrodicyclopenta[a,i]phenanthrene-1-carboxylic acid, (1R,2S,3aR,5aR,5bR,7aS,10R,12aR,12bR)-2-(3-carboxy-3-methylbutanoyloxy)-7a-(1-carboxyethylcarbamoyl)-3,3,5a,5b,12b-pentamethyl-10-(prop-1-en-2-yl)icosahydrodicyclopenta[a,i]phenanthrene-1-carboxylic acid, and pharmaceutically acceptable salts thereof.

6. The compound according to claim 2, wherein substituted alkyl of $R^A$ is selected from:

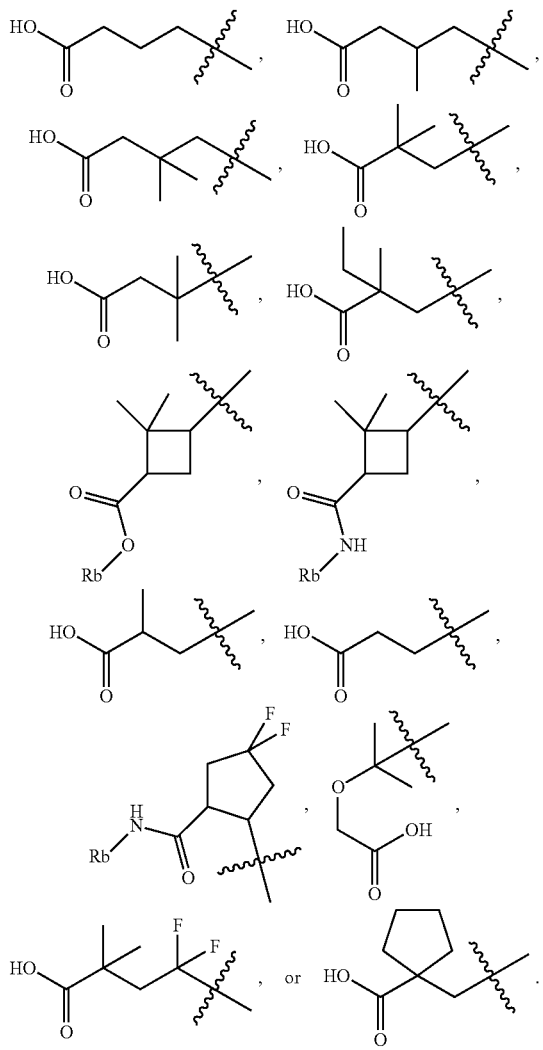

7. A compound which is
4-((1R,3aS,5aR,5bR,7aR,9S,11aR,11bR,13aR,13bR)-3a-((1R,3S)-2,2-dimethyl-3-(piperidine-1-carbonyl)cyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid, 4-((1R,3aS,5aR,5bR,7aR,9S,11aR,11bR,13aR,13bR)-3a-((1S,3R)-3-(4-ethylpiperazine-1-carbonyl)-2,2-dimethylcyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid, 4-((1R,3aS,5aR,5bR,7aR,9S,11aR,11bR,13aR,13bR)-3a-((1R,3S)-3-(4-ethylpiperazine-1-carbonyl)-2,2-dimethylcyclobutylcarbamoyl)-5a,5b,8,8,11a-pentamethyl-1-(prop-1-en-2-yl)icosahydro-1H-cyclopenta[a]chrysen-9-yloxy)-2,2-dimethyl-4-oxobutanoic acid, or 5-((1R,3aS,5aR,5bR,7aR,9S,11aR,11bR,13aR,13bR)-3a-((1R,3S)-3-((4-benzylpiperidin-1-yl)methyl)cyclopentylcarbamoyl)-5a,5b,8,8,11a-pentamethyl-1-(prop-1-en-2-yl)icosahydro-1H-cyclopenta[a]chrysen-9-yloxy)-3,3-dimethyl-5-oxopentanoic acid.

8. A pharmaceutical composition comprising a compound according to any one of claims 1-5 and a pharmaceutically acceptable excipient.

9. The pharmaceutical composition according to claim 8, wherein the pharmaceutically acceptable excipient is a carrier or diluent.

10. An Intermediate compound of the formula (3):

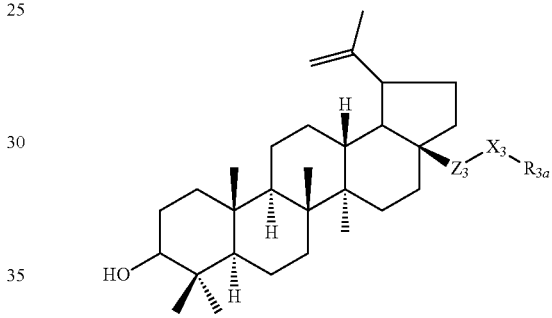

Formula (3)

wherein,
$R_{3a}$ is substituted or unsubstituted 4 or 5 membered cycloalkyl group, and if $R_{3a}$ is 4 membered cycloalkyl group then at least one of the carbon atom of the 4 membered cycloalkyl group must be substituted by two identical groups and which are selected from alkyl or halogen;

$X_3$ is selected from a bond, —O—, —NR"—, —C(O)—, —C(O)$_2$—, —(CH$_2$)$_n$—, or —C(O)NR"—;

n is 0-3;

$Z_3$ is selected from a bond, —O—, or —NR"—;

each R" is independently selected from H, —[CH(R''')]$_p$C(O)$_2$R''', substituted or unsubstituted alkyl, substituted or unsubstituted amino, substituted or unsubstituted aryl, substituted or unsubstituted cycloalkyl, or substituted or unsubstituted hetero cyclyl;

p is 0-3; and each R''' is independently selected from H, substituted or unsubstituted alkyl, or substituted or unsubstituted cycloalkyl; a pharmaceutically acceptable salt thereof, a tautomer thereof, a regioisomer thereof, or a stereoisomer thereof.

11. A method for ameliorating HIV infection in a subject in need thereof comprising administering to the subject a therapeutically effective amount of a compound according to any one of claims 1-5.

12. A method for ameliorating HIV infection in a subject in need thereof comprising administering to the subject a therapeutically effective amount of a compound according to claim 6.

13. A method for ameliorating HIV infection in a subject in need thereof comprising administering to the subject a therapeutically effective amount of a compound according to claim 7.

14. A method for ameliorating HIV infection in a subject in need thereof comprising administering to the subject a pharmaceutical composition according to claim 8.

15. A method for ameliorating HIV infection in a subject in need thereof comprising administering to the subject a pharmaceutical composition according to claim 9.

* * * * *